United States Patent
Du et al.

(10) Patent No.: US 11,718,614 B2
(45) Date of Patent: Aug. 8, 2023

(54) COMPOUNDS AND METHODS FOR TREATMENT OF HEDGEHOG PATHWAY ASSOCIATED CONDITIONS

(71) Applicant: Suzhou Mednes Pharma Tech Co., Ltd., Jiangsu (CN)

(72) Inventors: Fang Du, Suzhou (CN); Xiaowei Hu, Suzhou (CN); Yugang Liang, Suzhou (CN)

(73) Assignee: Suzhou Mednes Pharma Tech Co., Ltd., Suzhou (CN)

( * ) Notice: Subject to any disclaimer, the term of this patent is extended or adjusted under 35 U.S.C. 154(b) by 0 days.

(21) Appl. No.: 17/255,413

(22) PCT Filed: Jun. 25, 2019

(86) PCT No.: PCT/IB2019/055338
§ 371 (c)(1),
(2) Date: Dec. 22, 2020

(87) PCT Pub. No.: WO2020/003119
PCT Pub. Date: Jan. 2, 2020

(65) Prior Publication Data
US 2021/0214353 A1 Jul. 15, 2021

Related U.S. Application Data

(60) Provisional application No. 62/689,470, filed on Jun. 25, 2018.

(51) Int. Cl.
| | | |
|---|---|---|
| *C07D 209/24* | (2006.01) | |
| *C07D 209/30* | (2006.01) | |
| *C07D 471/04* | (2006.01) | |
| *C07D 235/10* | (2006.01) | |
| *C07D 235/12* | (2006.01) | |
| *C07D 235/16* | (2006.01) | |
| *C07D 403/06* | (2006.01) | |
| *C07D 413/06* | (2006.01) | |

(52) U.S. Cl.
CPC ......... *C07D 471/04* (2013.01); *C07D 209/24* (2013.01); *C07D 209/30* (2013.01); *C07D 235/10* (2013.01); *C07D 235/12* (2013.01); *C07D 235/16* (2013.01); *C07D 403/06* (2013.01); *C07D 413/06* (2013.01)

(58) Field of Classification Search
CPC .......................... C07D 209/24; C07D 209/30
See application file for complete search history.

(56) References Cited

U.S. PATENT DOCUMENTS

| 5,095,031 A | 3/1992 | Brooks et al. |
| 2013/0102636 A1 | 4/2013 | Hutchinson et al. |

FOREIGN PATENT DOCUMENTS

| CN | 101331117 A | 12/2008 |
| CN | 106456602 A | 2/2017 |
| CN | 109678785 A | 4/2019 |
| EP | 0166591 B1 | 11/1989 |
| EP | 0275667 B1 | 3/1992 |
| WO | 2007047207 A2 | 4/2007 |
| WO | 2014027053 A1 | 2/2014 |
| WO | 2014151451 A1 | 9/2014 |

OTHER PUBLICATIONS

AbdulHameed, et al. Journal of Chemical Information and Modeling (abstract) (2008) 48 (1), 179-185; retrieved from STN online database on Mar. 29, 2022. Accession No. 2007:1377089 ZCAPLUS.*
Gaur, et al. Sensors and Actuators, B: Chemical (abstract) (2017) 248, 690-698; retrieved from STN online database on Mar. 29, 2022. Accession No. 2017:655844 HCAPLUS.*
Zhu, et al. CN 106083830 (abstract) (Nov. 00, 2016), retrieved from STN online databases on Mar. 29, 2022. Accession No. 2016:1797398 HCAPLUS.*
Mirskova, et al. Open Chemistry (abstract) (2015), 13 (1), 149-155, retrieved from STN online databases on Mar. 29, 2022. Accession No. 2015:505884 HCAPLUS.*
Hutchinson, et al. WO 2007056220 (abstract) May 18, 2007, retrieved from STN online databases on Mar. 29, 2022. Accession No. 2012:577154 HCAPLUS.*
Serkan Levent, et al., Synthesis and biological evaluation of C(5)-substituted derivatives of leukotriene biosynthesis inhibitor BRP-7, European Journal of Medicinal Chemistry, Elsevier, Amsterdam, NL, vol. 122, Jul. 5, 2016, pp. 510-519.
Amor A. San Juan, et al., HQSAR Study of Microsomal Prostaglandin E2 Synthase (mPGES-1) Inhibitors, Bulletin of the Korean Chemical Society, vol. 27, No. 10, Oct. 20, 2006, pp. 1531-1536.
Ana Naruha Skoda, et al., The role of the Hedgehog signaling pathway in cancer: A comprehensive review, Bosnian Journal of Basic Medical Sciences, vol. 18, No. 1, Feb. 20, 2018, pp. 8-20.
Extended European Search Report for European Application No. 19824574.8, filed Dec. 21, 2020 dated Nov. 9, 2021.
Gür et al., Identification of multi-target inhibitors of leukotriene and prostaglandin E2 biosynthesis by structural tuning of the FLAP inhibitor BRP-7, European Journal of Medicinal Chemistry, vol. 150, pp. 876-899, published on Mar. 17, 2018.

* cited by examiner

*Primary Examiner* — Shawquia Jackson
(74) *Attorney, Agent, or Firm* — Fox Rothschild LLP

(57) ABSTRACT

Provided herein is novel compounds of formula (I), (II), (III), (IV), and (V) as described in the specification, and pharmaceutically acceptable salts, solvates, and prodrugs and compositions thereof, and methods of measuring hedgehog pathway activation in tumor cells, examining tumor cell proliferation, differentiation and apoptosis and using the compounds and pharmaceutical compositions disclosed for treatment of diseases and disorders associated with the hedgehog signaling pathway.

4 Claims, No Drawings

COMPOUNDS AND METHODS FOR TREATMENT OF HEDGEHOG PATHWAY ASSOCIATED CONDITIONS

CROSS-REFERENCE TO RELATED APPLICATIONS

This application is a U.S. national phase application of International Application No. PCT/IB2019/055338, filed on Jun. 25, 2019, which claims priority to U.S. Provisional Patent Application No. 62/689,470, filed on 25 Jun. 2018, the disclosures of which are incorporated herein by reference in their entirety.

FIELD OF THE INVENTION

This invention relates to compounds, pharmaceutical compositions, and methods for treatment of hedgehog pathway associated malignancies.

BACKGROUND OF THE INVENTION

Medulloblastoma is the most common malignant brain tumor in children. Despite current tumor therapies including surgery, chemotherapy and radiotherapy, a significant proportion of patients still succumb to this disease. Moreover, patients who survive medulloblastoma, often suffer from long-term side effects including cognitive deficits and endocrine disorders. Improved strategies to treat medulloblastoma are still urgently needed.

Approximately 30% of human medulloblastoma is associated with aberrant activation of hedgehog (Hh) pathway. Hh pathway activation is also found in many other human malignancies such as basal cell carcinoma and pancreatic cancers. Currently two Hh pathway antagonists are FDA approved including vismodegib and sonidegib.

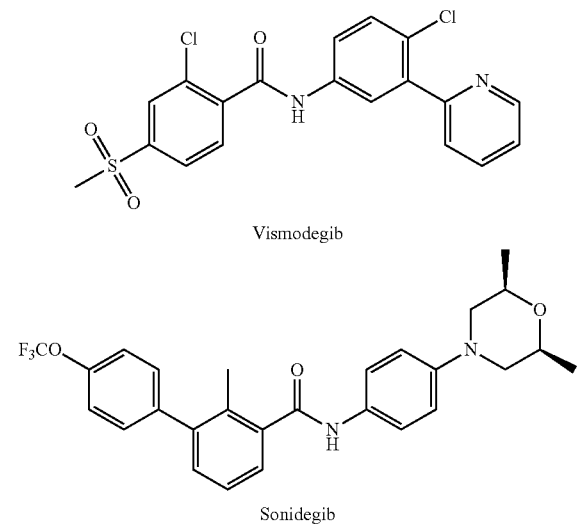

Although these antagonists exhibited promising efficacies in inhibiting medulloblastoma growth in the initial stage of clinical trial, patients often developed resistant rapidly. Moreover, vismodegib and sonidegib unspecifically inhibited Hh pathway in tumor cells and normal cells, which caused severe adverse effects, in particular, permanently compromised bone development. Due to the above reasons, these two drugs are currently not approved to be used for medulloblastoma treatment.

Therefore, there is a clear need to develop new therapeutic agents for treatment of such Hh pathway-associated diseases and disorders.

SUMMARY OF THE INVENTION

This invention meets the foregoing need by providing novel compounds as Hh pathway antagonists, which inhibit Hh signaling and repress medulloblastma cell growth. Therefore, the present invention represents a new type of chemotherapeutic approach to treat hedgehog pathway-associated malignancies. Different from conventional chemotherapeutic drugs that directly kill tumor cells by cytotoxicity, these compounds repress tumor cell growth through induction of tumor cells differentiation.

In one aspect, the present invention provides a compound of formula (I):

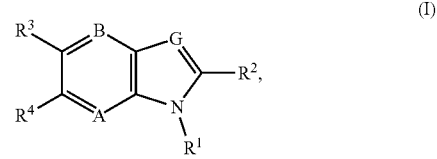

or a pharmaceutically acceptable salt, solvate, or prodrug thereof, wherein:

G is N or $CR^5$;

A is N or $CR^6$;

B is N or $CR^7$;

$R^1$ is $C_{1-8}$ alkyl, $C_{3-6}$ cycloalkyl, 5- to 10-membered heteroaryl, $C_{6-10}$ aryl, —($C_{1-6}$ alkylene)-$C_{3-6}$ cycloalkyl, —($C_{1-6}$ alkylene)-$C_{6-10}$ aryl, or —($C_{1-6}$ alkylene)-(5- to 10-membered heteroaryl or heterocyclyl), each optionally substituted;

$R^2$ is hydrogen, $C_{1-8}$ alkyl, $C_{6-10}$ aryl, —C(O)$OR^B$, —C(O)$NR^aR^b$, —($C_{1-6}$ alkylene)-$C_{6-10}$ aryl, —($C_{1-6}$ alkylene)-(5- to 10-membered heteroaryl or heterocyclyl), —($C_{1-6}$ alkylene)-C(O)$OR^B$, or —($C_{1-6}$ alkylene)-C(O)$NR^aR^b$, each except hydrogen optionally substituted;

$R^3$ is hydrogen, halogen, hydroxyl, optionally substituted $C_{1-6}$ alkyl, $C_{1-4}$ alkoxy, optionally substituted $C_{3-6}$ cycloalkyl, or —C(O)$OR^{11}$;

$R^4$ is hydrogen, halogen, hydroxyl, or optionally substituted $C_{1-6}$ alkyl;

$R^5$ is hydrogen, optionally substituted $C_{1-8}$ alkyl, optionally substituted $C_{6-10}$ aryl, optionally substituted 5- to 10-membered heteroaryl, —C(O)$OR^B$, —C(O)$R^9$, or —S(O)$_nR^{10}$ (n is 0, 1, or 2);

$R^6$ is hydrogen, halogen, or optionally substituted $C_{1-6}$ alkyl;

$R^7$ is hydrogen, halogen, or optionally substituted $C_{1-6}$ alkyl;

$R^8$ is hydrogen, $C_{1-6}$ alkyl, $C_{6-10}$ aryl, 5- to 10-membered heteroaryl, or —($C_{1-6}$ alkylene)-$C_{6-10}$ aryl, each exception hydrogen optionally substituted;

$R^9$ is hydrogen, $C_{1-8}$ alkyl, $C_{3-8}$ cycloalkyl, $C_{6-10}$ aryl, 3- to 10-membered heterocyclyl, 5- to 10-membered heteroaryl, or —($C_{1-6}$ alkylene)-$C_{6-10}$ aryl;

$R^{10}$ is $C_{1-10}$ alkyl, $C_{3-8}$ cycloalkyl, $C_{6-10}$ aryl, 5- to 10-membered heteroaryl, or —($C_{1-6}$ alkylene)-$C_{6-10}$ aryl, each exception hydrogen optionally substituted;

wherein any said optionally substituted alkyl or cycloalkyl is optionally substituted by one or two substituents independently selected from the group consisting of $C_{6-10}$ aryl, 5- to 10-membered heteroaryl, C(O)OR$^{11}$, OR$^{12}$, and C(O)NR$^a$R$^b$; and any said optionally substituted aryl or heteroaryl is optionally substituted by one, two or three substituents independently selected from the group consisting of halogen, hydroxyl, $C_{1-6}$ alkyl, $C_{1-6}$ haloalkyl, $C_{1-6}$ alkoxy, $C_{1-6}$ haloalkoxy, cyano, —C(O)OR$^{11}$, —($C_{1-6}$ alkylene)-OR$^{12}$, —($C_{1-6}$ alkylene)-CN, —($C_{1-6}$ alkylene)-C(O)OR$^{11}$, and —($C_{1-6}$ alkylene)-C(O)NR$^a$R$^b$;

R$^{11}$ is hydrogen or $C_{1-6}$ alkyl;

R$^{12}$ is hydrogen or $C_{1-6}$ alkyl; and

R$^a$ and R$^b$ are each independently hydrogen, $C_{1-6}$ alkyl, $C_{6-10}$ aryl, or benzyl.

In one aspect, the present invention provides Exemplified compounds in Table 1 and Examples in List 1 (below), and pharmaceutically acceptable salts, solvates, or prodrugs thereof.

In one aspect, the present invention provides a pharmaceutical composition comprising a compound according to any embodiments disclosed here, or a pharmaceutically acceptable salt, solvate or prodrug thereof, and a pharmaceutically acceptable carrier.

In another aspect, the present invention provides a method of treating a disease or disorder associated with hedgehog pathway, the method comprising administering to a subject in need of treatment a therapeutically effective amount of a compound according to any one embodiment disclosed herein, or a pharmaceutically acceptable salt, solvate, prodrug, or pharmaceutical composition thereof.

In another aspect, the present invention provides use of the compounds disclosed herein, or a pharmaceutically acceptable salt, solvate or prodrug thereof, in the manufacture of a medicament for treatment of a disease or disorder associated with hedgehog signaling pathway.

Other aspects or advantages of the present invention will be better appreciated in view of the following detailed description, Examples, and claims.

DETAILED DESCRIPTION OF THE INVENTION

The present invention, in one aspect, provides novel heterocyclic compounds, including, including but not limited to indole and benzimidazole compounds, among others, and analogs, especially those characterized by formula (I), useful as therapeutic agents for treatment of diseases or disorders associated with hedgehog signaling pathway based on a new discovery that these compounds can inhibit hedgehog signaling pathway in a mammalian animal.

In some embodiments, the present invention provides an indole compound of formula (II):

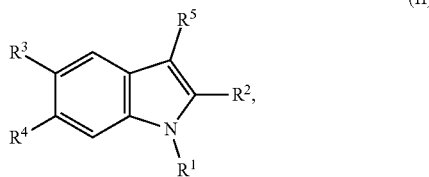

or a pharmaceutically acceptable salt, solvate, or prodrug thereof, wherein:

R$^1$ is $C_{1-8}$ alkyl, $C_{3-6}$ cycloalkyl, 5- to 10-membered heteroaryl, $C_{6-10}$ aryl, —($C_{1-6}$ alkylene)-$C_{3-6}$ cycloalkyl, —($C_{1-6}$ alkylene)-$C_{6-10}$ aryl, or —($C_{1-6}$ alkylene)-(5- to 10-membered heteroaryl or heterocyclyl);

R$^2$ is hydrogen, $C_{1-8}$ alkyl, $C_{6-10}$ aryl, —C(O)OR$^B$, —C(O)NR$^a$R$^b$, —($C_{1-6}$ alkylene)-$C_{6-10}$ aryl, —($C_{1-6}$ alkylene)-(5- to 10-membered heteroaryl or heterocyclyl), —($C_{1-6}$ alkylene)-C(O)OR$^8$, or —($C_{1-6}$ alkylene)-C(O)NR$^a$R$^b$;

R$^3$ is hydrogen, halogen, hydroxyl, $C_{1-6}$ alkyl, $C_{1-4}$ alkoxy, $C_{3-6}$ cycloalkyl, or —C(O)OR$^{11}$;

R$^4$ is hydrogen, halogen, hydroxyl, or $C_{1-6}$ alkyl;

R$^5$ is hydrogen, $C_{1-8}$ alkyl, $C_{6-10}$ aryl, 5- to 10-membered heteroaryl, —C(O)OR$^8$, —C(O)R$^9$, or —S(O)$_n$R$^{10}$ (n is 0, 1, or 2);

R$^8$ is hydrogen, $C_{1-6}$ alkyl, $C_{6-10}$ aryl, 5- to 10-membered heteroaryl, or —($C_{1-6}$ alkylene)-$C_{6-10}$ aryl;

R$^9$ is hydrogen, $C_{1-8}$ alkyl, $C_{3-8}$ cycloalkyl, $C_{6-10}$ aryl, 3- to 10-membered heterocyclyl, 5- to 10-membered heteroaryl, or —($C_{1-6}$ alkylene)-$C_{6-10}$ aryl;

R$^{10}$ is $C_{1-10}$ alkyl, $C_{3-8}$ cycloalkyl, $C_{6-10}$ aryl, 5- to 10-membered heteroaryl, or —($C_{1-6}$ alkylene)-$C_{6-10}$ aryl;

wherein any said alkyl or cycloalkyl is optionally substituted by one or two substituents independently selected from the group consisting of $C_{6-10}$ aryl, 5- to 10-membered heteroaryl, C(O)OR$^{11}$, OR$^{12}$, and C(O)NR$^a$R$^b$; and any said aryl or heteroaryl is optionally substituted by one, two or three substituents independently selected from the group consisting of halogen, hydroxyl, $C_{1-6}$ alkyl, $C_{1-6}$ haloalkyl, $C_{1-6}$ alkoxy, $C_{1-6}$ haloalkoxy, cyano, —C(O)OR$^{11}$, —($C_{1-6}$ alkylene)-OR$^{12}$, —($C_{1-6}$ alkylene)-CN, —($C_{1-6}$ alkylene)-C(O)OR$^{11}$, and —($C_{1-6}$ alkylene)-C(O)NR$^a$R$^b$;

R$^{11}$ is hydrogen or $C_{1-6}$ alkyl;

R$^{12}$ is hydrogen or $C_{1-6}$ alkyl; and

R$^a$ and R$^b$ are each independently hydrogen, $C_{1-6}$ alkyl, $C_{6-10}$ aryl, or benzyl;

provided, however, that the following compounds are excluded:

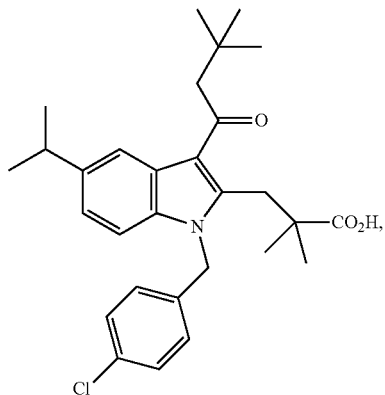

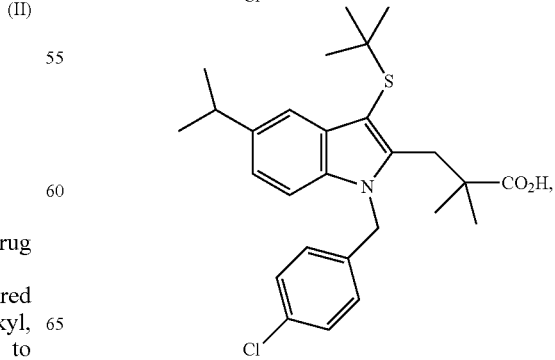

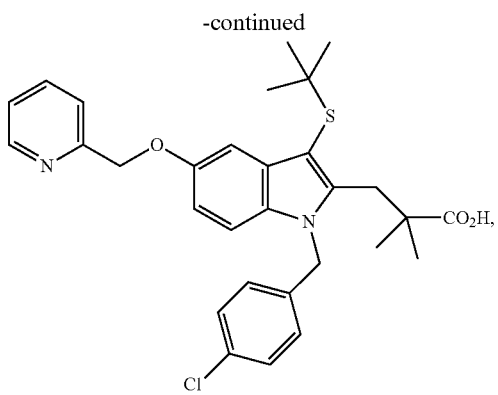

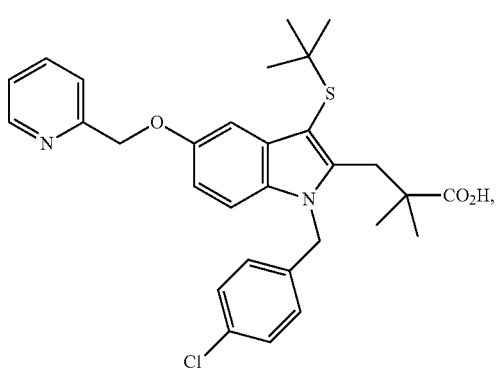

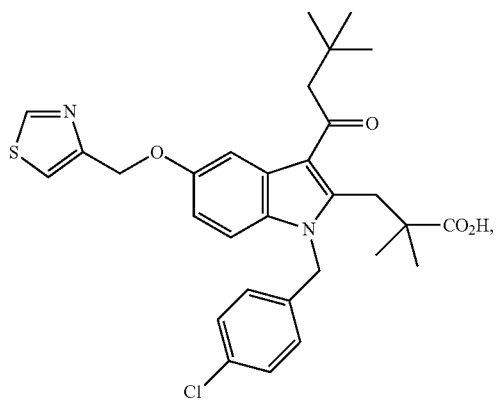

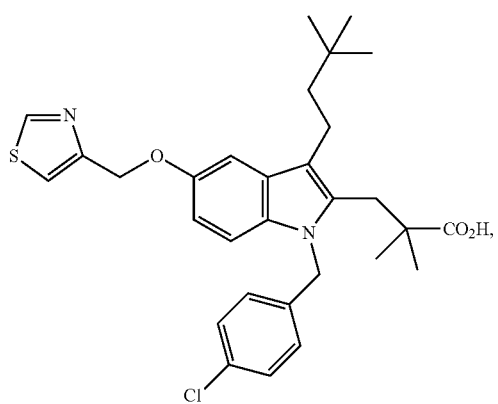

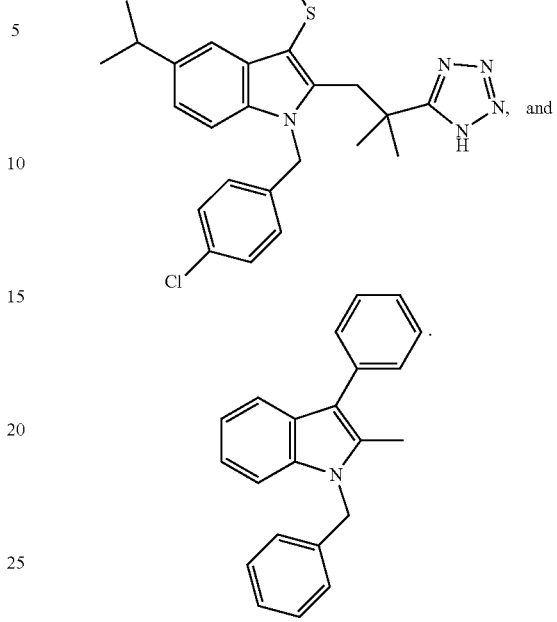

In some embodiments of this aspect, the compounds of formula (II) are further defined as follows:

$R^1$ is selected from the group consisting of benzyl, $C_{3-6}$ cycloalkyl-methyl, 5- or 6-membered heterocyclyl-methyl, and 5 or 6-membered heteroaryl-methyl, each optionally substituted; and $R^2$ is $C_{1-6}$ alkyl, phenyl, or 5-membered heteroaryl, wherein the $C_{1-8}$ alkyl is optionally substituted by one or two substituents independently selected from the group consisting of phenyl, 5- or 6-membered heteroaryl, $C(O)OR^{11}$, $OR^{12}$, and $C(O)NR^aR^b$; and any said heteroaryl or phenyl is optionally substituted by one or two substituents independently selected from the group consisting of halogen, hydroxyl, cyano, $C_{1-4}$ alkyl, $C_{1-4}$ alkoxy, —$C(O)OR^{11}$, —($C_{1-4}$ alkylene)-$OR^{12}$, —($C_{1-4}$ alkylene)-CN, and —($C_{1-4}$ alkylene)-$C(O)OR^{11}$;

$R^3$ is hydrogen, $C_{1-6}$ alkyl, halogen, hydroxyl, $C_{1-4}$ alkoxy, $C_{3-6}$ cycloalkyl, or —$C(O)OR^{11}$;

$R^4$ is hydrogen, halogen, hydroxyl, or $C_{1-6}$ alkyl;

$R^5$ is $C_{1-8}$ alkyl, phenyl optionally substituted by a $C_{1-6}$ alkyl, 5- to 6-membered heteroaryl, —$C(O)OR^B$, —$C(O)R^9$, or —$S(O)_nR^{10}$ (n is 0, 1, or 2), wherein the $C_{1-8}$ alkyl is optionally substituted by one or two substituents independently selected from the group consisting of $C_{6-10}$ aryl, 5- to 10-membered heteroaryl, $C(O)OR^{11}$, $OR^{12}$, $C(O)NR^aR^b$, and —($C_{1-8}$ alkyl)-($C_{6-10}$ aryl); and any aryl or heteroaryl is optionally substituted by one or two substituents independently selected from the group consisting of halogen, hydroxyl, $C_{1-4}$ alkyl, $C_{1-4}$ haloalkyl, $C_{1-4}$ alkoxy, $C_{1-4}$ haloalkoxy, and cyano;

$R^8$ is hydrogen, $C_{1-6}$ alkyl, $C_{6-10}$ aryl, 5- to 10-membered heteroaryl, or benzyl;

$R^9$ is hydrogen, $C_{1-6}$ alkyl, $C_{3-6}$ cycloalkyl, 3- to 6-membered heterocyclyl, phenyl, 5- to 10-membered heteroaryl, or —($C_{1-4}$ alkylene)-phenyl;

$R^{10}$ is $C_{1-8}$ alkyl, $C_{3-6}$ cycloalkyl, $C_{6-10}$ aryl, 5- to 10-membered heteroaryl, or benzyl;

$R^{11}$ is hydrogen or $C_{1-6}$ alkyl;

$R^{12}$ is hydrogen or $C_{1-6}$ alkyl; and $R^a$ and $R^b$ are independently hydrogen or $C_{1-6}$ alkyl.

In some embodiments, the present invention provides a benzimidazole compound of formula (III):

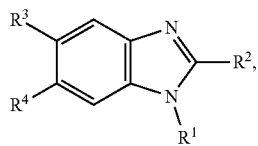
(III)

or a pharmaceutically acceptable salt, solvate or prodrug thereof, wherein:

$R^1$ is benzyl with its phenyl group optionally substituted by one or more halogen atoms;

$R^2$ is $C_{1-6}$ alkyl optionally substituted by phenyl or —C(O)OR$^8$, wherein phenyl is optionally substituted by one or two substituents independently selected from the group consisting of halogen, $C_{1-6}$ alkyl, —CN, —C(O)OR$^{11}$, —($C_{1-4}$ alkylene)-OR$^{12}$, —($C_{1-4}$ alkylene)-CN, and —($C_{1-4}$ alkylene)-C(O)OR$^{11}$;

$R^3$ is halogen, —OR$^{12}$, or —C(O)OR$^{11}$;

$R^4$ is hydrogen;

$R^8$ at each occurrence is independently hydrogen or $C_{1-4}$ alkyl;

$R^{11}$ is hydrogen or $C_{1-6}$ alkyl; and $R^{12}$ is hydrogen or $C_{1-6}$ alkyl;

provided, however, that the following compounds are excluded:

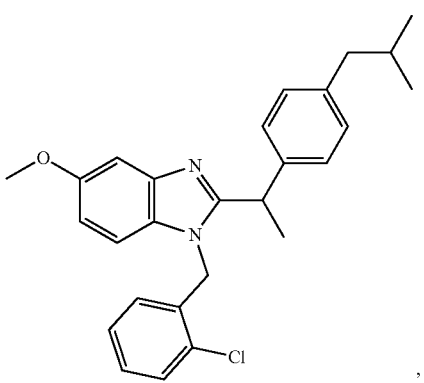

,

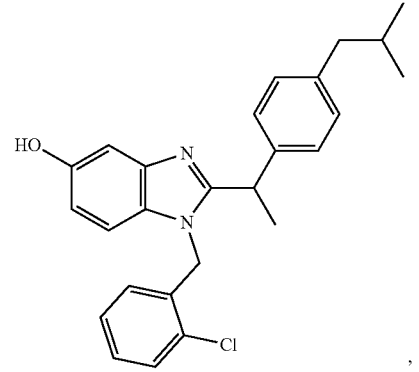

,

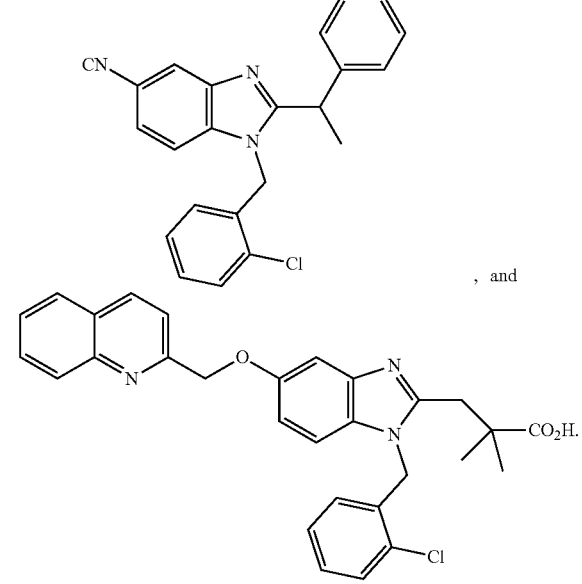

, and

In some embodiments, the present invention provides a pyrrolo[2,3-b]pyridine compound of formula (IV):

(IV)

or a pharmaceutically acceptable salt, solvate or prodrug thereof, wherein:

$R^1$ is benzyl with its phenyl group optionally substituted by one or more halogen atoms;

$R^2$ is $C_{1-6}$ alkyl optionally substituted by phenyl or —C(O)OR$^8$, wherein phenyl is optionally substituted by one or two substituents independently selected from the group consisting of halogen, $C_{1-6}$ alkyl, —CN, —C(O)OR$^{11}$, —($C_{1-4}$ alkylene)-OR$^{12}$, —($C_{1-4}$ alkylene)-CN, and —($C_{1-4}$ alkylene)-C(O)OR$^{11}$;

$R^3$ is halogen, $C_{1-6}$ alkyl, or —OR$^{12}$;

$R^4$ is hydrogen;

$R^5$ is $C_{1-8}$ alkyl, phenyl optionally substituted by a $C_{1-6}$ alkyl, 5- to 6-membered heteroaryl, —C(O)OR$^8$, or —C(O)R$^9$, wherein the $C_{1-8}$ alkyl is optionally substituted by one or two substituents independently selected from the group consisting of $C_{6-10}$ aryl, 5- to 10-membered heteroaryl, C(O)OR$^{11}$, OR$^{12}$, C(O)NR$^a$R$^b$, and —($C_{1-8}$ alkyl)-($C_{6-10}$ aryl); and any aryl or heteroaryl is optionally substituted by one or two substituents independently selected from the group consisting of halogen, hydroxyl, $C_{1-4}$ alkyl, $C_{1-4}$ haloalkyl, $C_{1-4}$ alkoxy, $C_{1-4}$ haloalkoxy, and cyano;

$R^8$ at each occurrence is independently hydrogen or $C_{1-4}$ alkyl;

$R^9$ is hydrogen, $C_{1-6}$ alkyl, $C_{3-6}$ cycloalkyl, 3- to 6-membered heterocyclyl, phenyl, 5- to 10-membered heteroaryl, or —($C_{1-4}$ alkylene)-phenyl;

$R^{11}$ is hydrogen or $C_{1-6}$ alkyl;
$R^{12}$ is hydrogen or $C_{1-6}$ alkyl; and
$R^a$ and $R^b$ are independently hydrogen or $C_{1-6}$ alkyl.

In some embodiments, the present invention provides a pyrrolo[3,2-b]pyridine compound of formula (V):

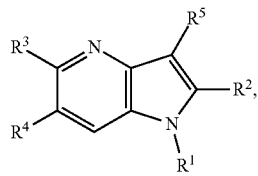

(V)

or a pharmaceutically acceptable salt, solvate or prodrug thereof, wherein:

wherein $R^1$ is benzyl with its phenyl group optionally substituted by one or more halogen atoms;

$R^2$ is $C_{1-6}$ alkyl optionally substituted by phenyl or —C(O)OR$^B$, wherein phenyl is optionally substituted by one, two, or three substituents independently selected from the group consisting of halogen, $C_{1-6}$ alkyl, —CN, —C(O)OR$^{11}$, —($C_{1-6}$ alkylene)-OR$^{12}$, —($C_{1-6}$ alkylene)-CN, and —($C_{1-6}$ alkylene)-C(O)OR$^{11}$;

$R^3$ is halogen, $C_{1-6}$ alkyl, or —OR$^{12}$;

$R^4$ is hydrogen;

$R^5$ is $C_{1-8}$ alkyl, phenyl optionally substituted by a $C_{1-6}$ alkyl, 5- to 6-membered heteroaryl, —C(O)OR$^B$, or —C(O)R$^9$, wherein the $C_{1-8}$ alkyl is optionally substituted by one or two substituents independently selected from the group consisting of $C_{6-10}$ aryl, 5- to 10-membered heteroaryl, C(O)OR$^{11}$, OR$^{12}$, C(O)NR$^a$R$^b$, and —($C_{1-8}$ alkyl)-($C_{6-10}$ aryl); and any aryl or heteroaryl is optionally substituted by one, two or three substituents independently selected from the group consisting of halogen, hydroxyl, $C_{1-4}$ alkyl, $C_{1-4}$ haloalkyl, $C_{1-4}$ alkoxy, $C_{1-4}$ haloalkoxy, and cyano;

$R^8$ is independently hydrogen or $C_{1-4}$ alkyl;

$R^9$ is hydrogen, $C_{1-6}$ alkyl, $C_{3-6}$ cycloalkyl, 3- to 6-membered heterocyclyl, phenyl, 5- to 10-membered heteroaryl, or —($C_{1-4}$ alkylene)-phenyl;

$R^{11}$ is hydrogen or $C_{1-6}$ alkyl; and
$R^{12}$ is hydrogen or $C_{1-6}$ alkyl; and
$R^a$ and $R^b$ are independently hydrogen or $C_{1-6}$ alkyl.

In some embodiments, sometimes preferred, the present invention provides a compound according to any one of Formulas (I), (II), (III), (IV), and (V), wherein (where applicable):

$R^1$ is selected from the group consisting from $C_1$-$C_6$ alkyl,

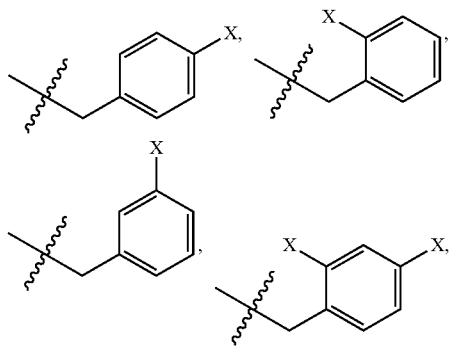

-continued

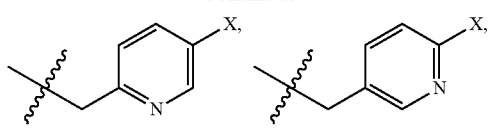

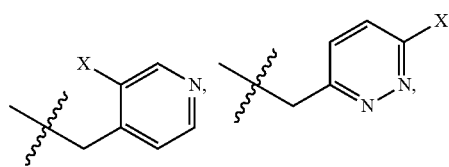

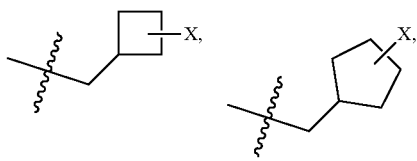

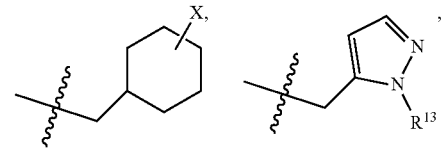

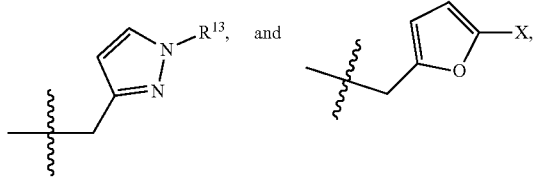

wherein each is independently hydrogen, halogen, $C_1$-$C_6$ alkyl, $C_1$-$C_6$ alkoxy, $C_1$-$C_6$ haloalkyl, or CN; and each $R^{13}$ is independently hydrogen, $C_1$-$C_6$ alkyl, or $C_1$-$C_6$ haloalkyl;

$R^2$ is selected from the group consisting of hydrogen, $C_1$-$C_6$ alkyl,

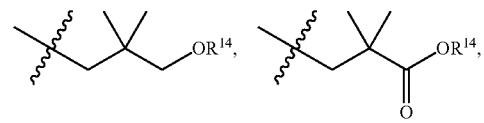

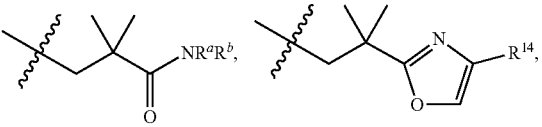

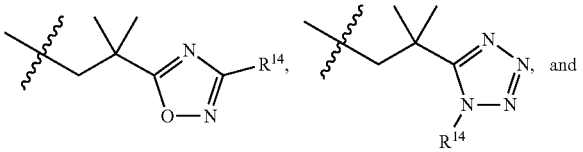

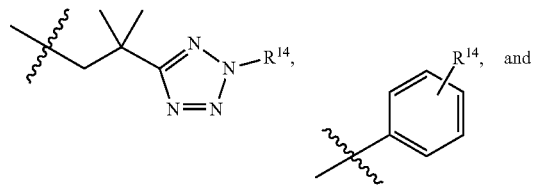

-continued

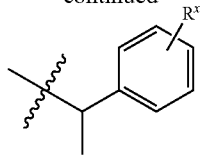

($R^x$ is halogen, —$(CH_2)_n$CN, or —$(CH_2)_n OR^{14}$) wherein each n is 0, 1, or 2; each $R^{14}$ is independently H or $C_1$-$C_6$ alkyl; and $R^a$ and $R^b$ are independently hydrogen or $C_{1-6}$ alkyl;

$R^3$ is selected from the group consisting of hydrogen, $C_1$-$C_6$ alkyl, hydroxyl, $C_1$-$C_6$ alkoxy, $C_1$-$C_6$ haloalkyl, and —C(O)O$R^{15}$ ($R^{15}$ is H or $C_1$-$C_6$ alkyl);

$R^4$ is selected from the group consisting of hydrogen, halogen, $C_1$-$C_6$ alkyl, $C_3$-$C_6$ cycloalkyl, hydroxyl, and $C_1$-$C_6$ alkoxy; and/or $R^5$ is selected from the group consisting of hydrogen, $C_1$-$C_8$ alkyl, 5-membered heteroaryl,

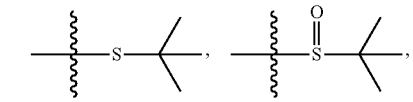

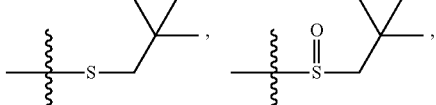

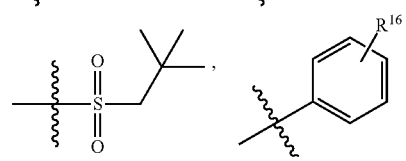

($R^{15}$ is halogen or $C_1$-$C_6$ alkyl),

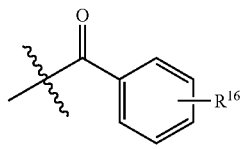

($R^{16}$ is halogen or $C_1$-$C_6$ alkyl),

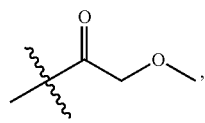 [SMILES: *C(=O)COC]

and —C(O)—$R^9$, where $R^9$ is $C_1$-$C_8$ alkyl or $C_3$-$C_6$ cycloalkyl;

provided, however, the provisos in any of the embodiments described herein will apply.

In some embodiments, the present invention provides exemplified compounds in Table 1 and the following list (List 1), and pharmaceutically acceptable salts, solvates, or prodrugs thereof:

List 1

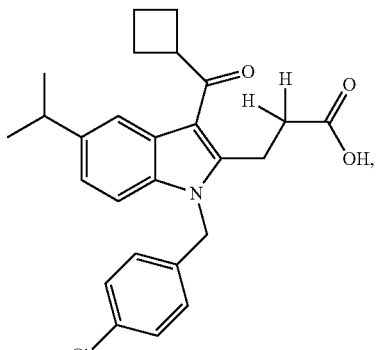

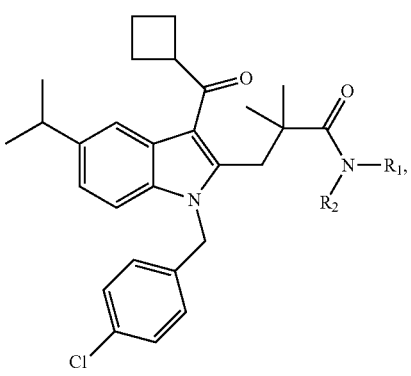

R1, R2 = H or alkyl

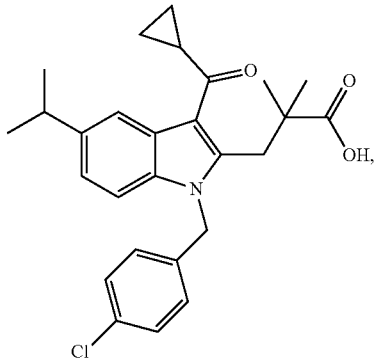

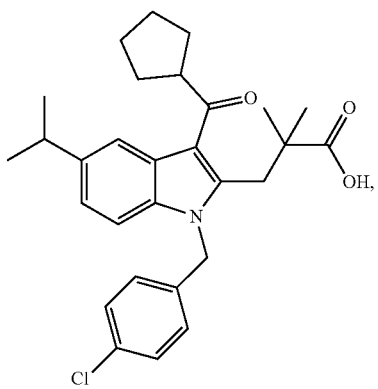

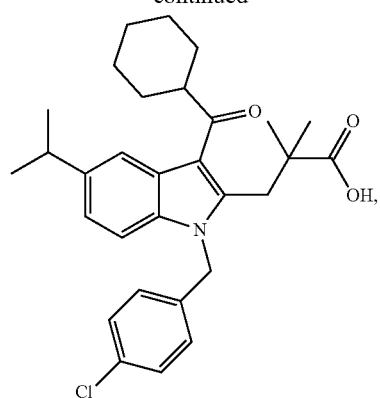
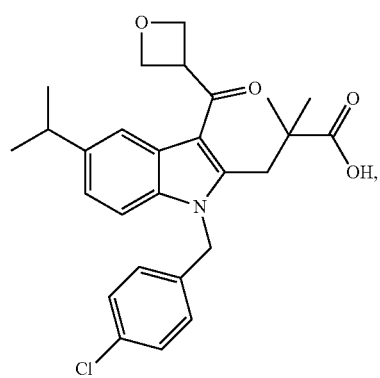
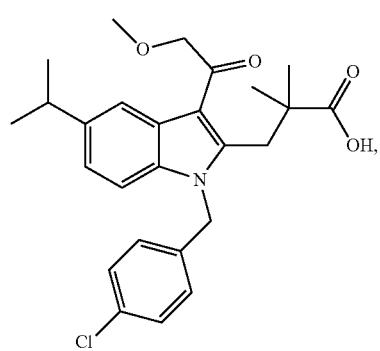
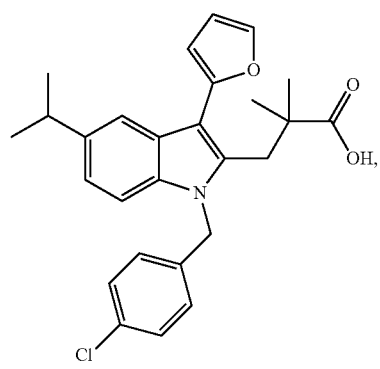
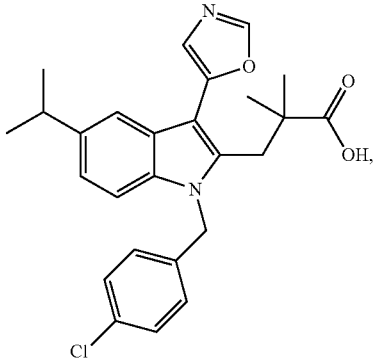
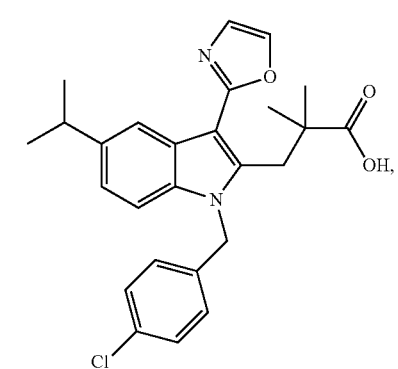
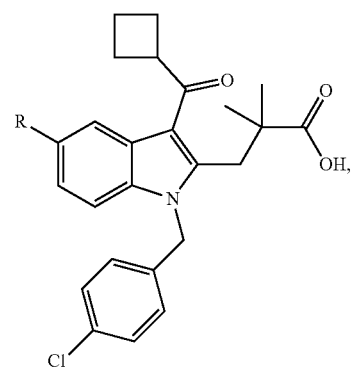
R = F, Cl, Br
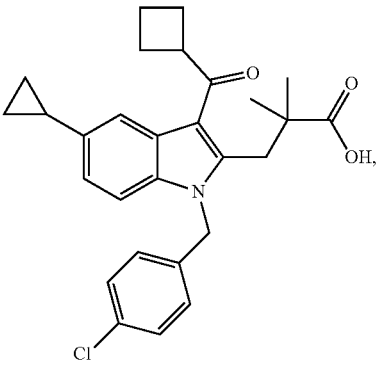

-continued
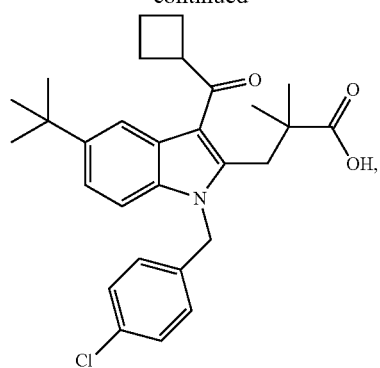
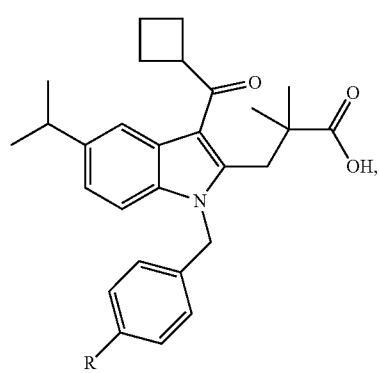
R = F, Br, I
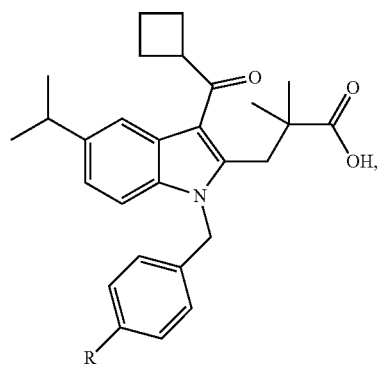
R = H or alkyl
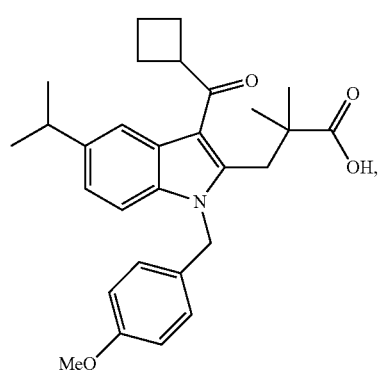
-continued
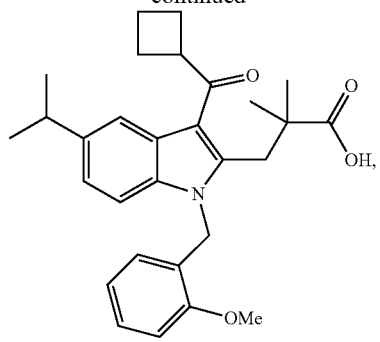
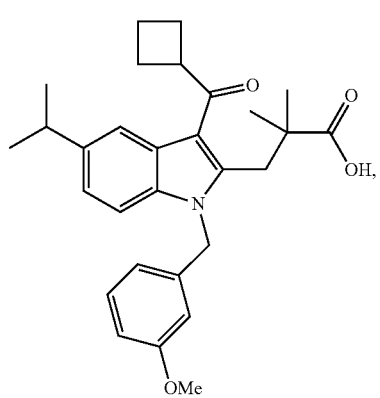
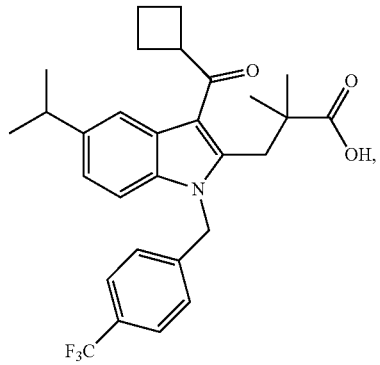
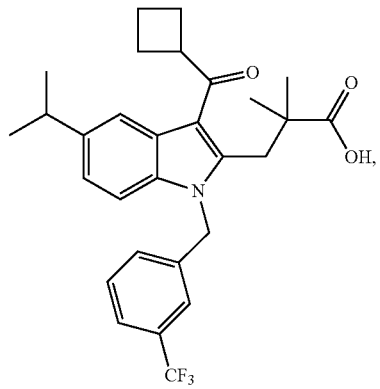

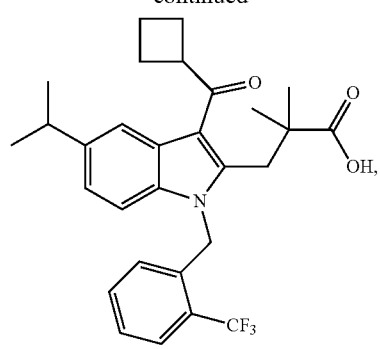
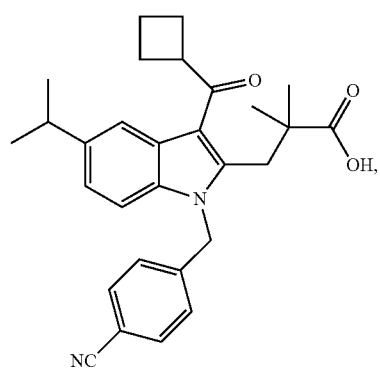
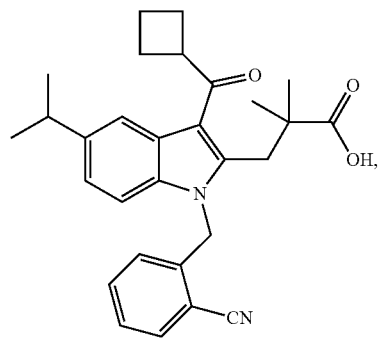
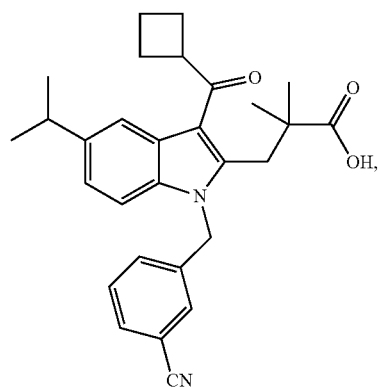
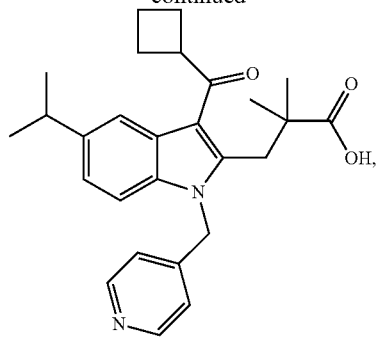
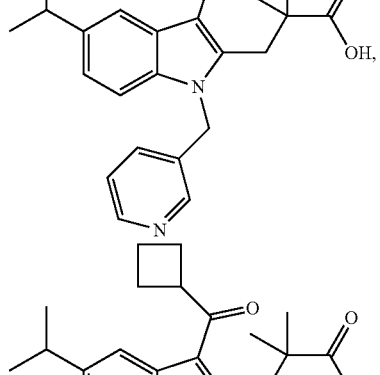
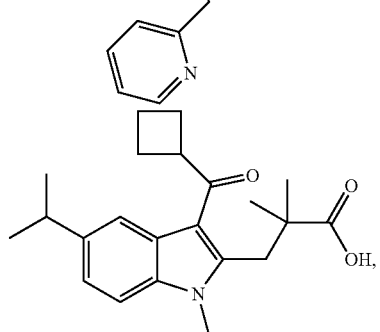
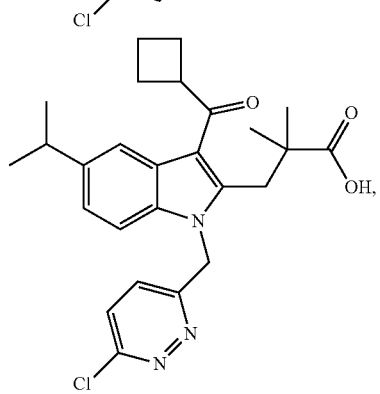

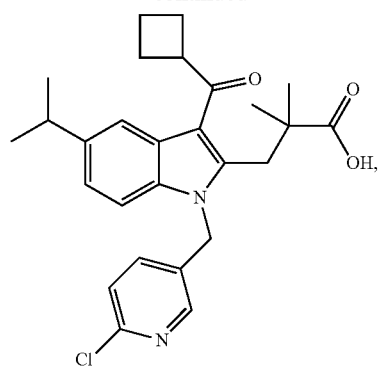
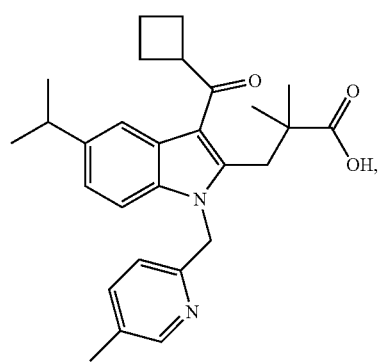
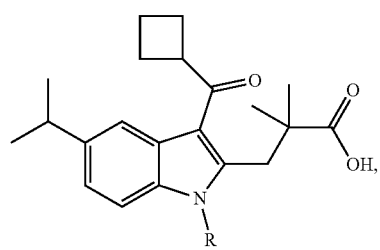
R = alkyl
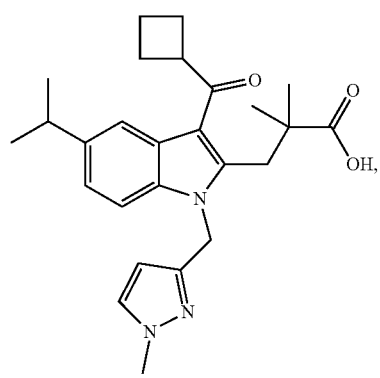
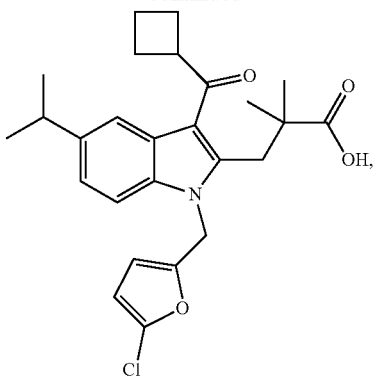
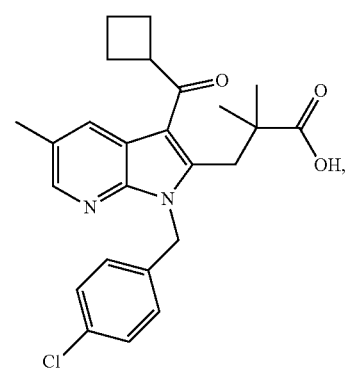
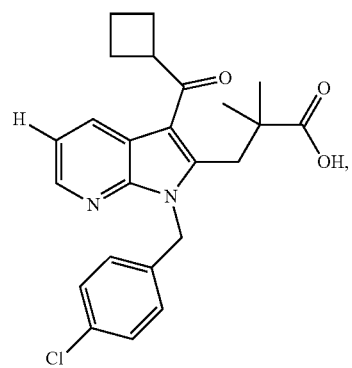
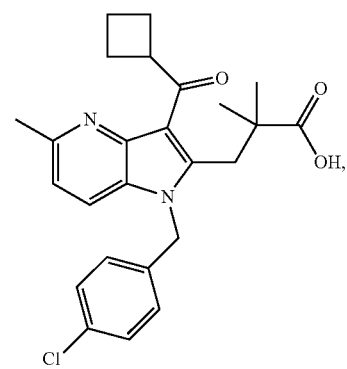

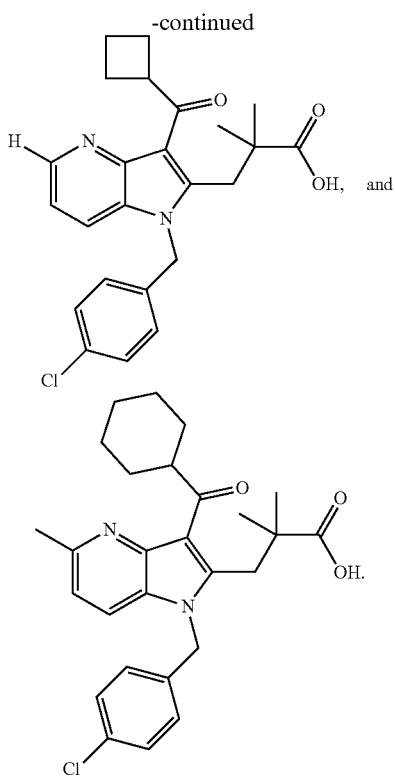

In one aspect, the present invention provides a pharmaceutical composition comprising a compound according to any embodiments disclosed here, or a pharmaceutically acceptable salt, solvate or prodrug thereof, and a pharmaceutically acceptable carrier.

In another aspect, the present invention provides a method of treating a disease or disorder associated with hedgehog pathway, comprising administering to a subject in need of treatment a therapeutically effective amount of a compound according to any one embodiment disclosed herein, or a pharmaceutically acceptable salt, solvate, prodrug, or pharmaceutical composition thereof.

In another aspect, the present invention provides use of any of the compounds disclosed herein, or a pharmaceutically acceptable salt, solvate or prodrug thereof, in the manufacture of a medicament for treatment of a disease or disorder associated with hedgehog signaling pathway.

The diseases and disorders that can be treated using the compounds disclosed herein include, but are not limited to, malignancies associated with hedgehog signaling pathway, for example, medulloblastoma, basal cell carcinoma, ovarian cancer, breast cancer, pancreatic cancer, advanced stomach cancer, oesophageal cancer, glioblastoma multiforme, acute leukemia, chronic myeloid leukemia, myelofibrosis, essential thrombocythaemia, metastatic colorectal cancer, small-cell lung cancer, and chondrosarcoma, etc.

The preferred subjects for treatment include mammalian animals, including humans, horses, dogs, cats, or the like, and more preferably humans.

Pharmaceutical compositions or formulations of the present invention include those suitable for oral, nasal, topical (including buccal and sublingual), rectal, vaginal and/or parenteral administration. Regardless of the route of administration selected, the active ingredient(s) are formulated into pharmaceutically acceptable dosage forms by methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly mixing the active ingredient(s) into liquid carriers, or finely divided solid carriers, or both, and then, if necessary, shaping the product.

Exemplary, non-limiting examples of formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s).

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers known to those of skill in the art. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

Any terms in the present application, unless specifically defined, will take the ordinary meanings as understood by a person of ordinary skill in the art.

As used herein, the singular forms "a", "an", and "the" include plural reference, and vice versa, unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group such as benzyl may be substituted as described in the definition of the term "aryl."

The term "alkoxy," as used herein, refers to an alkyl group attached to the parent molecular moiety through an oxygen atom. Representative examples of alkoxy group include, but are not limited to, methoxy ($CH_3O$—), ethoxy ($CH_3CH_2O$—), or the like.

The term "alkyl," as used herein, refers to a group derived from a straight or branched chain saturated hydrocarbon by removal of a hydrogen from one of the saturated carbons. The alkyl group preferably contains from one to ten, sometimes preferably one to six, and sometimes more preferably one to four, carbon atoms. Representative examples of alkyl group include, but are not limited to, methyl, ethyl, isopropyl, and tert-butyl.

The term "aryl," as used herein, refers to a group derived from an aromatic carbocycle by removal of a hydrogen atom from an aromatic ring. The aryl group can be monocyclic, bicyclic or polycyclic. Representative examples of aryl groups include phenyl and naphthyl, sometimes more preferably phenyl.

The term "benzyl," as used herein, refers to a methyl group on which one of the hydrogen atoms is replaced by a phenyl group, wherein said phenyl group may be substituted by one or more substituents. Representative examples of benzyl group include, but are not limited to, $PhCH_2$—, 4-MeO—$C_6H_4CH_2$—, and 2,4,6-tri-methyl-$C_6H_4CH_2$—.

The term "cyano," as used herein, refers to —CN.

The term "cycloalkyl," as used herein, refers to a group derived from a monocyclic saturated carbocycle, having preferably three to eight, and sometimes more preferably three to six carbon atoms, by removal of a hydrogen atom from the saturated carbocycle. Representative examples of cycloalkyl groups include, but are not limited to, cyclopropyl, cyclopentyl, cyclohexyl.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl ($CF_3$—), 2,2,2-trifluoroethyl ($CF_3CH_2$—).

The term "heteroaryl," as used herein, refers to a group derived from a monocyclic or bicyclic compound comprising at least one aromatic ring comprising one or more, preferably one to three, heteroatoms independently selected from nitrogen, oxygen, and sulfur, by removal of a hydrogen atom from the aromatic ring. As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, pyrimidinyl, furyl, thienyl, isoxazolyl, thiazolyl, isoxazolyl, oxazolyl, indolyl, quinolinyl, isoquinolinyl, benzisoxazolyl, benzothiazolyl, and benzothienyl.

The term "heterocyclyl," as used herein, refers to a group derived from a monocyclic or bicyclic compound comprising at least one nonaromatic ring comprising one or more, preferably one to three, heteroatoms independently selected from nitrogen, oxygen, and sulfur, by removal of a hydrogen atom from the nonaromatic ring. The heterocyclyl groups of the present disclosure can be attached to the parent molecular moiety through a carbon atom or a nitrogen atom in the group. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl.

The terms "hydroxy" or "hydroxyl," as used herein, refer to —OH.

The term "nitro," as used herein, refers to —$NO_2$.

When any group, for example, alkyl, alkenyl, "cycloalkyl," "aryl," "heterocyclyl," or "heteroaryl", is said to be "optionally substituted," unless specifically defined, it means that the group is or is not substituted by from one to five, preferably one to three, substituents independently selected from halogen, $C_{1-6}$ alkyl, $C_{1-6}$ alkoxy, $C_{1-6}$ haloalkyl, $C_{1-6}$ haloalkoxy, hydroxy, oxo, $C_{1-6}$ acyl, cyano, nitro, and amino (optionally substituted by one or two $C_{1-6}$ alkyl groups), or the like, provided that such substitution would not violate the conventional bonding principles known to a person of ordinary skill in the art. When the phrase "optionally substituted" is used before a list of groups, it means that each one of the groups listed may be optionally substituted.

The compounds of the present disclosure can exist as pharmaceutically acceptable salts or solvates. The term "pharmaceutically acceptable salt," as used herein, means any non-toxic salt that, upon administration to a recipient, is capable of providing the compounds or the prodrugs of a compound of this invention. The salts can be prepared during the final isolation and purification of the compounds or separately by reacting a suitable nitrogen atom with a suitable acid. Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include, but are not limited to, lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, and N-methylmorpholine.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Synthetic Methods

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

Abbreviations or terms used in the following synthetic schemes or processes take the meanings as commonly understood by those skilled in the art.

EXAMPLES

Example 1. 3-(1-(4-chlorobenzyl)-3-(cyclobutanecarbonyl)-5-isopropyl-1H-indol-2-yl)-2,2-dimethylpropanoic Acid

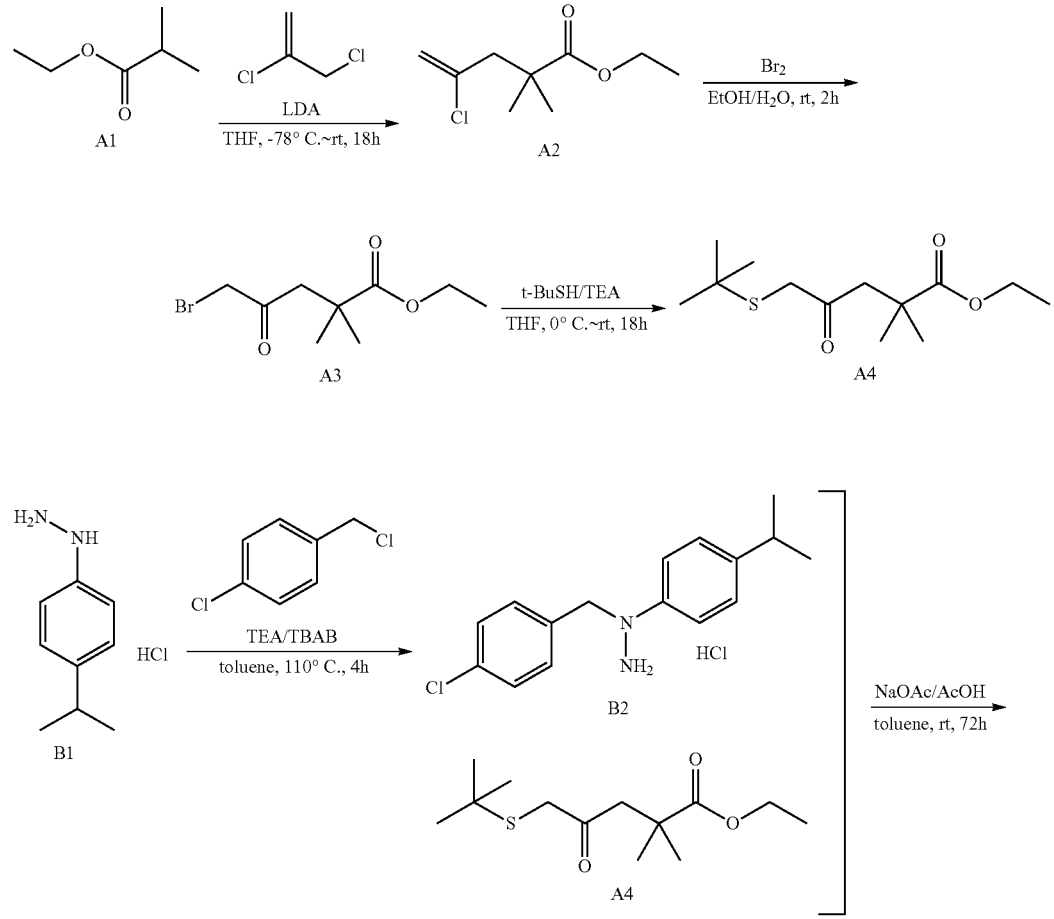

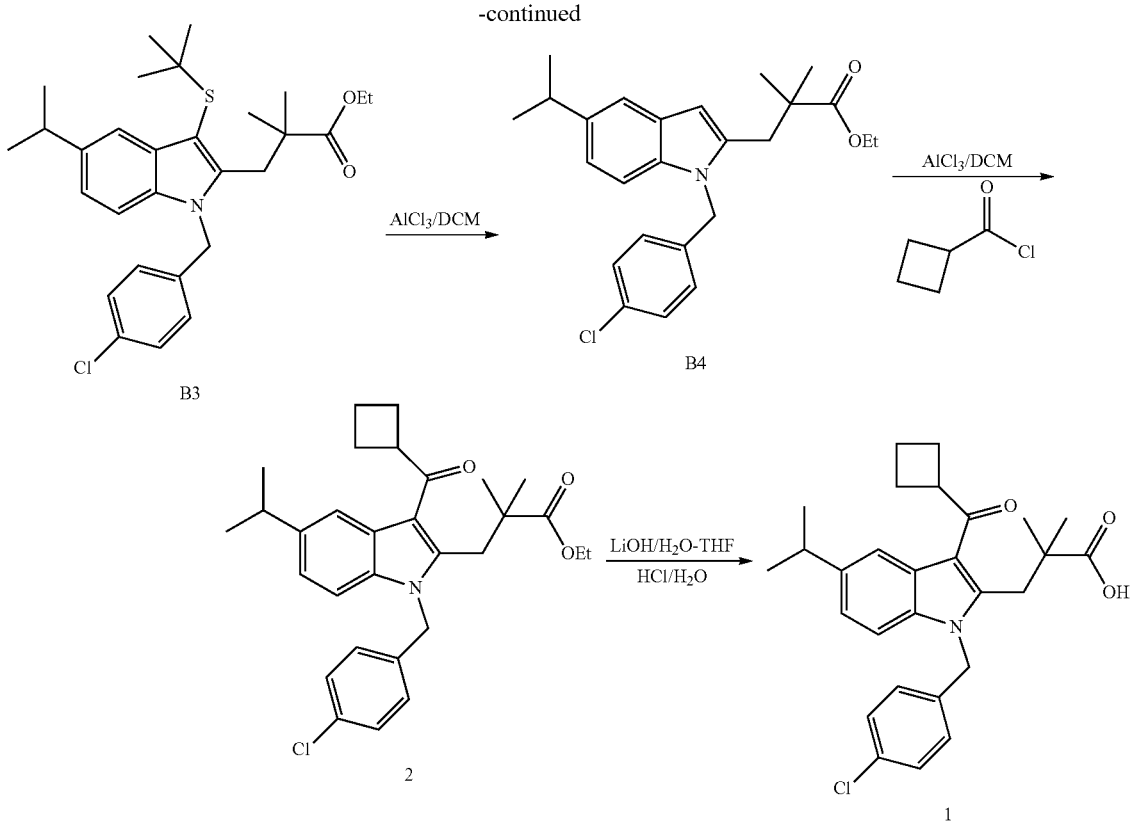

1.1. Preparation of Ethyl 4-chloro-2,2-dimethylpent-4-enoate

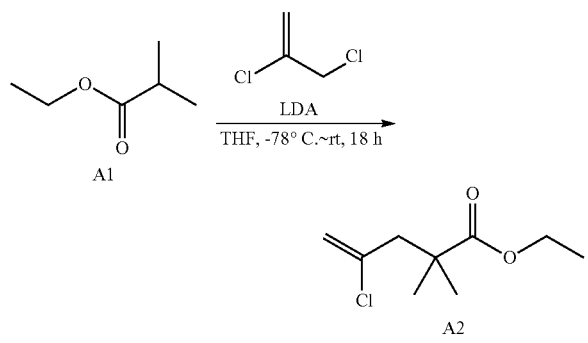

To a solution of THF (500 mL) was added LDA (150 mL, 0.3 mol, 2M in THF). The mixture was cooled to −78° C. Ethyl isobutyrate A1 (33 g, 0.284 mol) was added dropwise and the temperature was kept below −60° C. After addition, the mixture was stirred at −70~−65° C. for 20 min. 2,3-dichloroprop-1-ene (31 g, 0.279 mol) was added dropwise. The reaction mixture was then allowed to warm to room temperature and stirred for 18 hours. The mixture was quenched with sat. NH$_4$Cl(aq). The organic layer was separated and the aqueous layer was extracted with DCM (2×300 mL). The organic extracts were combined and dried over anhydrous Na$_2$SO$_4$. It was filtered and the filtrate was concentrated to give ethyl 4-chloro-2,2-dimethylpent-4-enoate A2 (59 g, 0.279 mol, 93% yield) as brown oil, which was used in the next step without further purification. $^1$H NMR (400 MHz, CDCl$_3$): δ (ppm) 1.24-1.28 (m, 9H), 2.65 (s, 2H), 4.15 (q, 4H), 5.13 (s, 1H), 5.24 (s, 1H).

1.2. Preparation of Ethyl 5-bromo-2,2-dimethyl-4-oxopentanoate

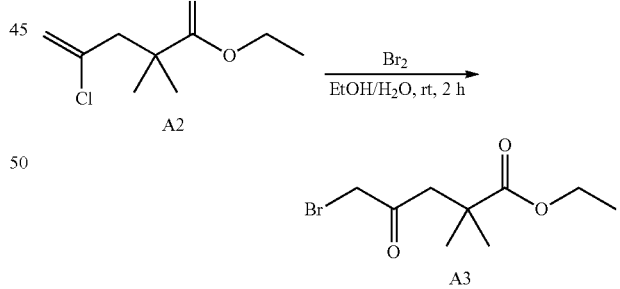

To a mixture of ethyl 4-chloro-2,2-dimethylpent-4-enoate A2 (59 g, 0.279 mol) in EtOH (300 mL) was added water (200 mL). The mixture was cooled −5-0° C. Br$_2$ (48 g, 0.300 mol) was added dropwise. The reaction mixture was stirred for 2 h at room temperature. Water (500 mL) was added and the mixture was extracted with DCM (3×300 mL). The combined extracts were washed with 5% Na$_2$CO$_3$ (aq) and dried over anhydrous Na$_2$SO$_4$. It was filtered and the filtrate was concentrated to give ethyl 5-bromo-2,2-dimethyl-4-oxopentanoate A3 (78 g, 0.279 mol, 100% yield) as brown oil, which was used in the next step without further purification. ¹H NMR (400 MHz, CDCl₃): δ (ppm) 1.18-1.25 (m, 9H), 2.59 (s, 2H), 3.85 (s, 2H), 4.11 (q, J=7.2 Hz, 2H).

1.3. Preparation of Ethyl 5-(tert-butylthio)-2,2-dimethyl-4-oxopentanoate

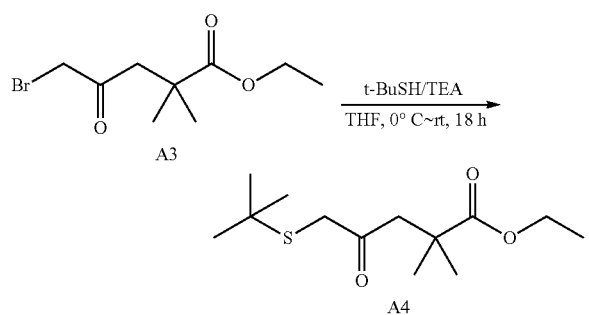

A mixture of ethyl 5-bromo-2,2-dimethyl-4-oxopentanoate A3 (78 g, 0.279 mol) in THF (500 mL) was cooled 0-5° C. TEA (45 mL, 0.324 mol) and t-BuSH (35 mL, 0.310 mol) was added dropwise. The reaction mixture was stirred for 18 h at room temperature. PE (300 mL) was added and the reaction mixture was filtered. The filtrate was evaporated and the residue was purified by flash column chromatography on silica gel (PE:EtOAc=20:1) to give ethyl-5-(tert-butylthio)-2,2-dimethyl-4-oxopentanoate A4 (71.2 g, 0.273 mol, 98% yield) as brown oil. ¹H NMR (400 MHz, CDCl₃): δ (ppm) 1.24-1.20 (m, 9H), 1.31 (s, 9H), 2.94 (s, 2H), 3.27 (s, 2H), 4.11 (q, J=6.8 Hz, 2H).

1.4. Preparation of 1-(4-chlorobenzyl)-1-(4-isopropylphenyl)hydrazine

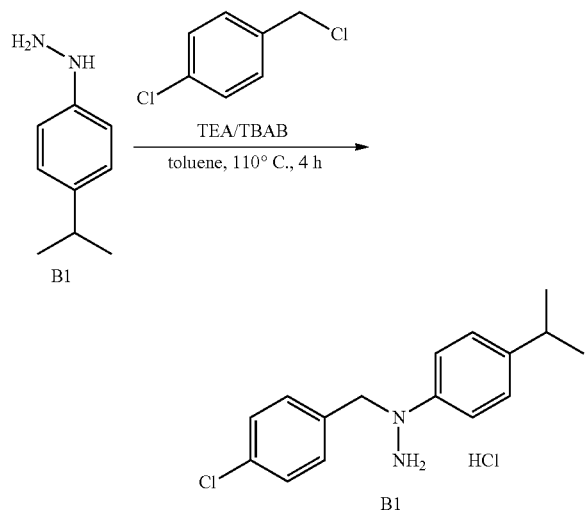

To a mixture of (4-isopropylphenyl)hydrazine hydrochloride B1 (5.8 g, 31.1.0 mmol) and 1-chloro-4-(chloromethyl) benzene (5.0 g, 31.1 mmol) in tolune (100 mL) was added TEA (9 mL, 64.7 mmol), followed by TBAB (100 mg, 0.31 mmol). The mixture was heated to reflux (110° C., oil bath) for 4 h and the reaction mixture was cooled to room temperature. The mixture was concentrated and the residue was diluted in EtOAc (15 mL) and PE (100 mL). The mixture was filtered and to the filtrate was added 6.0 N HCl in 1,4-dioxane (10 mL). The mixture was stirred for 2 h at room temperature and filtered to give 1-(4-chlorobenzyl)-1-(4-isopropylphenyl)hydrazine (HC salt) B2 (6.5 g, 23.7 mmol, 64% yield) as a white solid.

1.5. Preparation of Ethyl 3-(3-(tert-butylthio)-1-(4-chlorobenzyl)-5-isopropyl-1H-indol-2-yl)-2,2-dimethylpropanoate

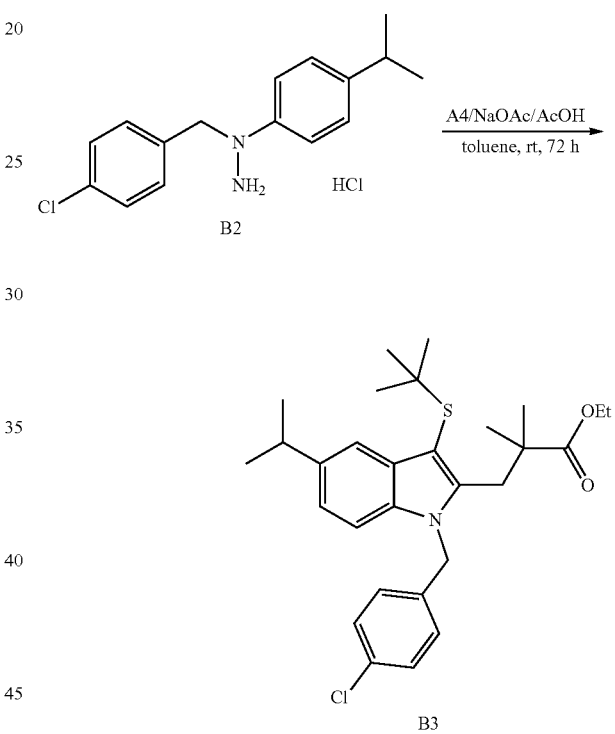

To a mixture of 1-(4-chlorobenzyl)-1-(4-isopropylphenyl) hydrazine (HCl salt) B2 (3.2 g, 10.3 mmol) and ethyl 5-(tert-butylthio)-2,2-dimethyl-4-oxopentanoate A4 (3.0 g, 11.5 mmol) in AcOH (25 mL) was added tolune (50 mL) and AcONa (1.0 g, 12.2 mmol). The reaction mixture was stirred for 72 h at room temperature. The mixture was concentrated and the residue was purified by column chromatography on silica gel (eluent: EA:PE=1:30) to give ethyl 3-(3-(tert-butylthio)-1-(4-chlorobenzyl)-5-isopropyl-1H-indol-2-yl)-2,2-dimethylpropanoateB3 (2.7 g, 5.4 mmol, 52% yield) as yellow solid. LCMS (ESI): m/z 500.3[M+1]+. ¹HNMR (400 MHz, DMSO-d₆): δ (ppm) 1.15-1.09 (m, 9H), 1.19 (s, 9H), 1.22 (d, J=7.2 Hz, 6H), 2.85-3.00 (m, 1H), 3.23 (s, 2H), 4.04 (q, J=7.2 Hz, 2H), 5.46 (s, 2H), 6.86 (d, J=8.8 Hz, 2H), 6.987 (dd, J=8.8, 1.6 Hz, 1H), 7.25 (d, J=8.4 Hz, 1H), 7.34-7.32 (d, J=8.4 Hz, 2H), 7.47 (s, 1H).

1.6. Preparation of Ethyl 3-(1-(4-chlorobenzyl)-5-isopropyl-1H-indol-2-yl)-2,2-dimethylpropanoate

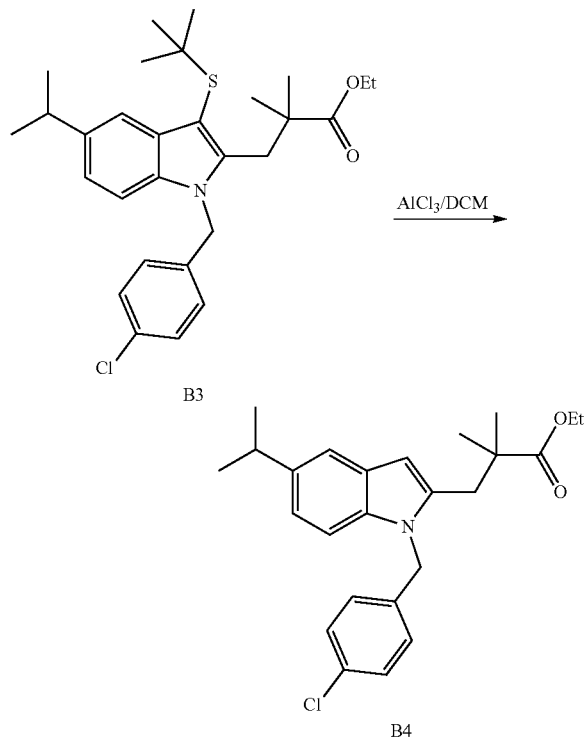

To a mixture of ethyl 3-(3-(tert-butylthio)-1-(4-chlorobenzyl)-5-isopropyl-1H-indol-2-yl)-2,2-dimethylpropanoate B3 (1.0 g, 2.0 mmol) in DCM (50 mL) was cooled to 0-5° C. in an ice bath. AlCl₃ (2.0 g, 15.0 mmol) was added in portions. After addition, the mixture was stirred for 18 h at room temperature. The mixture was quenched with Sat. NH₄Cl (aq). The organic layer was separated, dried over anhydrous Na₂SO₄. It was filtered and the filtrate was concentrated. The residue was purified by preparation TLC (PE:EA=10:1) to give ethyl 3-(1-(4-chlorobenzyl)-5-isopropyl-1H-indol-2-yl)-2,2-dimethylpropanoate (B4) (620 mg, 1.5 mmol, 75% yield) as brown oil. LCMS (ESI): m/z 412.4[M+H]⁺.

1.7. Preparation of Ethyl 3-(1-(4-chlorobenzyl)-3-(cyclobutanecarbonyl)-5-isopropyl-1H-indol-2-yl)-2,2-dimethylpropanoate

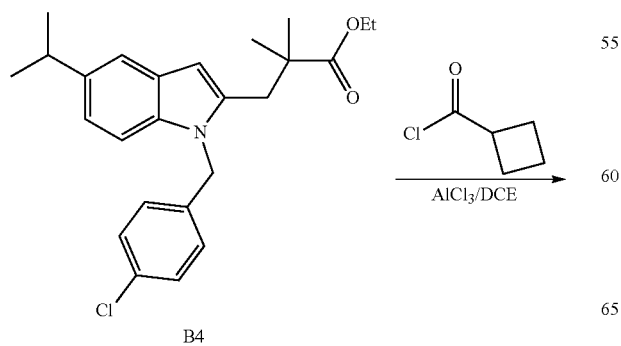

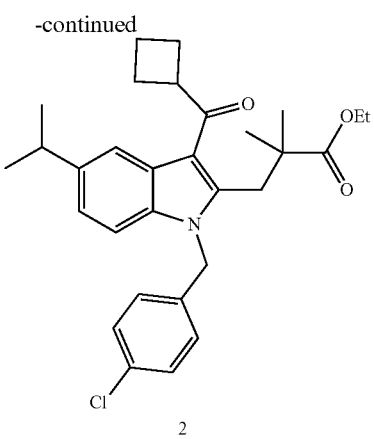

To a mixture of ethyl 3-(1-(4-chlorobenzyl)-3-(3,3-dimethylbutanoyl)-5-isopropyl-1H-indol-2-yl)-2,2-dimethylpropanoate B4 (500 mg, 1.21 mmol) in DCE (30 mL) was added AlCl₃ (600 mg, 4.49 mmol) and cyclobutanecarbonyl chloride (500 mg, 4.22 mmol). The mixture was heated to reflux for 4 h. The mixture was quenched with water (50 mL). The organic layer was separated, dried over anhydrous Na₂SO₄. It was filtered and the filtrate was concentrated. The residue was purified by preparation TLC (PE:EA=10:1) to give ethyl 3-(1-(4-chlorobenzyl)-3-(cyclobutanecarbonyl)-5-isopropyl-1H-indol-2-yl)-2,2-dimethylpropanoate (2) (170 mg, 0.34 mmol, 28% yield) as yellow oil. LCMS (ESI): m/z 494.3[M+Na]⁺. ¹HNMR (400 MHz, DMSO-d₆): δ (ppm) 1.06 (t, J=6.8 Hz, 3H), 1.14 (s, 6H), 1.22 (d, J=6.8 Hz, 6H), 1.85-1.90 (m, 1H), 1.95-1.99 (m, 1H), 2.35-2.25 (m, 4H), 2.92-2.97 (m, 1H), 3.55 (s, 2H), 3.88-4.01 (m, 3H), 5.25 (s, 2H), 6.70 (d, J=7.6 Hz, 2H), 6.96 (s, 2H), 7.11 (d, J=7.2 Hz, 2H), 7.26 (s, 1H), 7.56 (s, 1H).

1.8. Preparation of 3-(1-(4-chlorobenzyl)-3-(cyclobutanecarbonyl)-5-isopropyl-1H-indol-2-yl)-2,2-dimethylpropanoic Acid

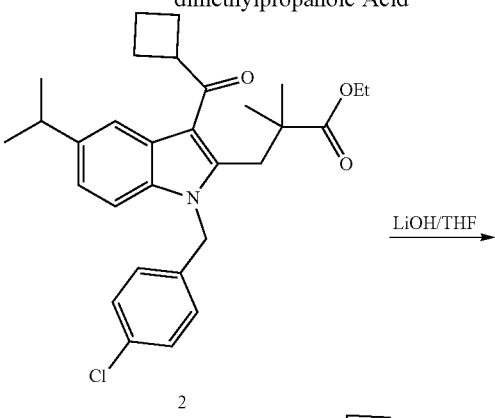

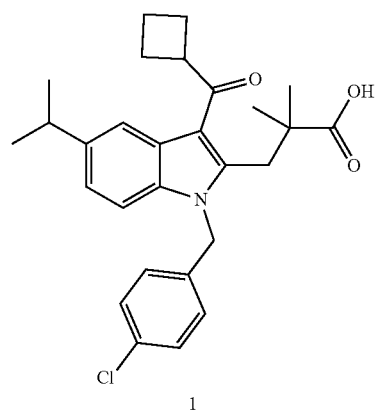

To a mixture of ethyl 3-(1-(4-chlorobenzyl)-3-(cyclobutanecarbonyl)-5-isopropyl-1H-indol-2-yl)-2,2-dimethylpropanoate 2 (50 mg, 0.10 mmol) in THF (1 mL) was added LiOH.H$_2$O (10 mg, 0.24 mmol) and water (1 mL). The mixture was heated to 65° C. for 18 h. After cooled to room temperature, the mixture was concentrated and the residue was purified by pre-HPLC to give 3-(1-(4-chlorobenzyl)-3-(cyclobutanecarbonyl)-5-isopropyl-1H-indol-2-yl)-2,2-dimethylpropanoic acid 1 (22 mg, 0.047 mmol, 47% yield) as white solid. LCMS (ESI): m/z 466.3[M+H]$^+$. $^1$HNMR (400 MHz, DMSO-d$_6$): δ (ppm) 1.12 (s, 6H), 1.26 (d, J=6.8 Hz, 6H), 1.85-1.90 (m, 1H), 1.98-2.05 (m, 1H), 2.20-2.35 (m, 4H), 2.99-3.05 (m, 1H), 3.59 (s, 2H), 4.03-4.08 (m, 1H), 5.49 (s, 2H), 6.91 (d, J=7.6 Hz, 2H), 7.06 (d, J=8.4 Hz, 1H), 7.30-7.36 (m, 3H), 7.63 (s, 1H), 12.49 (br s, 1H).

Example 2. 3-(1-(4-chlorobenzyl)-3-isobutyryl-5-isopropyl-1H-indol-2-yl)-2,2-dimethyl propanoic Acid 2.1. Preparation of Ethyl 3-(1-(4-chlorobenzyl)-3-isobutyryl-5-isopropyl-1H-indol-2-yl)-2,2-dimethyl-propanoate

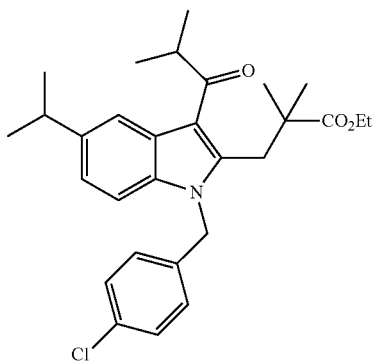

10

The compound 10 was prepared by the method similar to the compound ethyl 3-(1-(4-chlorobenzyl)-3-(cyclobutanecarbonyl)-5-isopropyl-1H-indol-2-yl)-2,2-dimethylpropanoate (compound 2) in the step 1.7, but using isobyryl chloride. LCMS (ESI): m/z 482.4[M+Na]+. $^1$HNMR (400 MHz, CDCl$_3$): δ (ppm) 1.55 (t, J=7.2 Hz, 3H), 1.23 (s, 6H), 1.31 (t, J=6.0 Hz, 12H), 3.08-3.00 (m, 1H), 3.70-2.55 (m, 3H), 4.03-3.98 (m, 2H), 5.36 (s, 2H), 6.80 (d, J=8.0 Hz, 2H), 7.06 (s, 2H), 7.21 (d, J=8.0 Hz, 2H), 7.71 (s, 1H).

2.2. Preparation of 3-(1-(4-chlorobenzyl)-3-isobutyryl-5-isopropyl-1H-indol-2-yl)-2,2-dimethylpropanoic Acid

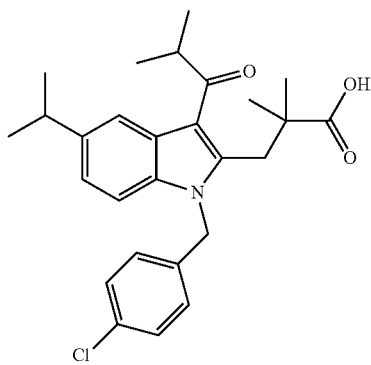

9

The compound 9 was prepared by the method similar to the example 1, but using ethyl 3-(1-(4-chlorobenzyl)-3-isobutyryl-5-isopropyl-1H-indol-2-yl)-2,2-dimethylpropanoate in the step 1.8. LCMS (ESI): m/z 454.4[M+H]$^+$. $^1$HNMR (400 MHz, DMSO-d$_6$): δ (ppm) 1.10 (s, 6H), 1.18 (d, J=6.8 Hz, 6H), 1.26 (d, J=6.8 Hz, 6H), 3.05-2.98 (m, 1H), 3.60-3.53 (m, 3H), 5.51 (s, 2H), 6.92 (d, J=8.0 Hz, 2H), 7.08 (d, J=8.8 Hz, 2H), 7.36 (d, J=8.4 Hz, 2H), 7.67 (s, 1H), 12.42 (brs, 1H).

Example 3. 3-(1-(4-chlorobenzyl)-5-isopropyl-3-(neopentylsulfonyl)-1H-indol-2-yl)-2,2-dimethylpropanoic Acid Scheme 3. Synthetic route for example 3

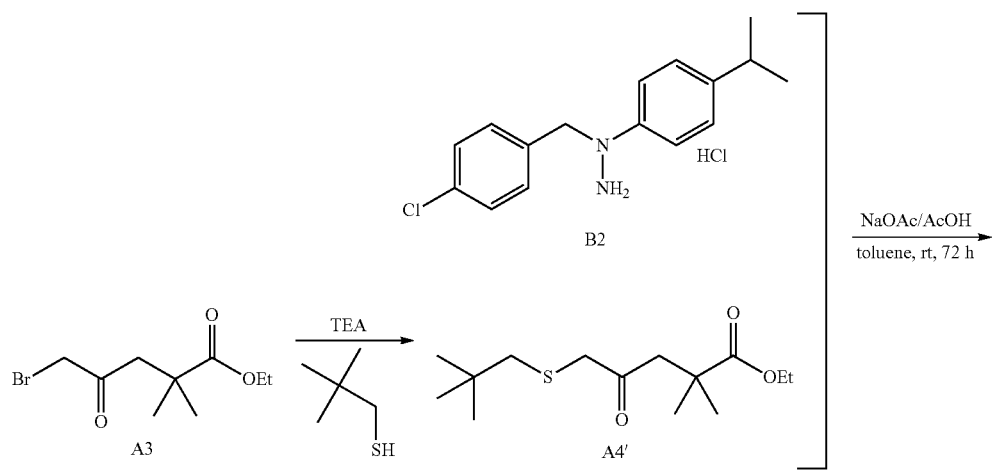

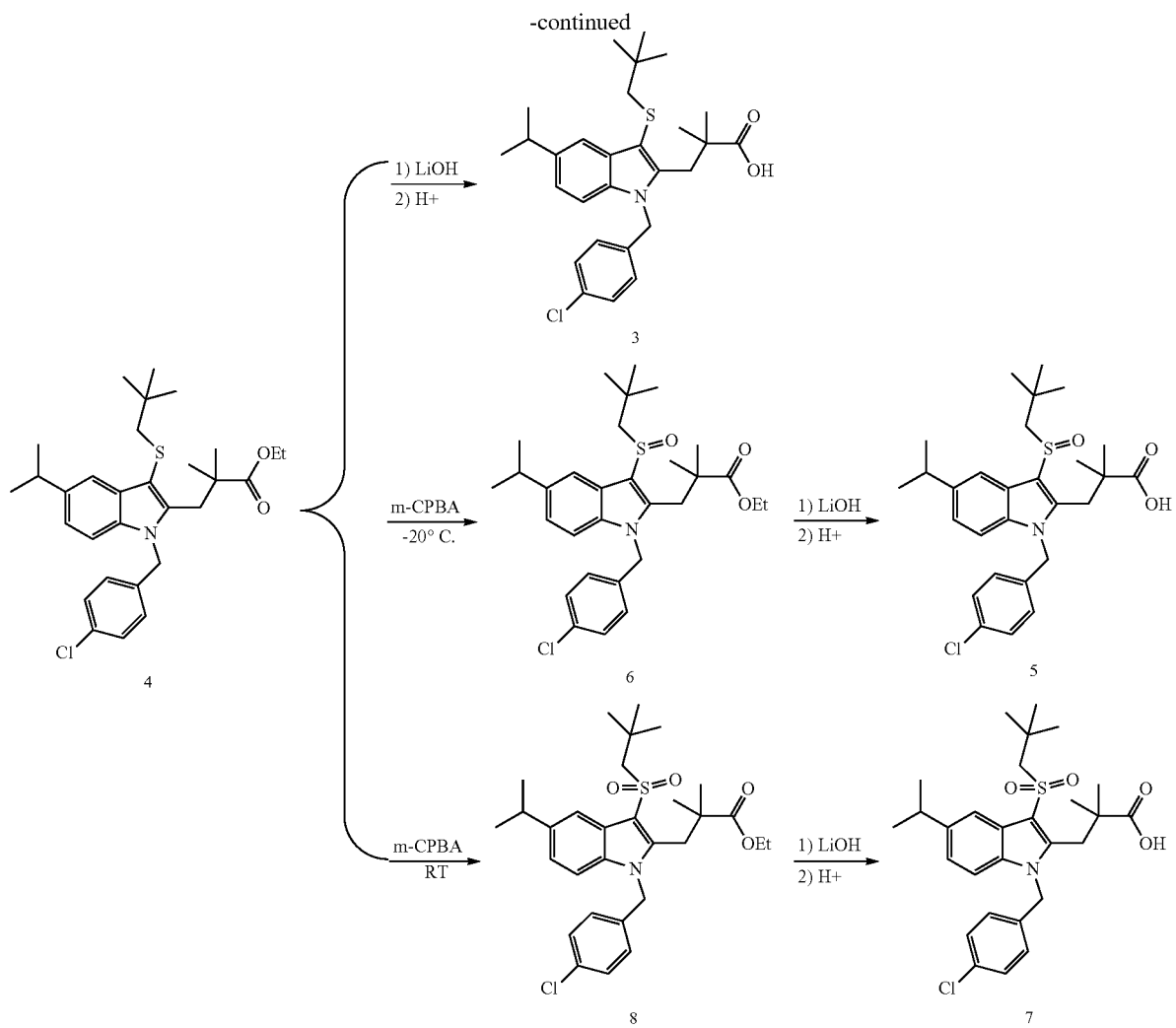

3.1. Preparation of Ethyl 2,2-dimethyl-5-(neopentylthio)-4-oxopentanoate

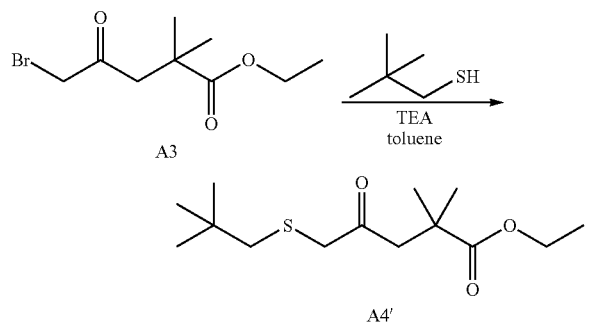

To a mixture of 2,2-dimethylpropane-1-thiol (210 mg, 2.0 mmol) in toluene (8 mL)/Et2O (15 mL) was added TEA (607 mg, 6.0 mmol). Ethyl 5-bromo-2,2-dimethyl-4-oxopentanoate (552.2 mg, 2.2 mmol) was then added dropwise. The reaction mixture was stirred for 18 h at room temperature. The mixture was concentrated and the residue was re-dissolved in EtOAc (30 mL) and washed with water (20 mL), followed by brine (20 mL). The organics were dried over anhydrous Na2SO4. It was filtered and the filtrate was concentrated. The crude product was purified by pre-TLC (PE:EA=20:1) to give ethyl 2,2-dimethyl-5-(neopentylthio)-4-oxopentanoate (220 mg, 0.8 mmol, 39.8% yield) as yellow oil. 1H NMR (400 MHz, CDCl3): δ (ppm) 4.14-4.12 (q, 2H), 3.46-3.55 (m, 2H), 3.14 (s, 2H), 2.41 (s, 2H), 1.26 (s, 6H), 0.97 (s, 9H), 0.91-0.93 (m, 3H).

3.2. Preparation of Ethyl 3-(1-(4-chlorobenzyl)-5-isopropyl-3-(neopentylthio)-1H-indol-2-yl)-2,2-dimethylpropanoate

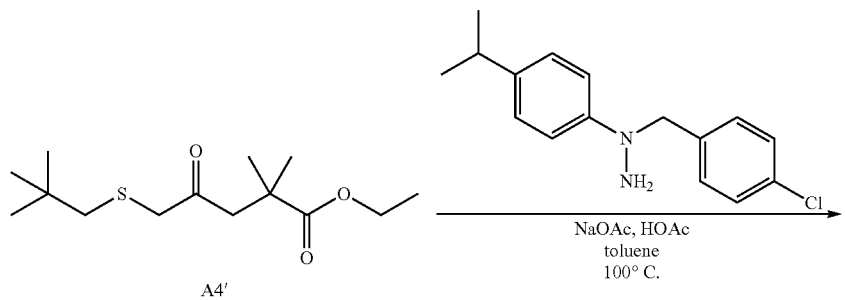

To a mixture of 1-(4-chlorobenzyl)-1-(4-isopropylphenyl) hydrazine (HCl salt)(360.5 mg, 1.31 mmol) and 2,2-dimethyl-5-(neopentylthio)-4-oxopentanoate (300 mg, 1.09 mmol) in AcOH (5 mL) was added tolune (15 mL) and AcONa (322 mg, 3.28 mmol). The reaction mixture was stirred for 16 h at 20° C. The mixture was concentrated and the residue was re-dissolved in EtOAc (50 mL). The resulting solution was washed with water (15 mL), followed by brine (15 mL), dried over anhydrous $Na_2SO_4$. It was filtered and the filtrate was concentrated. The crude product was purified by pre-TLC (PE:EA=20:1) to give ethyl 3-(1-(4-chlorobenzyl)-5-isopropyl-3-(neopentylthio)-1H-indol-2-yl)-2,2-dimethylpropanoate (160 mg, 0.31 mmol, 28.5% yield) as yellow oil. LCMS (ESI): m/z 514.4 [M+1]$^+$. $^1$HNMR (400 MHz, $CDCl_3$): δ (ppm) 1.05 (s, 9H), 1.19 (t, J=14.0 Hz, 3H), 1.24 (s, 6H), 1.32 (d, J=7.2 Hz, 6H), 2.71 (s, 2H), 3.02-3.05 (m, 1H), 3.22 (s, 2H), 4.02-4.08 (m, 2H), 5.30 (s, 2H), 6.73 (d, J=8.4 Hz, 2H), 7.02 (s, 2H), 7.18 (d, J=8.4 Hz, 2H), 7.58 (s, 1H).

3.3. Preparation of 3-(1-(4-chlorobenzyl)-5-isopropyl-3-(neopentylthio)-1H-indol-2-yl)-2,2-dimethylpropanoic Acid

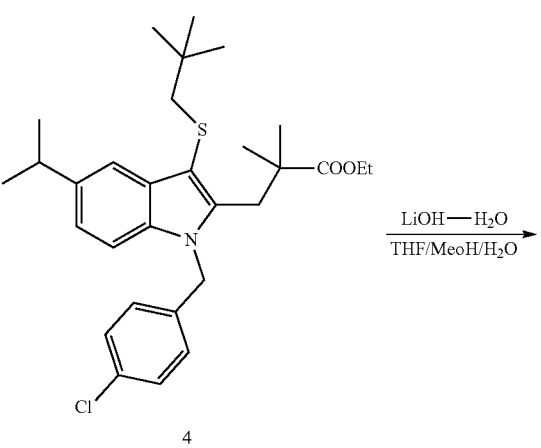

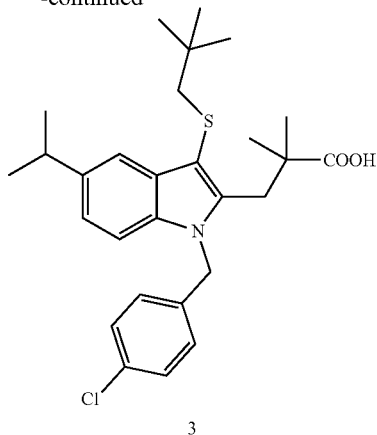

3

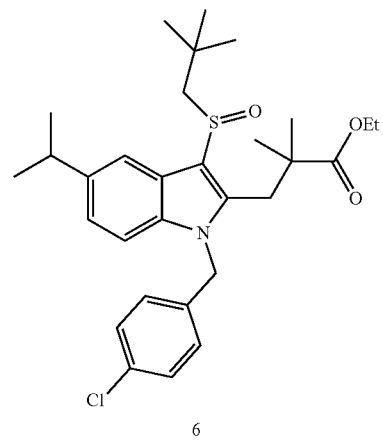

6

To a mixture of ethyl 3-(1-(4-chlorobenzyl)-5-isopropyl-3-(neopentylthio)-1H-indol-2-yl)-2,2-dimethylpropanoate (50 mg, 0.098 mmol) in THF (2 mL)/MeOH (3 mL)/H$_2$O (2 mL) was added LiOH. H$_2$O (16.3 mg, 0.39 mmol). The reaction mixture was stirred for 16 h at 60° C. After cooled to room temperature, the mixture was concentrated and the residue was diluted with water (5 mL). The solution was acidified with 2.0 N HCl (aq) to pH=6. The mixture was extracted with EtOAc (2×15 mL). The extracts were combined and dried over anhydrous Na$_2$SO$_4$. It was filtered and the filtrate was concentr-ated. The residue was purified by prep-HPLC to give 3-(1-(4-chlorobenzyl)-5-isopropyl-3-(neopentylthio)-1H-indol-2-yl)-2,2-dimethylpropanoic acid (25 mg, 0.05 mmol, 52.9% yield) as yellow solid. LCMS (ESI): m/z 486.3 [M+1]$^+$. $^1$HNMR (400 MHz, DMSO-d$_6$): δ (ppm) 0.99 (s, 9H), 1.14 (s, 6H), 1.24 (d, J=7.2 Hz, 6H), 2.65 (s, 2H), 2.96-2.99 (m, 1H), 3.16 (s, 2H), 5.43 (s, 2H), 6.82 (d, J=8.0 Hz, 2H), 7.01 (d, J=9.2 Hz, 2H), 7.25 (d, J=8.4 Hz, 2H), 7.31 (d, J=8.4 Hz, 2H), 7.42 (s, 1H), 12.47 (s, 1H).

3.4. Preparation of Ethyl 3-(1-(4-chlorobenzyl)-5-isopropyl-3-(neopentylsulfinyl)-1H-indol-2-yl)-2,2-dimethylpropanoate To a mixture of ethyl 3-(1-(4-chlorobenzyl)-5-isopropyl-3-(neopentylthio)-1H-indol-2-yl)-2,2-dimethylpropanoate (250 mg, 0.49 mmol) in DCM (10 mL) was added m-CPBA (108.6 mg, 0.54 mmol) at −20° C. The reaction mixture was stirred for 2 h at −20° C. The mixture was then washed with NaHCO$_3$ (aq), dried over anhydrous Na$_2$SO$_4$ and concentrated. The residue was purified by pre-HPLC to give ethyl 3-(1-(4-chlorobenzyl)-5-isopropyl-3-(neopentylsulfinyl)-1H-indol-2-yl)-2,2-dimethylpropanoate (108 mg, 0.2 mmol, 41.9% yield) as a yellow oil. LCMS (ESI): m/z 530.3 [M+1]$^+$. $^1$HNMR (400 MHz, CDCl$_3$): δ (ppm) 1.17-1.21 (m, 12H), 1.27-1.32 (m, 12H), 2.99-3.04 (m, 3H), 3.24 (d, J=2.0 Hz, 2H), 3.73 (d, J=13.2 Hz, 2H), 4.01-4.05 (m, 2H), 5.32 (s, 2H), 6.80 (d, J=8.4 Hz, 2H), 7.05-7.09 (m, 2H), 7.11 (d, J=8.0 Hz, 2H), 7.22 (d, J=8.4 Hz, 2H), 7.98 (s, 1H).

3.5. Preparation of 3-(1-(4-chlorobenzyl)-5-isopropyl-3-(neopentylsulfinyl)-1H-indol-2-yl)-2,2-dimethylpropanoic Acid

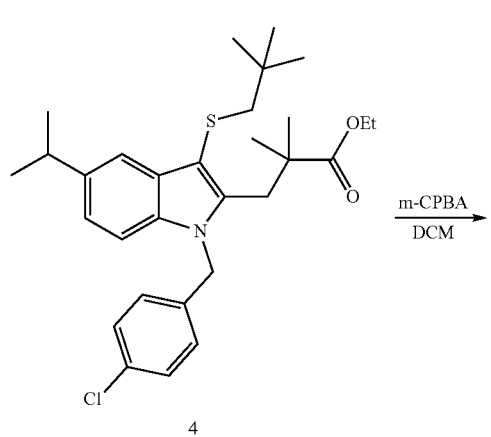

4

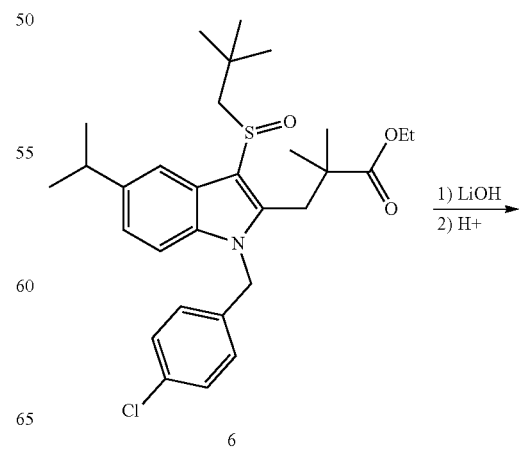

6

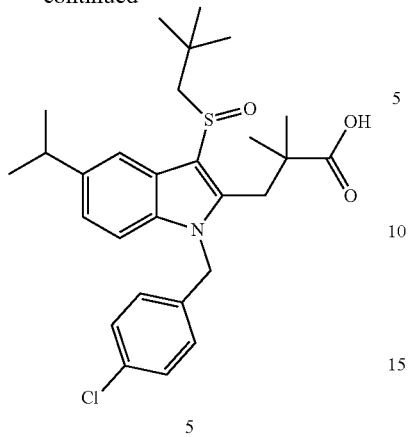

5

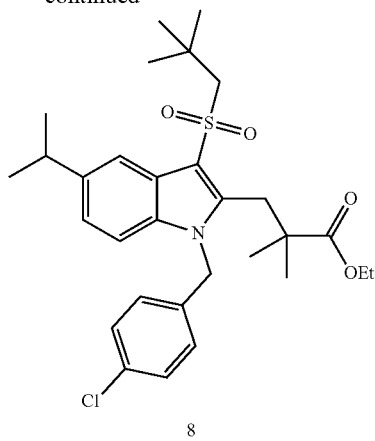

8

To a mixture of ethyl 3-(1-(4-chlorobenzyl)-5-isopropyl-3-(neopentylsulfinyl)-1H-indol-2-yl)-2,2-dimethylpropanoate (100 mg, 0.19 mmol) in in THF (3 mL)/MeOH (3 m)/H$_2$O (3 mL) was added LiOH. H$_2$O (31.7 mg, 0.75 mmol). The mixture was stirred for 16 h at 60° C. and then concentrated. The residue was diluted with water (5 mL). The solution was acidified with 1.0 N HCl (aq) to pH=6. The mixture was extracted with EtOAc (2×25 mL). The organic extracts were combined and dried over anhydrous Na$_2$SO$_4$. It was filtered and the filtrate was concentrated. The residue was purified by prep-HPLC to give 3-(1-(4-chlorobenzyl)-5-isopropyl-3-(neopentylsulfinyl)-1H-indol-2-yl)-2,2-dimethylpropanoic acid (40 mg, 0.08 mmol, 42.2% yield) as light yellow solid. LCMS (ESI): m/z 502.3 [M+1]$^+$. $^1$HNMR (400 MHz, DMSO-d$_6$): δ (ppm) 1.14 (s, 9H), 1.18 (d, J=12.0 Hz, 6H), 1.25 (d, J=6.8 Hz, 6H), 2.87 (d, J=13.2 Hz, 1H), 2.99 (m, 1H), 3.18 (d, J=4.8 Hz, 2H), 3.57 (d, J=13.2 Hz, 1H), 5.47 (s, 2H), 6.93 (d, J=8.8 Hz, 2H), 7.09-7.11 (m, 2H), 7.32-7.36 (m, 3H), 7.84 (s, 1H).

3.6. Preparation of Ethyl 3-(1-(4-chlorobenzyl)-5-isopropyl-3-(neopentylsulfonyl)-1H-indol-2-yl)-2,2-dimethylpropanoate To a mixture of ethyl 3-(1-(4-chlorobenzyl)-5-isopropyl-3-(neopentylthio)-1H-indol-2-yl)-2,2-dimethylpropanoate (250 mg, 0.49 mmol) in DCM (10 mL) was added m-CPBA (296 mg, 1.46 mmol) at 15° C. The reaction mixture was stirred for 16 h at 15° C. The mixture was treated with Na$_2$SO$_3$ (aq) and extracted with DCM (50 mL). The organic extract was washed with water (15 mL), followed by brine (15 mL), dried over anhydrous Na$_2$SO$_4$. It was filtered and the filtrate was concentrated. The crude product was purified by pre-HTPLC to give ethyl 3-(1-(4-chlorobenzyl)-5-isopropyl-3-(neopentylsulfonyl)-1H-indol-2-yl)-2,2-dimethylpropanoate (100 mg, 0.18 mmol, 37.7% yield) as yellow oil. LCMS (ESI): m/z 546.3 [M+1]$^+$. $^1$H NMR (400 MHz, CDCl$_3$): δ (ppm) 1.15 (t, J=14.0 Hz, 3H), 1.22 (s, 9H), 1.30-1.32 (m, 12H), 2.71 (s, 2H), 3.02-3.06 (m, 1H), 3.18 (s, 2H), 3.57 (s, 2H), 3.95-4.00 (m, 2H), 5.34 (s, 2H), 6.81 (d, J=8.4 Hz, 2H), 7.04 (d, J=8.4 Hz, 2H), 7.11 (d, J=8.0 Hz, 2H), 7.23 (d, J=8.8 Hz, 2H), 7.78 (s, 1H).

3.7 Preparation of 3-(1-(4-chlorobenzyl)-5-isopropyl-3-(neopentylsulfonyl)-1H-indol-2-yl)-2,2-dimethylpropanoic Acid

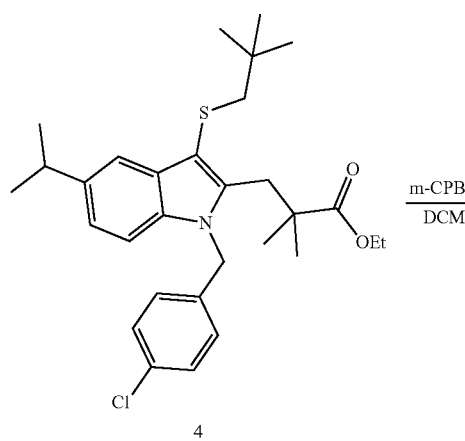

4

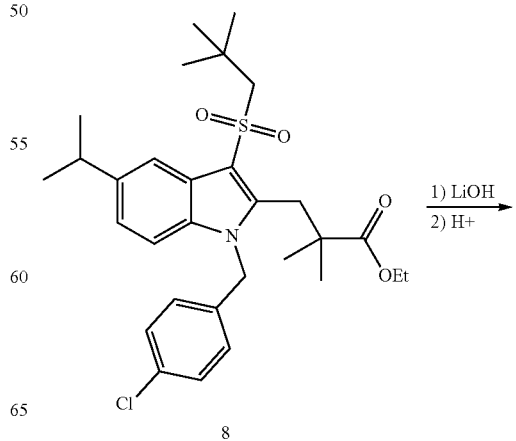

8

-continued

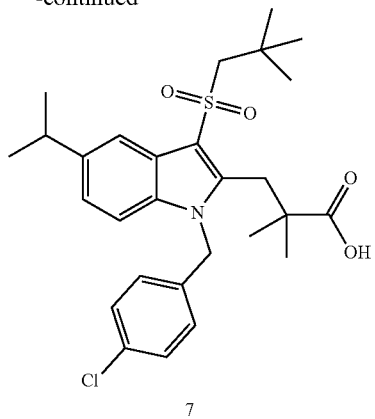

7

To a mixture of ethyl 3-(1-(4-chlorobenzyl)-5-isopropyl-3-(neopentylsulfinyl)-1H-indol-2-yl)-2,2-dimethylpropanoate (100 mg, 0.19 mmol) in THF (3 mL)/MeOH (3 mL)/H$_2$O (3 mL) was added LiOH.H$_2$O (31.7 mg, 0.75 mmol). The reaction mixture was stirred for 16 h at 60° C. and then concentrated. The residue was diluted with water (5 mL). The resulting solution was acidified with 1.0 N HCl (aq) to pH=6. The mixture was extracted with EtOAc (2×25 mL).

The organic extracts were combined and dried over anhydrous Na$_2$SO$_4$. It was filtered and the filtrate was concentrated. The residue was purified by pre-HPLC to give 3-(1-(4-chlorobenzyl)-5-isopropyl-3-(neopentylsulfonyl)-1H-indol-2-yl)-2,2-dimethylpropanoic acid (40 mg, 0.08 mmol, 42.2% yield) as light yellow solid. LCMS (ESI): m/z 518.3 [M+1]$^+$. $^1$HNMR (400 MHz, DMSO-d$_6$): δ (ppm) 1.11 (s, 9H), 1.18 (s, 6H), 1.24 (d, J=6.8 Hz, 6H), 2.98-3.01 (m, 1H), 3.20 (s, 2H), 3.47 (s, 2H), 5.49 (s, 2H), 6.96 (d, J=8.0 Hz, 2H), 7.14 (d, J=8.0 Hz, 2H), 7.36 (d, J=8.0 Hz, 2H), 7.62 (s, 1H), 12.60 (s, 1H).

Example 4: 3-(3-(tert-butylthio)-1-(4-chlorobenzyl)-5-isopropyl-1H-indol-2-yl) Propanoic Acid Scheme 4. Synthetic route for example 4

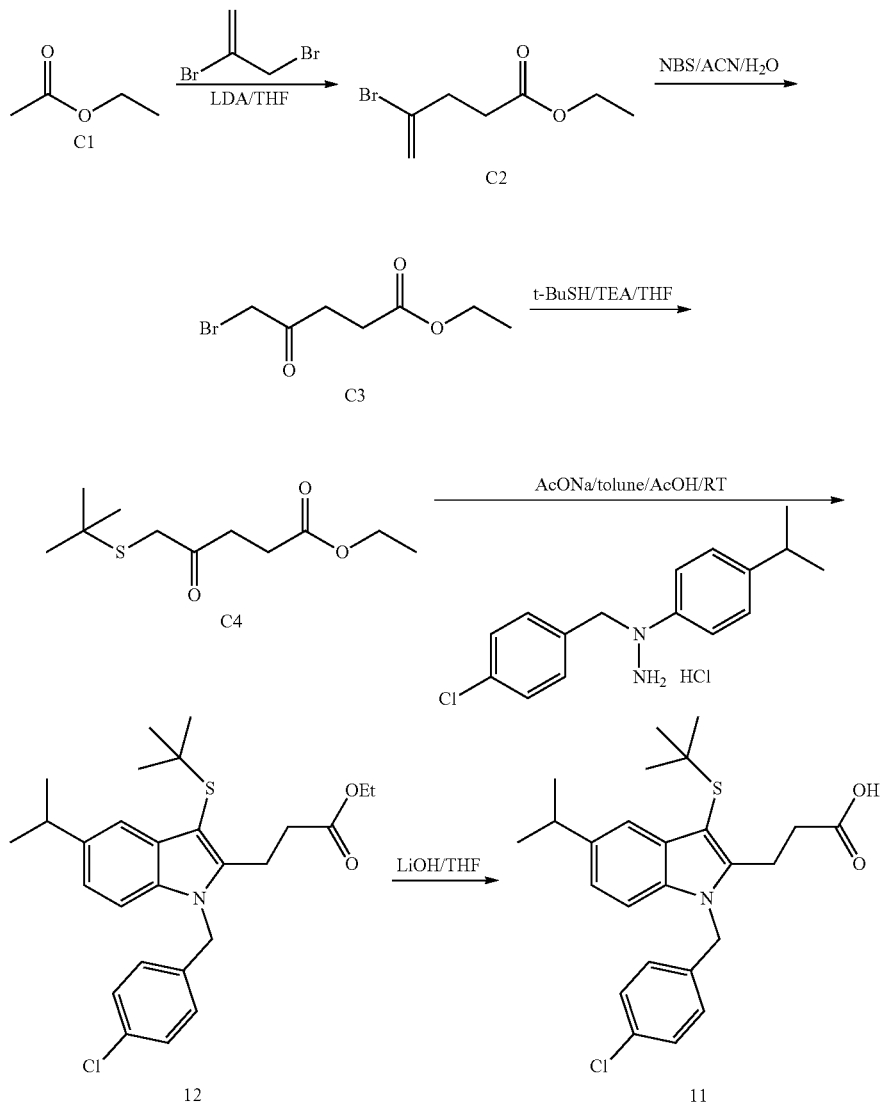

4.1. Preparation of Ethyl 4-bromopent-4-enoate

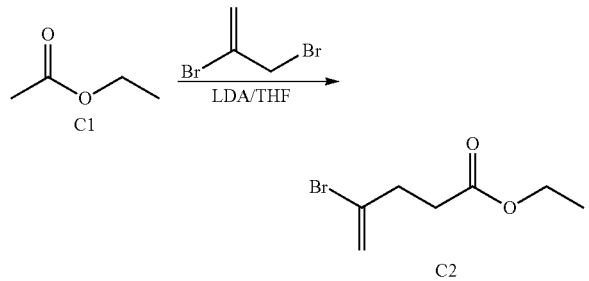

A solution of ethyl acetate (8 g, 90.9 mmol) in THF (150 mL) was cooled to −78° C. LDA (40 mL, 80 mmol, 2M in THF) was added dropwise. The mixture was stirred at −78° C. for 1 h. 2,3-dibromoprop-1-ene (13.5 g, 67.5 mmol) was added dropwise. The reaction mixture was then allowed to warm to −30° C. and stirred for 2 h. The mixture was quenched with water (300 mL). The organic layer was separated and the aqueous layer was extracted with EtOAc (3×150 mL). The combined organics were dried over anhydrous $Na_2SO_4$. It was filtered and the filtrate was concentrated to give ethyl 4-bromopent-4-enoate C2 (22 g) as yellow oil which was directly used in the next step without further purification.

4.2. Preparation of Ethyl 5-bromo-4-oxopentanoate

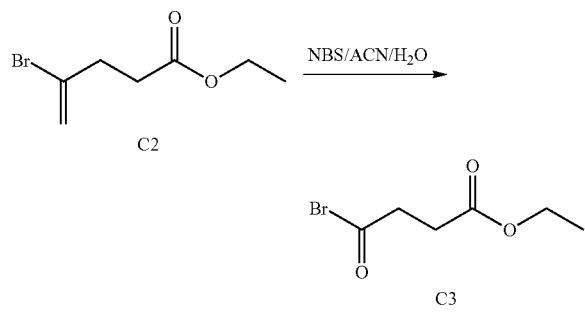

To a mixture of crude ethyl 4-bromopent-4-enoate (1 g, 4.83 mmol) in ACN (10 mL) was added water (2 mL) and NBS (1 g, 5.62 mmol). The reaction mixture was stirred for 3 h at room temperature and then concentrated. The residue was purified by column chromatography on silica gel (PE:EA=10:1) to give ethyl 5-bromo-4-oxopentanoate (C3) (180 mg, 0.81 mmol, 55% yield) as yellow oil.

4.3. Preparation of Ethyl 5-(tert-butylthio)-4-oxopentanoate

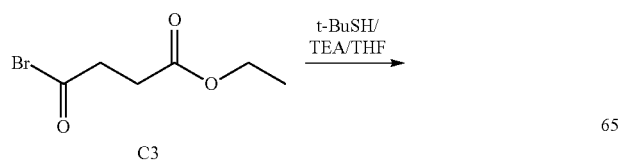

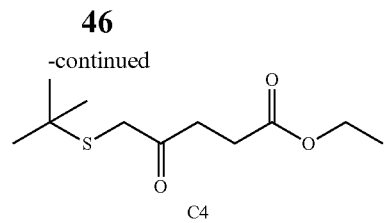

A mixture of ethyl 5-bromo-4-oxopentanoate (5.5 g, 24.7 mmol) in THF (50 mL) was cooled to 0~5° C. TEA (3.5 g, 34.6 mmol) and t-BuSH (3.5 g, 38.9 mmol) were added dropwise. The mixture was stirred for 18 h at room temperature. PE (300 mL) was added and the reaction mixture was filtered. The filtrate was evaporated and the residue was purified by flash column chromatography on silica gel (PE:EA=20:1) to give ethyl 5-(tert-butylthio)-4-oxopentanoate (C4) (2.0 g, 8.6 mmol, 35% yield) as yellow oil.

4.4. Preparation of Ethyl 3-(3-(tert-butylthio)-1-(4-chlorobenzyl)-5-isopropyl-1H-indol-2-yl)-2,2-dimethylpropanoate

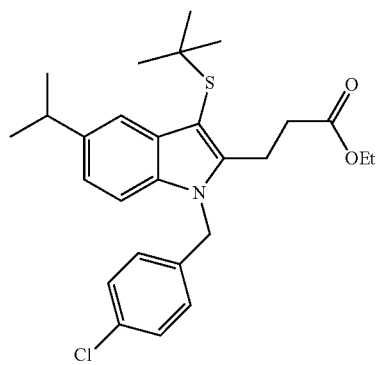

The compound 12 was prepared by the method similar to the compound ethyl 3-(1-(4-chlorobenzyl)-5-isopropyl-3-(neopentylthio)-1H-indol-2-yl)-2,2-dimethylpropanoate in the step 3.2, but using ethyl 5-(tert-butylthio)-4-oxopentanoate (C4). LCMS (ESI): m/z 472.3[M+1]⁺. ¹H NMR (400 MHz, $CDCl_3$): δ (ppm) 1.23 (t, J=7.2 Hz, 3H), 1.35-1.29 (m, 15H), 2.46 (t, J=8.0 Hz, 2H), 3.04-3.00 (m, 1H), 3.23 (t, J=8.0 Hz, 2H), 5.36 (s, 2H), 6.90 (d, J=8.4 Hz, 2H), 7.09-7.02 (m, 2H), 7.24 (d, J=8.4 Hz, 2H), 7.62 (s, 1H).

4.5. Preparation of 3-(3-(tert-butylthio)-1-(4-chlorobenzyl)-5-isopropyl-1H-indol-2-yl) Propanoic Acid

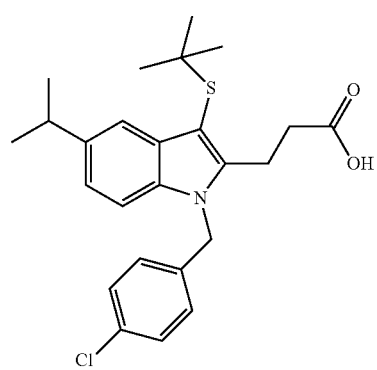

The compound 11 was prepared by the method similar to the compound ethyl 3-(1-(4-chlorobenzyl)-5-isopropyl-3-(neopentylthio)-1H-indol-2-yl)-2,2-dimethylpropanoate in the step 3.3, but using compound ethyl 3-(3-(tert-butylthio)-1-(4-chlorobenzyl)-5-isopropyl-1H-indol-2-yl)-2,2-dimethylpropanoate. LCMS (ESI): m/z 444.2[M+H]+. $^1$H NMR (400 MHz, DMSO-$d_6$): δ (ppm) 1.25-1.22 (m, 15H), 2.36 (t, J=8.4 Hz, 2H), 2.98-2.94 (m, 1H), 3.14 (t, J=7.6 Hz, 2H), 5.51 (s, 2H), 7.02-6.94 (m, 3H), 7.26 (d, J=8.4 Hz, 1H), 7.39 (d, J=8.0 Hz, 2H), 7.46 (s, 1H), 12.28 (brs, 1H).

Example 5. 2-(3-(tert-butylthio)-1-(4-chlorobenzyl)-5-isopropyl-1H-indol-2-yl) Acetic Acid Scheme 5. Synthetic route for example 5

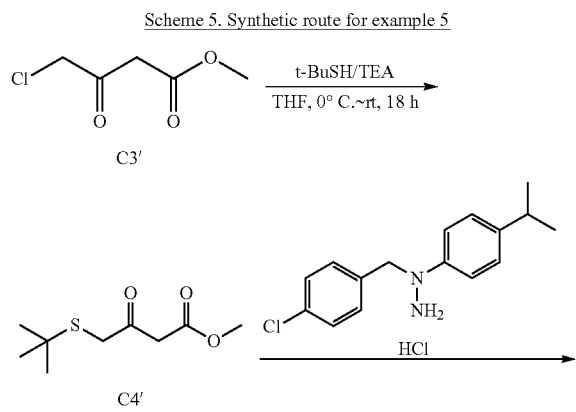

5.1. Preparation of Methyl 4-(tert-butylthio)-3-oxobutanoate

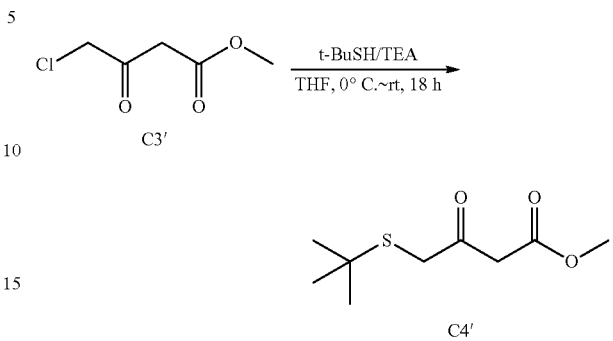

A mixture of methyl 4-chloro-3-oxobutanoate (1.0 g, 6.62 mmol) in THF (20 mL) was cooled 0~5° C. TEA (2.0 g, 19.9 mmol) was then added, followed by t-BuSH (1.7 g, 13.4 mmol) dropwise. The reaction mixture was stirred for 18 h at room temperature. PE (300 mL) was added and the mixture was filtered. The filtrate was concentrated and the residue was purified by flash column chromatography on silica gel (PE:EA=20:1) to give methyl 4-(tert-butylthio)-3-oxobutanoate (1.2 g, 5.88 mmol, 89% yield) as yellow oil.

5.2. Preparation of Methyl 2-(3-(tert-butylthio)-1-(4-chlorobenzyl)-5-isopropyl-1H-indol-2-yl)acetate

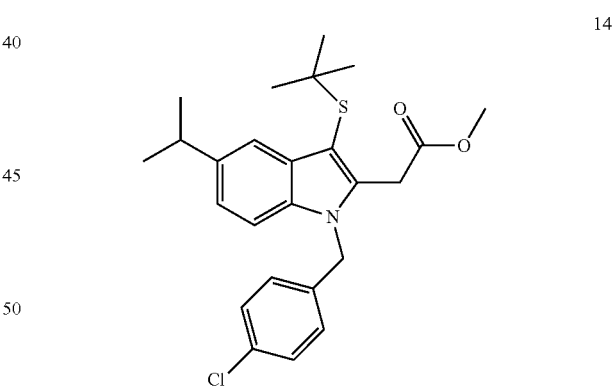

14

The compound 14 was prepared by the method similar with ethyl 3-(1-(4-chlorobenzyl)-5-isopropyl-3-(neopentylthio)-1H-indol-2-yl)-2,2-dimethylpropanoate (compound 4) in step 3.2, but using methyl 4-(tert-butylthio)-3-oxobutanoate (C4'). LCMS (ESI): m/z 444.3[M+1]+. $^1$H NMR (400 MHz, CDCl$_3$): δ (ppm) 7.65 (s, 1H), 7.22-7.25 (m, 2H), 7.08-7.11 (t, J=11.6 Hz, 2H), 6.88-6.90 (d, J=8.4 Hz, 2H), 5.35 (s, 2H), 4.02 (s, 2H), 3.55 (s, 3H), 3.01-3.04 (m, 1H), 1.29-1.31 (d, J=8.0 Hz, 15H).

5.3. Preparation of 2-(3-(tert-butylthio)-1-(4-chlorobenzyl)-5-isopropyl-1H-indol-2-yl) Acetic Acid

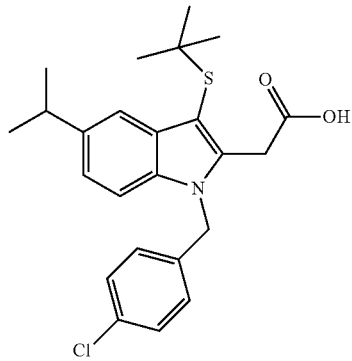

13

The compound 13 was prepared by the method similar to the compound 1 in the step 1.8, but using compound methyl 2-(3-(tert-butylthio)-1-(4-chlorobenzyl)-5-isopropyl-1H-indol-2-yl)acetate (compound 14). LCMS (ESI): m/z 430.3 [M+H]+. $^1$H NMR (400 MHz, DMSO-d$_6$): δ (ppm) 12.7 (brs, 1H), 7.48 (s, 1H), 7.35 (d, J=8.0 Hz, 2H), 7.23 (d, J=8.4 Hz, 2H), 7.02 (d, J=8.4 Hz, 3H), 5.45 (s, 2H), 3.97 (s, 2H), 2.50 (m, 1H), 1.22-1.24 (t, J=6.8 Hz, 15H).

Example 6. 3-(tert-butylthio)-1-(4-chlorobenzyl)-5-isopropyl-2-neopentyl-1H-indole Scheme 6. Synthetic route for example 6

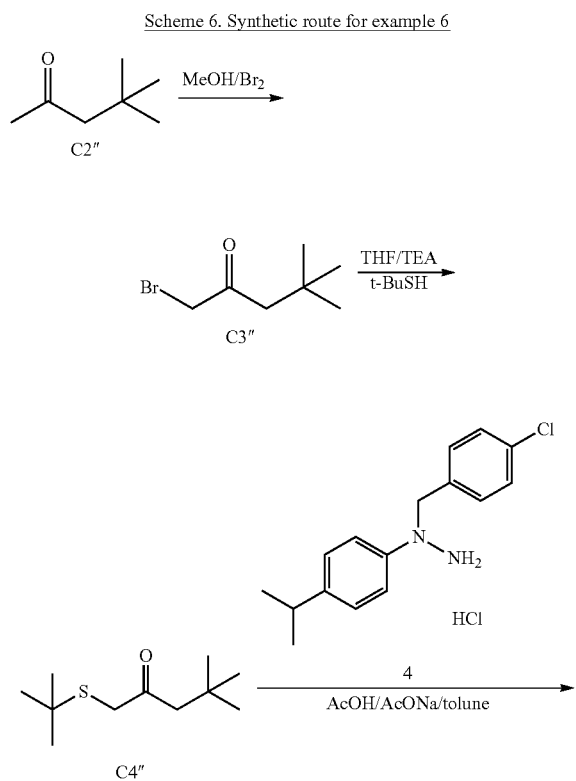

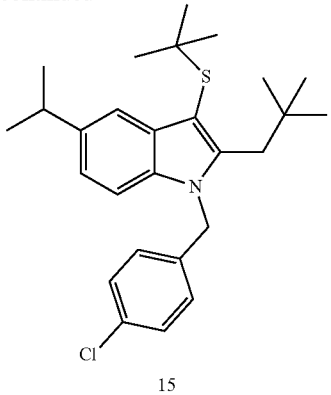

15

6.1. Preparation of 1-bromo-4,4-dimethylpentan-2-one

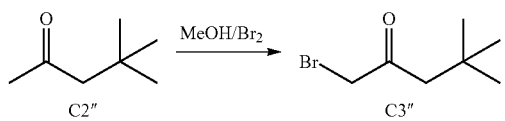

To a mixture of 4,4-dimethylpentan-2-one (1.2 g, 12.3 mmol) in MeOH (2.5 mL) was added Br$_2$ (1.8 g, 11.3 mmol) in an ice-bath. After addition, the mixture was stirred at room temperature for 30 min and then quenched with water (30 mL). The mixture was extracted with DCM (2×20 mL). The organic extracts were combined and dried over anhydrous Na$_2$SO$_4$. It was filtered and the filtrate was concentrated to give 1-bromo-4,4-dimethylpentan-2-one C3" (1.6 g, 8.3 mmol, 73% yield) as yellow oil used as the intermediate without further purification.

6.2. Preparation of 1-(tert-butylthio)-4,4-dimethylpentan-2-one

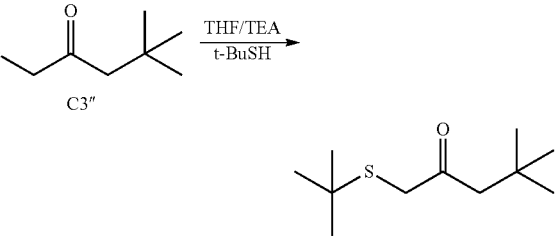

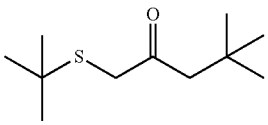

To a mixture of 1-bromo-4,4-dimethylpentan-2-one (C3") (1.6 g, 8.3 mmol) in THF (50 mL) was added TEA (2.8 mL, 20.2 mmol) and t-BuSH (1.3 mL, 11.5 mmol). The reaction mixture was stirred for 18 h at room temperature. It was filtered and the filtrate was concentrated to give 1-(tert-butylthio)-4,4-dimethylpentan-2-one (C4") (1.4 g, 6.9 mmol, 84% yield) as yellow oil used as the intermediate without further purification.

6.3. Preparation of 3-(tert-butylthio)-1-(4-chlorobenzyl)-5-isopropyl-2-neopentyl-1H-indole

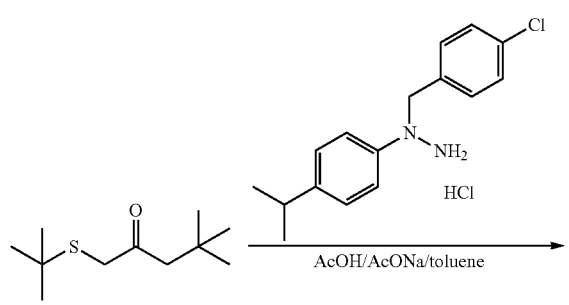

To a mixture of 1-(tert-butylthio)-4,4-dimethylpentan-2-one (500 mg, 2.48 mmol) and 1-(4-chlorobenzyl)-1-(4-isopropylphenyl)hydrazine hydrochloride (750 mg, 2.41 mmol) in AcOH (15 mL) was added toluene (25 mL) and AcONa (220 mg, 2.68 mol). The reaction mixture was stirred for 30 hours at room temperature and then concentrated. The residue was purified by flash column chromatography on silica gel (PE:EA=20:1) to give 3-(tert-butylthio)-1-(4-chlorobenzyl)-5-isopropyl-2-neopentyl-1H-indole (122 mg, 0.28 mmol, 11% yield) as white solid. LCMS (ESI): m/z 442.3[M+1]$^+$. $^1$HNMR (400 MHz, DMSO-d$_6$): δ (ppm) 0.99 (s, 9H), 1.26 (s, 9H), 1.30 (d, J=7.2 Hz, 6H), 2.88 (br s, 2H), 3.05-2.97 (m, 1H), 5.39 (s, 2H), 6.74 (d, J=8.4 Hz, 2H), 6.99 (d, J=8.4, 1.2 Hz, 1H), 7.04 (d, J=8.0 Hz, 2H), 7.20 (d, J=8.4 Hz, 2H), 7.64 (s, 1H).

Example 7. 3-(1-(4-chlorobenzyl)-3-(cyclobutanecarbonyl)-5-isopropyl-1H-pyrrolo[2,3-b]pyridin-2-yl)-2,2-dimethylpropanoic Acid Scheme 7. Synthetic route for example 7

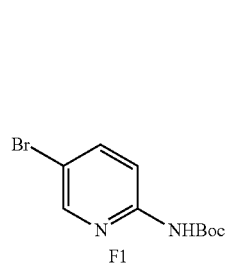

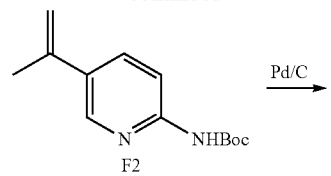

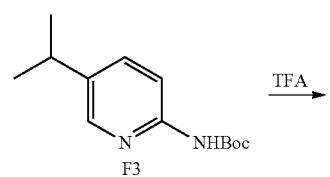

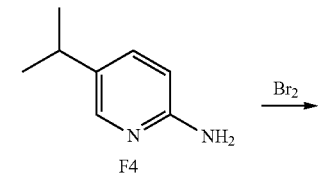

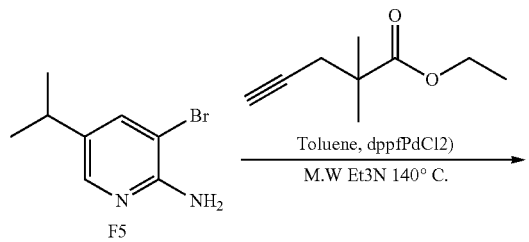

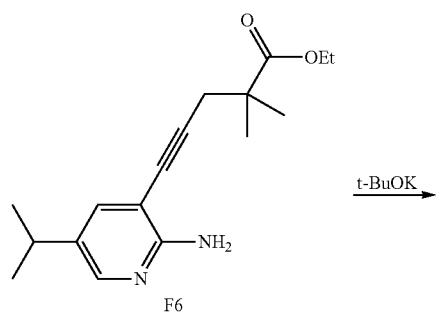

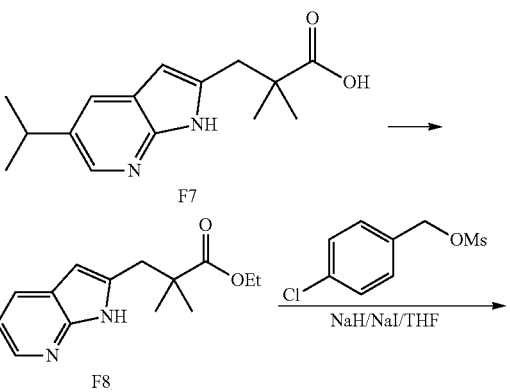

-continued

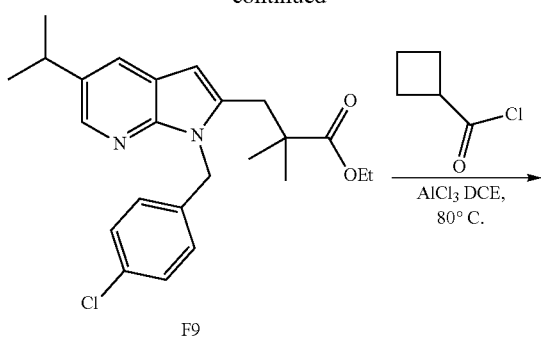

F9

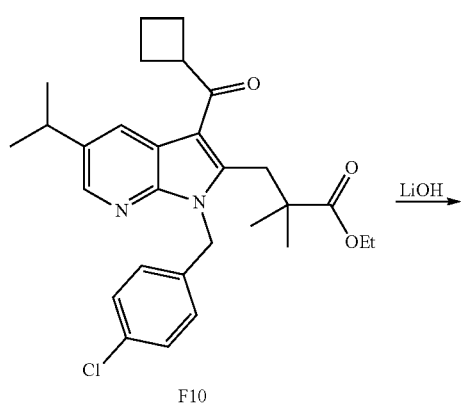

F10

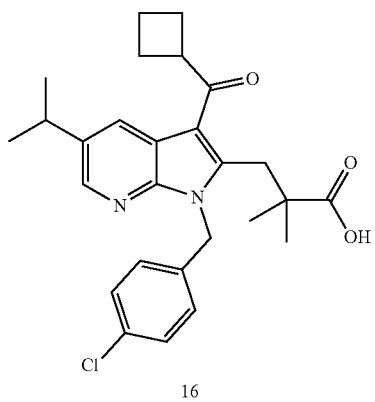

16

7.1. Preparation of Tert-Butyl (5-(prop-1-en-2-yl)pyridin-2-yl)carbamate

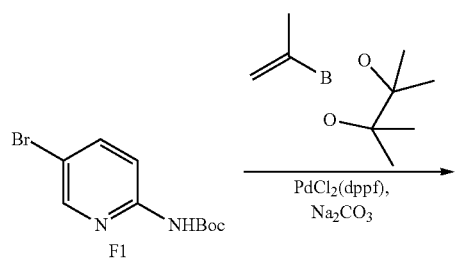

-continued

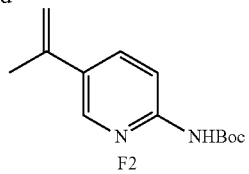

F2

To a solution of tert-butyl (5-bromopyridin-2-yl)carbamate (5.40 g, 20 mmol) in 1,4-dioxane (100 mL), 4,4,5,5-tetramethyl-2-(prop-1-en-2-yl)-1,3,2-dioxaborolane (3.40 g, 20 mmol), PdCl$_2$(dppf) (1.45 g, 2 mmol) and Na$_2$CO$_3$ (2.12 g, 20 mmol) were added. The mixture was stirred overnight at 110° C. under N2. After cooled to the room temperature, it was filtered, and the filtrate was concentrated. The residue was purified by column chromatography on silica gel (PE:EA=10:1) to give tert-butyl (5-(prop-1-en-2-yl)pyridin-2-yl)carbamate (2.57 g, 11 mmol, 5 5% yield) as oil. LCMS (ESI): m/z 235.4[M+1]$^+$.

7.2. Preparation of Tert-Butyl(5-isopropylpyridin-2-yl)carbamate

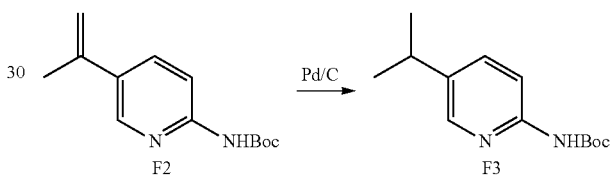

To a solution of tert-butyl (5-(prop-1-en-2-yl)pyridin-2-yl)carbamate (2.57 g, 11 mmol) in MeOH (30 mL), Pd/C (300 mg, 0.14 mmol) was added, the mixture was stirred overnight at 25° C. under N$_2$. It was filtrated, and the filtrate was concentrated to give tert-butyl (5-isopropylpyridin-2-yl)carbamate (2.36 g, 10 mmol, 90.9% yield) as oil used as the intermediate without further purification. LCMS (ESI): m/z 237.2[M+1]+.

7.3. Preparation of 5-isopropylpyridin-2-amine

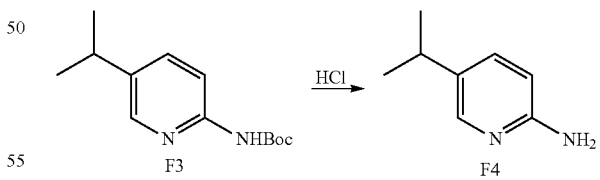

A solution of tert-butyl (5-isopropylpyridin-2-yl)carbamate (2.36 g, 10 mmol) in 6N HC/MeOH (50 mL) was stirred for 2 h. It was concentrated and H$_2$O (40 mL) was added. The mixture was basified with NaHCO$_3$ to PH=8. The mixture was extracted with DCM (3×20 mL). The organic extracts were washed with brine (20 mL), dried over anhydrous Na$_2$SO$_4$ and concentrated to give 5-isopropylpyridin-2-amine (1.20 g, 8.8 mmol, 88% yield) as oil used as the intermediate without further purification. LCMS (ESI): m/z 137.4[M+1]+.

7.4. Preparation of 3-bromo-5-isopropylpyridin-2-amine

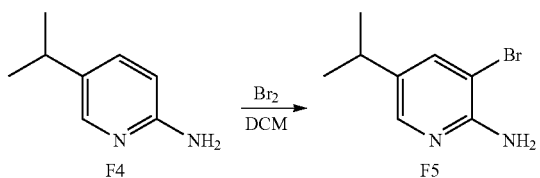

To a solution of 5-isopropylpyridin-2-amine (1.20 g, 8.8 mmol) in DCM (50 mL), Br$_2$ (1.40 g, 8.8 mmol) was added dropwise. The mixture was stirred for 1.0 hour at 10° C. The mixture was washed with NaHCO$_3$ (2×60 mL) and brine (40 m), dried over anhydrous Na$_2$SO$_4$. It was filtered and the filtrate was concentrated. The residue was purified by column chromatography on silica gel (PE:EA=5:1) to give 3-bromo-5-isopropylpyridin-2-amine (950 mg, 4.4 mmol, 50% yield) as oil. $^1$HNMR (400 MHz, CDCl$_3$): δ (ppm) 1.21 (d, J=6.8 Hz, 6H), 2.80 (m, 1H), 4.81 (s, 2H), 7.53 (d, J=1.6 Hz, 1H), 7.88 (d, J=1.6 Hz, 1H).

7.5. Preparation of Ethyl 5-(2-amino-5-isopropylpyridin-3yl)-2,2-dimethylpent-4-ynoate

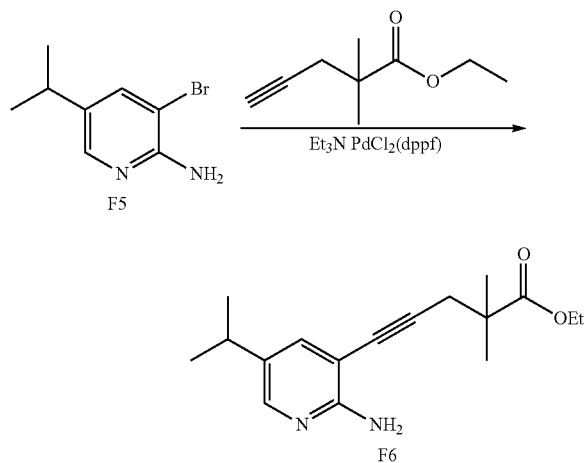

To a mixture of 3-bromo-5-isopropylpyridin-2-amine (500 mg, 2.33 mmol) and ethyl 2,2-dimethylpent-4-ynoate (770 mg. 5 mmol,) in toluene (5 mL), PdCl$_2$(dppf) (182 mg, 0.25 mmol) and Et$_3$N (378 mg, 3.75 mmol) was added. The reaction mixture was irritated via microwave reactor for 20 min at 140° C. under N$_2$. The mixture was concentrated and the residue was purified by prep TLC (PE:EA=3:1) to give ethyl 5-(2-amino-5-isopropylpyridin-3-yl)-2,2-dimethyl-pent-4-ynoate (210 mg, 0.73 mmol, 30.4% yield) as yellow solid. LCMS (ESI): m/z 289.4 [M+1]$^+$.

7.6. Preparation of Ethyl 3-(5-isopropyl-1H-pyrrolo[2,3-b]pyridin-2-yl)-2,2-dimethylpropanoate

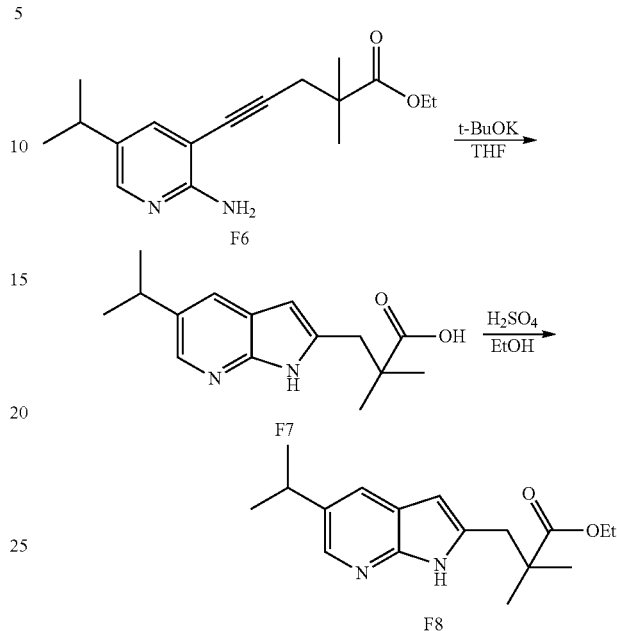

To a mixture of ethyl 5-(2-amino-5-isopropylpyridin-3-yl)-2,2-dimethylpent-4-ynoate (210 mg, 0.73 mmol) in THF (10 mL), t-BuOK (178 mg, 1.5 mmol) was added. The reaction mixture was heated to 60° C. for 1.0 hour. The mixture was concentrated and EtOH (10 mL) and H$_2$SO$_4$ (296 mg, 3 mmol) were added. The mixture was heated overnight at 80° c. The mixture was concentrated, and H$_2$O (20 mL) was added. The mixture was neutralized with NaHCO$_3$. It was extracted with DCM (3×20 mL). The organic extracts were washed with NaHCO$_3$ (20 mL) and brine (20 m), dried over anhydrous Na$_2$SO$_4$. It was filtered and the filtrate was concentrated. The residue was purified by column chromatography on silica gel (PE:EA=3:1) to give ethyl 3-(5-isopropyl-1H-pyrrolo [2,3-b]pyridin-2-yl)-2, 2-dimethylpropanoate (165 mg, 0.57 mmol, 78.4% yield) as oil. LCMS (ESI): m/z 289.4[M+1]+.

7.7. Preparation of Ethyl 3-(1-(4-chlorobenzyl)-5-isopropyl-H-pyrrolo[2,3-b]pyridin-2-yl)-2,2-dimethylpropanoate

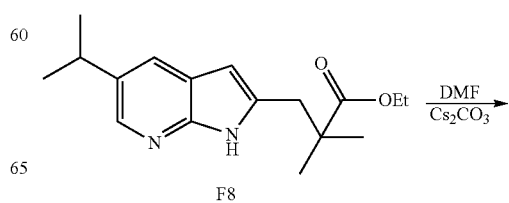

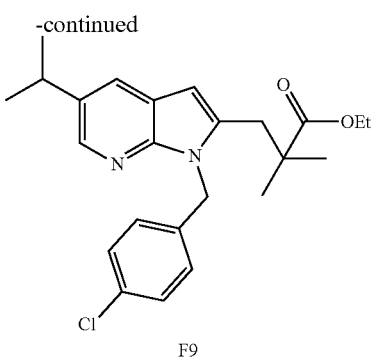

F9

To a mixture of ethyl 3-(5-isopropyl-1H-pyrrolo[2,3-b]pyridin-2-yl)-2,2-dimethylpropanoate (165 mg, 0.57 mmol) in DMF (3.0 mL), 1-chloro-4-(chloromethyl)benzene (92 mg, 0.57 mmol) and $Cs_2CO_3$ (370 mg, 1.14 mmol) were added. The mixture was stirred overnight at 60° C. $H_2O$ (15 mL) was added and the mixture was extracted with DCM (3×10 mL). The organic extracts were combined and washed with brine (2×10 mL), dried over $Na_2SO_4$ and concentrated. The residue was purified by column chromatography on silica gel (PE:EA=10:1) to give ethyl 3-(1-(4-chlorobenzyl)-5-isopropyl-1H-pyrrolo [2,3-b]pyridin-2-yl)-2,2-dimethylpropanoate (140 mg, 0.34 mmol, 59.6% yield) as yellow solid. LCMS (ESI): m/z 413.3[M+1]+.

7.8. Preparation of Ethyl 3-(1-(4-chlorobenzyl)-5-isopropyl-1H-pyrrolo-5-isopropyl-1H-pyrrolo[2,3-b]pyridin-2-yl)-2,2-dimethylpropanoate

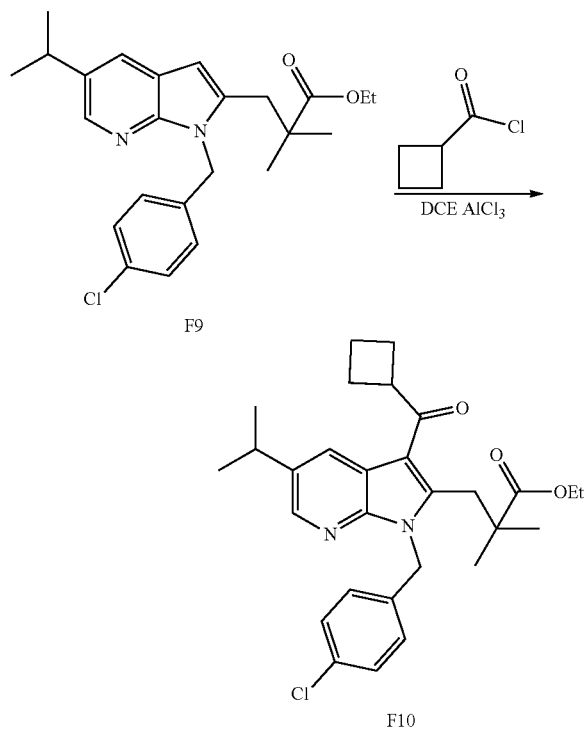

To a solution of ethyl 3-(1-(4-chlorobenzyl)-5-isopropyl-1H-pyrrolo [2,3-b]pyridin-2-yl)-2,2-dimethylpropanoate (120 mg, 0.29 mmol) in DCE (5 ml), $AlCl_3$ (193 mg, 1.45 mmol) was added under $N_2$. The mixture was heated to 80° C., then cyclobutanecarbonyl chloride (171 mg, 1.45 mmol) was added dropwise. After addition, the mixture was stirred overnight at 80° C., and then poured into ice slowly. 1.0 N HCl (10 mL) was added and the mixture extracted with $CH_2Cl_2$ (2×15 mL). The organic extracts were combined and washed with water (2×15 mL), dried ($MgSO_4$), and concentrated, purified by column chromatography on silica gel (PE:EA=10:1) to give ethyl 3-(1-(4-chlorobenzyl)-3-(cyclobutanecarbonyl)-5-isopropyl-1H-pyrrolo[2,3-b]pyridin-2-yl)-2,2-dimethylpropanoate (72 mg, 0.14 mmol, 50% yield) as yellow solid. LCMS (ESI): m/z 495.3[M+1]+.

7.9. Preparation of 3-(1-(4-chlorobenzyl)-3-(cyclobutanecarbonyl)-5-isopropyl-1H-pyrrolo[2,3-b]pyridin-2-yl)-2,2-dimethylpropanoic Acid

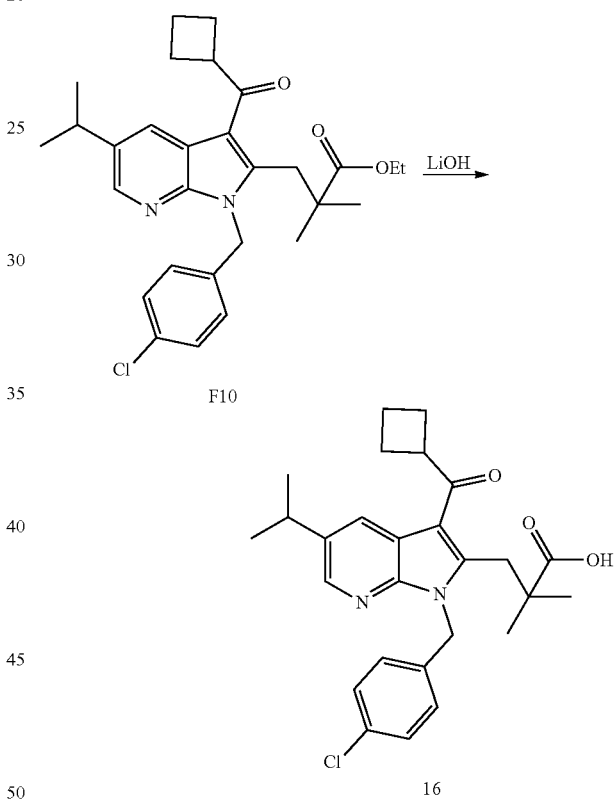

To a mixture of ethyl3-(1-(4-chlorobenzyl)-3-(cyclobutanecarbonyl)-5-isopropyl-1H-pyrrolo[2,3-b]pyridin-2-yl)-2,2-dimethylpropanoate (72 mg, 0.14 mmol) in THF (5 mL) was added $LiOH \cdot H_2O$ (50 mg, 1.19 mmol) and water (1.0 mL). The mixture was heated to 60° C. for 18 hours and concentrated. The residue was purified by preparation HPLC to give 3-(1-(4-chlorobenzyl)-3-(cyclobutanecarbonyl)-5-isopropyl-1H-pyrrolo-[2,3-b]pyridin-2-yl)-2,2-dimethylpropanoic acid (16) (14 mg, 0.030 mmol, 21% yield) as white solid. LCMS (ESI): m/z 467.3 [M+1]+. $^1$HNMR (400 MHz, DMSO-$d_6$): δ ppm 1.10 (s, 6H), 1.32-1.27 (d, J=6.8 Hz, 6H), 1.79 (m, 1H), 2.03-2.01 (m, 1H), 2.49-2.24 (m, 4H), 3.12-3.09 (m, 1H), 3.50 (s, 2H), 4.10-4.05 (m, 1H), 5.57 (s, 2H), 6.94 (d, J=8.8 Hz, 2H), 7.35 (d, J=8.4 Hz, 2H), 8.04 (d, J=2.0 Hz, 1H), 8.21 (d, J=1.6 Hz, 1H), 12.50 (s, 1H).

Example 8. 3-(3-(tert-butylthio)-1-(4-chlorobenzyl)-5-methoxy-1H-pyrrolo[2,3-b]pyridin-2-yl)-2,2-dimethylpropanoic Acid

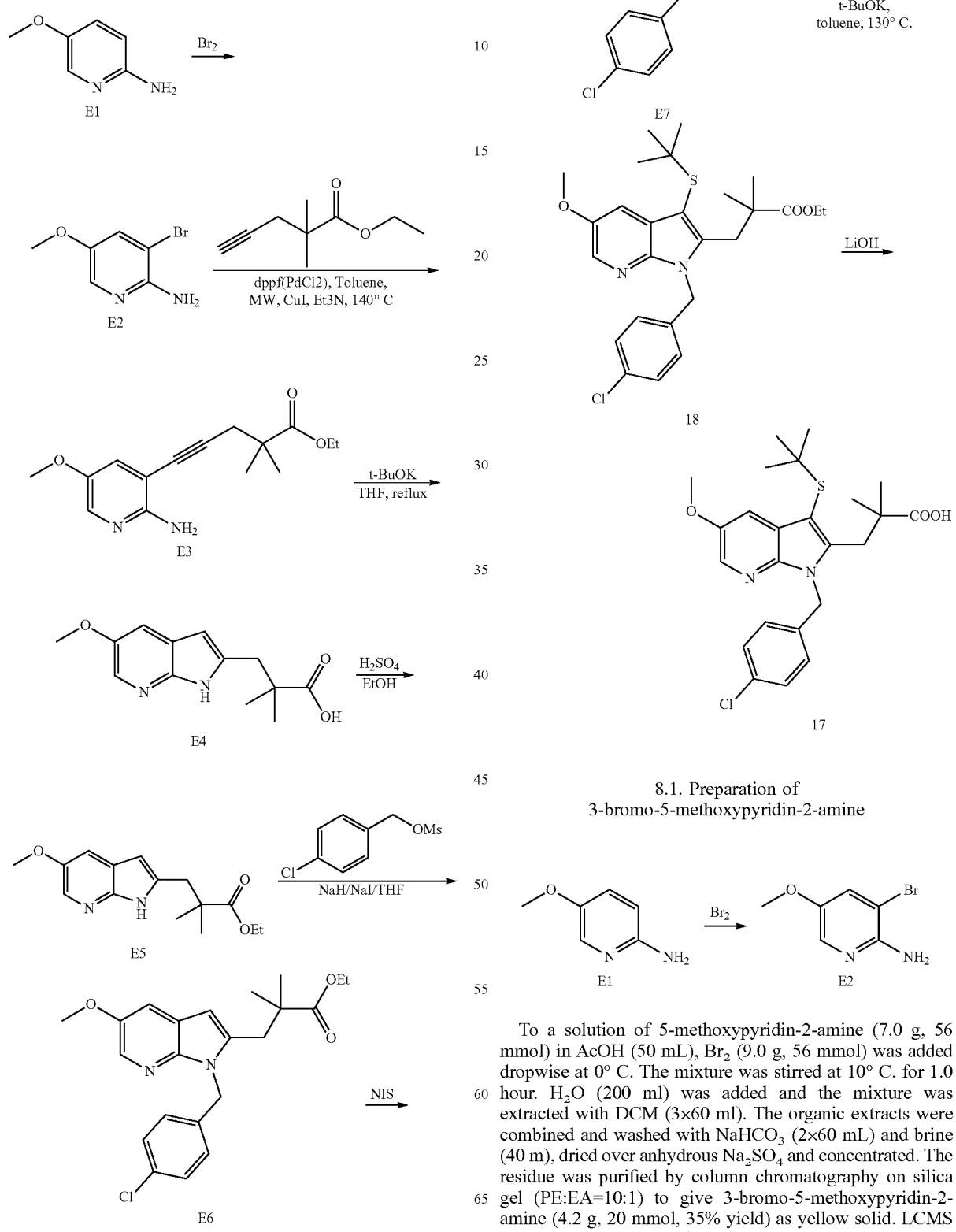

8.1. Preparation of 3-bromo-5-methoxypyridin-2-amine

To a solution of 5-methoxypyridin-2-amine (7.0 g, 56 mmol) in AcOH (50 mL), Br$_2$ (9.0 g, 56 mmol) was added dropwise at 0° C. The mixture was stirred at 10° C. for 1.0 hour. H$_2$O (200 ml) was added and the mixture was extracted with DCM (3×60 ml). The organic extracts were combined and washed with NaHCO$_3$ (2×60 mL) and brine (40 m), dried over anhydrous Na$_2$SO$_4$ and concentrated. The residue was purified by column chromatography on silica gel (PE:EA=10:1) to give 3-bromo-5-methoxypyridin-2-amine (4.2 g, 20 mmol, 35% yield) as yellow solid. LCMS (ESI): m/z 203.0 [M+1]$^+$.

8.2. Preparation of Ethyl 5-(2-amino-5-methoxy-pyridin-3-yl)-2,2-dimethylpent-4-ynoate

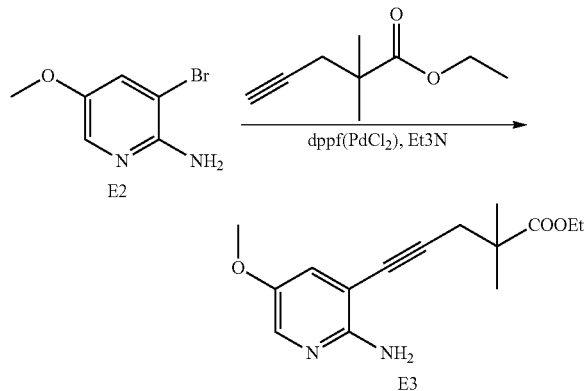

To a mixture of 3-bromo-5-methoxypyridin-2-amine (500 mg, 2.5 mmol) and ethyl 2,2-dimethylpent-4-ynoate (770 mg. 5 mmol) in toluene (5 mL), PdCl₂(dppf) (182 mg, 0.25 mmol) and Et₃N (378 mg, 3.75 mmol) were added, the mixture was irritated via microwave reactor for 20 min at 140° C. under N₂. The mixture was concentrated and the residue was purified by TLC (PE:EA=5:1) to give ethyl 5-(2-amino-5-methoxypyridin-3-yl)-2,2-dimethylpent-4-ynoate (210 mg, 0.76 mmol, 30.4% yield) as yellow solid. LCMS (ESI): m/z 277.3 [M+1]⁺.

8.3. Preparation of Ethyl 3-(5-methoxy-1H-pyrrolo[2,3-b]pyridin-2-yl)-2,2-dimethylpropanoate

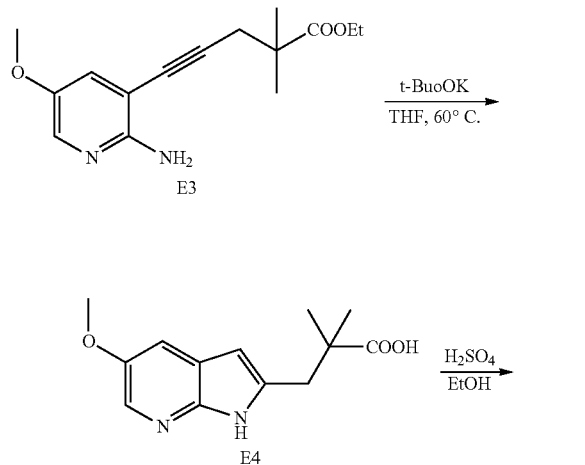

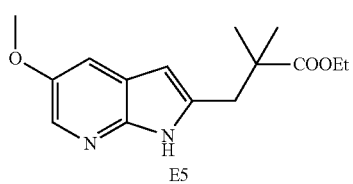

To a mixture of ethyl 5-(2-amino-5-methoxypyridin-3-yl)-2,2-dimethylpent-4-ynoate (1.20 g, 4.3 mmol) in THF (20 mL), t-BuOK (490 mg, 4.3 mmol) was added. The mixture was heated to 60° c. for 1.0 hour. The mixture was concentrated. EtOH (20 ml) and H₂SO₄ (1.05 g, 10.8 mmol) were added, and the mixture was heated to 80° c. overnight. The mixture was concentrate. H₂O (20 mL) was added and the mixture was neutralized with NaHCO₃, extracted with DCM (3×20 mL). The organic extracts were combined and washed with NaHCO₃ (20 ml) and brine (20 mL), dried over anhydrous Na₂SO₄ and filtered. The filtrate was concentrated. The residue was purified by column chromatography on silica gel (PE:EA=10:1) to give ethyl3-(5-methoxy-1H-pyrrolo [2,3-b]pyridin-2-yl)-2,2-dimethylpropanoate (910 mg, 3.3 mmol, 76.7% yield) as oil. LCMS (ESI): m/z 277.4 [M+1]⁺.

8.4. Preparation of Ethyl 3-(1-(4-chlorobenzyl)-5-methoxy-1H-pyrrolo[2,3-b] pyridin-2-yl)-2,2-dimethylpropanoate

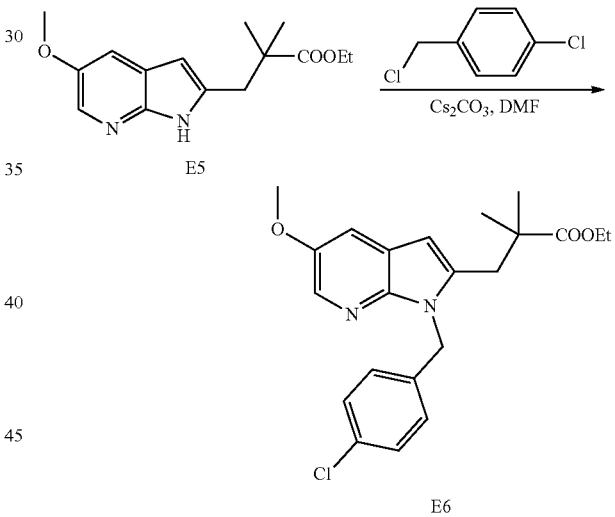

To a mixture of ethyl 3-(5-methoxy-1H-pyrrolo[2,3-b] pyridin-2-yl)-2,2-dimethylpropanoate (850 mg, 3.19 mmol) in DMF (10 mL), 1-chloro-4-(chloromethyl) benzene (615 mg, 3.8 mmol) and Cs₂CO₃ (2.08 g, 6.4 mmol) were added, the mixture was heated to 60° C. overnight. H₂O (100 mL) was added, and the mixture was extracted with DCM (3×30 mL). The organic extracts were combined and washed with brine (2×30 mL), dried over anhydrous Na₂SO₄ and concentrated. The residue was purified by column chromatography on silicagel (PE:EA=5:1) to give ethyl3-(1-(4-chlorobenzyl)-5-methoxy-1H-pyrrolo[2,3-b]pyridin-2-yl)-2,2-dimethylpropanoate (810 mg, 2.0 mmol, 62.5% yield) as yellow solid. LCMS (ESI): m/z 401.3 [M+1]+.

8.5. Preparation of Ethyl 3-(1-(4-chlorobenzyl)-3-iodo-5-methoxy-1H-pyrrolo[2,3-b]pyridin-2-yl)-2,2-dimethylpropanoate

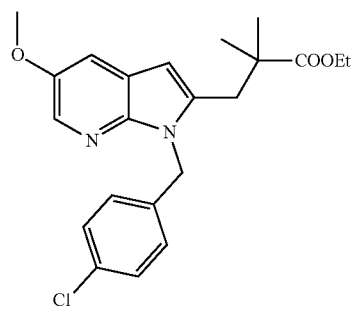

E6

NIS →

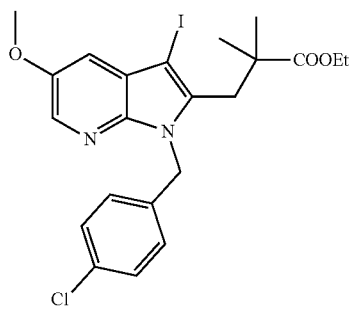

E7

To a mixture of ethyl 3-(1-(4-chlorobenzyl)-5-methoxy-1H-pyrrolo [2,3-b]pyridin-2-yl)-2,2-dimethylpropanoate (400 mg, 1 mmol) in acetonitrile (10 mL), NIS (270 mg, 1.2 mmol) was added. The mixture was stirred for 2.0 hours at 10° C. The mixture was concentrated and the residue was purified by column chromatography on silica gel (PE: EA=10:1) to give ethyl 3-(1-(4-chlorobenzyl)-3-iodo-5-methoxy-1H-pyrrolo[2,3-b] pyridin-2-yl)-2,2-dimethylpropanoate (410 mg, 0.78 mmol, 78% yield) as yellow solid. LCMS (ESI): m/z 527.2 [M+1]$^+$.

8.6. Preparation of Ethyl 3-(3-(tert-butylthio)-1-(4-chlorobenzyl)-5-methoxy-1H-pyrrolo[2,3-b]pyridin-2-yl)-2,2-dimethylpropanoate

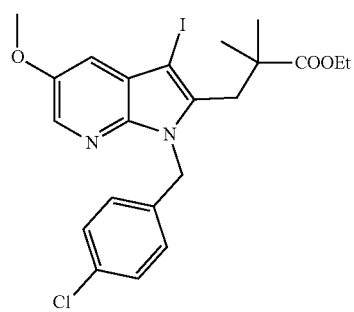

E7

→ SH t-BuOK / Pd$_2$(dba)$_3$ / P(Cy)$_3$HBF$_4$

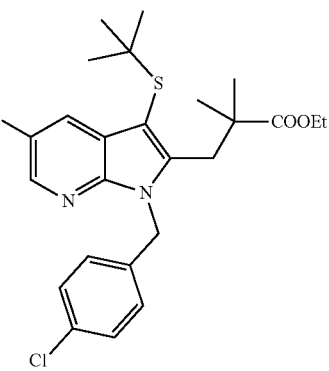

18

LiOH →

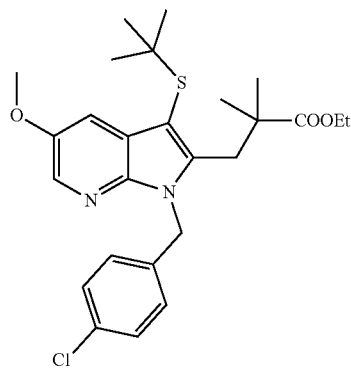

18

To a mixture of ethyl 3-(1-(4-chlorobenzyl)-3-iodo-5-methoxy-1H-pyrrolo[2,3-b] pyridin-2-yl)-2,2-dimethylpropanoate (410 mg, 0.78 mmol) in toluene (5 mL), t-BuOK (240 mg, 2 mmol), 2-methylpropane-2-thiol (270 mg, 3.0 mmol), Pd$_2$(dba)$_3$ (91 mg, 0.1 mmol) and Tricyclohexylphosphonium tetrafluoborate (36.8 mg, 0.1 mmol) were added. The mixture was irritated via microwave reactor at 140° C. under N$_2$. After cooled to room temperature, the mixture was concentrated. The residue was purified by preparation TLC (PE:EA=5:1) to give ethyl3-(3-(tert-butylthio)-1-(4-chlorobenzyl)-5-methoxy-1H-pyrrolo[2,3-b]pyridin-2-yl)-2,2-dimethylpropanoate (210 mg, 0.43 mmol, 55% yield) as yellow solid. LCMS (ESI): m/z 489.3[M+1]$^+$. $^1$HNMR (400 MHz, CDCl$_3$): δ ppm 1.18-1.15 (m, 3H), 1.21 (s, 6H), 1.23 (s, 9H), 3.18 (s, 2H), 3.90 (s, 3H), 4.12 (m, 2H), 5.54 (s, 2H), 6.76 (d, J=8.4 Hz, 2H), 7.19 (d, J=8.4 Hz, 2H), 7.53 (d, J=2.4 Hz, 1H), 8.04 (d, J=2.8 Hz, 1H).

8.7. Preparation of 3-(3-(tert-butylthio)-1-(4-chlorobenzyl)-5-methoxy-1H-pyrrolo[2,3-b]pyridin-2-yl)-2,2-dimethylpropanoic Acid

65

-continued

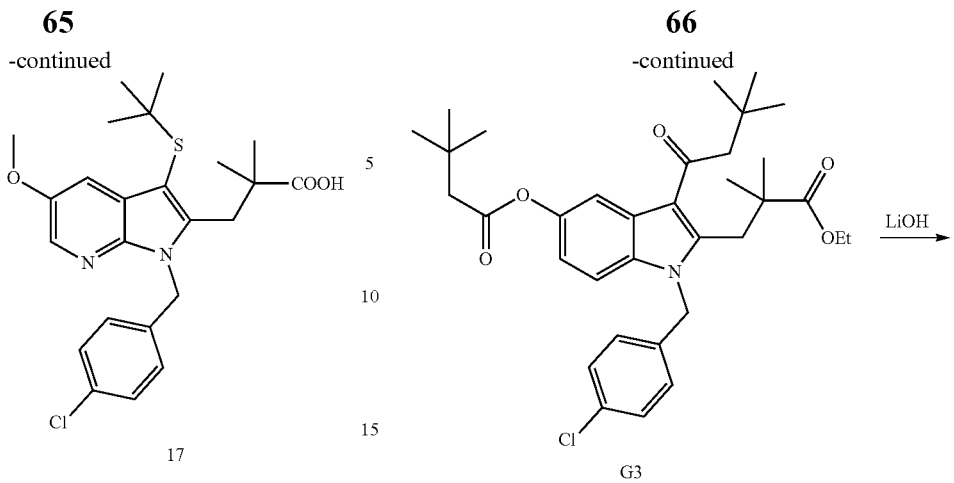

17

To a mixture of ethyl 3-(3-(tert-butylthio)-1-(4-chlorobenzyl)-5-methoxy-1H-pyrrolo[2,3-b]pyridin-2-yl)-2,2-dimethylpropanoate (50 mg, 0.1 mmol) in THF (5 mL) was added LiOH.H$_2$O (50 mg, 1.19 mmol) and water (1 mL). The mixture was heated to 60° C. for 18 hours. After cooled to room temperature, the mixture was concentrated. The residue was purified by preparation HPLC to give 3-(3-(tert-butylthio)-1-(4-chlorobenzyl)-5-methoxy-1H-pyrrolo[2,3-b]pyridin-2-yl)-2,2-dimethylpropanoic acid (14 mg, 0.030 mmol, 32% yield) as whitesolid. LCMS (ESI): m/z 461.2 [M+1]+. $^1$HNMR (400 MHz, DMSO-d$_6$): δ (ppm) 1.10 (s, 6H), 1.18 (s, 9H), 3.14 (s, 2H), 3.85 (s2, 3H), 5.56 (s, 2H), 6.84 (d, J=8.0 Hz, 2H), 7.34 (d, J=8.4 Hz, 2H), 7.50 (d, J=2.4 Hz, 1H), 8.00 (d, J=2.4 Hz, 1H), 12.51 (s, 1H).

Example 9. 1-(4-chlorobenzyl)-3-(3,3-dimethyl-butyl)-2-(3-hydroxy-2,2-dimethylpropyl)-1H-indol-5-ol Scheme 9. Synthetic route for example 9

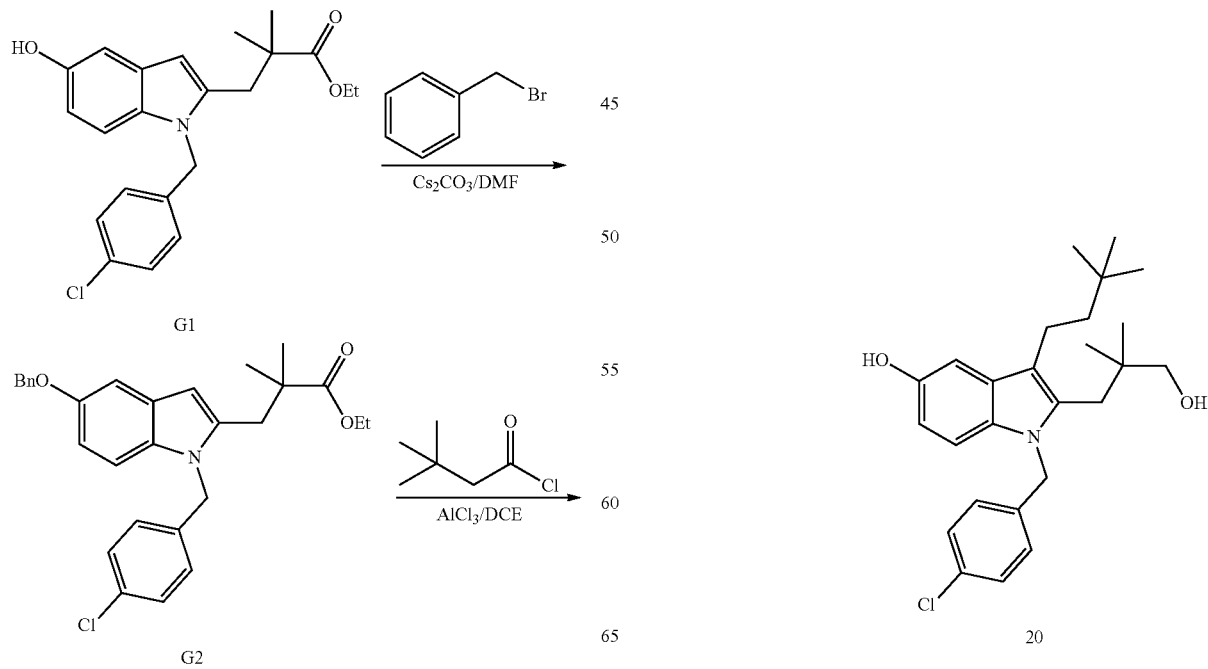

66

-continued

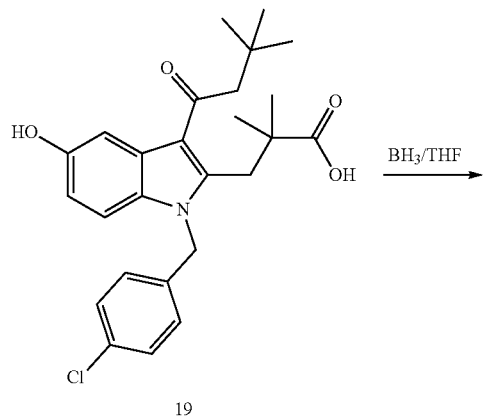

9.1. Preparation of Ethyl 3-(5-(benzyloxy)-1-(4-chlorobenzyl)-1H-indol-2-yl)-2,2-dimethylpropanoate

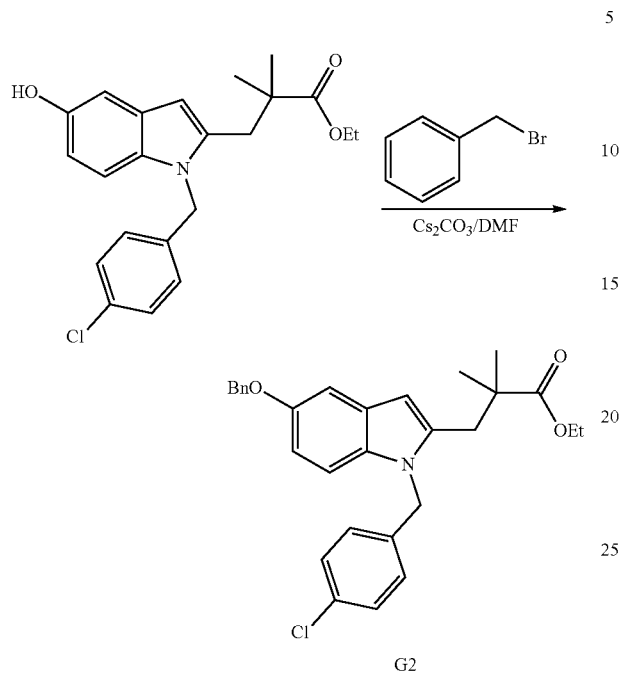

G2

To a solution of ethyl 3-(1-(4-chlorobenzyl)-5-hydroxy-1H-indol-2-yl)-2,2-dimethylpropanoate (2.0 g, 5.2 mmol) in DMF (50 mL) were added Cs$_2$CO$_3$ (5.1 g, 15.6 mmol), (bromomethyl)benzene (1.15 g, 6.8 mmol) and (n-Bu)$_4$NI (0.19 g, 0.52 mmol) at room temperature. After addition, the reaction mixture was stirred for 15 hours at room temperature. The mixture was concentrated and the residue was purified by column chromatography on silica gel (PE:EA=10:1) to give ethyl 3-(5-(benzyloxy)-1-(4-chlorobenzyl)-1H-indol-2-yl)-2,2-dimethylpropanoate (2.3 g, 4.8 mmol, 92% yield) as yellow oil. LCMS (ESI): m/z 476.3 [M+1]$^+$. $^1$HNMR (400 MHz, CDCl$_3$): δ (ppm) 1.20 (t, J=7.2 Hz, 3H), 1.25 (s, 6H), 2.92 (s, 2H), 4.11 (q, J=6.4 Hz, 2H), 5.08 (s, 2H), 5.29 (s, 2H), 6.78-6.85 (m, 3H), 7.00 (d, J=8.8 Hz, 1H), 7.11 (d, J=2 Hz, 2H), 7.21 (d, J=8.4 Hz, 1H), 7.31-7.33 (m, 1H), 7.36-7.40 (m, 2H), 7.45-7.47 (m, 2H).

9.2. Preparation of 1-(4-chlorobenzyl)-3-(3,3-dimethylbutanoyl)-2-(3-ethoxy-2,2-dimethyl-3-oxopropyl)-1H-indol-5-yl-3,3-dimethylbutanoate

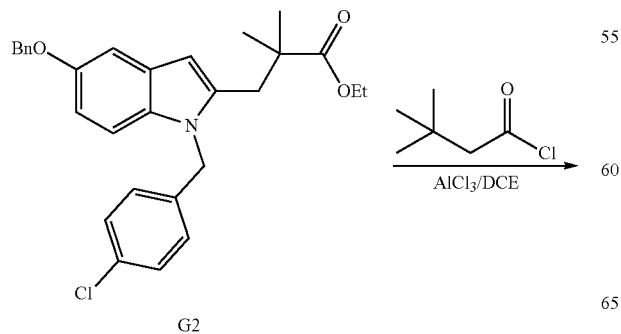

G2

-continued

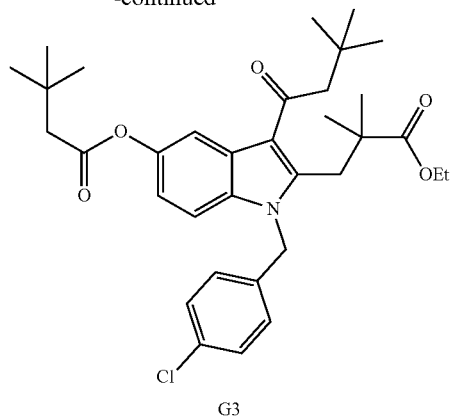

G3

To a solution of ethyl 3-(5-(benzyloxy)-1-(4-chlorobenzyl)-1H-indol-2-yl)-2,2-dimethylpropanoate (2.9 g, 6.1 mmol) in DCM (200 mL) were added AlCl$_3$ (4.1 g, 30.5 mmol) and 3,3-dimethylbutanoyl chloride (4.1 g, 30.5 mmol) at −70° C. After addition, the reaction mixture was stirred for 30 min at −70° C. The mixture was acidified with 1.0 N HCl (aq) to pH=4 and then extracted with DCM (2×10 mL). The organic extracts were combined and washed with brine (2×10 m), dried over anhydrous Na$_2$SO$_4$. It was filtered and the filtrate was concentrated to give 1-(4-chlorobenzyl)-3-(3,3-dimethylbutanoyl)-2-(3-ethoxy-2,2-dimethyl-3-oxopropyl)-1H-indol-5-yl3,3-dimethylbutanoate (3.5 g, 6 mmol, 98% yield) as yellow solid used as the intermediate without further purification. LCMS (ESI): m/z 582[M+1]+.

9.3. Preparation of 3-(1-(4-chlorobenzyl)-3-(3,3-dimethylbutanoyl)-5-hydroxy-1H-indol-2-yl)-2,2-dimethylpropanoic Acid

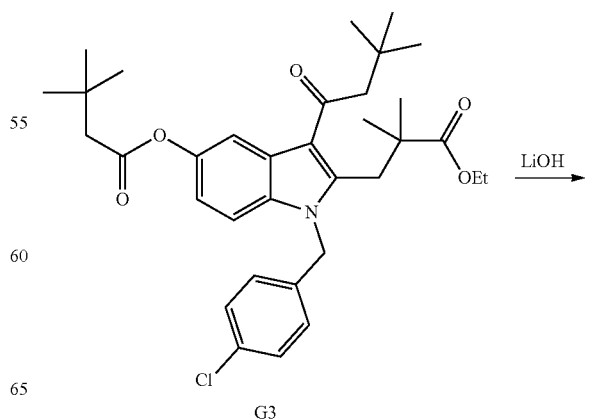

G3

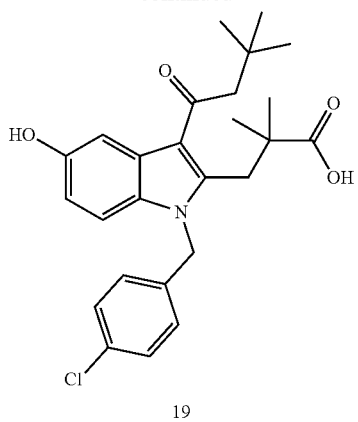

19

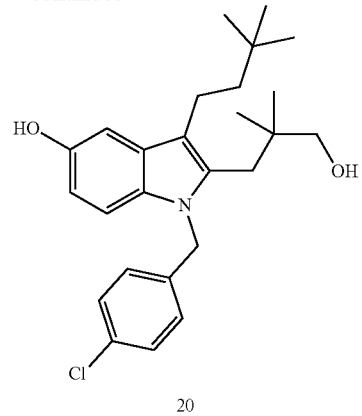 [SMILES: CC(C)(C)CCc1c(CC(C)(C)CO)n(Cc2ccc(Cl)cc2)c2ccc(O)cc12]

20

To a solution of 1-(4-chlorobenzyl)-3-(3,3-dimethylbutanoyl)-2-(3-ethoxy-2,2-dimethyl-3-oxopropyl)-1H-indol-5-yl 3,3-dimethylbutanoate (3.5 g, 6 mmol) in THF (50 mL) and MeOH (50 mL) was added water (100 mL) and LiOH.H$_2$O (2.5 g, 60 mmol) at room temperature. After addition, the reaction mixture was stirred at 60° C. for 15 h. The mixture was acidified with 1.0 N HCl (aq) to pH=4.0. It was then extracted with DCM (2×100 mL). The organic extracts were combined and washed with brine (2×100 mL), dried over anhydrous Na$_2$SO$_4$ and concentrated. The residue was purified by column chromatography on silica gel (PE:EA=1:1) to give 3-(1-(4-chlorobenzyl)-3-(3,3-dimethylbutanoyl)-5-hydroxy-1H-indol-2-yl)-2,2-dimethylpropanoic acid (2.2 g, 4.8 mmol, 80% yield) as white solid. LCMS (ESI): m/z 456.3 [M+1]$^+$. $^1$HNMR (400 MHz, DMSO-d$_6$): δ (ppm) 1.08 (s, 9H), 1.12 (s, 6H), 2.86 (s, 2H), 3.52 (s, 2H), 5.45 (s, 2H), 6.64 (d, J=7.2 Hz, 1H), 6.88 (d, J=8.0 Hz, 2H), 7.20 (d, J=8.8 Hz, 2H), 7.33 (m, 3H), 9.10 (s, 1H), 12.60 (s, 1H).

9.4. Preparation of 1-(4-chlorobenzyl)-3-(3,3-dimethylbutyl)-2-(3-hydroxy-2,2-dimethylpropyl)-1H-indol-5-ol To a solution of 3-(1-(4-chlorobenzyl)-3-(3,3-dimethylbutanoyl)-5-hydroxy-1H-indol-2-yl)-2,2-dimethylpropanoic acid (100 mg, 0.22 mmol) in THF (5 mL) was added BH$_3$/THF (1 M, 1.1 mL, 1.1 mmol) at 0° C. After addition, the reaction mixture was stirred for 16 hours at room temperature. The mixture was quenched with MeOH (10 mL), concentrated and the residue was purified on the prep-HPLC to give 1-(4-chlorobenzyl)-3-(3,3-dimethylbutyl)-2-(3-hydroxy-2,2-dimethylpropyl)-1H-indol-5-ol (51 mg, 0.12 mmol, 55% yield). LCMS (ESI): m/z 428.3 [M+1]$^+$. $^1$HNMR (400 MHz, DMSO-d$_6$): δ (ppm) 0.85 (s, 6H), 1.06 (s, 9H), 1.48 (m, 2H), 2.63 (m, 4H), 3.16 (s, 2H), 4.78 (m, 1H), 5.36 (s, 1H), 6.48 (m, 1H), 6.78 (m, 3H), 7.00 (d, J=8.4 Hz, 1H), 7.28 (d, J=8.4 Hz, 1H), 8.62 (s, 1H).

Example 10. 3-(1-(4-chlorobenzyl)-3-(3,3-dimethylbutanoyl)-5-methoxy-1H-indol-2-yl)-2,2-dimethylpropanoic A Scheme 10. Synthetic route for example 10

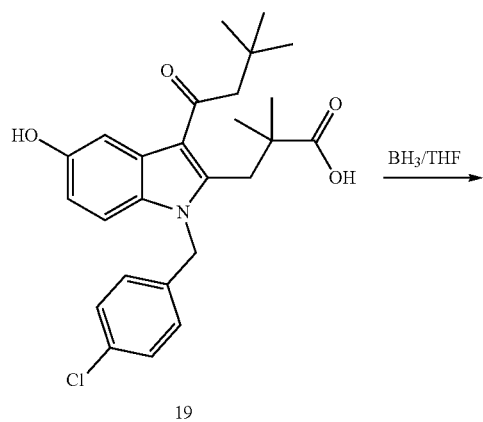

19

BH$_3$/THF →

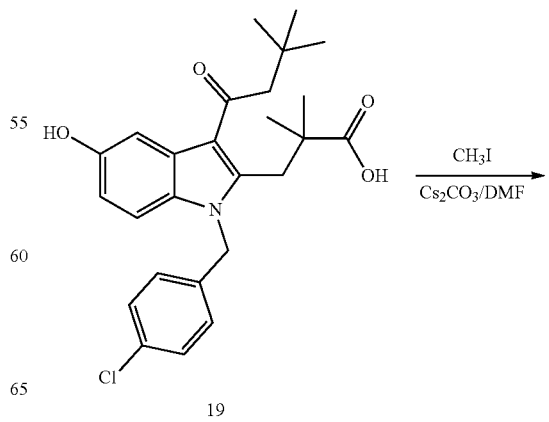

19

CH$_3$I
Cs$_2$CO$_3$/DMF →

10.1. Preparation of Methyl 3-(1-(4-chlorobenzyl)-3-(3,3-dimethylbutanoyl)-5-methoxy-1H-indol-2-yl)-2,2-dimethylpropanoate

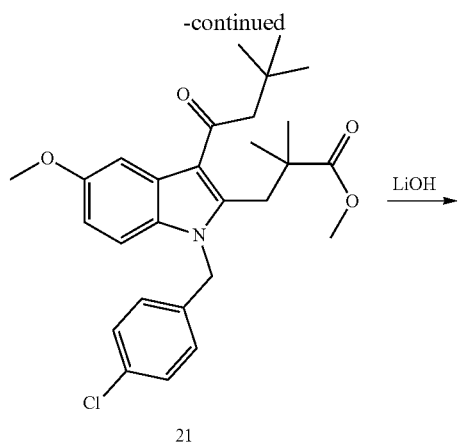

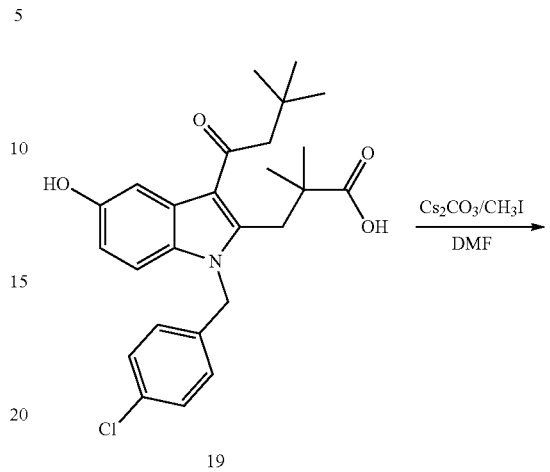

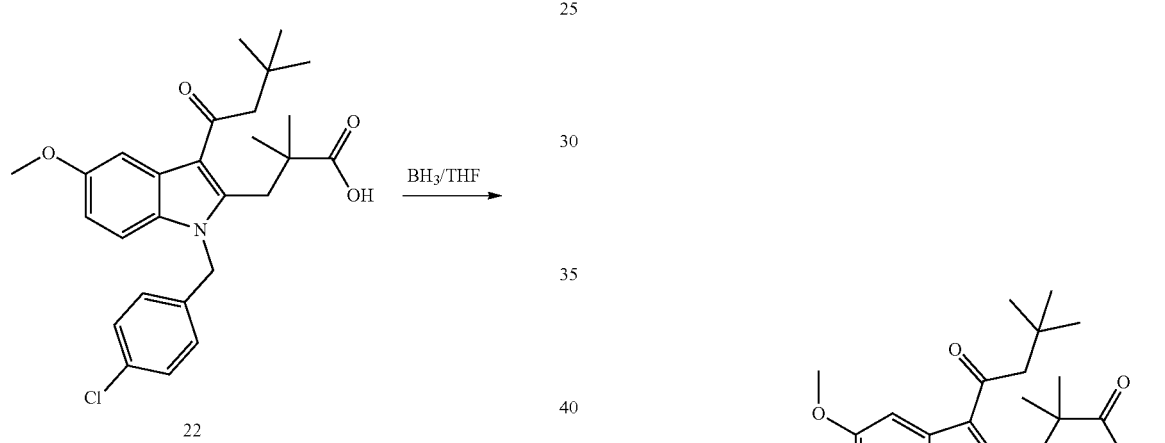

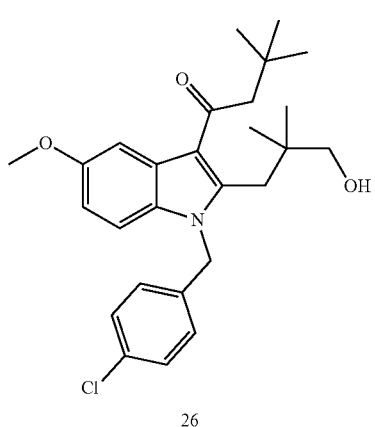

To a solution of 3-(1-(4-chlorobenzyl)-3-(3,3-dimethylbutanoyl)-5-hydroxy-1H-indol-2-yl)-2,2-dimethylpropanoic acid (2.2 g, 4.8 mmol) in DMF (50 mL) were added Cs$_2$CO$_3$ (4.7 g, 14.5 mmol) and iodomethane (2.1 g, 14.5 mmol). After addition, the reaction mixture was stirred for 2.0 hours at room temperature. The mixture was then concentrated and the residue was purified by column chromatography on silica gel (PE:EA=10:1) to give methyl 3-(1-(4-chlorobenzyl)-3-(3,3-dimethylbutanoyl)-5-methoxy-1H-indol-2-yl)-2,2-dimethylpropanoate (2.0 g, 4.1 mmol, 85% yield). $^1$HNMR (400 MHz, CDCl$_3$): δ (ppm) 1.07 (s, 9H), 1.17 (s, 6H), 2.91 (s, 2H), 3.54 (s, 2H), 3.57 (s, 3H), 3.80 (s, 3H), 5.48 (s, 2H), 6.88-6.90 (m, 3H), 7.32-7.38 (m, 4H).

10.2. Preparation of 3-(1-(4-chlorobenzyl)-3-(3,3-dimethylbutanoyl)-5-methoxy-1H-indol-2-yl)-2,2-dimethylpropanoic Acid

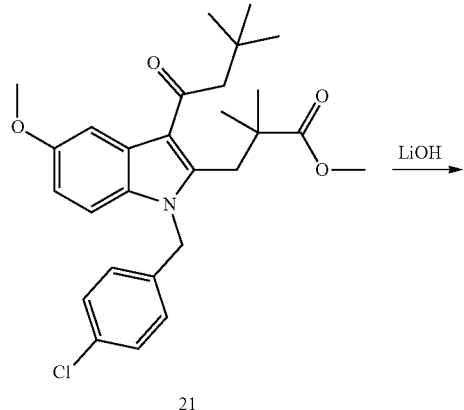

21

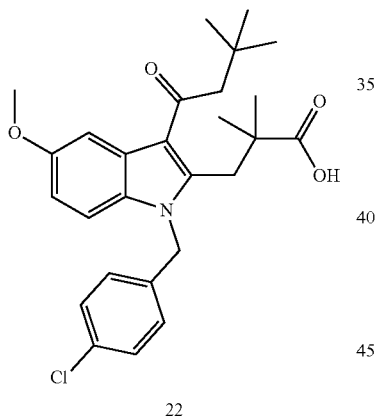

22

To a solution of methyl 3-(1-(4-chlorobenzyl)-3-(3,3-dimethylbutanoyl)-5-methoxy-1H-indol-2-yl)-2,2-dimethylpropanoate (150 mg, 0.3 mmol) in THF (5 mL) and MeOH (5 mL) was added water (10 mL), followed by LiOH.H$_2$O (130 mg, 3 mmol) at room temperature. After addition, the reaction mixture was stirred for 5 hours at 60° C. After cooled to room temperature, the mixture was acidified with 1.0 N HCl (aq) to pH=4.0 and extracted with DCM (2×10 mL). The organic extracts were combined and washed with brine (2×10 mL), dried over Na$_2$SO$_4$ and concentrated. The residue was purified on the pre-HPLC to give 3-(1-(4-chlorobenzyl)-3-(3,3-dimethylbutanoyl)-5-methoxy-1H-indol-2-yl)-2,2-dimethylpropanoic acid (70 mg, 0.15 mmol, 50% yield). LCMS (ESI): m/z 470.3 [M+1]+. $^1$HNMR (400 MHz, DMSO-d$_6$): δ (ppm) 1.07 (s, 9H), 1.12 (s, 6H), 2.92 (s, 2H), 3.53 (s, 2H), 3.80 (s, 3H), 5.50 (s, 2H), 6.83 (d, J=7.2 Hz, 1H), 6.88 (d, J=8.4 Hz, 2H), 7.32-7.38 (m, 4H).

10.3. Preparation of 3-(1-(4-chlorobenzyl)-3-(3,3-dimethylbutanoyl)-5-methoxy-1H-indol-2-yl)-2,2-dimethylpropanoic Acid

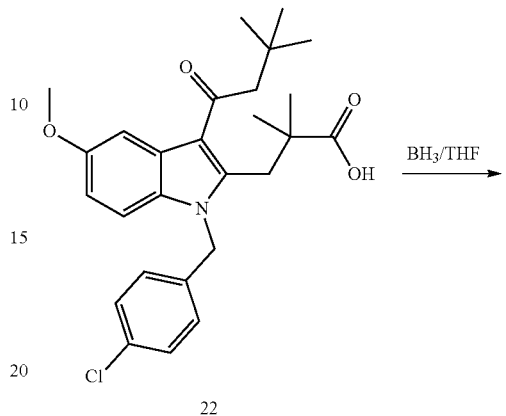

22

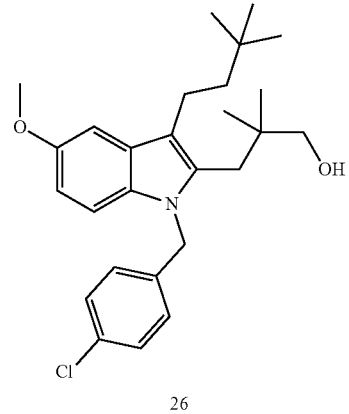

26

To a solution of 3-(1-(4-chlorobenzyl)-3-(3,3-dimethylbutanoyl)-5-methoxy-1H-indol-2-yl)-2,2-dimethylpropanoic acid (120 mg, 0.26 mmol) in THF (10 mL) was added BH$_3$/THF (1 M, 1.3 mL, 1.3 mmol) at 0° C. After addition, the reaction mixture was stirred for 16 hours at room temperature. The mixture was quenched with MeOH (10 mL), and concentrated. The residue was purified on the pre-HPLC to give 1-(4-chlorobenzyl)-3-(3,3-dimethylbutyl)-2-(3-hydroxy-2,2-dimethylpropyl)-1H-indol-5-ol (30 mg, 0.07 mmol, 27% yield). LCMS (ESI): m/z 442.3 [M+1]+. $^1$H NMR (400 MHz, CDCl$_3$): δ (ppm) 0.85 (s, 6H), 1.06 (s, 9H), 1.49 (m, 2H), 2.65 (m, 5H), 3.17 (s, 2H), 3.75 (s, 3H), 5.42 (s, 2H), 6.63-6.66 (m, 1H), 6.76 (d, J=8.4 Hz, 2H), 6.90 (s, 1H), 7.12 (d, J=9.2 Hz, 1H), 7.28 (d, J=8.4 Hz, 2H).

Example 11. 1-(1-(4-chlorobenzyl)-2-(3-hydroxy-2,2-dimethylpropyl)-5-methoxy-1H-indol-3-yl)-3,3-dimethylbutan-1-one

Example 12. 1-(1-(4-chlorobenzyl)-5-hydroxy-2-(3-hydroxy-2,2-dimethylpropyl)-1H-indol-3-yl)-3,3-dimethylbutan-1-one

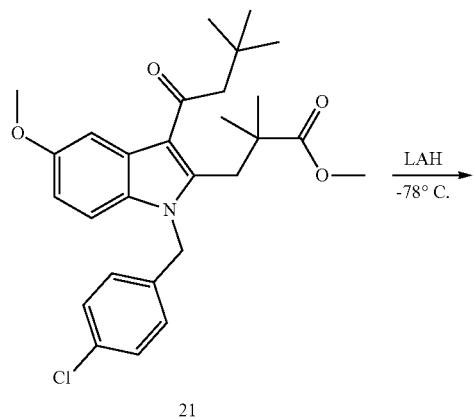

Scheme 11. Synthesis route for example 11

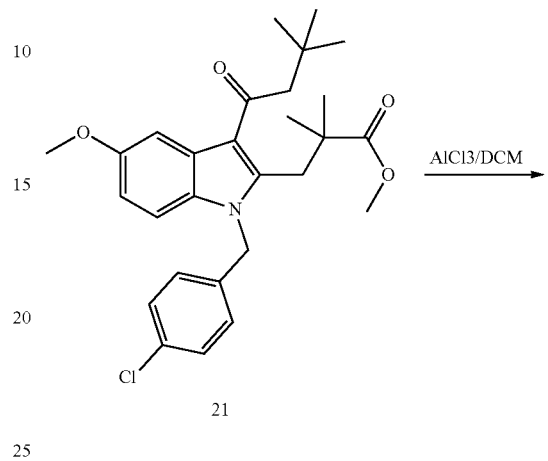

Scheme 12. Synthesis route for example 12

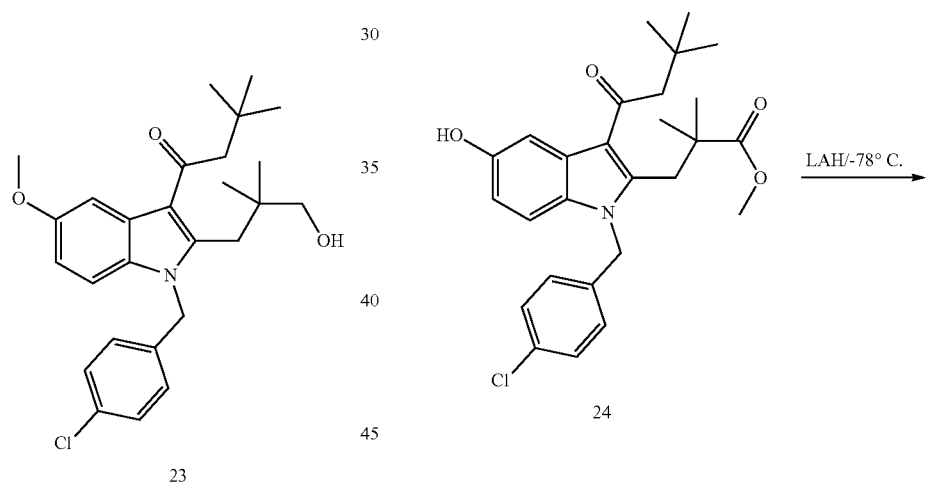

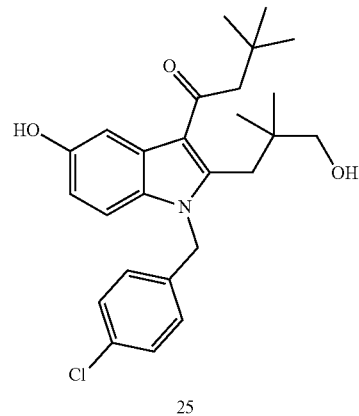

To a solution of methyl 3-(1-(4-chlorobenzyl)-3-(3,3-dimethylbutanoyl)-5-methoxy-1H-indol-2-yl)-2,2-dimethylpropanoate (300 mg, 0.62 mmol) in THF (10 mL) was added LAH (47 mg, 1.24 mmol) at −78° C. After addition, the mixture was stirred for 1.0 hour at −78° C. The mixture was quenched with saturated Na$_2$SO$_4$ (aq, 1.0 m). It was filtered and the filtrate was concentrated to give crude product which was then purified on the prep-HPLC (condition?) to give 1-(1-(4-chlorobenzyl)-2-(3-hydroxy-2,2-dimethylpropyl)-5-methoxy-1H-indol-3-yl)-3,3-dimethylbutan-1-one (98 mg, 0.22 mmol, 35% yield). LCMS (ESI): m/z 456.3 [M+1]+. $^1$HNMR (400 MHz, DMSO-d$_6$): δ (ppm) 0.83 (s, 6H), 1.07 (s, 9H), 2.91 (s, 2H), 3.15 (m, 2H), 3.39 (s, 2H), 3.79 (s, 3H), 4.91 (t, 1H), 5.60 (s, 2H), 6.79-6.81 (m, 1H), 6.88 (d, J=8.4 Hz, 2H), 7.30-7.39 (m, 4H).

12.1. Preparation of Methyl 3-(1-(4-chlorobenzyl)-3-(3,3-dimethylbutanoyl)-5-hydroxy-1H-indol-2-yl)-2,2-dimethylpropanoate

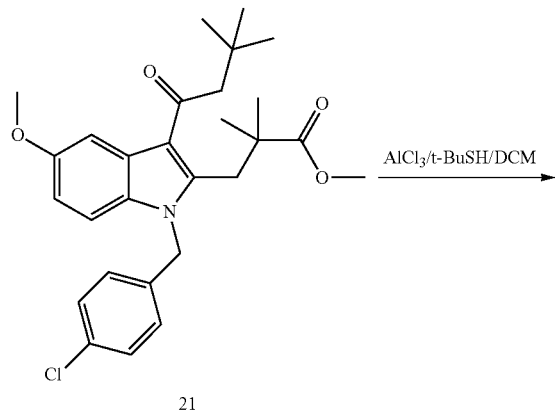

21

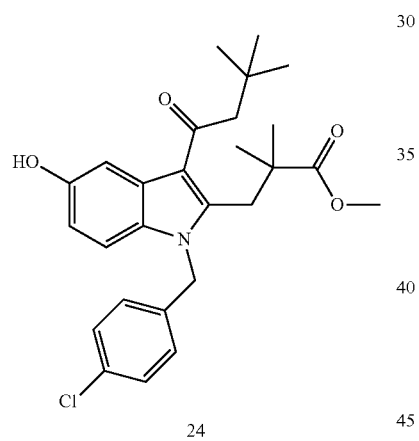

24

The methyl 3-(1-(4-chlorobenzyl)-3-(3,3-dimethylbutanoyl)-5-methoxy-1H-indol-2-yl)-2,2-dimethylpropanoate (1.2 g, 2.5 mmol) and t-butylthiol (2.2 g, 25 mmol) were dissolved in $CH_2Cl_2$ (50 mL) and cooled to 0° C. $AlCl_3$ (1.66 g, 12.5 mmol) was added in portions over 5 min. After addition, the mixture was stirred for 2.0 hours, and then poured into ice slowly. 1.0 N HCl (aq, 10 mL) was added and the mixture was extracted with $CH_2Cl_2$ (2×50 m). The organic extracts were combined and washed with water (2×50 mL), dried over anhydrous $MgSO_4$. It was filtered and the filtrate was concentrated. The residue was purified by column chromatography on silica gel (PE:EA=10:1) to give methyl 3-(1-(4-chlorobenzyl)-3-(3,3-dimethylbutanoyl)-5-hydroxy-1H-indol-2-yl)-2,2-dimethylpropanoate (780 mg, 1.7 mmol, 68% yield) as white solid. $^1$HNMR (400 MHz, DMSO-$d_6$): δ (ppm) 1.08 (s, 9H), 1.16 (s, 6H), 2.84 (s, 2H), 3.57 (s, 3H), 3.68 (s, 2H), 5.43 (s, 2H), 6.63-6.65 (m, 1H), 6.88 (d, J=8.4 Hz, 2H), 7.17 (d, J=8.8 Hz, 1H), 7.29 (s, 1H), 7.34 (d, J=8.4 Hz, 2H), 9.11 (s, 1H).

12.2. Preparation of 1-(1-(4-chlorobenzyl)-5-hydroxy-2-(3-hydroxy-2,2-dimethylpropyl)-1H-indol-3-yl)-3,3-dimethylbutan-1-one

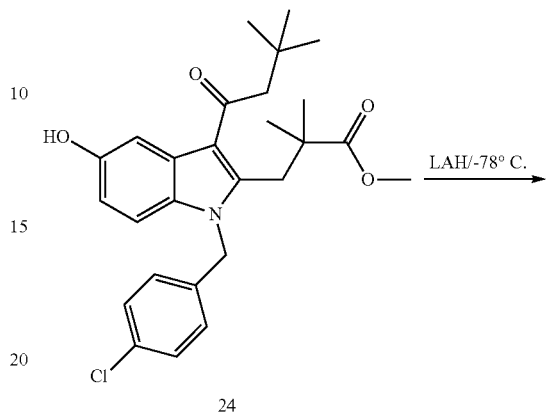

24

25

To a solution of methyl 3-(1-(4-chlorobenzyl)-3-(3,3-dimethylbutanoyl)-5-hydroxy-1H-indol-2-yl)-2,2-dimethylpropanoate (200 mg, 0.43 mmol) in THF (10 mL) was added LAH (49 mg, 1.28 mmol) at −78° C. After addition, the mixture was stirred for 1.0 hour at −78° C. It was then quenched with saturated $Na_2SO_4$ (aq, 1.0 mL), filtered and the filtrate was concentrated to give crude product which was purified on the pre-HPLC to give 1-(1-(4-chlorobenzyl)-5-hydroxy-2-(3-hydroxy-2,2-dimethylpropyl)-1H-indol-3-yl)-3,3-dimethylbutan-1-one (68 mg, 0.15 mmol, 35% yield). LCMS (ESI): m/z 441.3[M+1]$^+$. $^1$HNMR (400 MHz, DMSO-$d_6$): δ (ppm) 0.83 (s, 6H), 1.08 (s, 9H), 2.84 (s, 2H), 3.14 (s, 2H), 3.33 (s, 2H), 4.88 (m, 1H), 5.56 (s, 2H), 6.60-6.63 (m, 1H), 6.88 (d, J=8.4 Hz, 1H), 7.18 (d, J=8.4 Hz, 1H), 7.30-7.35 (m, 3H), 9.05 (s, 1H).

79

Example 13. 3-(3-(4-chlorobenzoyl)-1-(cyclobutylmethyl)-6-isopropyl-1H-indol-2-yl)-2,2-dimethylpropanoic Acid

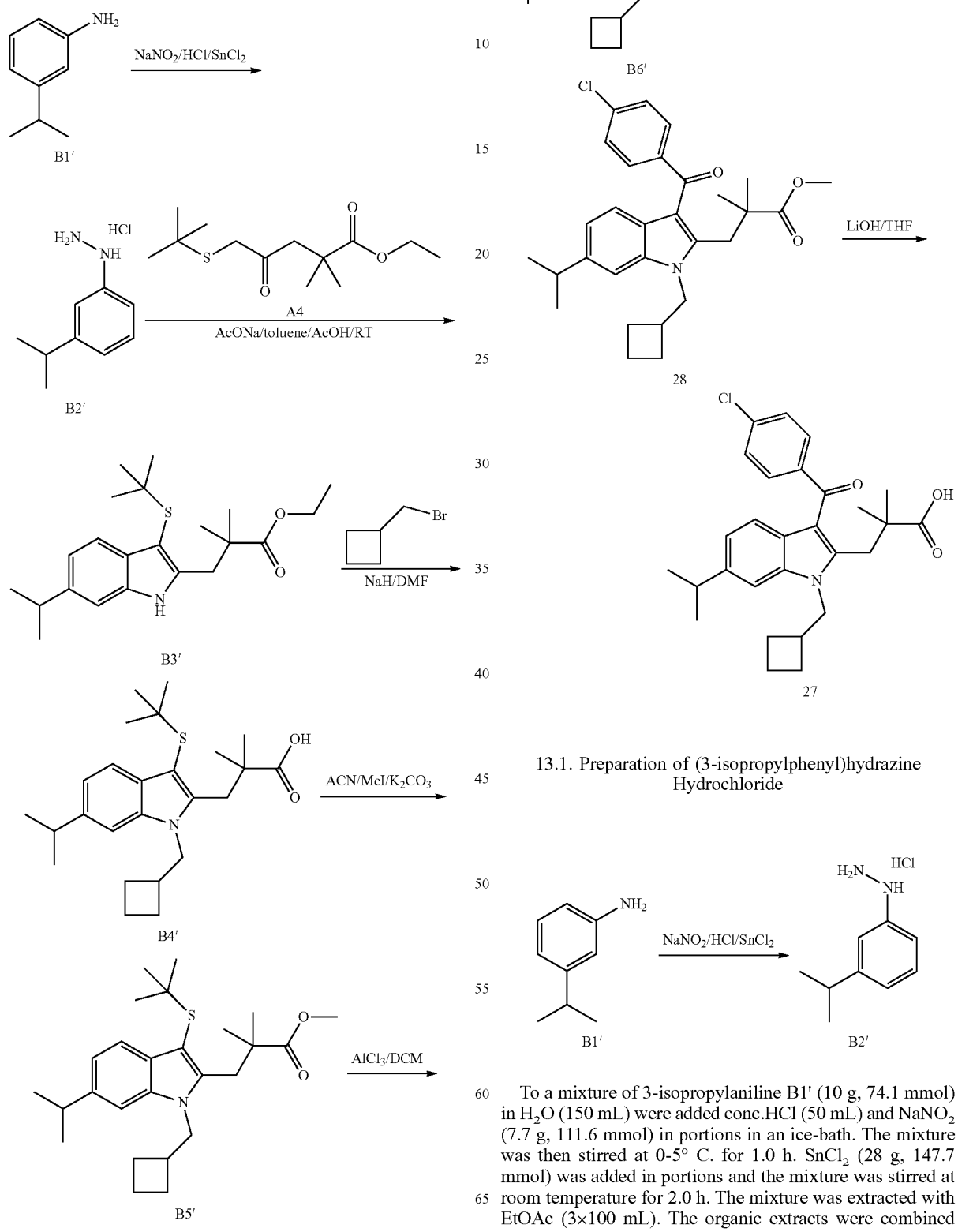

80

13.1. Preparation of (3-isopropylphenyl)hydrazine Hydrochloride

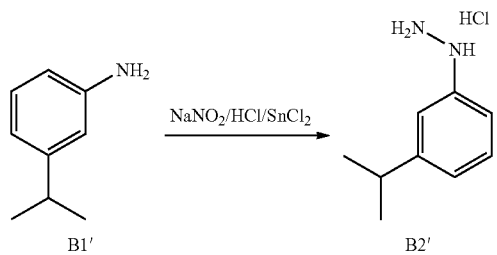

To a mixture of 3-isopropylaniline B1' (10 g, 74.1 mmol) in H$_2$O (150 mL) were added conc.HCl (50 mL) and NaNO$_2$ (7.7 g, 111.6 mmol) in portions in an ice-bath. The mixture was then stirred at 0-5° C. for 1.0 h. SnCl$_2$ (28 g, 147.7 mmol) was added in portions and the mixture was stirred at room temperature for 2.0 h. The mixture was extracted with EtOAc (3×100 mL). The organic extracts were combined and dried over anhydrous Na$_2$SO$_4$, filtered and the filtrate was concentrated. The residue was dissolved in EtOAc (50 mL) and PE (50 mL). 6M HC/1,4-dioxane (20 mL) was added. The mixture was stirred at room temperature for 2.0 h and filtered to give (3-isopropylphenyl)hydrazine hydrochloride 2 (11.3 g, 60.5 mmol, 82% yield) as white solid used as the intermediate without further purification.

13.2. Preparation of Ethyl 5-bromo-2,2-dimethyl-4-oxopentanoate

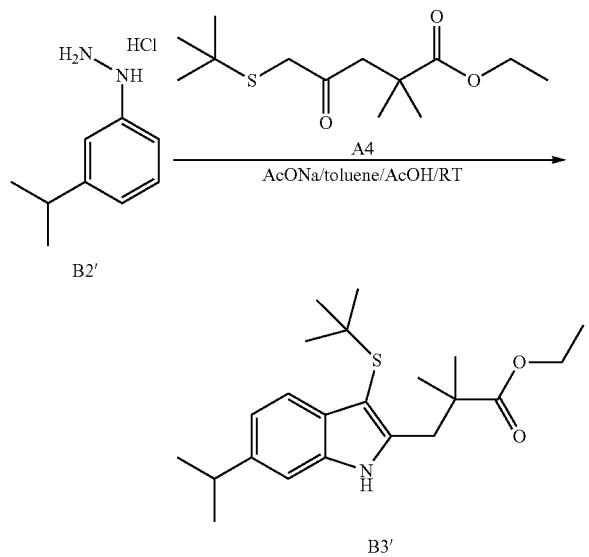

To a mixture of (3-isopropylphenyl)hydrazine hydrochloride B2' (4 g, 21.4 mmol) and ethyl 5-(tert-butylthio)-2,2-dimethyl-4-oxopentanoate A4 (6 g, 23.0 mmol) in AcOH (30 mL) were added tolune (60 mL) and AcONa (2 g, 24.4 mmol). The mixture was stirred for 72 hours at room temperature. The mixture was concentrated and the residue was purified by column chromatography on silica gel (PE: EA=30:1) to give ethyl 5-(tert-butylthio)-2,2-dimethyl-4-oxopentanoate B3' (1.9 g, 5.06 mmol, 24% yield) as yellow solid. LCMS (ESI): m/z 376.4[M+1]$^+$.

13.3. Preparation of 3-(3-(tert-butylthio)-1-(cyclobutylmethyl)-6-isopropyl-1H-indol-2-yl)-2,2-dimethylpropanoic Acid

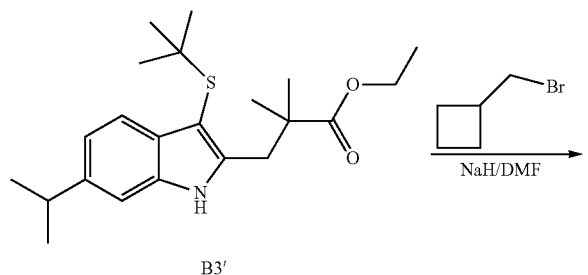

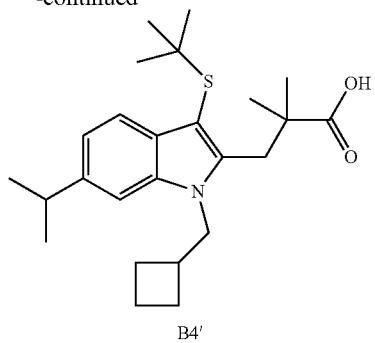

To a mixture of ethyl 3-(3-(tert-butylthio)-6-isopropyl-1H-indol-2-yl)-2,2-dimethylpropanoate B3' (500 mg, 1.33 mmol) in DMF (10 mL) were added NaH (100 mg, 2.50 mmol) and (bromomethyl)cyclobutane (250 mg, 1.68 mmol). The reaction mixture was stirred for 18 hours at room temperature. PE (60 mL) and EtOAc (10 mL) was added and the mixture was acidified by 2.0 N HCl (aq) to PH=4-5. The mixture was washed with water (2×40 mL), dried over anhydrous Na$_2$SO$_4$. It was filtered and the filtrate was concentrated to give 3-(3-(tert-butylthio)-1-(cyclobutylmethyl)-6-isopropyl-1H-indol-2-yl)-2,2-dimethylpropanoic acid B4' (380 mg, 0.91 mmol, 69% yield) as yellow oil used as the intermediate without further purification. LCMS (ESI): m/z 416.4[M+1]$^+$. $^1$HNMR (400 MHz, DMSO-d$_6$): δ (ppm) 0.96 (s, 6H), 1.16 (s, 9H), 1.27 (d, J=6.8 Hz, 6H), 1.70-1.60 (m, 2H), 1.82-1.70 (m, 4H), 2.55 (s, 2H), 2.75-2.63 (m, 1H), 3.03-2.95 (m, 1H), 4.26 (d, J=7.2 Hz, 2H), 6.99 (d, J=8.4 Hz, 1H), 7.30 (s, 1H), 7.49 (d, J=8.0 Hz, 1H), 12.44 (brs, 1H).

13.4. Preparation of Methyl 3-(3-(tert-butylthio)-1-(cyclobutylmethyl)-6-isopropyl-1H-indol-2-yl)-2,2-dimethylpropanoate

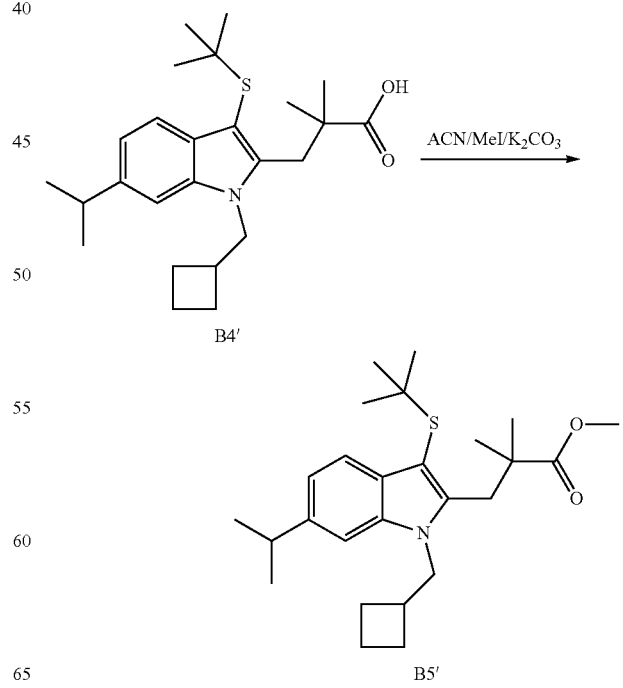

To a mixture of 3-(3-(tert-butylthio)-1-(cyclobutylmethyl)-6-isopropyl-1H-indol-2-yl)-2,2-dimethylpropanoic acid B4' (350 mg, 0.84 mmol) in DMF (5 mL) were added Cs$_2$CO$_3$ (400 mg, 1.23 mmol) and MeI (200 mg, 1.41 mmol). The mixture was stirred for 18 hours at room temperature. To the mixture were added PE (50 mL) and EtOAc (10 mL). The mixture was washed with water (2×40 m), dried over anhydrous Na$_2$SO$_4$, filtered and the filtrate was concentrated to give methyl 3-(3-(tert-butylthio)-1-(cyclobutylmethyl)-6-isopropyl-1H-indol-2-yl)-2,2-dimethylpropanoate B5' (360 mg, 0.84 mmol, 99% yield) as yellow oil. LCMS (ESI): m/z 430.5[M+1]$^+$. $^1$HNMR (400 MHz, CDCl$_3$): δ (ppm) 1.16 (s, 6H), 1.22 (s, 9H), 1.32 (d, J=6.8 Hz, 6H), 1.72-1.67 (m, 2H), 1.90-1.79 (m, 4H), 2.80-2.70 (m, 1H), 3.08-2.98 (m, 1H), 3.37 (s, 2H), 3.70 (s, 3H), 4.15 (d, J=7.2 Hz, 2H), 7.03 (d, J=8.0 Hz, 1H), 7.10 (s, 1H), 7.64 (d, J=8.4 Hz, 1H).

13.5. Preparation of Methyl 3-(1-(cyclobutylmethyl)-6-isopropyl-1H-indol-2-yl)-2,2-dimethylpropanoate

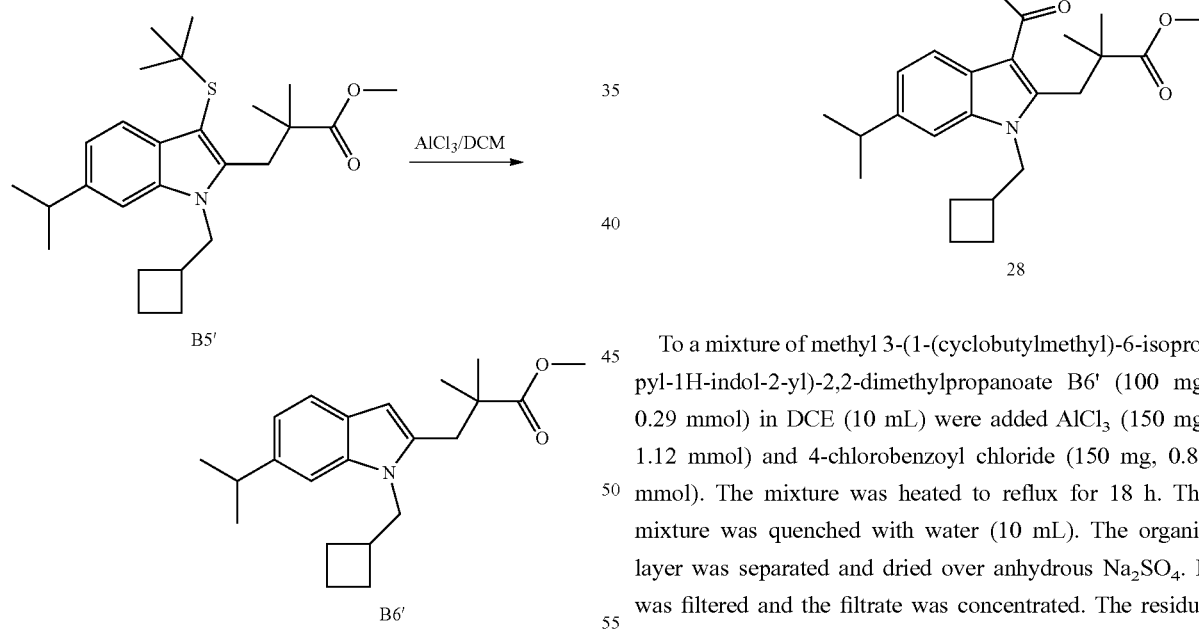

To a mixture of methyl 3-(3-(tert-butylthio)-1-(cyclobutylmethyl)-6-isopropyl-1H-indol-2-yl)-2,2-dimethylpropanoate B5' (360 mg, 0.84 mmol) in DCM (20 mL) was added AlCl$_3$ (800 mg, 5.99 mmol). The mixture was stirred for 18 h at room temperature. The mixture was quenched with water (20 mL). The organic layer was separated and dried over anhydrous Na$_2$SO$_4$. It was filtered and the filtrate was concentrated to give methyl 3-(1-(cyclobutylmethyl)-6-isopropyl-1H-indol-2-yl)-2,2-dimethylpropanoate B6' (190 mg, 0.56 mmol, 66% yield) as brown oil used as the intermediate without further purification.

13.6. Preparation of Methyl 3-(3-(4-chlorobenzoyl)-1-(cyclobutylmethyl)-6-isopropyl-1H-indol-2-yl)-2,2-dimethylpropanoate

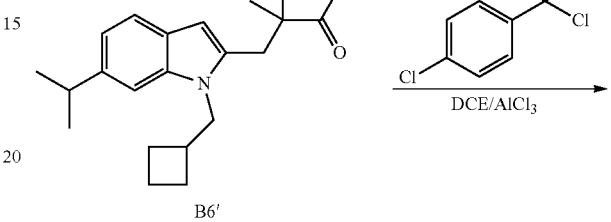

To a mixture of methyl 3-(1-(cyclobutylmethyl)-6-isopropyl-1H-indol-2-yl)-2,2-dimethylpropanoate B6' (100 mg, 0.29 mmol) in DCE (10 mL) were added AlCl$_3$ (150 mg, 1.12 mmol) and 4-chlorobenzoyl chloride (150 mg, 0.86 mmol). The mixture was heated to reflux for 18 h. The mixture was quenched with water (10 mL). The organic layer was separated and dried over anhydrous Na$_2$SO$_4$. It was filtered and the filtrate was concentrated. The residue was purified by preparation TLC (PE:EA=5:1) to give methyl 3-(3-(4-chlorobenzoyl)-1-(cyclobutylmethyl)-6-isopropyl-1H-indol-2-yl)-2,2-dimethylpropanoate (28) (72 mg, 0.15 mmol, 51% yield) as yellow oil. LCMS (ESI): m/z 480.2[M+Na]$^+$. $^1$HNMR (400 MHz, CDCl$_3$): δ (ppm) 1.18 (s, 6H), 1.29 (d, J=6.8 Hz, 6H), 1.88-1.77 (m, 4H), 2.01-1.99 (m, 2H), 2.80-2.65 (m, 1H), 3.05-2.95 (m, 1H), 3.61 (s, 5H), 4.21 (d, J=6.8 Hz, 2H), 6.91 (s, 2H), 7.15 (s, 1H), 7.42 (d, J=8.4 Hz, 1H), 7.73 (d, J=8.4 Hz, 1H).

13.7. Preparation of 3-(3-(4-chlorobenzoyl)-1-(cyclobutylmethyl)-6-isopropyl-1H-indol-2-yl)-2,2-dimethylpropanoic Acid

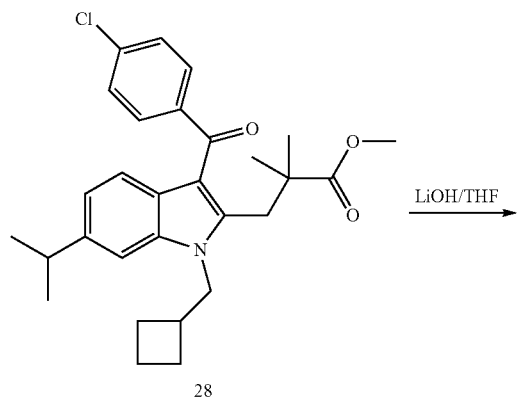

28

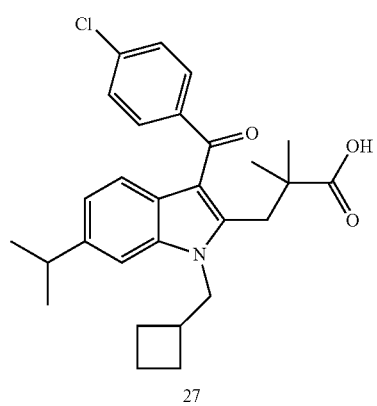

27

To a mixture of methyl 3-(3-(4-chlorobenzoyl)-1-(cyclobutylmethyl)-6-isopropyl-1H-indol-2-yl)-2,2-dimethylpropanoate 40 (50 mg, 0.104 mmol) in THF (5 mL) were added lithium hydroxide monohydrate (30 mg, 0.714 mmol) and water (1.0 mL). The mixture was heated to 60° C. for 18 h. After cooling to room temperature, the mixture was concentrated and the residue was purified by pre-HPLC to give 3-(3-(4-chlorobenzoyl)-1-(cyclobutylmethyl)-6-isopropyl-1H-indol-2-yl)-2,2-dimethylpropanoic acid (39) (24 mg, 0.052 mmol, 49% yield) as white solid. LCMS (ESI): m/z 466.3[M+H]$^+$. $^1$HNMR (400 MHz, DMSO-d$_6$): δ (ppm) 1.03 (s, 6H), 1.25 (d, J=6.8 Hz, 6H), 1.91-1.73 (m, 6H), 2.75-2.70 (m, 1H), 2.99-2.95 (m, 1H), 3.44 (s, 2H), 4.34 (d, J=6.4 Hz, 2H), 6.81 (d, J=8.4 Hz, 1H), 6.93 (d, J=8.0 Hz, 1H), 7.43 (s, 1H), 7.70-7.58 (m, 4H), 12.43 (brs, 1H).

Example 14. 3-(3-(4-chlorobenzoyl)-1-(cyclobutylmethyl)-6-hydroxy-1H-indol-2-yl)-2,2-dimethylpropanoic Acid

14.1. Preparation of 3-(3-(4-chlorobenzoyl)-1-(cyclobutylmethyl)-6-hydroxy-1H-indol-2-yl)-2,2-dimethylpropanoic Acid

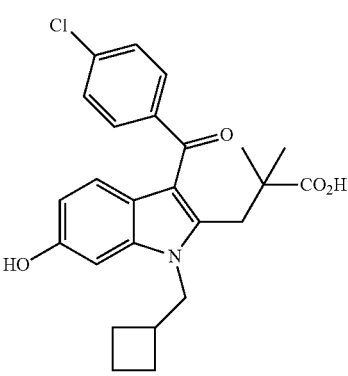

29

The compound 29 was prepared by the method similar to the compound 3-(3-(4-chlorobenzoyl)-1-(cyclobutylmethyl)-6-isopropyl-1H-indol-2-yl)-2,2-dimethylpropanoic acid, but using (3-methoxyphenyl)hydrazine hydrochloride (step 13.2). LCMS (ESI): m/z 440.3[M+1]$^+$. $^1$H NMR (400 MHz, DMSO-d$_6$): δ (ppm) 1.00 (s, 6H), 1.91-1.74 (m, 6H), 2.70-2.65 (m, 1H), 3.39 (s, 2H), 4.21 (d, J=7.2 Hz, 2H), 6.55 (d, J=2.0 Hz, 1H), 6.72 (d, J=8.8 Hz, 1H), 6.86 (d, J=1.6 Hz, 1H), 7.65-7.57 (m, 4H), 9.24 (s, 1H), 12.39 (brs, 1H).

14.2. Preparation of Ethyl 3-(3-(4-chlorobenzoyl)-1-(cyclobutylmethyl)-6-hydroxy-1H-indol-2-yl)-2,2-dimethylpropanoate

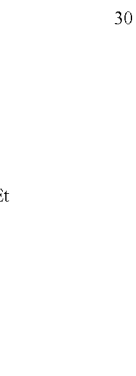

30

The compound 30 was prepared by the method similar to the compound methyl 3-(3-(4-chlorobenzoyl)-1-(cyclobutylmethyl)-6-isopropyl-1H-indol-2-yl)-2,2-dimethylpropanoate, but using (3-methoxyphenyl)hydrazine hydrochloride (step 13.2). LCMS (ESI): m/z 468.2[M+1]$^+$. $^1$H NMR (400 MHz, CDCl$_3$+CD$_3$OD): δ ppm 1.23 (t, J=6.8 Hz, 3H), 1.29 (s, 6H), 1.85-1.74 (m, 4H), 1.98-1.94 (m, 2H), 2.76-2.73 (m, 1H), 3.06 (s, 2H), 3.38 (s, 2H), 4.18-4.11 (m, 2H), 6.23 (s, 1H), 6.89-6.87 (m, 1H), 7.15 (s, 1H), 7.52-7.49 (m, 3H), 8.19-8.16 (m, 2H).
Example 15. 3-(tert-butylthio)-1-(4-chlorobenzyl)-2-(2-methyl-2-(4-methyloxazol-2-yl)propyl)-1H-indol-5-ol
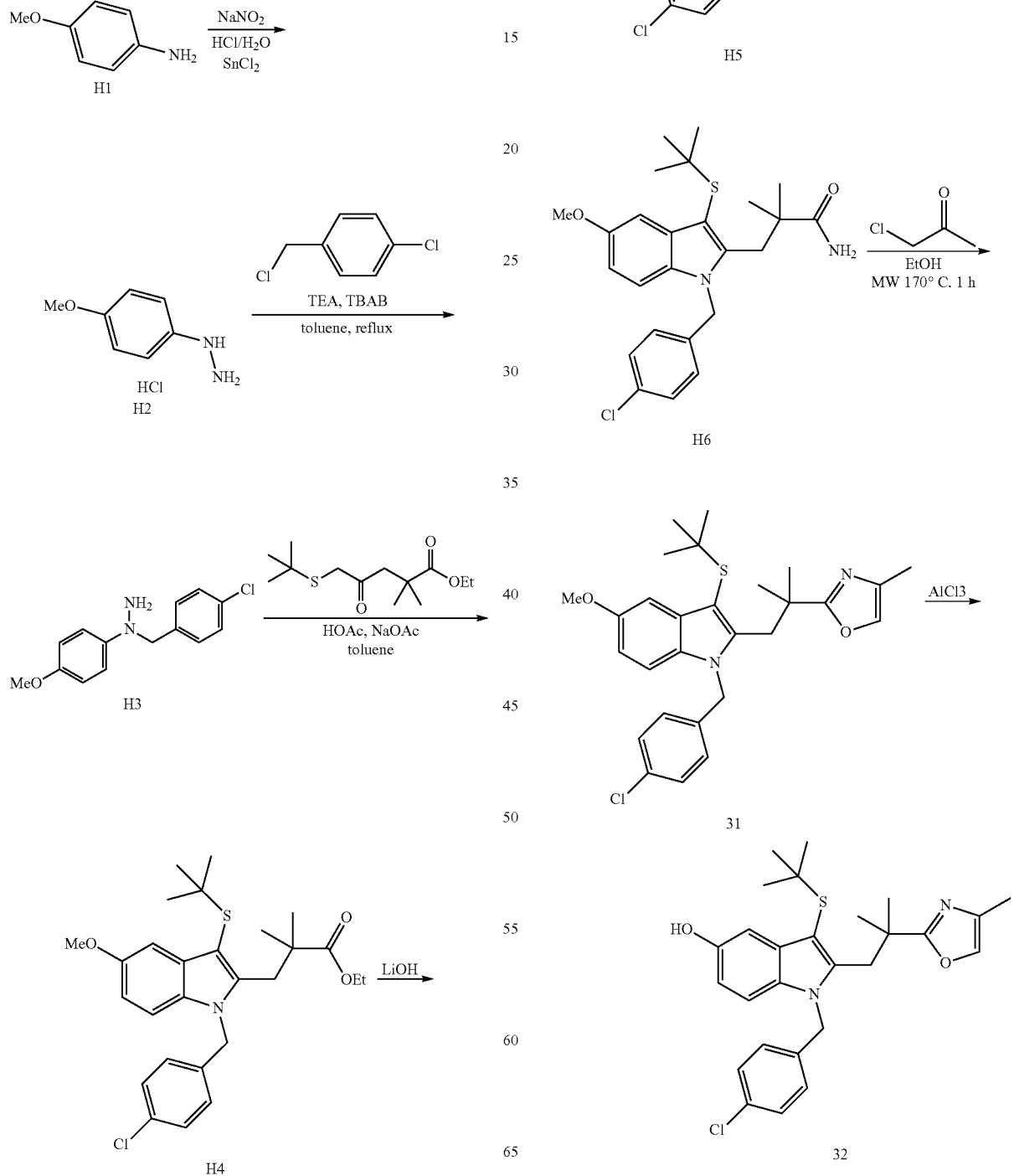

15.1 Preparation of Ethyl 3-(3-(tert-butylthio)-1-(4-chlorobenzyl)-5-methoxy-1H-indol-2-yl)-2,2-dimethylpropanoate

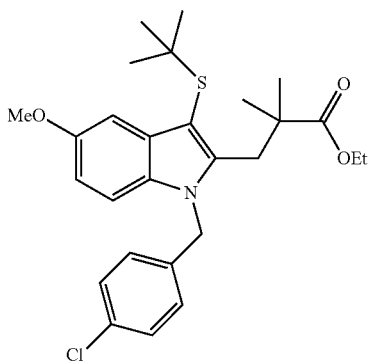
H4

The compound H4 was prepared by the method similar to the compound B3 in example 1, but using different aniline as the starting material. LCMS (ESI): m/z 488.3[M+1]$^+$.

15.2. Preparation of 3-(3-(tert-butylthio)-1-(4-chlorobenzyl)-5-methoxy-1H-indol-2-yl)-2,2-dimethylpropanoic Acid

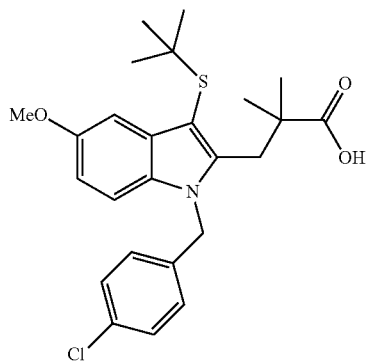
H5

The compound H5 was prepared by the similar method to the prepararat on of compound 1 in the step 1.8. LCMS (ESI): m/z 460.2[M+1]$^+$.

15.3. Preparation of 3-(3-(tert-butylthio)-1-(4-chlorobenzyl)-5-methoxy-1H-indol-2-yl)-2,2-dimethylpropanamide

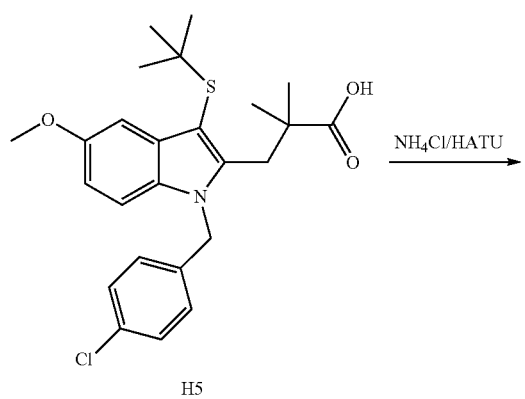
H5

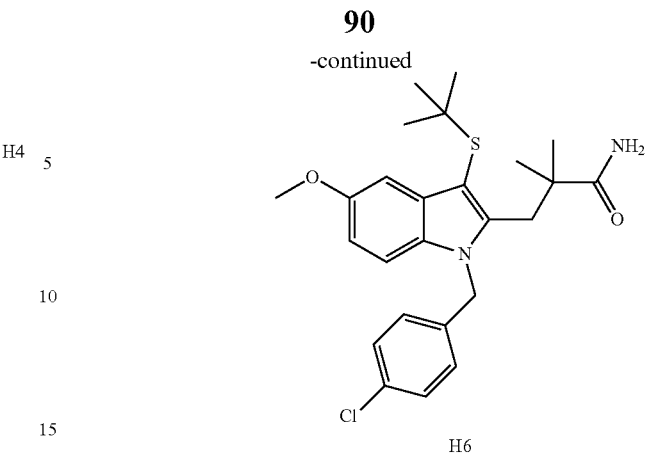
H6

To a mixture of 3-(3-(tert-butylthio)-1-(4-chlorobenzyl)-5-methoxy-1H-indol-2-yl)-2,2-dimethylpropanoic acid (6 g, 13.0 mmol) in THF (100 mL) was added NH$_4$Cl (1.05 g, 19.6 mmol), HATU (7.5 g, 19.7 mmol) and TEA (3 g, 29.7 mmol). The mixture was stirred at room temperature for 18 hours. The mixture was concentrated and the residue was purified by column chromatography on silica gel (PE:EA=2:1) to give 3-(3-(tert-butylthio)-1-(4-chlorobenzyl)-5-methoxy-1H-indol-2-yl)-2,2-dimethylpropanamide H6 (5.6 g, 12.2 mmol, 93% yield) as yellow solid. LCMS (ESI): m/z 459.2[M+H]$^+$.

15.4. Preparation of 2-(1-(3-(tert-butylthio)-1-(4-chlorobenzyl)-5-methoxy-1H-indol-2-yl)-2-methylpropan-2-yl)-4-methyloxazole

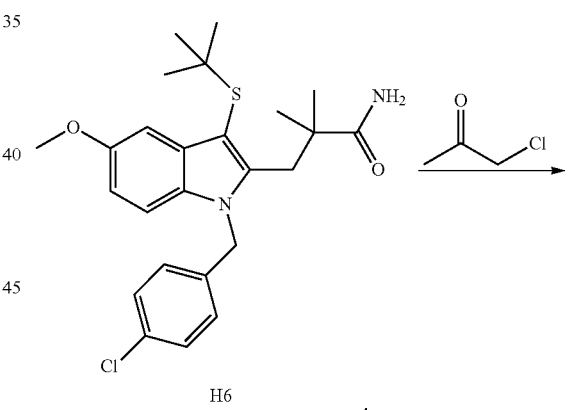
H6

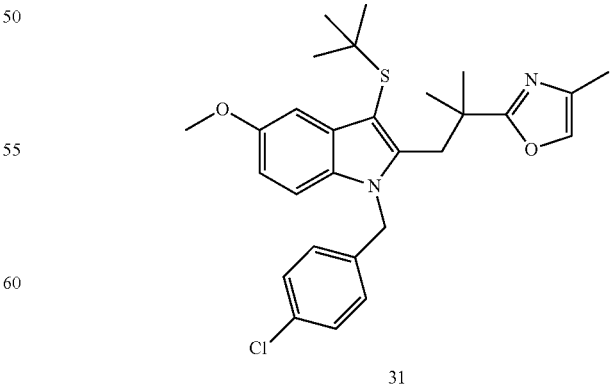
31

To a mixture of 3-(3-(tert-butylthio)-1-(4-chlorobenzyl)-5-methoxy-1H-indol-2-yl)-2,2-dimethylpropanamide (200 mg, 0.44 mmol) in toluene (10 mL) was added 1-chloropropan-2-one (300 mg, 3.24 mmol). The mixture was heated to 110° C. for 18 hours. After cooling to room temperature, the mixture was concentrated and the residue was purified by prep-HPLC to give 2-(1-(3-(tert-butylthio)-1-(4-chlorobenzyl)-5-methoxy-1H-indol-2-yl)-2-methylpropan-2-yl)-4-methyloxazole (38 mg, 0.076 mmol, 17% yield) as white solid. LCMS (ESI): m/z 497.3 [M+H]⁺. ¹HNMR (400 MHz, CDCl₃): δ (ppm) 1.26 (s, 9H), 1.42 (s, 6H), 2.17 (s, 3H), 3.32 (s, 2H), 3.86 (s, 3H), 4.89 (s, 2H), 6.63 (d, J=8.4 Hz, 2H), 6.77-6.74 (m, 1H), 6.94 (d, J=8.8 Hz, 1H), 7.16 (d, J=8.4 Hz, 2H), 7.26-7.24 (m, 2H).

15.5. Preparation of 3-(tert-butylthio)-1-(4-chlorobenzyl)-2-(2-methyl-2-(4-methyloxazol-2-yl)propyl)-1H-indol-5-ol

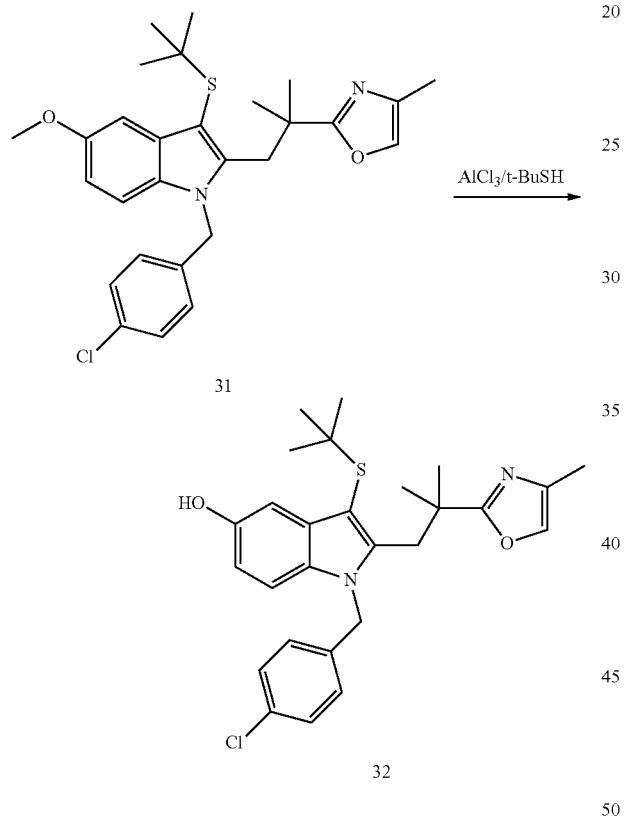

To a mixture of 2-(1-(3-(tert-butylthio)-1-(4-chlorobenzyl)-5-methoxy-1H-indol-2-yl)-2-methylpropan-2-yl)-4-methyloxazole (60 mg, 0.12 mmol) in DCM (10 mL) were added t-BuSH (300 mg, 3.33 mmol) and AlCl₃ (200 mg, 1.50 mmol). The mixture was stirred for 18 hours at room temperature. The mixture was diluted with water (10 mL) and extracted with dichloromethane. The organic extract was dried over anhydrous Na₂SO₄, filtered and the filtrate was concentrated. The residue was purified by preparation HPLC to give 3-(tert-butylthio)-1-(4-chlorobenzyl)-2-(2-methyl-2-(4-methyloxazol-2-yl)propyl)-1H-indol-5-ol (32 mg, 0.066 mmol, 55% yield) as white solid. LCMS (ESI): m/z 483.2[M+H]⁺. ¹HNMR (400 MHz, DMSO-d₆): δ (ppm) 1.18 (s, 9H), 1.28 (s, 6H), 2.05 (s, 3H), 3.23 (s, 2H), 4.95 (s, 2H), 6.58-6.55 (m, 1H), 6.77-6.74 (m, 2H), 6.97 (d, J=2.4 Hz, 1H), 7.10 (d, J=8.8 Hz, 1H), 7.30 (d, J=8.4 Hz, 2H), 7.68 (d, J=1.2 Hz, 1H), 8.84 (brs, 1H).

Example 16. 3-(tert-butylthio)-1-(4-chlorobenzyl)-2-(2-(3-ethyl-1,2,4-oxadiazol-5-yl)-2-methylpropyl)-1H-indol-5-ol

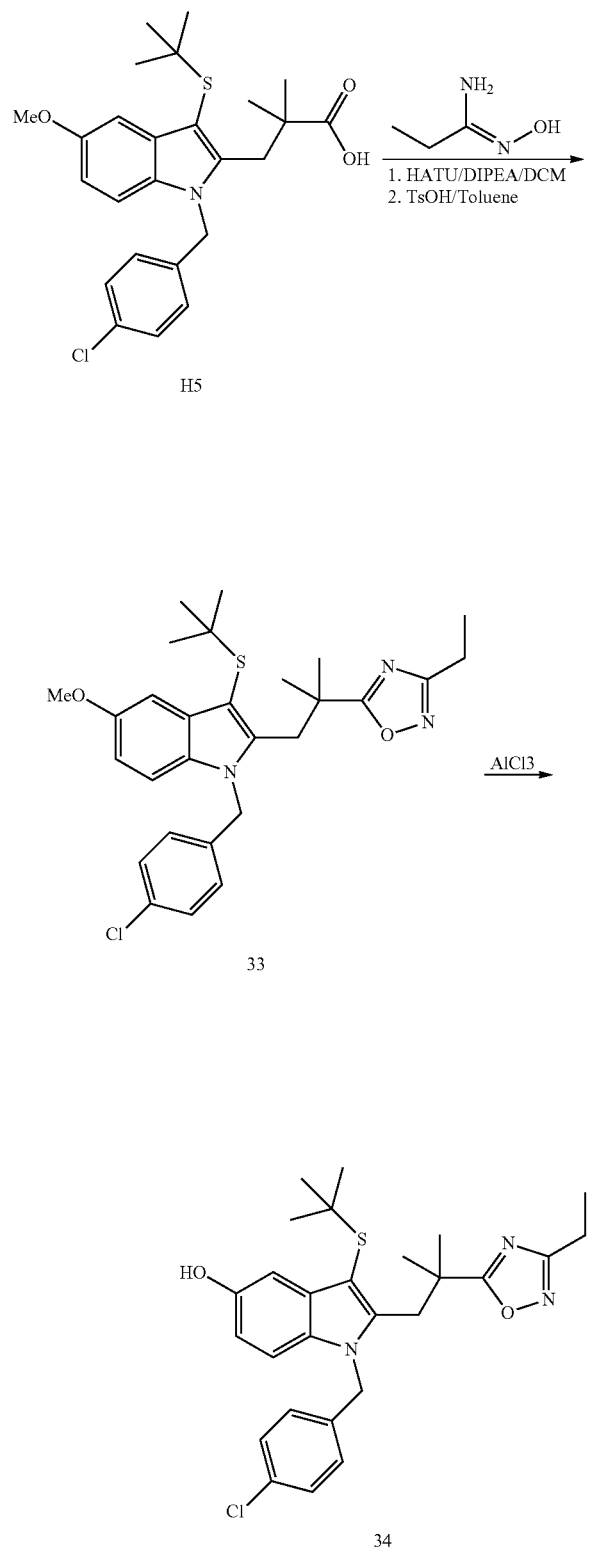

16.1. Preparation of 5-(1-(3-(tert-butylthio)-1-(4-chlorobenzyl)-5-methoxy-1H-indol-2-yl)-2-methyl-propan-2-yl)-3-ethyl-1,2,4-oxadiazole

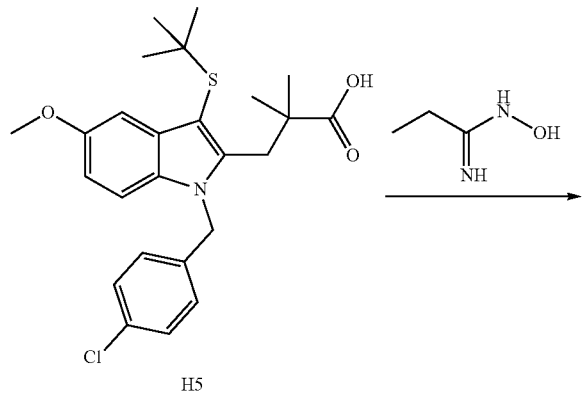

H5

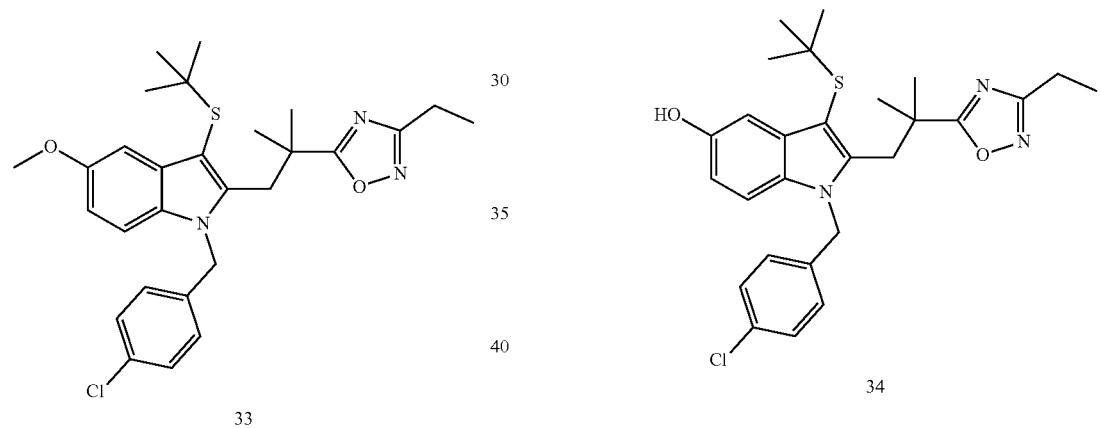

33

To a mixture of 3-(3-(tert-butylthio)-1-(4-chlorobenzyl)-5-methoxy-1H-indol-2-yl)-2,2-dimethylpropanoic acid (500 mg, 1.09 mmol) in DCM (10 mL) was added N-hydroxypropionimidamide (150 mg, 1.70 mmol), HATU (700 mg, 1.84 mmol) and TEA (500 mg, 4.95 mmol). The mixture was stirred for 18 hours at room temperature. The mixture was concentrated and the residue was purified by preparation HPLC to give 5-(1-(3-(tert-butylthio)-1-(4-chlorobenzyl)-5-methoxy-1H-indol-2-yl)-2-methylpropan-2-yl)-3-ethyl-1,2,4-oxadiazole (62 mg, 0.12 mmol, 11% yield) as white solid. LCMS (ESI): m/z 512.2 [M+H]$^+$. $^1$HNMR (400 MHz, DMSO-d$_6$): δ (ppm) 1.17 (s, 9H), 1.21 (t, J=7.2 Hz, 3H), 1.41 (s, 6H), 2.70-2.63 (q, J=7.6 Hz, 2H), 3.36 (s, 2H), 3.75 (s, 3H), 5.27 (s, 2H), 6.75-6.72 (m, 1H), 6.82 (d, J=8.8 Hz, 2H), 7.06 (d, J=2.4 Hz, 1H), 7.24 (d, J=8.8 Hz, 1H), 7.32 (d, J=8.4 Hz, 2H).

16.2 Preparation of 3-(tert-butylthio)-1-(4-chlorobenzyl)-2-(2-(3-ethyl-1,2,4-oxadiazol-5-yl)-2-methylpropyl)-1H-indol-5-ol

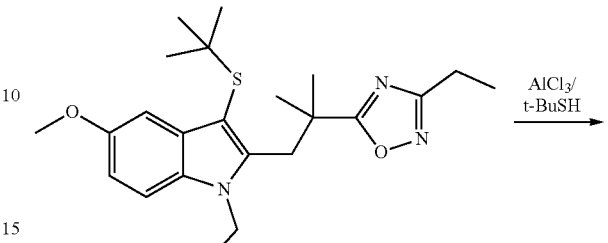

33

34

To a mixture of 5-(1-(3-(tert-butylthio)-1-(4-chlorobenzyl)-5-methoxy-1H-indol-2-yl)-2-methylpropan-2-yl)-3-ethyl-1,2,4-oxadiazole (50 mg, 0.10 mmol) in DCM (10 mL) was added t-BuSH (300 mg, 3.33 mmol) and AlCl$_3$ (200 mg, 1.50 mmol). The mixture was stirred for 18 hours at room temperature. The mixture was diluted with water (10 mL) and extracted with DCM. The organic extract was dried over anhydrous Na$_2$SO$_4$, filtered and the filtrate was concentrated. The residue was purified by prep-HPLC to give 3-(tert-butylthio)-1-(4-chlorobenzyl)-2-(2-(3-ethyl-1,2,4-oxadiazol-5-yl)-2-methylpropyl)-1H-indol-5-ol (15 mg, 0.030 mmol, 30% yield) as white solid. LCMS (ESI): m/z 498.2[M+H]$^+$. $^1$HNMR (400 MHz, DMSO-d$_6$): δ (ppm) 1.16 (s, 9H), 1.21 (t, J=7.6 Hz, 6H), 1.42 (s, 6H), 2.70-2.63 (q, 2H), 3.34 (s, 2H), 5.22 (s, 2H), 6.60-6.56 (m, 1H), 6.81 (d, J=8.4 Hz, 2H), 6.95 (d, J=2.0 Hz, 1H), 7.12 (d, J=8.8 Hz, 1H), 7.33-7.30 (m, 2H), 8.89 (brs, 1H).

Example 17. 3-(tert-butylthio)-1-(4-chlorobenzyl)-2-(2-methyl-2-(1-methyl-1H-tetrazol-5-yl)propyl)-1H-indol-5-ol and 3-(tert-butylthio)-1-(4-chlorobenzyl)-2-(2-methyl-2-(2-methyl-2H-tetrazol-5-yl)propyl)-1H-indol-5-ol
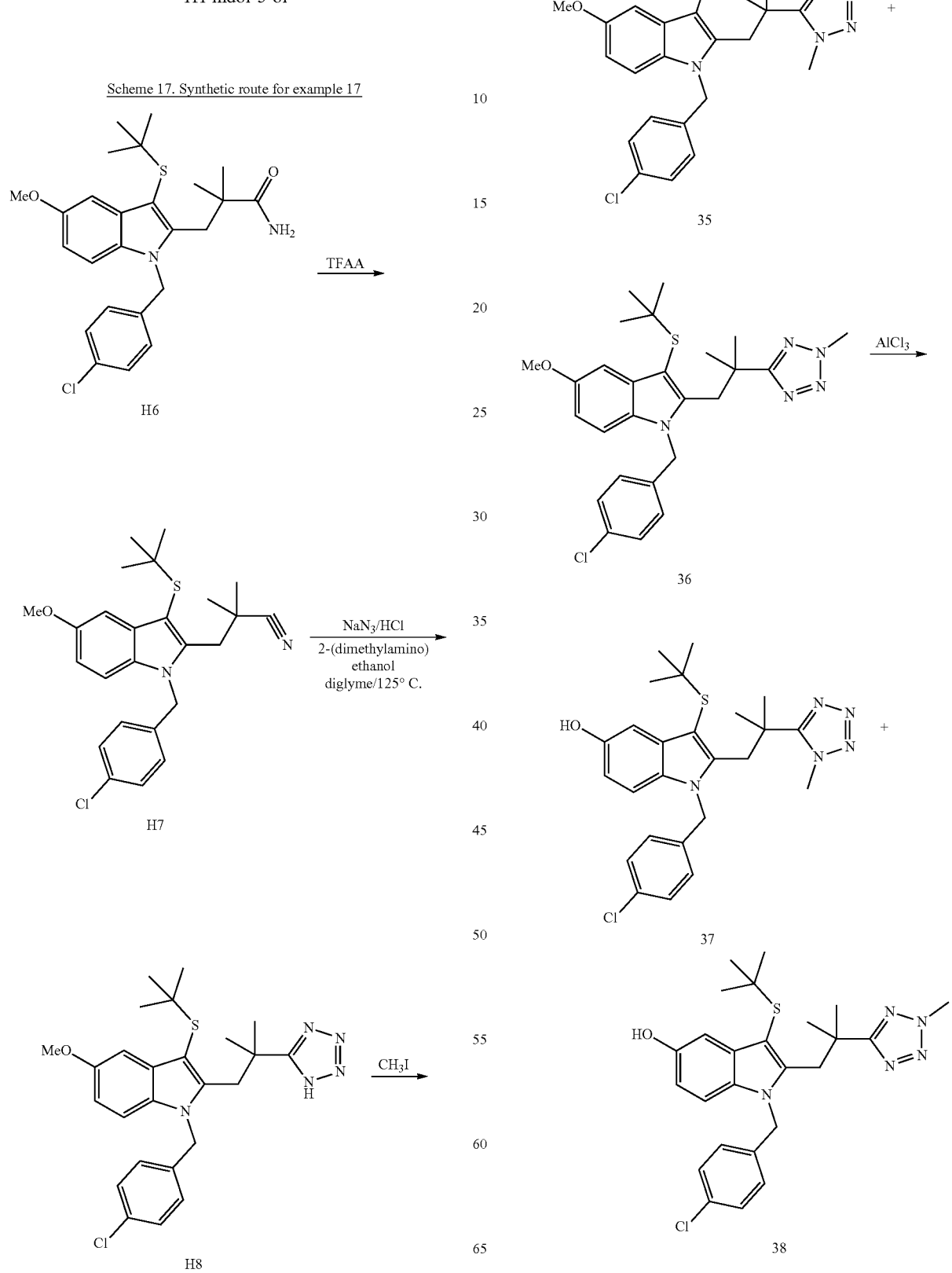
Scheme 17. Synthetic route for example 17

17.1. Preparation of 3-(3-(tert-butylthio)-1-(4-chlorobenzyl)-5-methoxy-1H-indol-2-yl)-2,2-dimethylpropanenitrile

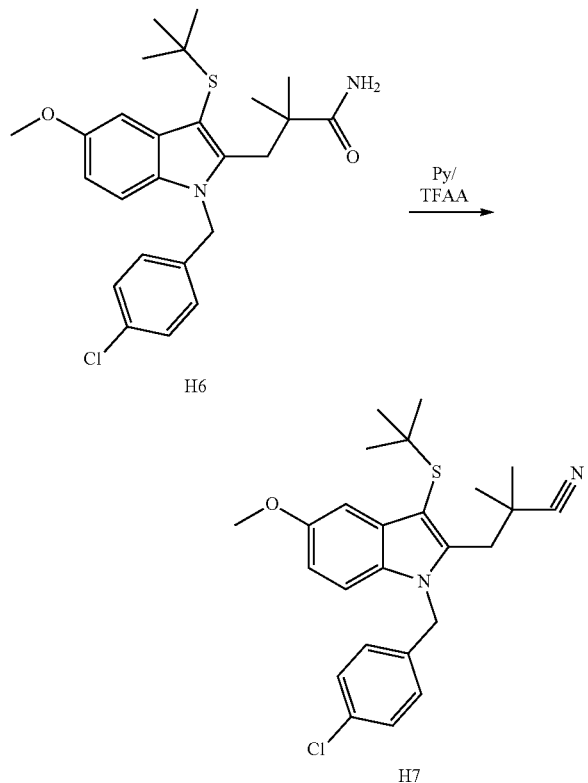

To a mixture of 3-(3-(tert-butylthio)-1-(4-chlorobenzyl)-5-methoxy-1H-indol-2-yl)-2,2-dimethylpropanamide (1.0 g, 2.18 mmol) in DCM (50 mL) was added pyridine (5 mL) and TFAA (1.5 g, 7.14 mmol) dropwise in an ice-bath. The mixture was stirred for 1.0 hour at room temperature and then washed with 1.0 N HCl (3×50 mL). The organic layer was dried over anhydrous $Na_2SO_4$, filtered and the filtrate was concentrated to give 3-(3-(tert-butylthio)-1-(4-chlorobenzyl)-5-methoxy-1H-indol-2-yl)-2,2-dimethylpropanenitrile (620 mg, 1.41 mmol, 64% yield) as yellow solid. LCMS (ESI): m/z 441.2[M+H]$^+$.

17.2. Preparation of 3-(tert-butylthio)-1-(4-chlorobenzyl)-5-methoxy-2-(2-methyl-2-(1H-tetrazol-5-yl)propyl)-1H-indole

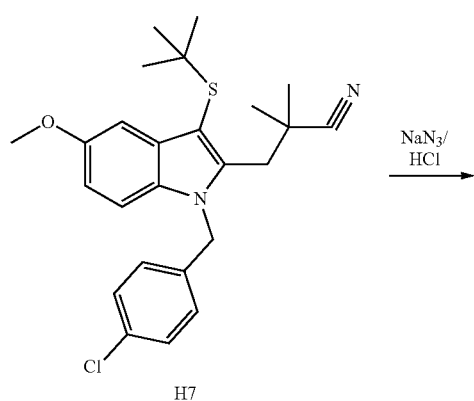

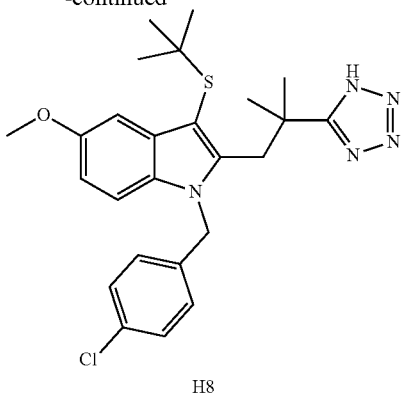

To a mixture of 3-(3-(tert-butylthio)-1-(4-chlorobenzyl)-5-methoxy-1H-indol-2-yl)-2,2-dimethylpropanenitrile (500 mg, 1.13 mmol) and 2-(dimethylamino)ethanol (100 mg, 1.12 mmol) in diglyme (10 mL) was added HC/1,4-dioxane (1 mL, 4 mmol, 4.0 M). The mixture was stirred for 15 min at room temperature. 2-(dimethylamino)ethanol (300 mg, 3.37 mmol) and $NaN_3$ (180 mg, 2.77 mmol) were added. The mixture was heated to 130° C. for 72 hours. After cooling to room temperature, the mixture was concentrated. The residue was diluted with water (50 mL) and extracted with DCM (3×30 mL). The combined organic extracts were dried over anhydrous $Na_2SO_4$, filtered and the filtrate was concentrated to give 3-(tert-butylthio)-1-(4-chlorobenzyl)-5-methoxy-2-(2-methyl-2-(1H-tetrazol-5-yl)propyl)-1H-indole (420 mg, 0.87 mmol, 77% yield) as yellow oil used in the next step without further purification. LCMS (ESI): m/z 484.3 [M+H]$^+$.

17.3. Preparation of 3-(tert-butylthio)-1-(4-chlorobenzyl)-5-methoxy-2-(2-methyl-2-(1-methyl-1H-tetrazol-5-yl)propyl)-1H-indole and 3-(tert-butylthio)-1-(4-chlorobenzyl)-5-methoxy-2-(2-methyl-2-(2-methyl-2H-tetrazol-5-yl)propyl)-1H-indole

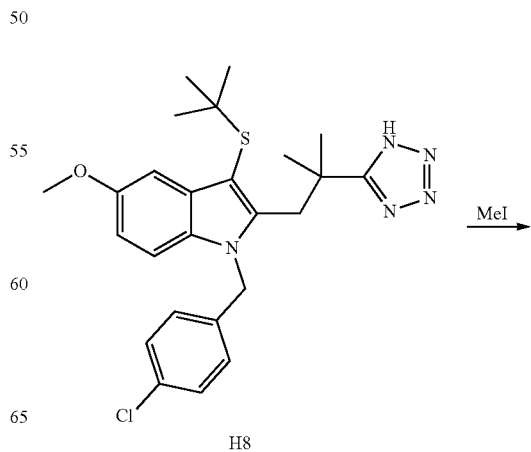

-continued

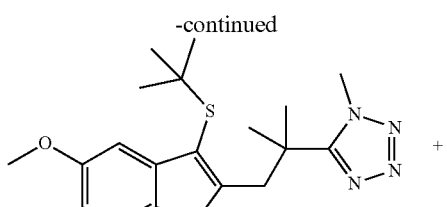
35

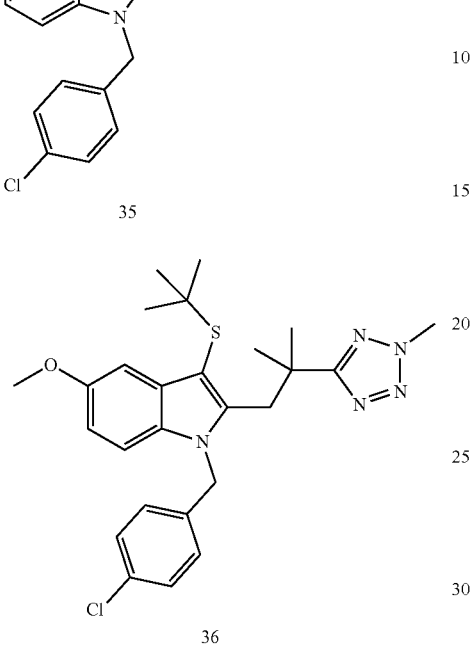
36

To a mixture of 3-(tert-butylthio)-1-(4-chlorobenzyl)-5-methoxy-2-(2-methyl-2-(1H-tetrazol-5-yl)propyl)-1H-indole H8 (500 mg, 1.03 mmol) in DMF (10 mL) was added Cs$_2$CO$_3$ (1 g, 3.08 mmol) and MeI (1.2 g, 8.51 mmol). The reaction mixture was heated to 50° C. for 18 hours. After cooling to room temperature, the mixture was diluted with PE (50 mL) and EtOAc (50 mL). The resulting solution was washed with water (3×50 mL), dried over anhydrous Na$_2$SO$_4$, filtered and the filtrate was concentrated to give crude product (700 mg). The crude product (200 mg) was purified by pre-HPLC to give 3-(tert-butylthio)-1-(4-chlorobenzyl)-5-methoxy-2-(2-methyl-2-(1-methyl-1H-tetrazol-5-yl)propyl)-1H-indole 35 (10 mg, 0.020 mmol, 7% yield) and 3-(tert-butylthio)-1-(4-chlorobenzyl)-5-methoxy-2-(2-methyl-2-(2-methyl-2H-tetrazol-5-yl)propyl)-1H-indole 36 (22 mg, 0.044 mmol, 15% yield) as white solid. LCMS (ESI) (compound 35): m/z 498.3 [M+H]$^+$. $^1$HNMR (400 MHz, CDCl$_3$): δ (ppm) 1.27 (s, 9H), 1.66 (s, 6H), 3.33-3.20 (m, 5H), 3.87 (s, 3H), 4.52 (s, 2H), 6.54 (d, J=8.4 Hz, 2H), 6.83-6.79 (m, 1H), 6.98 (d, J=8.8 Hz, 1H), 7.14 (d, J=8.4 Hz, 2H), 7.26-7.24 (m, 1H). LCMS (ESI) (compound 36): m/z 498.3[M+H]$^+$. $^1$HNMR (400 MHz, CDCl$_3$): δ (ppm) 1.25 (s, 9H), 1.47 (s, 6H), 3.42 (s, 2H), 3.86 (s, 3H), 4.20 (s, 3H), 5.08 (s, 2H), 6.54 (d, J=8.4 Hz, 2H), 6.76-6.73 (m, 1H), 6.91 (d, J=8.8 Hz, 1H), 7.16 (d, J=8.4 Hz, 2H), 7.26-7.24 (m, 1H).

17.4. Preparation of 3-(tert-butylthio)-1-(4-chlorobenzyl)-2-(2-methyl-2-(1-methyl-1H-tetrazol-5-yl)propyl)-1H-indol-5-ol and 3-(tert-butylthio)-1-(4-chlorobenzyl)-2-(2-methyl-2-(2-methyl-2H-tetrazol-5-yl)propyl)-1H-indol-5-ol

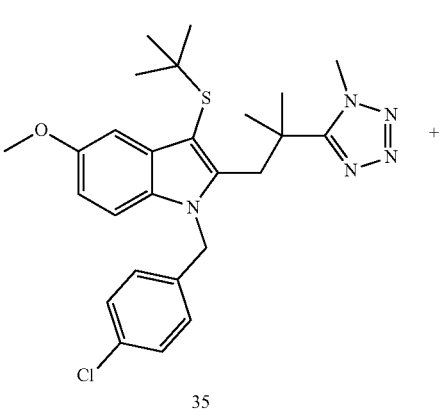
35

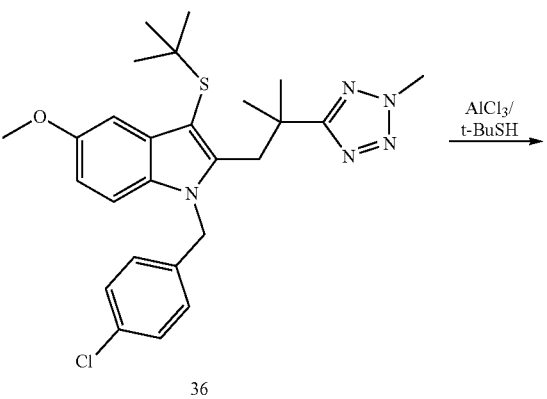
36

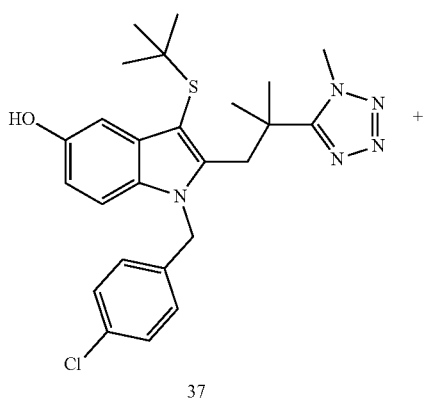
37

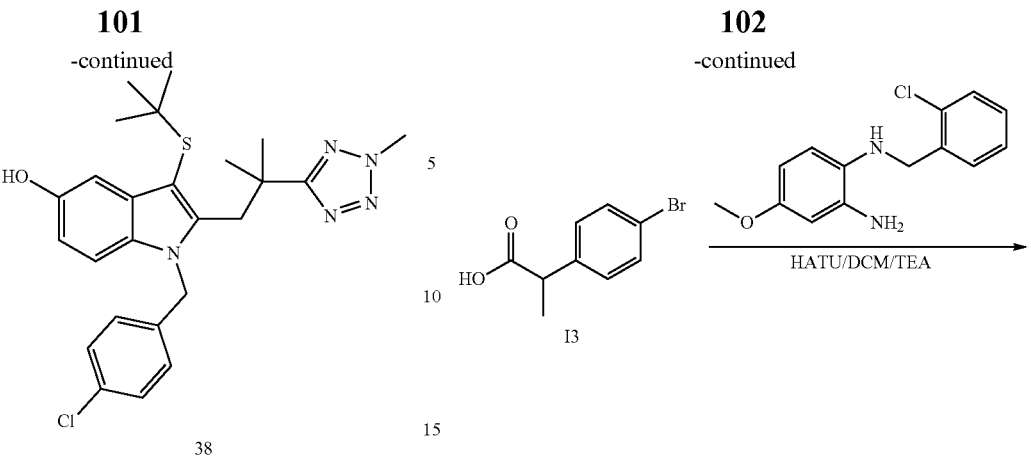
38

To a mixture of two isomers 35 and 36 (500 mg, 0.74 mmol) in DCM (30 mL) was added t-BuSH (3 g, 33.3 mmol) and AlCl$_3$ (1.8 g, 13.5 mmol). The reaction mixture was stirred for 18 hours at room temperature. The mixture was washed with water (20 mL), dried over anhydrous Na$_2$SO$_4$, filtered, the filtrate was concentrated. The residue was purified by preparation HPLC to give 3-(tert-butylthio)-1-(4-chlorobenzyl)-2-(2-methyl-2-(1-methyl-1H-tetrazol-5-yl)propyl)-1H-indol-5-ol (62 mg, 0.13 mmol, 17% yield) and 3-(tert-butylthio)-1-(4-chlorobenzyl)-2-(2-methyl-2-(2-methyl-2H-tetrazol-5-yl)propyl)-1H-indol-5-ol (120 mg, 0.25 mmol, 34% yield) as white solid. LCMS (ESI) (compound 37): m/z 484.3 [M+H]$^+$. $^1$HNMR (400 MHz, DMSO-d$_6$): δ (ppm) 1.14 (s, 9H), 1.50 (s, 6H), 4.05-3.75 (m, 5H), 5.26 (s, 2H), 6.60-6.57 (m, 1H), 6.82 (d, J=8.4 Hz, 2H), 6.90 (d, J=2.0 Hz, 1H), 7.15 (d, J=8.0 Hz, 1H), 7.31 (d, J=8.4 Hz, 2H), 8.88 (brs, 1H). LCMS (ESI) (compound 38): m/z 484.3[M+H]$^+$. $^1$HNMR (400 MHz, DMSO-d$_6$): δ (ppm) 1.16 (s, 7H), 1.20 (s, 2H), 1.40 (s, 6H), 3.27-3.30 (s, 2H), 4.29 (s, 3H), 5.07 (s, 1.49H), 5.58 (s, 0.45H), 6.55-6.63 (m1H), 6.77 (d, J=8.4 Hz, 1.53H), 6.88 (d, J=8.4 Hz, 0.49H), 6.95-7.01 (m, 1H), 7.07 (d, J=8.8 Hz, 0.8H), 7.18 (d, J=8.8 Hz, 0.26H), 7.28-7.34 (m, 2H).

Example 18. 2-(4-(1-(1-(2-chlorobenzyl)-5-methoxy-1H-benzo[d]imidazol-2-yl)ethyl)phenyl)ethanol

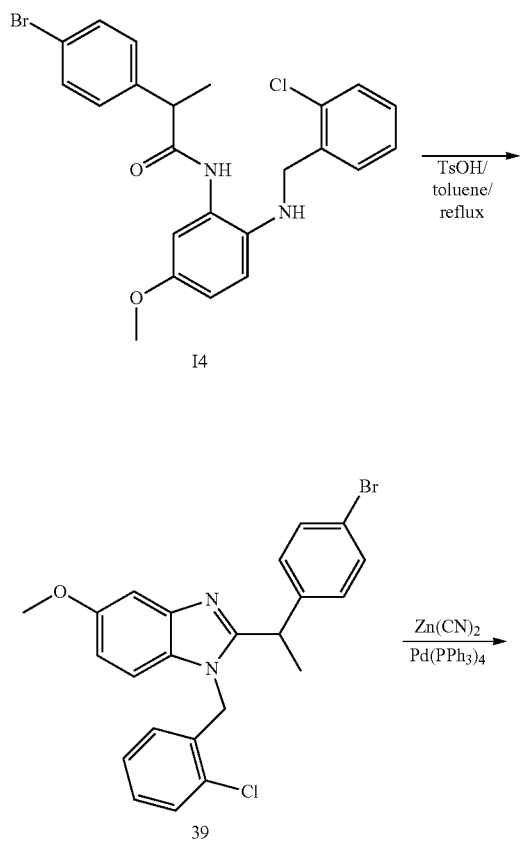

Scheme 18. Synthetic route for example 18

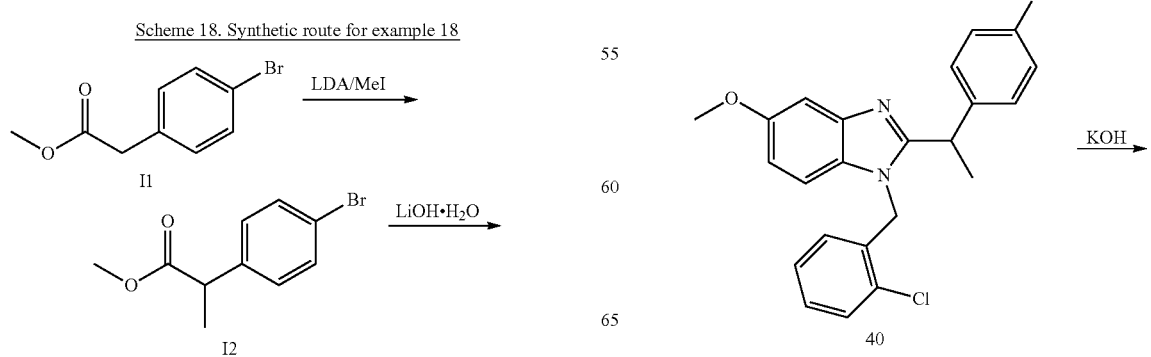

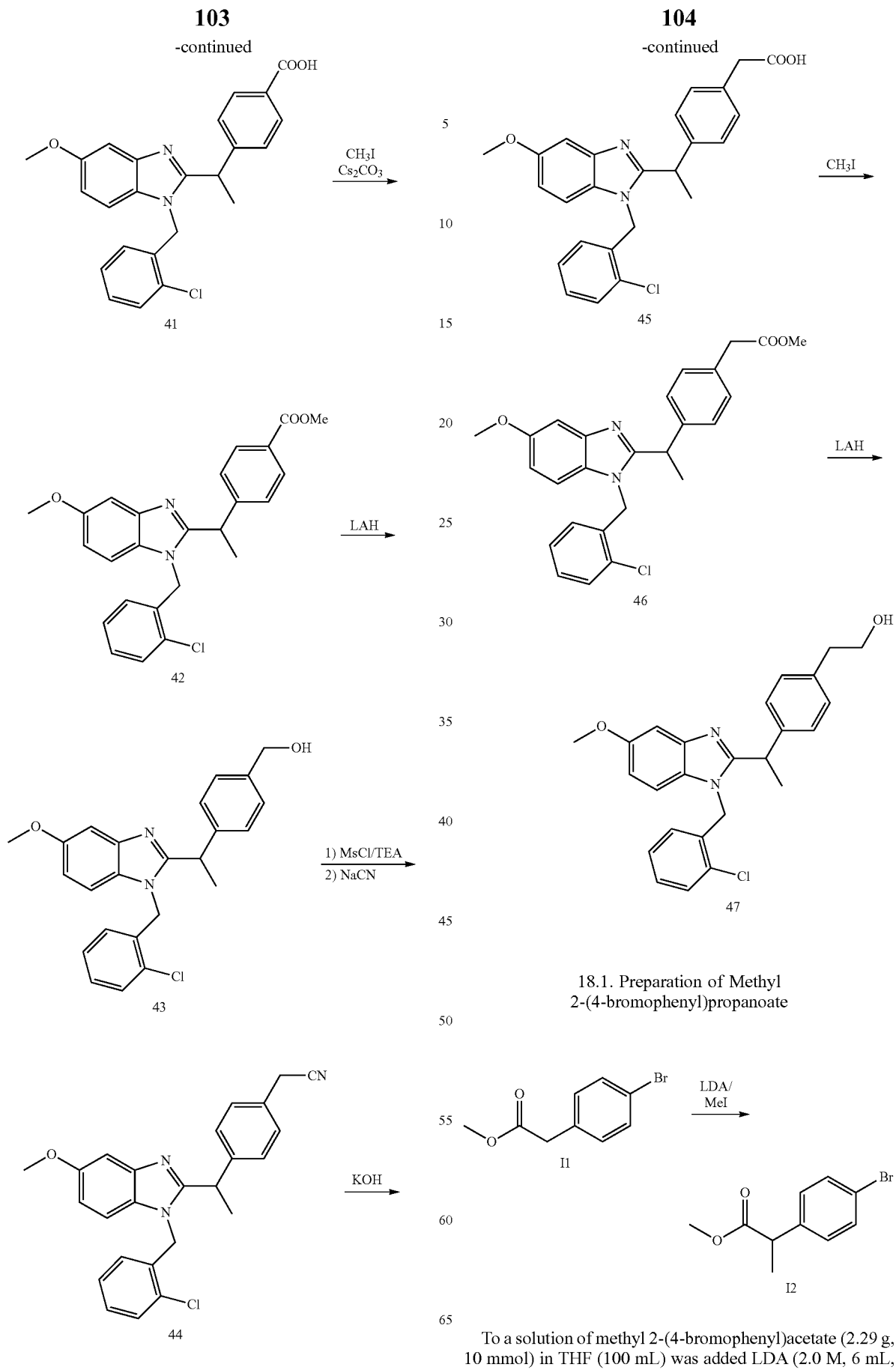
18.1. Preparation of Methyl 2-(4-bromophenyl)propanoate
To a solution of methyl 2-(4-bromophenyl)acetate (2.29 g, 10 mmol) in THF (100 mL) was added LDA (2.0 M, 6 mL, 12 mmol) at −70° C. under N₂. After addition, the reaction mixture was stirred for 30 min at 0° C. The mixture was then cooled to −70° C. again and iodomethane (1.7 g, 12 mmol) was added. After addition, the reaction mixture was stirred for 1.0 hour at 0° C. The mixture was quenched with water (50 mL) and extracted with EtOAc (3×50 mL). The organic extracts were washed with brine (2×50 mL), dried over anhydrous Na₂SO₄ and concentrated to give methyl 2-(4-bromophenyl) propanoate (2.3 g, 9.5 mmol, 95% yield) as yellow oil used as the intermediate without further purification. ¹H NMR (400 MHz, CDCl₃): δ (ppm) 1.48 (d, J=7.2 Hz, 3H), 3.65-3.71 (m, 4H), 7.17 (d, J=8.4 Hz, 2H), 7.48 (d, J=8.4 Hz, 2H).

18.2. Preparation of 2-(4-bromophenyl)propanoic Acid

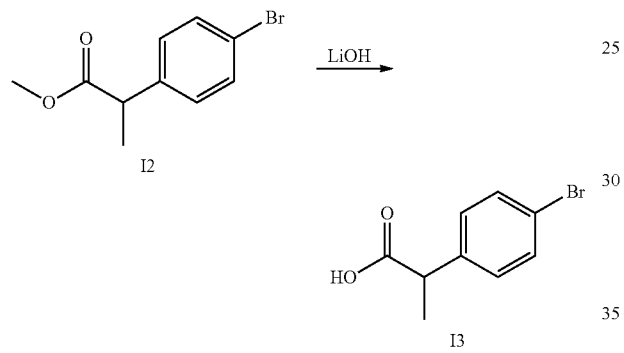

To a mixture of methyl 2-(4-bromophenyl)propanoate (2.3 g, 9.5 mmol) in THF (20 mL) and MeOH (20 mL) were added LiOH.H₂O (4.0 g, 95 mmol) and water (40 m). The mixture was heated to 65° C. for 3 hours. After cooling to room temperature, the mixture was concentrated. The residue was diluted with water and acidified with 1.0 N HCl (aq) to pH=4. The resulting mixture was extracted with DCM (2×50 mL) and the organic extracts were washed with brine (2×50 mL), dried over anhydrous Na₂SO₄ and concentrated to give crude 2-(4-bromophenyl)propanoic acid (2.2 g, 9.5 mmol, 100% yield) as yellow oil used as the intermediate without further purification. LCMS (ESI): m/z 229[M+1]+.

18.3. Preparation of 2-(4-bromophenyl)-N-(2-((2-chlorobenzyl)amino)-5-methoxyphenyl) Propanamide

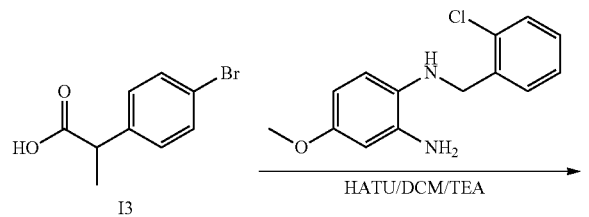

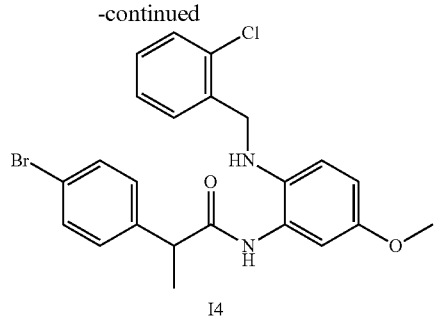

To a solution of N1-(2-chlorobenzyl)-4-methoxybenzene-1,2-diamine (2.62 g, 10 mmol) in DCM (50 mL) were added 2-(4-bromophenyl)propanoic acid (2.2 g, 9.6 mmol), TEA (5.05 g, 50 mmol) and HATU (5.7 g, 15 mmol) at room temperature. After addition, the reaction mixture was stirred for 24 hours at room temperature. Then it was concentrated, and the residue was purified by column chromatography on silica gel (PE:EA=1:2) to give 2-(4-bromophenyl)-N-(2-((2-chlorobenzyl)amino)-5-methoxyphenyl)propanamide (4.1 g, 8.7 mmol, 91% yield) as brown solid. ¹H NMR (400 MHz, DMSO-d₆): δ (ppm) 1.42 (d, J=6.8 Hz, 3H), 3.62 (s, 3H), 3.88-3.93 (m, 1H), 4.29 (d, J=6.0 Hz, 2H), 4.93-4.96 (m, 1H), 6.43 (d, J=8.8 Hz, 1H), 6.61 (d, J=8.8 Hz, 1H), 6.85 (d, J=2.8 Hz, 1H), 7.27-7.37 (m, 5H), 7.44-7.51 (m, 3H), 9.48 (s, 1H).

18.4. Preparation of 2-(1-(4-bromophenyl)ethyl)-1-(2-chlorobenzyl)-5-methoxy-1H-benzo[d]imidazole

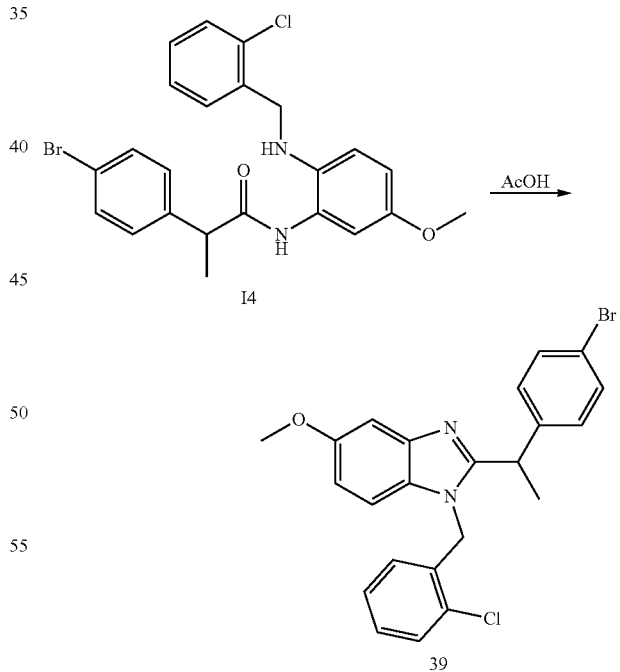

The mixture of 2-(4-bromophenyl)-N-(2-((2-chlorobenzyl)amino)-5-methoxyphenyl) propanamide (20 g, 4.2 mmol) in AcOH (40 mL) was stirred for 16 h at 120° C. After cooling to room temperature, the mixture was concentrated, and the residue was purified by column chromatography on silicagel (PE:EA=5:1) to give 2-(1-(4-bromophenyl)ethyl)-1-(2-chlorobenzyl)-5-methoxy-1H-benzo[d]imidazole (1.5 g, 3.3 mmol, 79% yield). LCMS (ESI): m/z 455.1 [M+1]+. 1HNMR (400 MHz, CDCl3): δ (ppm) 1.94 (d, J=7.2 Hz, 3H), 3.91 (s, 3H), 4.40-4.46 (m, 1H), 5.36 (s, 2H), 6.14 (d, J=7.6 Hz, 1H), 6.97-7.04 (m, 2H), 7.03-7.13 (m, 3H), 7.24-7.27 (m, 1H), 7.32 (d, J=8.8 Hz, 2H), 7.41 (d, J=8.4 Hz, 1H), 7.60 (d, J=2.4 Hz, 1H).

18.5. Preparation of 4-(1-(1-(2-chlorobenzyl)-5-methoxy-1H-benzo[d]imidazol-2-yl)ethyl)benzonitrile

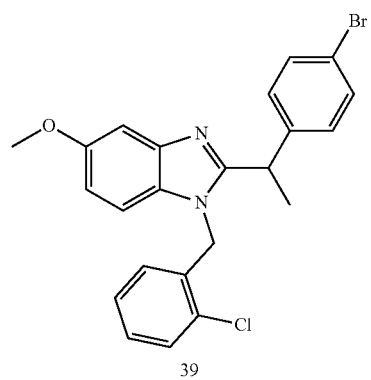
39

Zn(CN)2
Pd(PPh3)4

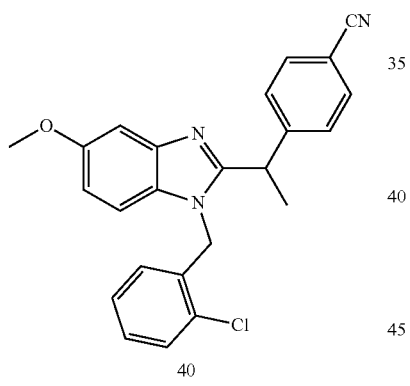
40

To a solution of 2-(1-(4-bromophenyl)ethyl)-1-(2-chlorobenzyl)-5-methoxy-1H-benzo[d]imidazole (1.9 g, 4.2 mmol) in DMF (50 mL) were added Pd(PPh3)4 (473 mg, 0.42 mmol) and Zn(CN)2 (490 mg, 4.2 mmol) at room temperature under N2. After addition, the reaction mixture was stirred for 16 hours at 80° C. The mixture was concentrated and the residue was purified by column chromatography on silica gel (PE:EA=3:1) to give 4-(1-(1-(2-chlorobenzyl)-5-methoxy-1H-benzo[d]imidazol-2-yl)ethyl)benzonitrile (1.5 g, 3.7 mmol, 88% yield). LCMS (ESI): m/z 402.2[M+1]+. 1HNMR (400 MHz, CDCl3): δ (ppm) 1.87 (d, J=7.2 Hz, 3H), 3.90 (s, 3H), 4.33-4.34 (m, 1H), 5.20-5.35 (m, 2H), 6.11 (d, J=7.6 Hz, 1H), 6.90-6.96 (m, 2H), 7.07 (d, J=9.2 Hz, 1H), 7.17-7.2 (m, 1H), 7.31 (d, J=8.4 Hz, 2H), 7.37 (d, J=7.2 Hz, 1H), 7.42-7.47 (m, 3H).

18.6. Preparation of 4-(1-(1-(2-chlorobenzyl)-5-methoxy-1H-benzo[d]imidazol-2-yl)ethyl)benzoic Acid

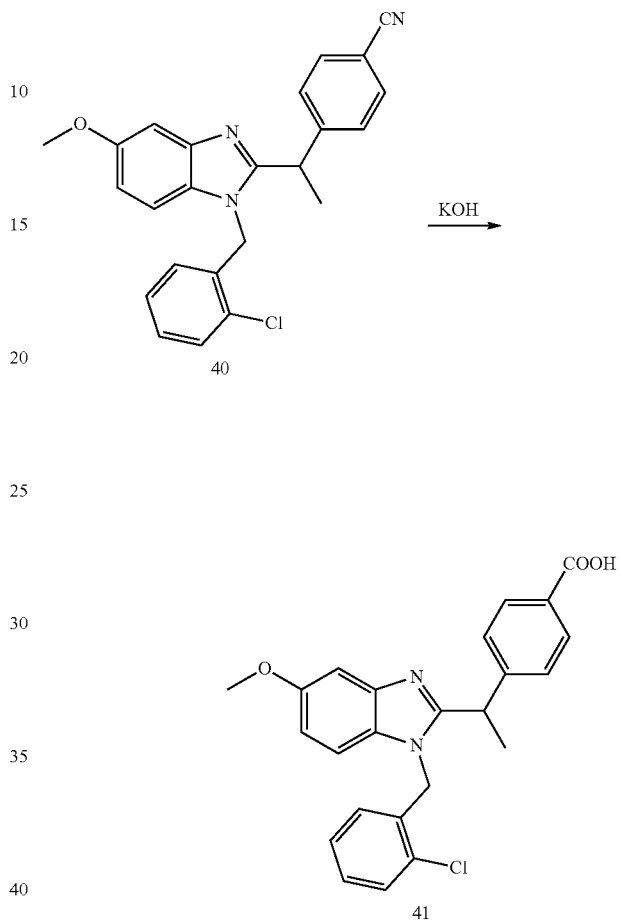

To a solution of 4-(1-(1-(2-chlorobenzyl)-5-methoxy-1H-benzo[d]imidazol-2-yl)ethyl)benzonitrile (1.5 g, 3.74 mmol) in MeOH (20 mL) were added water (50 mL) and KOH (4.19 g, 7.48 mmol). The mixture was heated to 115° C. for 24 hours. After cooling to room temperature, the organic solvent was evaporated and the residue was acidified with 1.0N HCl (aq) to pH=4. The resulting mixture was extracted with DCM (2×50 mL), and the organic extracts were washed with brine (2×50 m), dried over Na2SO4 and concentrated to give 4-(1-(1-(2-chlorobenzyl)-5-methoxy-1H-benzo[d]imidazol-2-yl)ethyl)benzoic acid (1.4 g, 3.3 mmol, 88% yield). LCMS (ESI): m/z 421.3[M+1]+. 1H NMR (400 MHz, DMSO-d6): δ (ppm) 1.74 (d, J=7.2 Hz, 3H), 3.84 (s, 3H), 4.77-4.79 (m, 1H), 5.55-5.66 (m, 2H), 6.24 (d, J=7.6 Hz, 1H), 6.97-7.01 (m, 2H), 7.18-7.22 (m, 1H), 7.30-7.37 (m, 4H), 7.43 (d, J=7.6 Hz, 1H), 7.73 (d, J=8.4 Hz, 2H), 13.20 (s, 1H).

18.7. Preparation of Methyl 4-(1-(1-(2-chlorobenzyl)-5-methoxy-1H-benzo [d]imidazol-2-yl)ethyl)benzoate

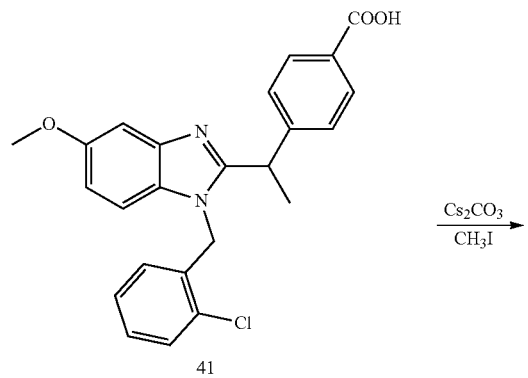

41

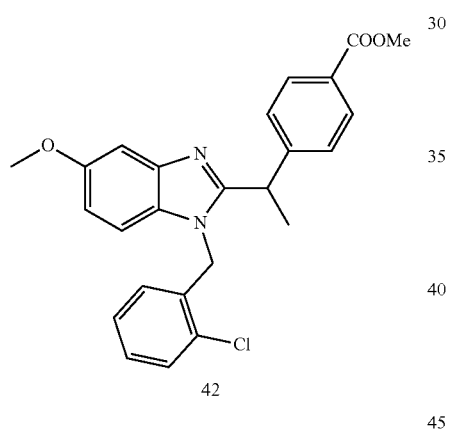

42

To a solution of 4-(1-(1-(2-chlorobenzyl)-5-methoxy-1H-benzo[d]imidazol-2-yl) ethyl)benzoic acid (1.2 g, 2.9 mmol) in DMF (50 mL) were added $Cs_2CO_3$ (2.9 g, 8.6 mmol) and iodomethane (618 mg, 4.35 mmol). After addition, the reaction mixture was stirred for 2 hours at room temperature. It was then concentrated and the residue was purified by column chromatography on silica gel (PE:EA=5:1) to give methyl 4-(1-(1-(2-chlorobenzyl)-5-methoxy-1H-benzo[d] imidazol-2-yl)ethyl)benzoate (1.2 g, 2.8 mmol, 96% yield). LCMS (ESI): m/z 435.2[M+1]+. $^1$H NMR (400 MHz, $CDCl_3$): δ (ppm) 1.88 (d, J=7.2 Hz, 3H), 3.88 (s, 3H), 3.89 (s, 3H), 4.30-4.36 (m, 1H), 5.20-5.31 (m, 2H), 6.18 (d, J=7.6 Hz, 1H), 6.91-6.95 (m, 2H), 7.04 (d, J=8.8 Hz, 1H), 7.14-7.18 (m, 1H), 7.27 (d, J=8.0 Hz, 2H), 7.37 (d, J=8.0 Hz, 1H), 7.50 (s, 1H), 7.85 (d, J=8.4 Hz, 2H).

18.8. Preparation of (4-(1-(1-(2-chlorobenzyl)-5-methoxy-1H-benzo[d]imidazol-2-yl)ethyl)phenyl)methanol

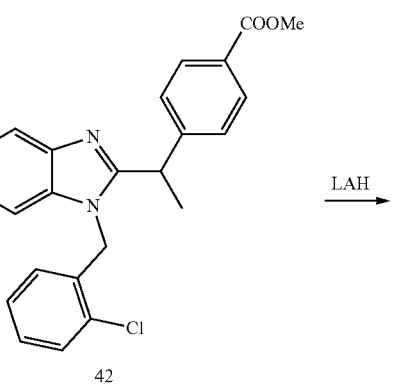

42

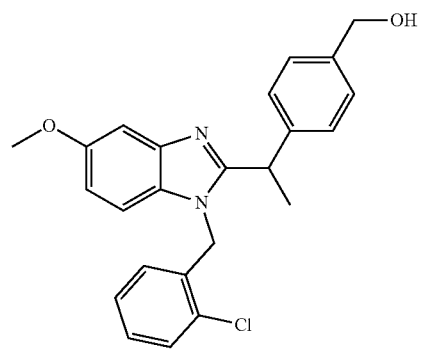

43

To a solution of methyl 4-(1-(1-(2-chlorobenzyl)-5-methoxy-1H-benzo[d]imidazole-2-yl)ethyl)benzoate (1.1 g, 2.5 mmol) in THF (50 mL) was added LAH (193 mg, 5 mmol) at 0° C. After addition, the reaction mixture was stirred for 2 h at room temperature. It was then quenched with 1.0 N NaOH (1.0 mL), filtered and concentrated to give (4-(1-(1-(2-chlorobenzyl)-5-methoxy-1H-benzo[d]imidazol-2-yl)ethyl)phenyl)methanol (0.9 g, 2.2 mmol, 88% yield). LCMS (ESI): m/z 407.3[M+1]+. $^1$HNMR (400 MHz, $CDCl_3$): δ (ppm) 7.61 (s, 1H), 7.42 (d, J=8.0 Hz, 1H), 7.22-7.24 (m, 5H), 7.08 (d, J=8.8 Hz, 1H), 7.00-7.04 (m, 3H), 6.21 (d, J=7.6 Hz, 1H), 5.36 (s, 2H), 4.60 (s, 2H), 4.46-4.48 (m, 1H), 3.89 (s, 3H), 1.95 (d, J=7.2 Hz, 3H).

18.9. Preparation of 2-(4-(1-(1-(2-chlorobenzyl)-5-methoxy-1H-benzo[d]imidazol-2-yl) ethyl)phenyl) acetonitrile

18.10. Preparation of 2-(4-(1-(1-(2-chlorobenzyl)-5-methoxy-1H-benzo[d]imidazol-2-yl)ethyl)phenyl) acetic Acid

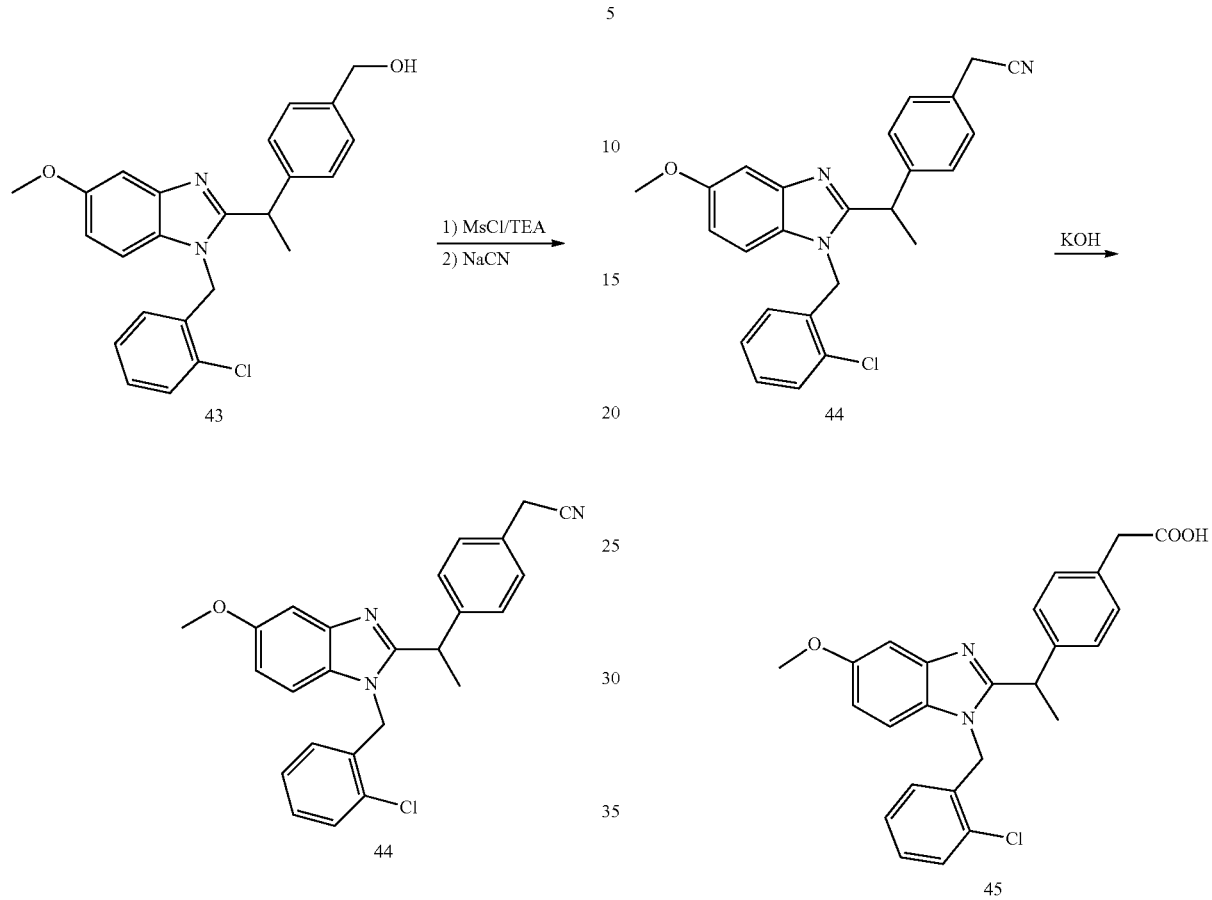

To a solution of (4-(1-(1-(2-chlorobenzyl)-5-methoxy-1H-benzo[d]imidazol-2-yl) ethyl)phenyl)methanol (0.8 g, 2.0 mmol) in DCM (20 mL) were added TEA (1.0 g, 10 mmol) and MsCl (344 mg, 3.0 mmol) at 0° C. After addition, the reaction mixture was stirred for 2 h at 0° C. The mixture was then concentrated to give the intermediate 4-(1-(1-(2-chlorobenzyl)-5-methoxy-1H-benzo[d]imidazol-2-yl)ethyl) benzyl methanesulfonate. The above intermediate was dissolved in DMF (20 mL) and NaCN (196 mg, 4.0 mmol) was added at room temperature. The reaction mixture was stirred for 16 h at room temperature, and then it was concentrated. The crude product was purified by column chromatography on silica gel (PE:EA=5:1) to give 2-(4-(1-(1-(2-chlorobenzyl)-5-methoxy-1H-benzo[d]imidazol-2-yl) ethyl)phenyl) acetonitrile (260 mg, 0.7 mmol, 35% yield). LCMS (ESI): m/z 415.3[M+1]$^+$. $^1$H NMR (400 MHz, CDCl$_3$): δ (ppm) 1.96 (d, J=7.2 Hz, 3H), 3.64 (s, 2H), 3.91 (s, 3H), 4.49-4.54 (m, 1H), 5.40 (m, 2H), 6.18 (d, J=7.6 Hz, 1H), 7.00-7.08 (m, 2H), 7.14-7.20 (m, 3H), 7.25-7.28 (m, 3H), 7.43 d, J=8.0 Hz, 1H), 7.53 (s, 1H).

To a solution of 2-(4-(1-(1-(2-chlorobenzyl)-5-methoxy-1H-benzo[d]imidazol-2-yl)ethyl)phenyl) acetonitrile (250 mg, 0.6 mmol) in MeOH (10 mL) were added water (20 mL) and KOH (337 mg, 6 mmol). The reaction mixture was heated to 115° C. for 24 h. After cooling to room temperature, the organic solvent was evaporated and the aqoues layer was acidified with 1.0 N HCl (aq) to pH=4.0. The resulting mixture was extracted with DCM (2×50 mL). The organic extracts were washed with brine (2×50 mL), dried over anhydrous Na$_2$SO$_4$ and concentrated to give 2-(4-(1-(1-(2-chlorobenzyl)-5-methoxy-1H-benzo[d]imidazol-2-yl) ethyl)phenyl)acetic acid (20 mg, 0.05 mmol, 9% yield). LCMS (ESI): m/z 435.3[M+1]$^+$. $^1$HNMR (400 MHz, DMSO-d$_6$): δ (ppm) 1.68 (d, J=6.8 Hz, 3H), 3.44 (s, 2H), 3.81 (s, 3H), 4.93-4.51 (m, 1H), 5.40-5.82 (m, 2H), 6.19 (d, J=8.0 Hz, 1H), 6.88 (d, J=7.6 Hz, 1H), 6.09-7.04 (m, 1H), 7.08 (d, J=8.0 Hz, 2H), 7.14 (d, J=7.2 Hz, 2H), 7.25-7.27 (m, 2H), 7.17-7.28 (m, 3H), 7.46 (d, J=7.6 Hz, 1H), 12.50 (s, 1H).

18.11. Preparation of methyl 2-(4-(1-(1-(2-chlorobenzyl)-5-methoxy-1H-benzo[d]imidazol-2-yl)ethyl)phenyl)acetate

18.12. Preparation of 2-(4-(1-(1-(2-chlorobenzyl)-5-methoxy-1H-benzo[d]imidazol-2-yl)ethyl)phenyl)ethanol

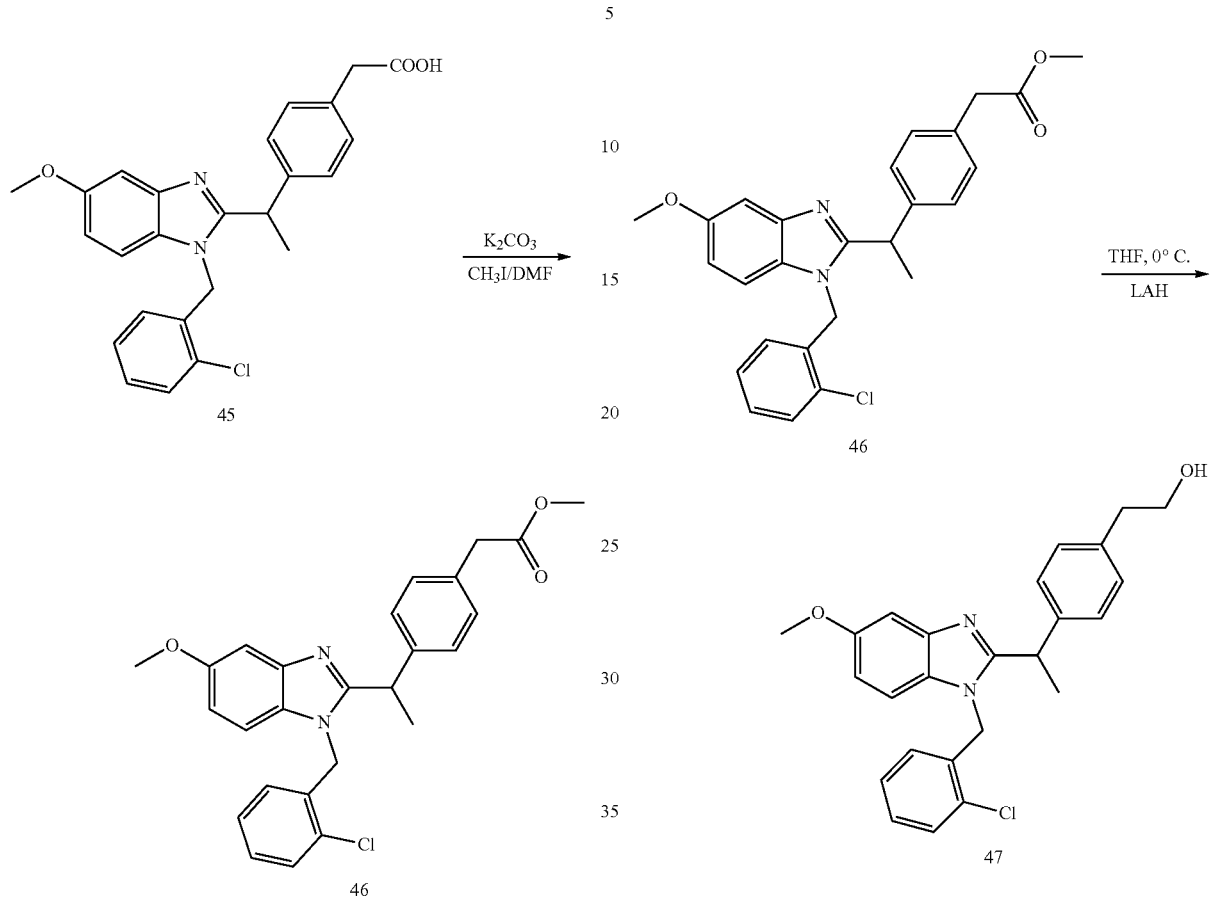

To a solution of 2-(4-(1-(1-(2-chlorobenzyl)-5-methoxy-1H-benzo[d]imidazol-2-yl)ethyl)phenyl)acetic acid (380 mg, 0.87 mmol) in DMF (5 mL) were added $K_2CO_3$ (120 mg, 0.87 mmol) and iodomethane (127 mg, 0.87 mmol). After addition, the reaction mixture was stirred for 2 h at room temperature. The mixture was diluted with water and extracted with ethyl acetate. The organic extract was washed with water and dried over anhydrous $Na_2SO_4$. It was filtered and the filtrate was concentrated and the residue was purified by column chromatography on silica gel (PE:EA=5:1) to give methyl 2-(4-(1-(1-(2-chlorobenzyl)-5-methoxy-1H-benzo[d]imidazol-2-yl)ethyl)phenyl) acetate (310 mg, 0.69 mmol, 79% yield) as white solid. LCMS (ESI): m/z 449.2 [M+1]$^+$. $^1$HNMR (400 MHz, DMSO-$d_6$): δ (ppm) 1.72 (d, J=7.2 Hz, 2H), 3.56 (s, 2H), 3.59 (s, 3H), 3.83 (s, 3H), 4.64 (m, 1H), 5.46-5.65 (m, 2H), 6.27 (d, J=7.6 Hz, 1H), 6.94 (m, 1H), 7.03 (m, 1H), 7.08 (d, J=8.4 Hz, 2H). 7.19 (d, J=8.4 Hz, 2H), 7.22 (m, 1H), 7.29-7.33 (m, 2H), 7.45 (d, J=8.0 Hz, 2H).

To a solution of methy 2-(4-(1-(1-(2-chlorobenzyl)-5-methoxy-1H-benzo[d]imidazol-2-yl)ethyl)phenyl)acetate (100 mg, 0.22 mmol) in THF (5 mL) was added LAH (9 mg, 0.22 mmol) at 0° C. After addition, the reaction mixture was stirred for 2 h at room temperature. The mixture was quenche with 1.0 N NaOH (1.0 mL), filtrated and concentrated. The residue was purified by pre-HPLC to give 2-(4-(1-(1-(2-chlorobenzyl)-5-methoxy-1H-benzo[d]imidazol-2-yl)ethyl)phenyl)ethanol (10 mg, 0.023 mmol, 10.8% yield) as white solid. LCMS (ESI): m/z 421.2 [M+1]$^+$. $^1$HNMR (400 MHz, DMSO-$d_6$): δ (ppm) 1.72 (d, J=6.8 Hz, 3H), 2.62 (t, d, J=7.2 Hz, 2H), 3.48 (d, J=7.2 Hz, 2H), 3.83 (s, 3H), 4.64 (m, 1H), 5.61 (m, 2H), 6.24 (d, J=7.6 Hz, 1H), 7.05-6.96 (m, 4H), 7.14-7.10 (d, J=8.0 Hz, 2H), 7.22-7.28 (m, 2H), 7.34 (d, J=8.8 Hz, 1H), 7.47 (d, J=8.0 Hz, 1H).

Example 19. 1-(3-chlorobenzyl)-2-(1-(4-isobutylphenyl)ethyl)-1H-indol-5-ol

Scheme 19. Synthetic route for example 19

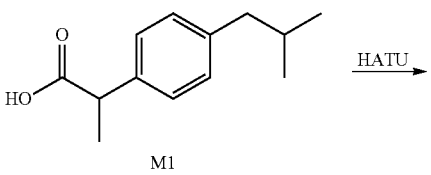

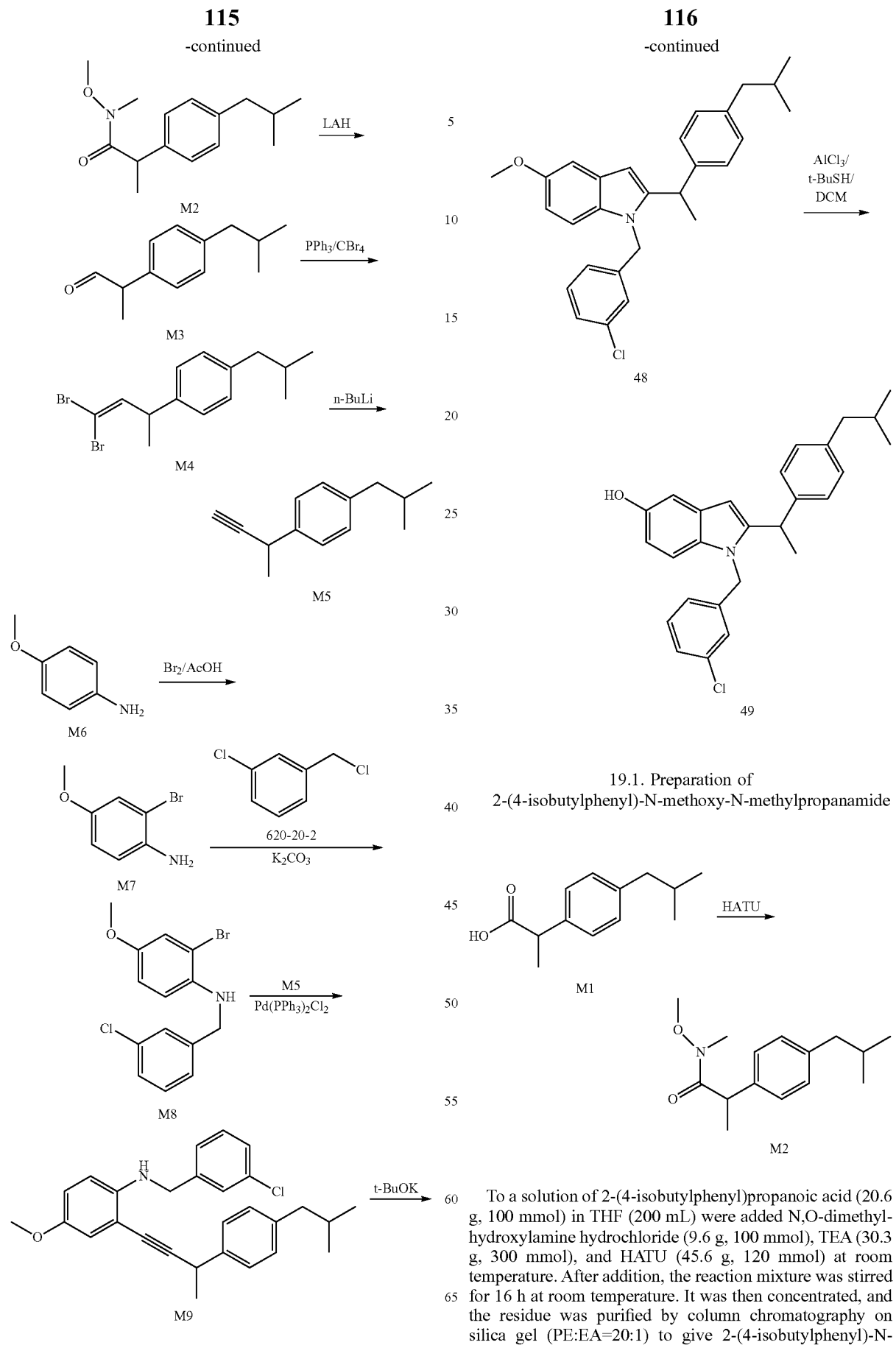

19.1. Preparation of 2-(4-isobutylphenyl)-N-methoxy-N-methylpropanamide

To a solution of 2-(4-isobutylphenyl)propanoic acid (20.6 g, 100 mmol) in THF (200 mL) were added N,O-dimethylhydroxylamine hydrochloride (9.6 g, 100 mmol), TEA (30.3 g, 300 mmol), and HATU (45.6 g, 120 mmol) at room temperature. After addition, the reaction mixture was stirred for 16 h at room temperature. It was then concentrated, and the residue was purified by column chromatography on silica gel (PE:EA=20:1) to give 2-(4-isobutylphenyl)-N- methoxy-N-methylpropanamide (24.0 g, 96 mmol, 96% yield) as colorless oil. LCMS (ESI): m/z 250.1[M+1]+.

19.2. Preparation of 2-(4-isobutylphenyl)propanal

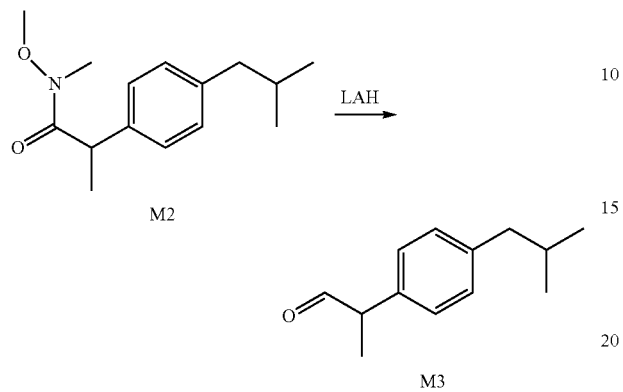

To a solution of 2-(4-isobutylphenyl)-N-methoxy-N-methylpropanamide (20.6 g, 83 mmol) in THF (200 mL) was added LAH (3.14 g, 83 mmol) at 0° C. After addition, the reaction mixture was stirred for 1.0 h at room temperature. The mixture was quenched with saturated Na$_2$SO$_4$ (aq, 6 mL), filtered and concentrated to give 2-(4-isobutylphenyl)propanal (14.8 g, 78 mmol, 94% yield) as colorless oil used as the intermediate without further purification. $^1$HNMR (400 MHz, CDCl$_3$): δ (ppm) 0.90 (d, J=8.0 Hz, 6H), 1.42 (d, J=6.8 Hz, 3H), 1.82-1.89 (m, 1H), 2.46 (d, J=7.2 Hz, 2H), 3.57-3.61 (m, 1H), 7.10-7.17 (m, 4H), 9.67 (s, 1H).

19.3. Preparation of 1-(4,4-dibromobut-3-en-2-yl)-4-isobutylbenzene

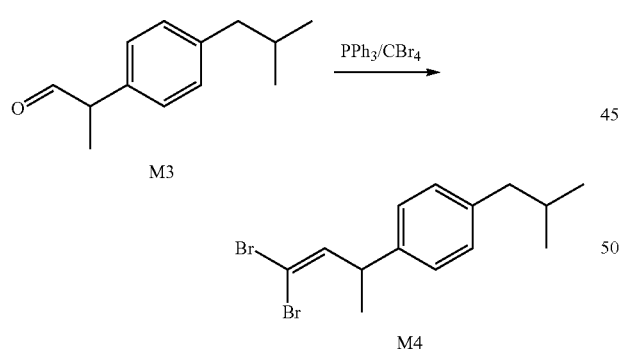

To a solution of CBr$_4$ (5.05 g, 15.2 mmol) in DCM (30 mL) was added the solution of PPh$_3$ (3.98 g, 15.2 mmol) in DCM (20 mL) at 0° C. After addition, the reaction mixture was stirred for 30 min at 0° C. The solution of 2-(4-isobutylphenyl)propanal (2.4 g, 12.6 mmol) in DCM (20 mL) was then added at 0° C. After addition, the reaction mixture was stirred at 0° C. for 2 h, and then quenched with water (50 mL). The organic layer was separated and dried over anhydrous Na$_2$SO$_4$. It was filtered and the filtrate was concentrated. The residue was purified by column chromatography on silica gel (PE:EA=30:1) to give 1-(4,4-dibromobut-3-en-2-yl)-4-isobutylbenzene (3.1 g, 9 mmol, 71% yield) as colorless oil. $^1$HNMR (400 MHz, CDCl$_3$): δ (ppm) 0.90 (d, J=6.4 Hz, 6H), 1.38 (d, J=6.8 Hz, 3H), 1.82-1.88 (m, 1H), 2.44 (d, J=7.2 Hz, 2H), 3.71-3.75 (m, 1H), 6.49 (d, J=9.6 Hz, 1H), 7.08-7.26 (m, 4H).

19.4. Preparation of 1-but-3-yn-2-yl)-4-isobutylbenzene

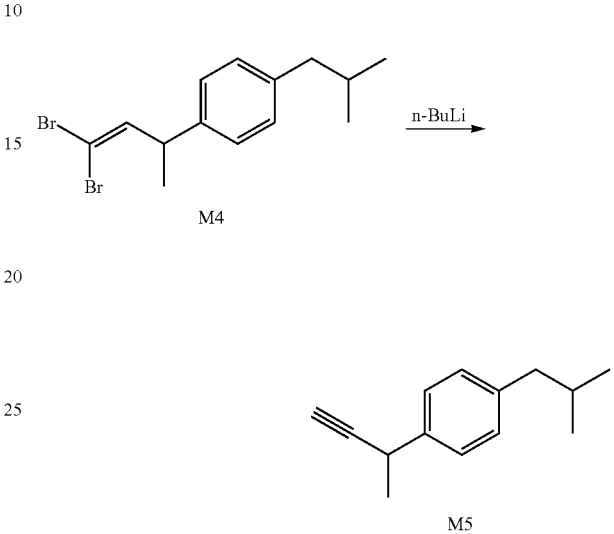

To a solution of 1-(4,4-dibromobut-3-en-2-yl)-4-isobutylbenzene (3.1 g, 9 mmol) in THF (80 mL) was added n-BuLi (22.5 mL, 36 mmol) at −70° C. After addition, the reaction mixture was stirred at −70° C. for 2 h. Then it was quenched with NH$_4$Cl (aq, 60 mL), extracted with EOAc (2×50 mL). The organic extracts were concentrated to give 1-(but-3-yn-2-yl)-4-isobutylbenzene (2.0 g, 9 mmol, 100% yield) as yellow oil. $^1$HNMR (400 MHz, CDCl$_3$): δ (ppm) 0.90 (d, J=6.8 Hz, 6H), 1.49 (d, J=7.2 Hz, 3H), 1.81-1.88 (m, 1H), 2.25 (d, J=2.4 Hz, 1H), 2.45 (d, J=7.2 Hz, 2H), 3.71-3.77 (m, 1H), 7.10 (d, J=8.0 Hz, 1H), 7.28 (d, J=8.0 Hz, 1H).

19.5. Preparation of 2-bromo-4-methoxyaniline

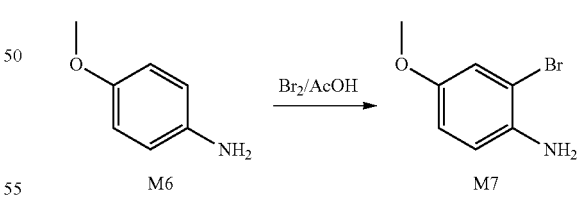

To a solution of 4-methoxyaniline (12.3 g, 100 mmol) in AcOH (100 mL) was added bromine (16 g, 100 mmol) at 0° C. After addition, the reaction mixture was stirred at 0° C. for 2 h. Then it was quenched with water (100 mL), extracted with EtOAc (2×50 mL). The organic extracts were combined and concentrated. The residue was purified by column chromatography on silica gel (PE:EA=10:1) to give 2-bromo-4-methoxyaniline (7.8 g, 39 mmol, 39% yield). $^1$H NMR (400 MHz, DMSO-d$_6$): δ (ppm) 3.65 (s, 3H), 4.82 (s, 2H), 6.74-6.78 (m, 2H), 6.97 (d, J=2.4 Hz, 1H).

19.6. Preparation of 2-bromo-N-(3-chlorobenzyl)-4-methoxyaniline

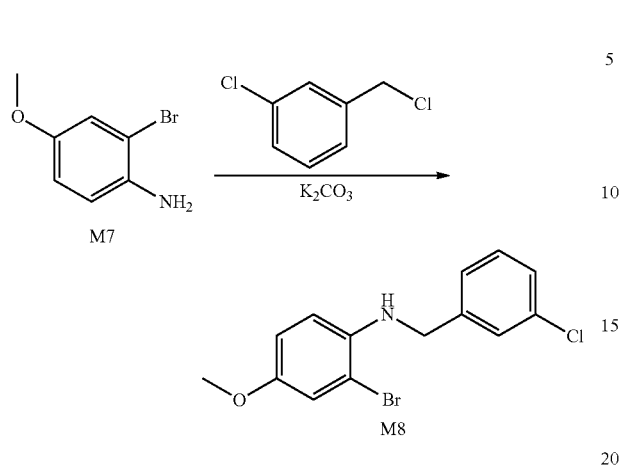

To a solution of 2-bromo-4-methoxyaniline (3.0 g, 14.9 mmol) in DMF (80 mL) were added 1-chloro-3-(chloromethyl)benzene (2.4 g, 14.9 mmol) and $K_2CO_3$ (6.15 g, 44.6 mmol) at room temperature. After addition, the reaction mixture was stirred at 80° C. for 12 h. Then it was quenched with water (100 mL), extracted with EtOAc (2×50 mL). The organic extracts were combined and concentrated. The residue was purified by column chromatography on silicagel (PE:EA=20:1) to give 2-bromo-N-(3-chlorobenzyl)-4-methoxyaniline (2.0 g, 6 mmol, 42% yield) as yellow oil. LCMS (ESI): m/z 328.1 [M+1]+.

19.7. Preparation of N-(3-chlorobenzyl)-2-(3-(4-isobutylphenyl)but-1-yn-1-yl)-4-methoxyaniline

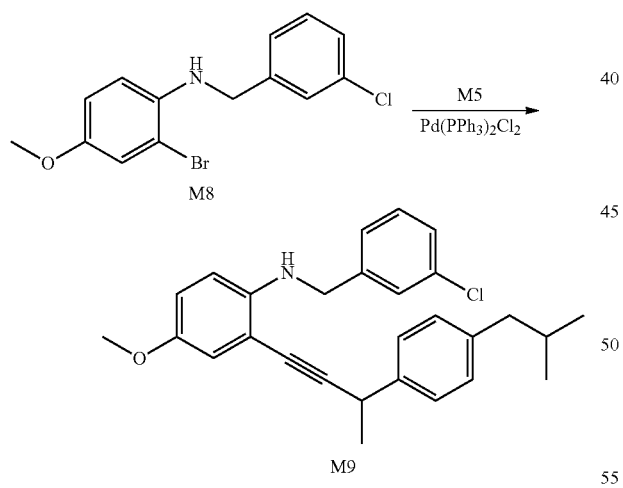

To a solution of 2-bromo-N-(3-chlorobenzyl)-4-methoxyaniline (2.0 g, 6 mmol) in THF (50 mL) was added 1-(but-3-yn-2-yl)-4-isobutylbenzene (1.14 g, 6 mmol), Pd(PPh$_3$)$_2$Cl$_2$ (500 mg), CuI (50 mg) and TEA (1.8 g, 18 mmol) at room temperature under N$_2$, after addition, the reaction mixture was stirred at 80° C. for 24 h. After cooling to room temperature, the mixture was concentrated and the residue was purified by column chromatography on silica gel (PE:EA=10:1) to give N-(3-chlorobenzyl)-2-(3-(4-isobutylphenyl)but-1-yn-1-yl)-4-methoxyaniline (1.0 g, 2.3 mmol, 38% yield) as yellow oil.

19.8. Preparation of 1-(3-chlorobenzyl)-2-(1-(4-isobutylphenyl)ethyl)-5-methoxy-1H-indole

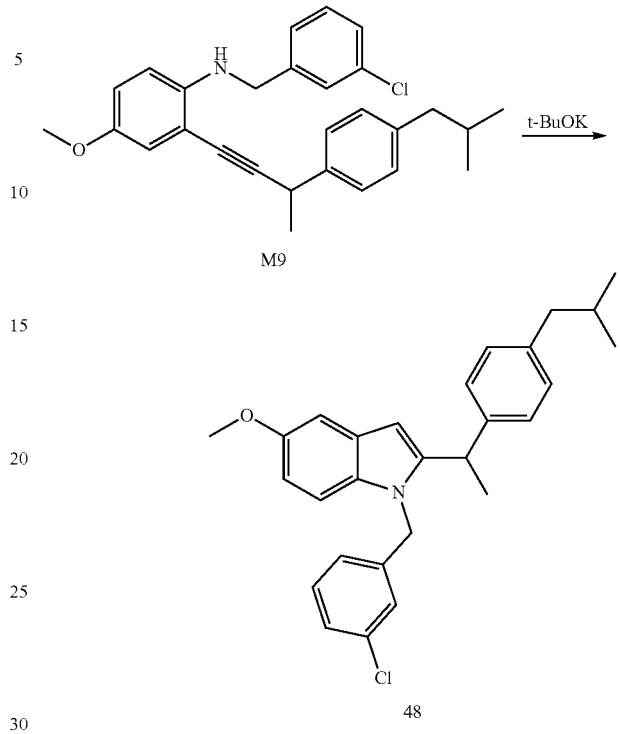

To a solution of crude N-(3-chlorobenzyl)-2-(3-(4-isobutylphenyl)but-1-yn-1-yl)-4-methoxyaniline (1.0 g, 2.3 mmol) in DME (40 mL) was added potassium 2-methylpropan-2-olate (515 mg, 4.6 mmol) at room temperature. After addition, the reaction mixture was stirred for 14 h at 50° C. It was then concentrated and the residue was purified by column chromatography on silica gel (PE:EA=20:1) to give 1-(3-chlorobenzyl)-2-(1-(4-isobutylphenyl)ethyl)-5-methoxy-1H-indole (300 mg, 0.7 mmol, 30% yield) as white solid. LCMS (ESI): m/z 432.3[M+1]+. $^1$HNMR (400 MHz, DMSO-d$_6$): δ (ppm) 0.80-0.82 (m, 6H), 1.58 (d, J=7.2 Hz, 3H), 1.71-1.78 (m, 1H), 2.34 (d, J=7.6 Hz, 2H), 3.75 (s, 3H), 4.17-4.22 (m, 1H), 5.04-5.38 (m, 2H), 6.50 (s, 1H), 6.65-6.72 (m, 3H), 6.97-6.99 (m, 2H), 7.05-7.08 (m, 3H), 7.17-7.21 (m, 2H).

18.9. Preparation of 1-(3-chlorobenzyl)-2-(1-(4-isobutylphenyl)ethyl)-1H-indol-5-ol

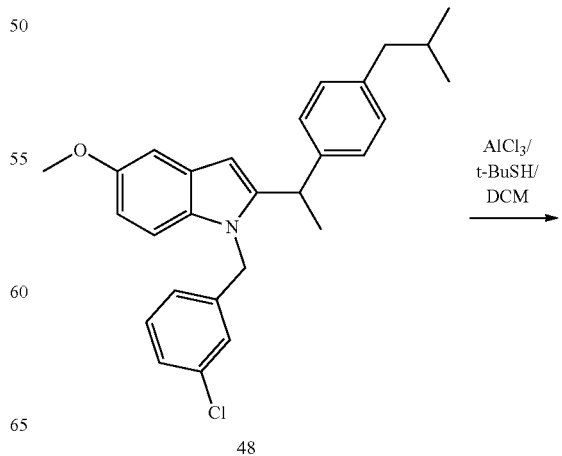

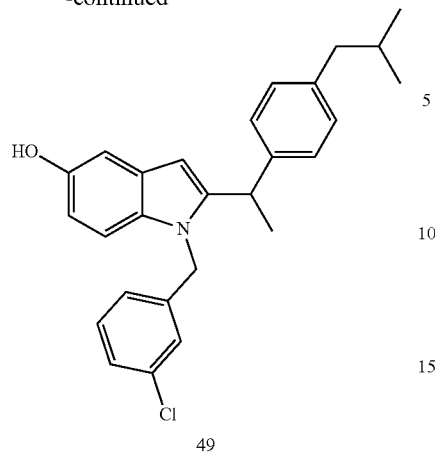

49

The 1-(3-chlorobenzyl)-2-(1-(4-isobutylphenyl)ethyl)-5-methoxy-1H-indole (300 mg, 0.7 mmol) and t-butylthiol (0.48 g, 5.3 mmol) were dissolved in CH$_2$Cl$_2$ (20 mL) and cooled to 0° C. AlCl$_3$ (0.36 mg, 2.7 mmol) was added in portions over 5 min. The mixture stirred for 2 h, and then poured into ice slowly. 1.0 N HCl (10 mL) was added and the mixture extracted with CH$_2$Cl$_2$ (2×20 mL). The organic extracts were washed with water (2×20 mL), dried (MgSO$_4$), and concentrated. The crude product was purified by column chromatography on silica gel (PE:EA=10:1) to give 1-(3-chlorobenzyl)-2-(1-(4-isobutylphenyl)ethyl)-1H-indol-5-ol (180 mg, 0.42 mmol, 60% yield) as white solid. LCMS (ESI): m/z 418.3[M+1]$^+$. $^1$HNMR (400 MHz, DMSO-d$_6$): δ (ppm) 0.80-0.83 (m, 6H), 1.52-1.57 (m, 3H), 1.71-1.78 (m, 1H), 2.34 (d, J=6.8 Hz, 2H), 4.14-4.19 (m, 1H), 5.00-5.33 (m, 2H), 6.40 (s, 1H), 6.51-6.53 (m, 1H), 6.65 (s, 1H), 6.71-6.73 (m, 1H), 6.88 (d, J=2.0 Hz, 1H), 6.93-6.99 (m, 3H), 7.07 (d, J=8.0 Hz, 2H), 7.12-7.21 (m, 2H), 8.66 (s, 1H).

Example 20. 1-(2-chlorobenzyl)-2-(4-isobutylphenyl)-1H-benzo[d]imidazol-5-ol Scheme 20. Synthetic route for example 20

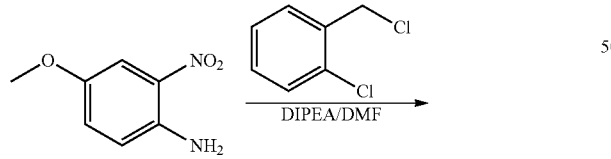

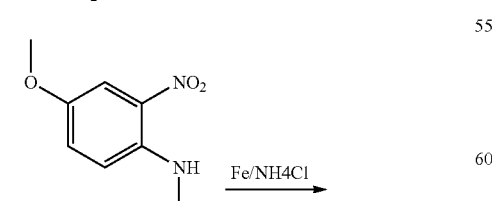

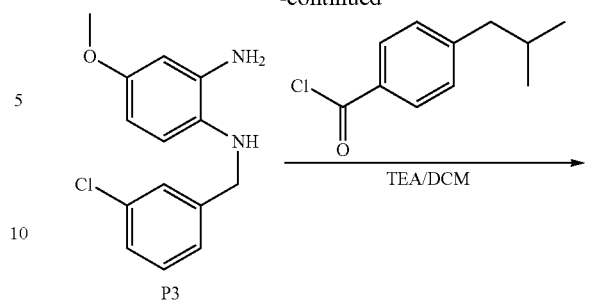

P3

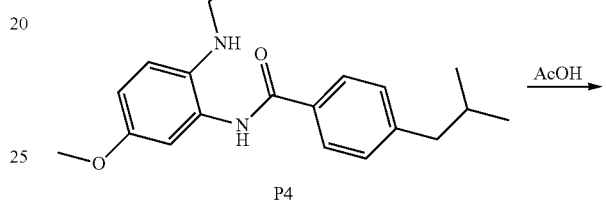

P4

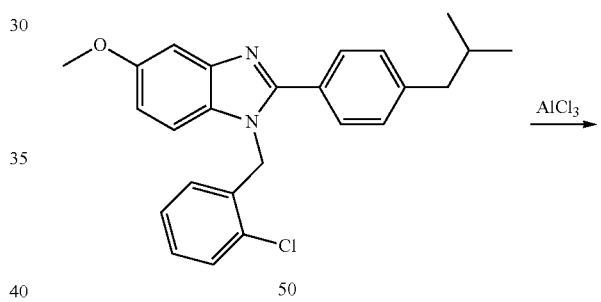

50

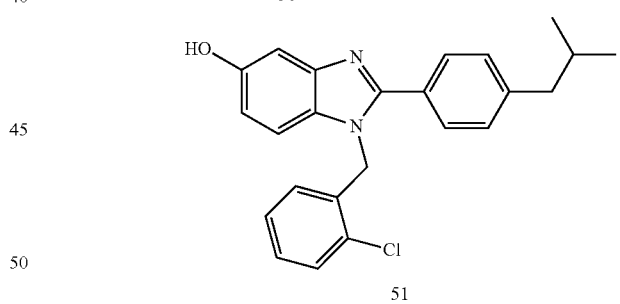

51

20.1. Preparation of N-(2-chlorobenzyl)-4-methoxy-2-nitroaniline

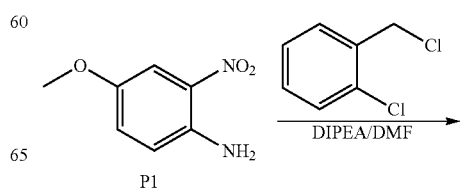

P1

123

-continued

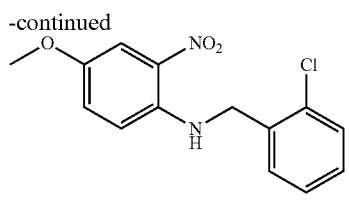

P2

To a solution of 4-methoxy-2-nitroaniline (5.04 g, 30 mmol) and 1-chloro-2-(chloromethyl)benzene (4.83 g, 30 mmol) in DMF (100 mL) was added DIPEA (1.65 mL, 90 mmol) at room temperature under $N_2$. After addition, the reaction mixture was stirred for 48 h at 140° C. After cooling to room temperature, the mixture was quenched with water (100 mL), extracted with EtOAc (3×100 mL). The organic extracts were combined and washed with brine (3×100 mL), dried over anhydrous $Na_2SO_4$ and concentrated. The residue was purified by column chromatography on silica gel (PE: EA=10:1) to give N-(2-chlorobenzyl)-4-methoxy-2-nitroaniline (4.0 g, 14 mmol, 46% yield) as red solid. $^1$HNMR (400 MHz, DMSO-$d_6$): δ (ppm) 3.74 (s, 3H), 4.67 (d, J=6.0 Hz, 2H), 6.79 (d, J=9.6 Hz 1H), 7.23 (dd, J=9.2, 2.8 Hz, 1H), 7.28-7.32 (m, 3H), 7.47-7.51 (m, 1H), 7.55 (d, J=2.8 Hz, 1H), 8.54 (t, J=6.0 Hz, 1H).

20.2. Preparation of N1-(2-chlorobenzyl)-4-methoxybenzene-1,2-diamine

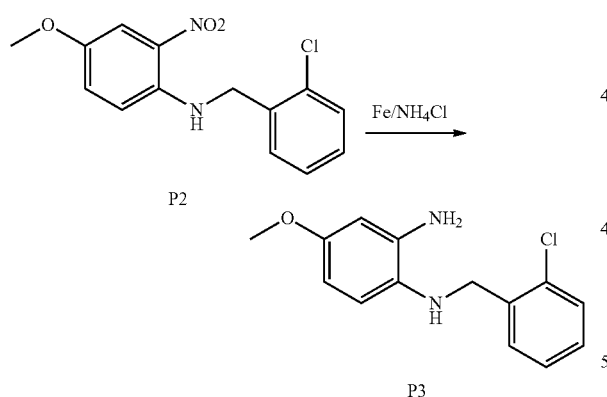

To a solution of N-(2-chlorobenzyl)-4-methoxy-2-nitroaniline (1.45 g, 5 mmol) in EtOH (50 mL) were added Fe (2.78 g, 50 mmol), $NH_4Cl$ (5.3 g, 100 mmol) and water (10 mL) at room temperature. After addition, the reaction mixture was stirred for 4 hours at 80° C. After cooling to room temperature, the reaction mixture was extracted with ethyl acetate (3×100 mL). The organic extracts were combined and washed with brine (3×100 m), dried over anhydrous $Na_2SO_4$ and concentrated to give N1-(2-chlorobenzyl)-4-methoxybenzene-1,2-diamine (1.4 g, 5 mmol, 100% yield) as brown oil used as the intermediate without further purification. LCMS (ESI): m/z 263.3 [M+1]$^+$.

124

20.3. Preparation of N-(2-((2-chlorobenzyl)amino)-5-methoxyphenyl)-4-isobutylbenzamide

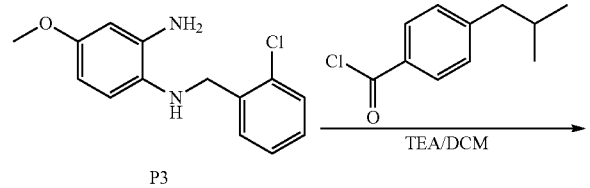

P3

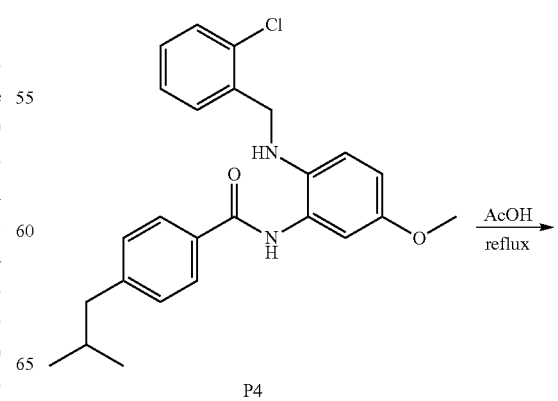

P4

To a solution of N1-(2-chlorobenzyl)-4-methoxybenzene-1,2-diamine (1.3 g, 5.0 mmol) in DCM (30 mL) were added TEA (3.5 mL, 25 mmol) and the solution of 4-isobutylbenzoyl chloride (1.0 g, 5.0 mmol) in DCM (20 mL) at 0° C. After addition, the reaction mixture was stirred for 18 h at room temperature. It was then quenched with water (50 mL) and extracted with DCM (3×50 mL). The extracts were combined, washed with brine (2×100 mL), and dried over anhydrous $Na_2SO_4$. It was filtered and the filtrate was concentrated. The residue was purified by column chromatography on silica gel (PE:EA=10:1) to give N-(2-((2-chlorobenzyl)amino)-5-methoxyphenyl)-4-isobutylbenzamide (1.3 g, 3.1 mmol, 62% yield) as yellow solid. LCMS (ESI): m/z 423.3[M+1]$^+$.

20.4. Preparation of 1-(2-chlorobenzyl)-2-(4-isobutylphenyl)-5-methoxy-1H-benzo[d]imidazole

P4

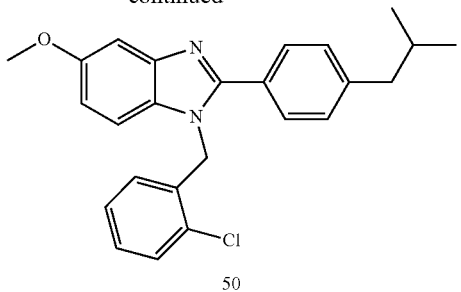

50

A mixture of N-(2-((2-chlorobenzyl)amino)-5-methoxyphenyl)-4-isobutylbenzamide (1.2 g, 2.8 mmol) in AcOH was stirred for 16 h at 120° C. After cooling to room temperature, the mixture was concentrated, and the residue was purified by column chromatography on silica gel (PE:EA=15:1) to give 1-(2-chlorobenzyl)-2-(4-isobutylphenyl)-5-methoxy-1H-benzo[d]imidazole (0.8 g, 2.0 mmol, 72% yield). LCMS (ESI): m/z 405.2[M+1]$^+$. $^1$HNMR (400 MHz, CDCl$_3$): δ (ppm) 0.95 (d, J=6.8 Hz, 6H), 1.92-1.96 (m, 1H), 2.57 (d, J=7.2 Hz, 2H), 6.95 (s, 3H), 5.63 (s, 2H), 6.81 (d, J=7.6 Hz, 1H), 7.06-7.09 (m, 1H), 7.18 (d, J=8.8 Hz, 1H), 7.25-7.27 (m, 1H), 7.37-7.40 (m, 3H), 7.55 (d, J=7.2 Hz, 1H), 7.64-7.68 (m, 3H).

20.5. Preparation of 1-(2-chlorobenzyl)-2-(4-isobutylphenyl)-1H-benzo[d]imidazol-5-ol

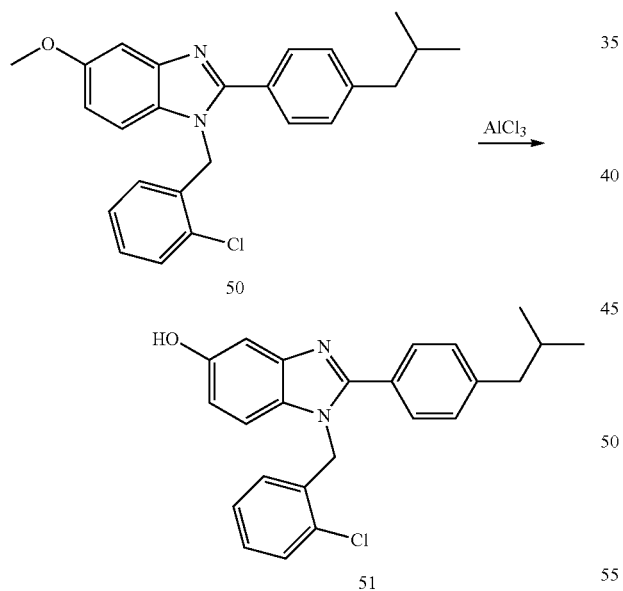

A mixture of 1-(2-chlorobenzyl)-2-(4-isobutylphenyl)-5-methoxy-1H-benzo[d]imidazole (600 mg, 1.5 mmol) and t-butylthiol (1.3 g, 15 mmol) in CH$_2$Cl$_2$ (40 mL) was cooled to 0° C. AlCl$_3$ (959 mg, 7.19 mmol) was added in portions over 5 min. After addition, the reaction mixture was stirred for 2 h, and then poured into the ice slowly. 1.0 N HCl (10 mL) was added and the mixture was extracted with CH$_2$Cl$_2$ (2×50 mL). The organic extracts were combined and washed with water (2×50 mL), dried (MgSO$_4$), and concentrated. The crude product was purified by column chromatography on silica gel (PE:EA=10:1) to give 1-(2-chlorobenzyl)-2-(4-isobutylphenyl)-1H-benzo[d]imidazol-5-ol (400 mg, 1.0 mmol, 69% yield) as white solid. LCMS (ESI): m/z 391.3 [M+1]$^+$. $^1$HNMR (400 MHz, DMSO-d6): δ (ppm) 0.86 (d, J=6.4 Hz, 6H), 1.84-1.90 (m, 1H), 2.53 (d, J=6.4 Hz, 2H), 5.62 (s, 2H), 6.92-6.89 (m, 2H), 7.10 (d, J=2.4 Hz, 1H), 7.23-7.27 (m, 1H), 7.32-7.37 (m, 4H), 7.51 (d, J=7.2 Hz, 1H), 7.59 (d, J=8.4 Hz, 2H).

Example 21. 1-(2-chlorobenzyl)-2-(1-(4-isobutylphenyl)ethyl)-1H-benzo[d]imidazole-5-carboxylic Acid Scheme 21. Synthetic route for example 21

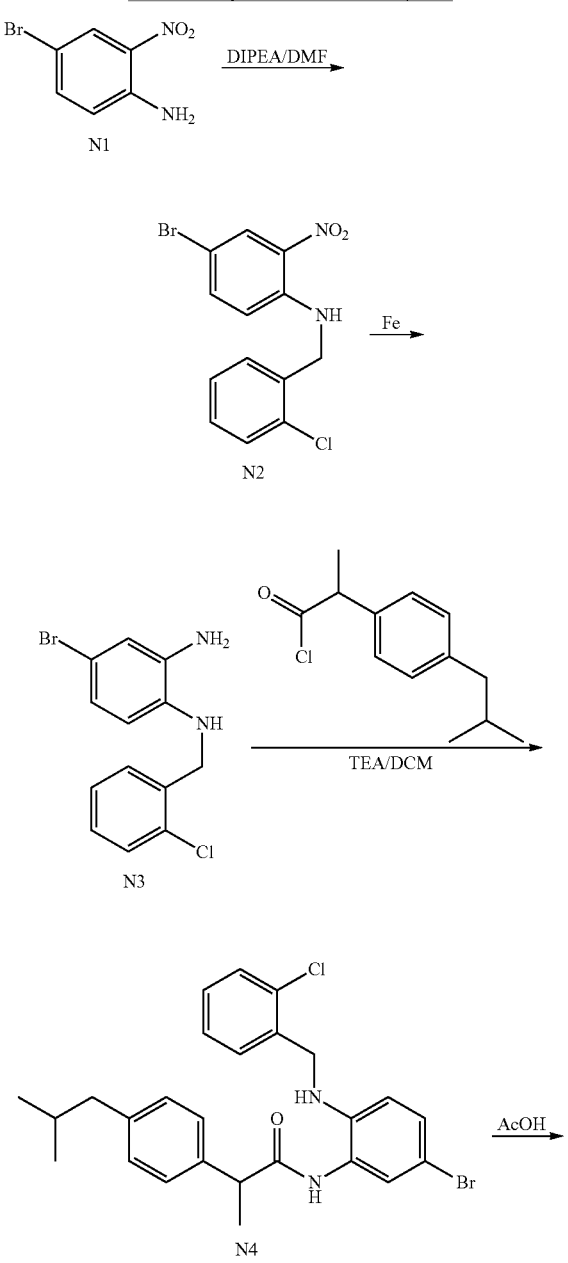

-continued

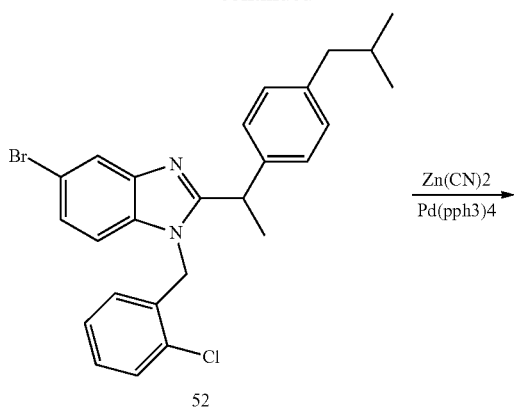

52

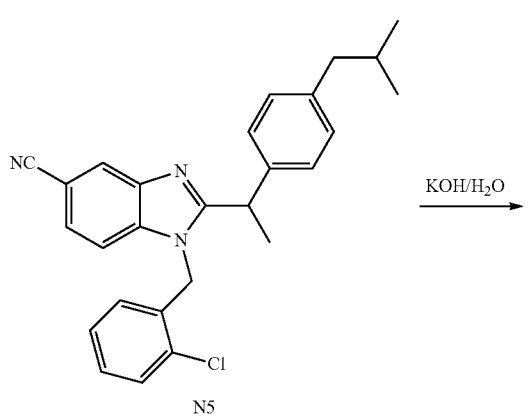

N5

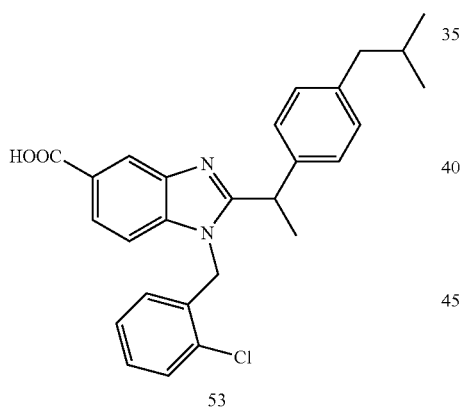

53

21.1. Preparation of
4-bromo-N-(2-chlorobenzyl)-2-nitroaniline

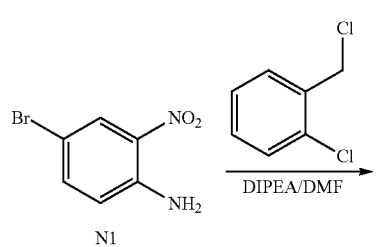

-continued

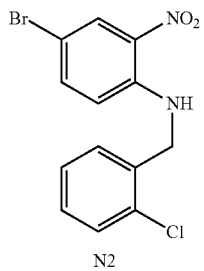

N2

To a solution of 4-bromo-2-nitroaniline (5.0 g, 23 mmol) and 1-chloro-2-(chloromethyl)benzene (3.7 g, 23 mmol) in DMF (100 mL) was added DIPEA (1.65 mL, 90 mmol) at room temperature under $N_2$. After addition, the reaction mixture was stirred for 48 h at 140° C. After cooling to room temperature, the mixture was quenched with water (100 mL) and extracted with EtOA (3×100 mL). The organic extracts were combined and washed with brine (3×100 mL), dried over anhydrous $Na_2SO_4$ and concentrated. The residue was purified by column chromatography on silica gel (PE:EA=10:1) to give 4-bromo-N-(2-chlorobenzyl)-2-nitroaniline (2.7 g, 8 mmol, 35% yield) as red solid. LCMS (ESI): m/z 343[M+1]+.

21.2. Preparation of
4-bromo-N1-(2-chlorobenzyl)benzene-1,2-diamine

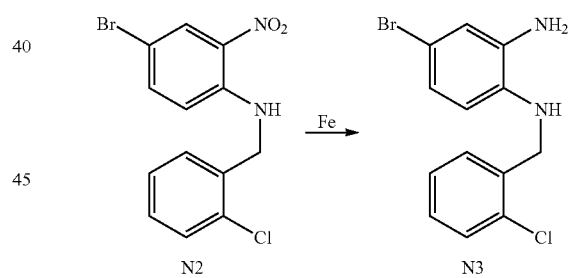

N2    N3

To a solution of 4-bromo-N-(2-chlorobenzyl)-2-nitroaniline (2.7 g, 7.9 mmol) in EtOH (50 mL) were added Fe (4.43 g, 79 mmol), $NH_4Cl$ (8.5 g, 158 mmol) and water (10 mL) at room temperature. After addition, the reaction mixture was stirred for 4 h at 80° C. After cooling to room temperature, the mixture was extracted with EtOAc (3×100 mL). The organic extracts were combined and washed with brine (3×100 mL), dried over $Na_2SO_4$ and concentrated. The residue was purified by column chromatography on silica gel (PE:EA=3:1) to give 4-bromo-N1-(2-chlorobenzyl) benzene-1, 2-diamine (0.7 g, 2.2 mmol, 28% yield) as brown oil. LCMS (ESI): m/z 313.3[M+1]+.

21.3. Preparation of N-(5-bromo-2-((2-chlorobenzyl)amino)phenyl)-2-(4-isobutylphenyl) Propanamide

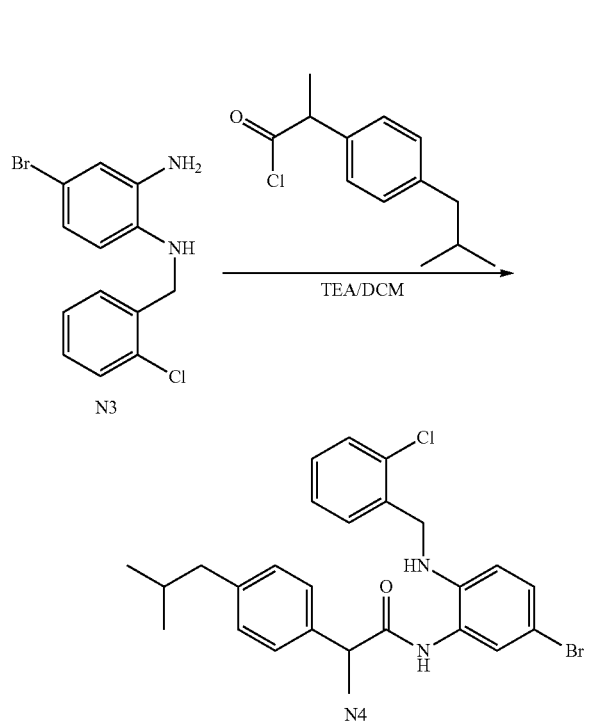

To a solution of 4-bromo-N1-(2-chlorobenzyl) benzene-1,2-diamine 0.7 g, 2.3 mmol) in DCM (30 mL) were added TEA (3.7 mL, 26.5 mmol) and the solution of 2-(4-isobutylphenyl)propanoyl chloride (0.6 g, 2.25 mmol) in DCM (20 mL) at 0° C. After addition, the reaction mixture was stirred for 18 h at room temperature. The mixture was quenched with water (50 mL) and extracted with DCM (3×50 mL). The organic extracts were washed with brine (2×100 mL), dried over anhydrous $Na_2SO_4$ and concentrated. The residue was purified by column chromatography on silica gel (PE:EA=5:1) to give N-(5-bromo-2-((2-chlorobenzyl)amino)phenyl)-2-(4-isobutylphenyl)propanamide (720 mg, 1.45 mmol, 66% yield). LCMS (ESI): m/z 501.2 [M+1]$^+$.

21.4. Preparation of 5-bromo-1-(2-chlorobenzyl)-2-(1-(4-isobutylphenyl)ethyl)-1H-benzo[d]imidazole

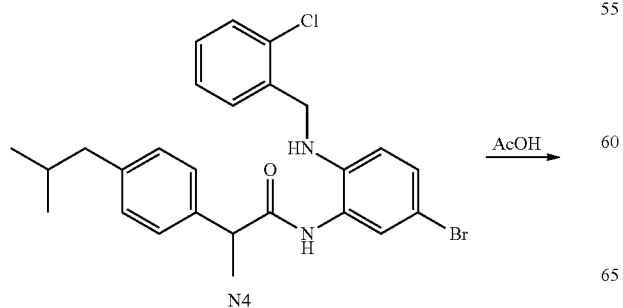

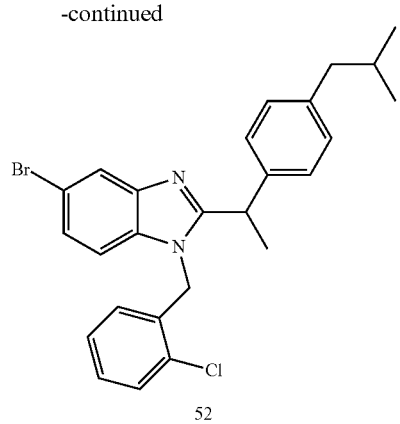

A mixture of N-(5-bromo-2-((2-chlorobenzyl)amino)phenyl)-2-(4-isobutylphenyl) propanamide (0.7 g, 1.4 mmol) in AcOH (20 mL) was stirred for 16 h at 120° C. After cooling to room temperature, the mixture was concentrated, and the residue was purified by column chromatography on silica gel (PE:EA=10:1) to give 5-bromo-1-(2-chlorobenzyl)-2-(1-(4-isobutylphenyl)ethyl)-1H-benzo[d]imidazole (0.6 g, 1.3 mmol, 93% yield). LCMS (ESI): m/z 483.2[M+1]$^+$. $^1$H NMR (400 MHz, CDCl$_3$): δ (ppm) 0.84 (d, J=6.4 Hz, 6H), 1.72-1.79 (m, 1H), 1.88 (d, J=6.8 Hz, 3H), 2.35 (d, J=7.2 Hz, 2H), 4.33-4.38 (m, 1H), 5.32 (s, 2H), 6.14 (d, J=7.2 Hz, 1H), 6.94-7.03 (m, 3H), 7.11 (d, J=7.6 Hz, 2H), 7.18-7.22 (m, 1H), 7.39-7.43 (m, 2H), 8.20 (s, 1H).

21.5. Preparation of 1-(2-chlorobenzyl)-2-(1-(4-isobutylphenyl)ethyl)-1H-benzo[d]imidazole-5-carbonitrile

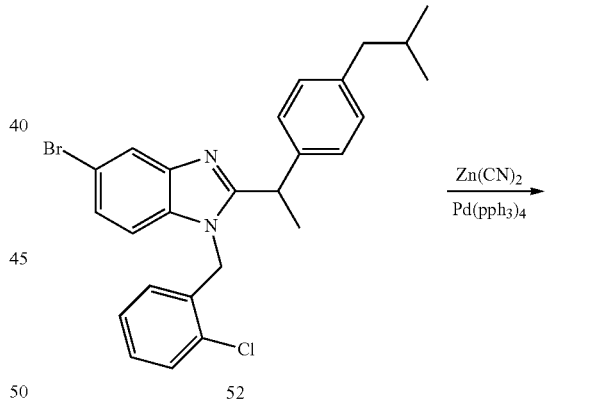

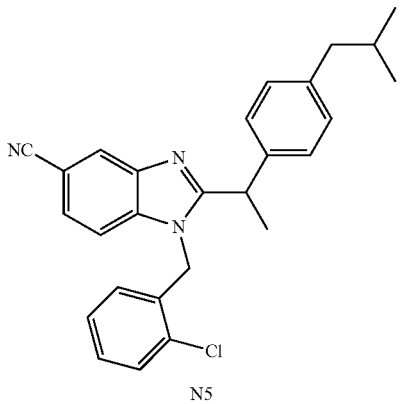

To a solution of 5-bromo-1-(2-chlorobenzyl)-2-(1-(4-isobutylphenyl)ethyl)-1H-benzo[d]imidazole (520 mg, 1.08 mmol) in DMF (20 mL) were added Pd(PPh$_3$)$_4$ (122 mg, 0.1 mmol) and Zn(CN)$_2$ (127 mg, 1.08 mmol) at room temperature under N2. After addition, the reaction mixture was stirred for 16 hours at 80° C. After cooling to room temperature, the mixture was concentrated and the residue was purified by column chromatography on silica gel (PE:EA=5:1) to give 1-(2-chlorobenzyl)-2-(1-(4-isobutylphenyl)ethyl)-1H-benzo[d]imidazole-5-carbonitrile (280 mg, 0.7 mmol, 70% yield). LCMS (ESI): m/z 428.3[M+1]$^+$. $^1$HNMR (400 MHz, CDCl$_3$): δ (ppm) 0.84 (d, J=6.4 Hz, 6H), 1.72-1.79 (m, 1H), 1.84 (d, J=7.2 Hz, 3H), 2.35 (d, J=7.2 Hz, 2H), 4.22-4.27 (m, 1H), 5.30 (s, 2H), 6.11 (d, J=7.2 Hz, 1H), 6.94-7.00 (m, 3H), 7.06-7.08 (m, 2H), 7.16-7.21 (m, 2H), 7.39-7.41 (m, 1H), 7.48-7.50 (m, 1H), 8.27 (s, 1H).

21.6. Preparation of 1-(2-chlorobenzyl)-2-(1-(4-isobutylphenyl)ethyl)-1H-benzo[d]imidazole-5-carboxylic Acid

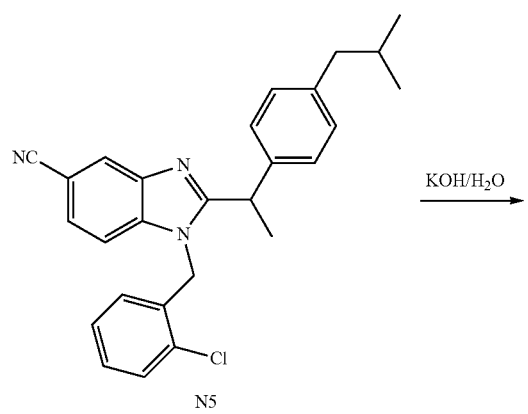

N5

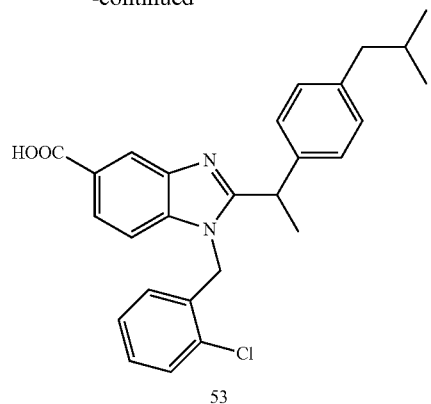

53

To a solution of 1-(2-chlorobenzyl)-2-(1-(4-isobutylphenyl)ethyl)-1H-benzo[d]imidazole-5-carbonitrile (200 mg, 0.5 mmol) in MeOH (3 mL) were added water (10 mL) and KOH (263 mg, 5 mmol). The mixture was heated to 115° C. for 24 h and the organic solvente was evaporated. The residue was acidified by 1.0 N HCl (aq) to pH=4. The resulting mixture was extracted with DCM (2×10 mL). The organic extracts were combined and washed with brine (2×10 mL), dried over anhydrous Na$_2$SO$_4$ and concentrated. The residue was purified by pre-HPLC to give 1-(2-chlorobenzyl)-2-(1-(4-isobutylphenyl)ethyl)-1H-benzo[d]imidazole-5-carboxylic acid (71 mg, 0.16 mmol, 32% yield). LCMS (ESI): m/z 447.2[M+1]$^+$. $^1$HNMR (400 MHz, DMSO-d$_6$): δ (ppm) 0.78 (d, J=7.2 Hz, 6H), 1.68-1.72 (m, 4H), 2.30 (d, J=6.8 Hz, 2H), 4.45-4.50 (m, 1H), 5.38-5.62 (m, 2H), 6.10 (d, J=7.6 Hz, 1H), 6.94-7.0 (m, 3H), 7.10 (d, J=8.0 Hz, 1H), 7.11-7.23 (m, 1H), 7.37 (d, J=7.2 Hz, 1H), 7.44 (d, J=7.2 Hz, 1H), 7.80-7.83 (m, 1H), 8.31 (s, 1H), 12.98 (s, 1H).

Example 22. 1-(2-chlorobenzyl)-3-(4-isobutylphenyl)-2-methyl-1H-indol-5-ol

Scheme 22. Synthetic route for example 22

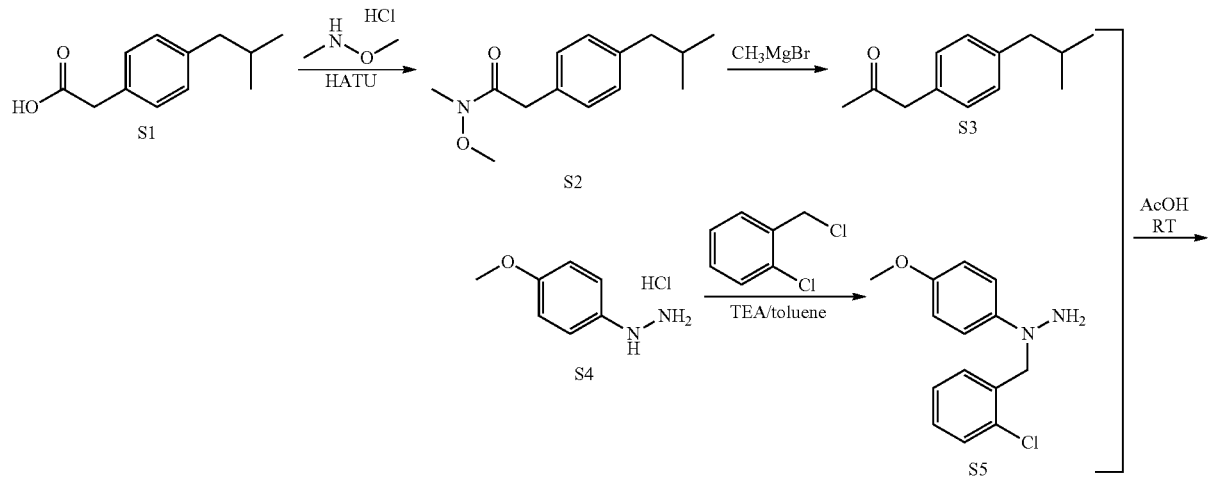

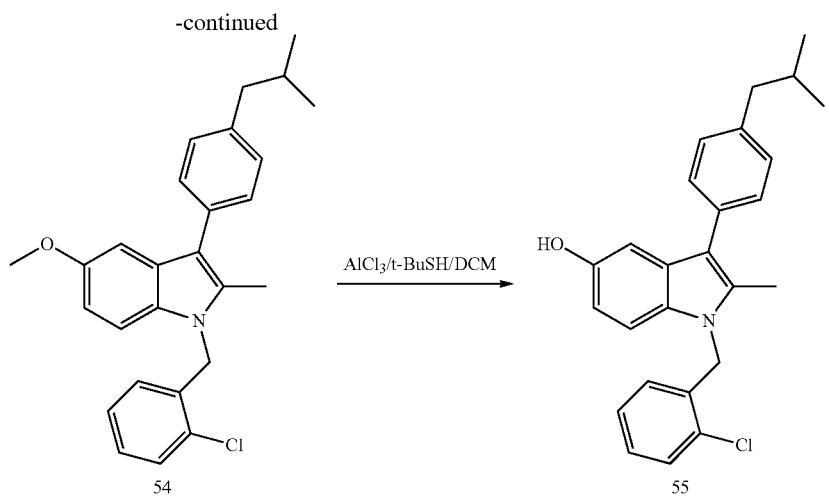

22.1. Preparation of 2-(4-isobutylphenyl)-N-methoxy-N-methylacetamide

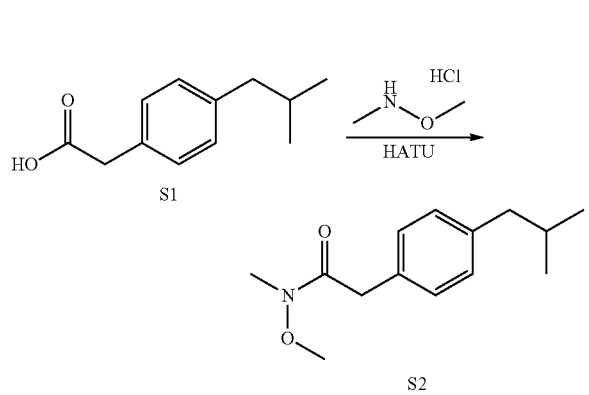

To a solution of 2-(4-isobutylphenyl)acetic acid (1.5 g, 7.8 mmol) in THF (50 mL) was added TEA (3.94 g, 39 mmol), N,O-dimethylhydroxylamine hydrochloride (0.94 g, 9.4 mmol) and HATU (4.45 g, 11.7 mmol) at room temperature. After addition, the reaction mixture was stirred for 18 h at room temperature. The mixture was concentrated and the residue was purified by column chromatography on silica gel (PE:EA=15:1) to give 2-(4-isobutylphenyl)-N-methoxy-N-methylacetamide (1.9 g, 8 mmol, 100% yield) as colorless oil. $^1$HNMR (400 MHz, CDCl$_3$): δ (ppm) 0.88 (d, J=6.4 Hz, 6H), 1.76-1.85 (m, 1H), 2.44 (d, J=7.2 Hz, 2H), 3.19 (s, 3H), 3.59 (s, 3H), 3.74 (s, 2H), 7.09 (d, J=8.0 Hz, 2H), 7.19 (d, J=8.0 Hz, 2H).

22.2. Preparation of 1-(4-isobutylphenyl)propan-2-one

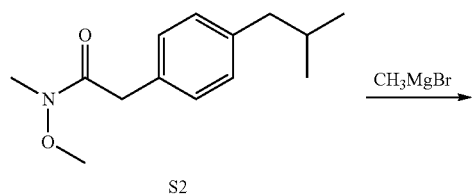

To a solution of 2-(4-isobutylphenyl)-N-methoxy-N-methylacetamide (1.9 g, 8 mmol) in THF (50 mL) was added methylmagnesium bromide (12 mL, 12 mmol) at 0° C. After addition, the reaction mixture was stirred for 1 h at room temperature. It was quenched with saturated NH$_4$Cl (aq, 50 mL) and extracted with EtOAc (3×50 mL). The organic extracts were washed with brine (2×50 mL), dried over anhydrous Na$_2$SO$_4$ and concentrated. The residue was purified by column chromatography on silica gel (PE:EA=10:1) to give 1-(4-isobutyl phenyl)propan-2-one (1.1 g, 5.8 mmol, 73% yield) as colorless oil. $^1$HNMR (400 MHz, CDCl$_3$): δ (ppm) 0.89 (d, J=6.4 Hz, 6H), 1.82-1.88 (m, 1H), 2.14 (s, 3H), 2.45 (d, J=7.2 Hz 2H), 3.66 (s, 2H), 7.11 (s, 4H).

22.3. Preparation of 1-(2-chlorobenzyl)-1-(4-methoxyphenyl)hydrazine

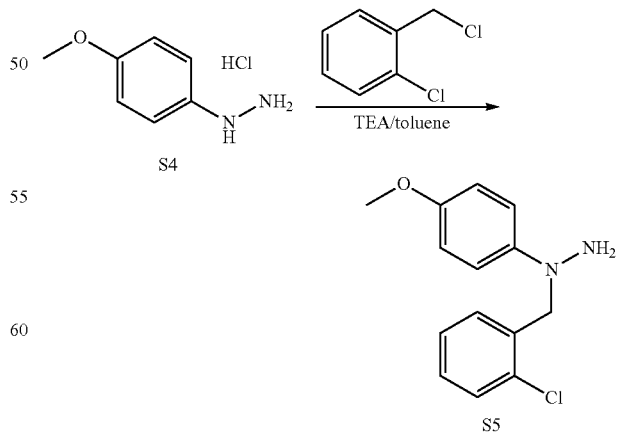

To a suspension of (4-methoxyphenyl)hydrazine hydrochloride (8.75 g, 50 mmol) and 1-chloro-2-(chloromethyl)

benzene (8.0 g, 50 mmol) in toluene (100 mL) was added triethylamine (13.78 mL, 100 mmol) and (n-Bu)₄NI (0.55 g, 1.5 mmol) at room temperature. After addition, the temperature was allowed to slowly increase to 120° C., The reaction mixture was stirred for 4 h at 120° C. After cooling to room temperature, the mixture was concentrated and the residue was purified by column chromatography on silica gel (PE: EA=5:1) to give 1-(2-chlorobenzyl)-1-(4-methoxyphenyl) hydrazine (10.0 g, 38.5 mmol, 77% yield) as brown solid. LCMS (ESI): m/z 263.3[M+1]⁺.

22.4. Preparation of 1-(2-chlorobenzyl)-3-(4-isobutylphenyl)-5-methoxy-2-methyl-1H-indole

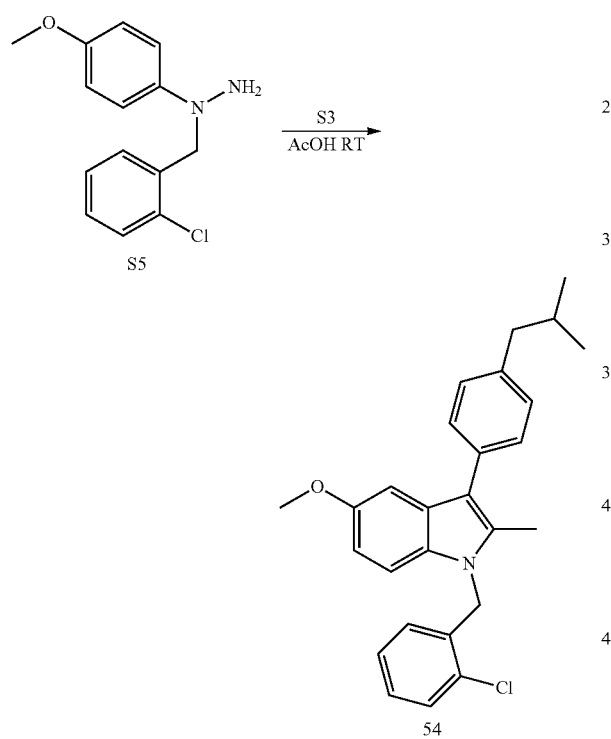

To a mixture of 1-(2-chlorobenzyl)-1-(4-methoxyphenyl) hydrazine (1.5 g, 5.8 mmol) in toluene (40 mL) were added 1-(4-isobutyl phenyl)propan-2-one (1.1 g, 5.8 mmol) and AcOH (20 mL). After addition, the reaction mixture was stirred for 24 h at room temperature. The mixture was concentrated and the residue was purified by column chromatography on silica gel (PE:EA=10:1) to give 1-(2-chlorobenzyl)-3-(4-isobutylphenyl)-5-methoxy-2-methyl-1H-indole (2.1 g, 5 mmol, 86% yield) as white solid. LCMS (ESI): m/z 418.4[M+1]⁺. ¹HNMR (400 MHz, CDCl₃): δ (ppm) 0.97 (d, J=7.2 Hz, 6H), 1.91-1.97 (m, 1H), 2.38 (s, 3H), 2.54 (d, J=7.2 Hz, 2H), 3.83 (s, 3H), 5.39 (s, 2H), 6.34 (d, J=7.6 Hz, 1H), 6.79-6.82 (m, 1H), 7.03-7.09 (m, 2H), 7.16-7.20 (m, 2H), 7.25-7.27 (m, 2H), 7.40-7.45 (m, 3H).

22.5. Preparation of 1-(2-chlorobenzyl)-3-(4-isobutylphenyl)-2-methyl-1H-indol-5-ol

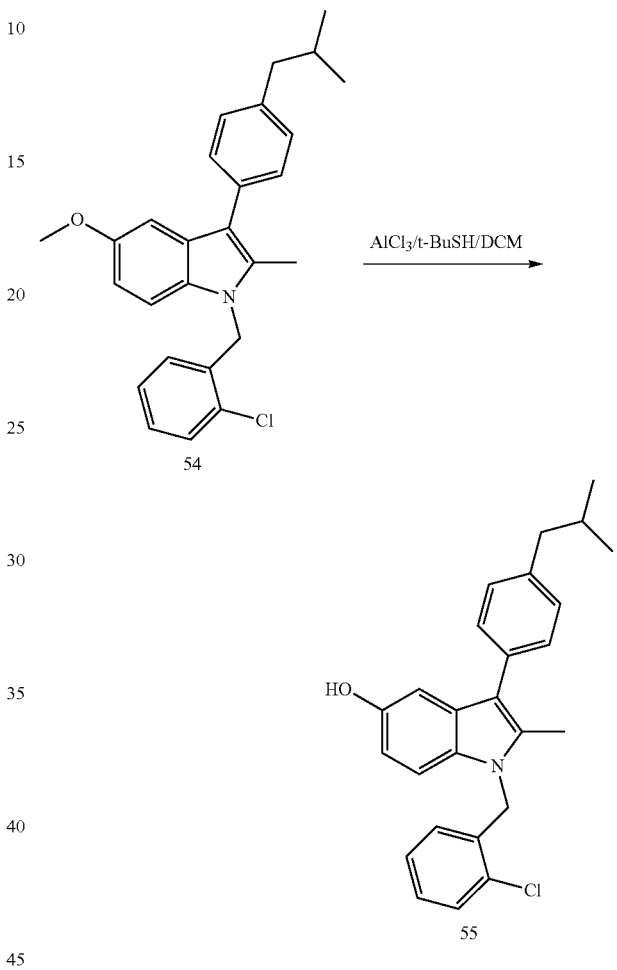

A solution of 1-(2-chlorobenzyl)-3-(4-isobutylphenyl)-5-methoxy-2-methyl-1H-indole (600 mg, 1.44 mmol) and t-butylthiol (1.3 g, 14.4 mmol) in CH₂Cl₂ (40 mL) was cooled to 0° C. AlCl₃ (959 mg, 7.19 mmol) was added in portions over 5 min. The reaction mixture stirred for 2 h, and then poured into the ice slowly. 1.0 N HCl (aq, 10 mL) was added and the mixture was extracted with DCM (2×50 mL). The organic extracts were washed with water (2×50 mL), dried over anhydrous MgSO₄, and concentrated. The crude product was purified by column chromatography on silica gel (PE:EA=3:1) to give 1-(2-chlorobenzyl)-3-(4-isobutylphenyl)-2-methyl-1H-indol-5-ol (400 mg, 1 mmol, 69% yield) as white solid. LCMS (ESI): m/z 404.3[M+1]⁺. ¹HNMR (400 MHz, CDCl₃): δ (ppm) 0.96 (d, J=6.8 Hz, 6H), 1.91-1.95 (m, 1H), 2.38 (s, 3H), 2.53 (d, J=7.2 Hz, 2H), 5.38 (s, 2H), 6.34 (d, J=7.6 Hz, 1H), 6.70-6.72 (m, 1H), 7.02-7.07 (m, 2H), 7.14-7.20 (m, 2H), 7.23-7.25 (m, 2H), 7.40-7.42 (m, 3H).

137

Example 23. 1-(2-chlorobenzyl)-3-(4-isobutylphenyl)-5-methoxy-1H-indole

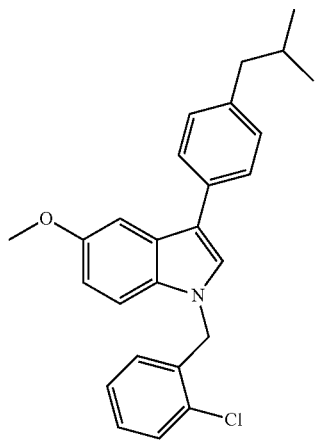

56

The compound 56 was prepared by the method similar to example 22. LCMS (ESI): m/z 404.3[M+1]$^+$. $^1$HNMR (400 MHz, DMSO-d$_6$): δ (ppm) 0.90 (d, J=6.4, 6H), 1.89-1.84 (m, 1H), 2.47 (d, J=7.2, 2H), 3.79 (s, 3H), 5.51 (s, 2H), 6.74 (d, J=6.8, 1H), 6.84-6.81 (m, 1H), 7.24-7.21 (m, 3H), 7.35-7.28 (m, 3H), 7.51 (d, J=7.6 Hz, 1H), 7.57 (d, J=8.0 Hz, 2H), 7.70 (s, 1H).

Example 24. 3-(1-(2-chlorobenzyl)-5-methoxy-1H-benzo[d]imidazol-2-yl)-2,2-dimethyl Propanoic Acid

138

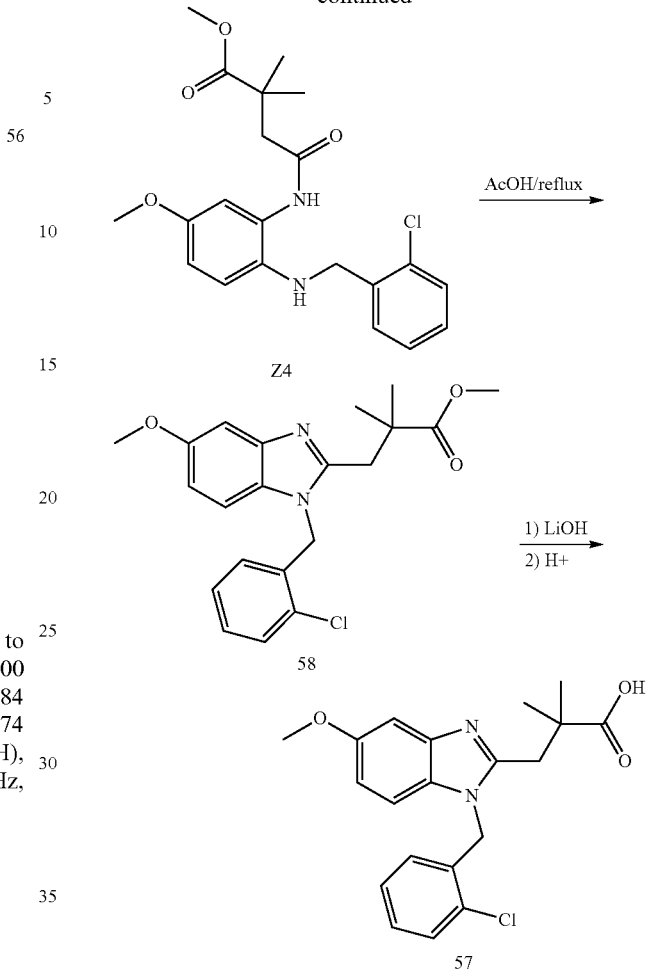

24.1. Preparation of dimethyl 2,2-dimethylsuccinate

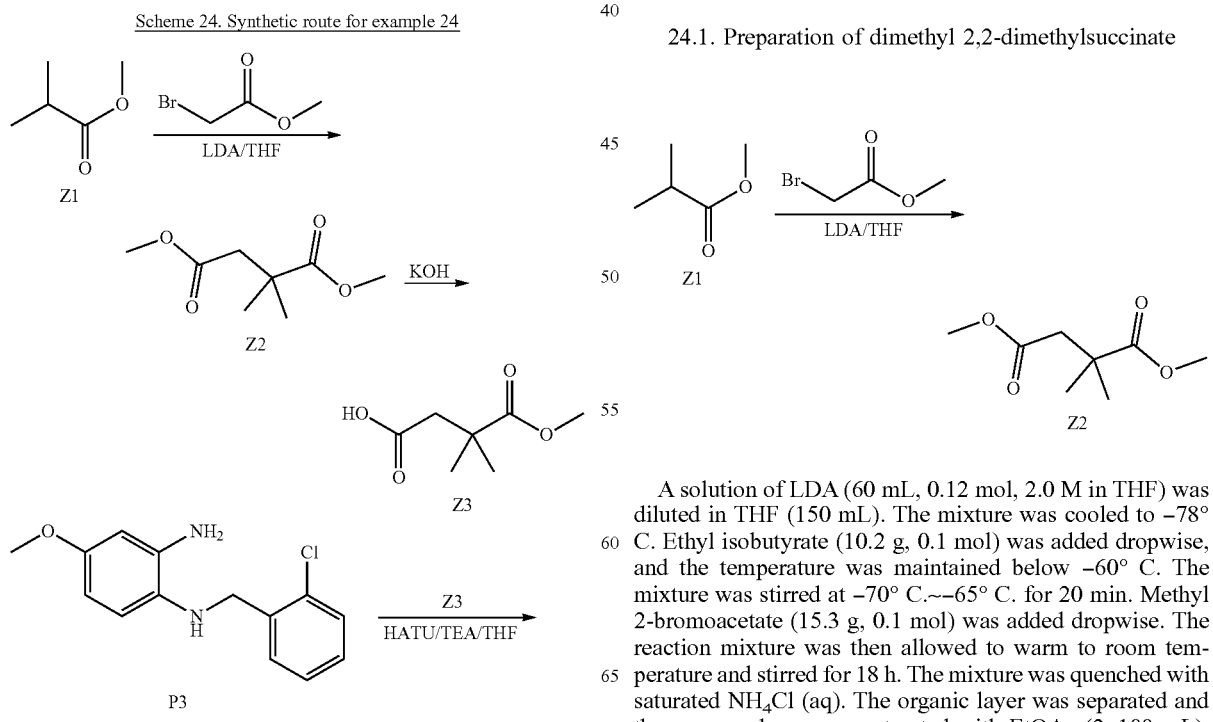

A solution of LDA (60 mL, 0.12 mol, 2.0 M in THF) was diluted in THF (150 mL). The mixture was cooled to −78° C. Ethyl isobutyrate (10.2 g, 0.1 mol) was added dropwise, and the temperature was maintained below −60° C. The mixture was stirred at −70° C.~−65° C. for 20 min. Methyl 2-bromoacetate (15.3 g, 0.1 mol) was added dropwise. The reaction mixture was then allowed to warm to room temperature and stirred for 18 h. The mixture was quenched with saturated NH$_4$Cl (aq). The organic layer was separated and the aqueous layer was extracted with EtOAc (2×100 mL).

The organic layers were combined and dried over anhydrous Na₂SO₄, filtered and concentrated to give dimethyl 2,2-dimethylsuccinate (10 g, 57 mmol) as brown oil used as the intermediate without further purification. ¹HNMR (400 MHz, CDCl₃): δ (ppm) 1.27 (s, 6H), 2.60 (s, 2H), 3.66 (s, 3H), 3.72 (s, 3H).

24.2. Preparation of 4-methoxy-3,3-dimethyl-4-oxobutanoic Acid

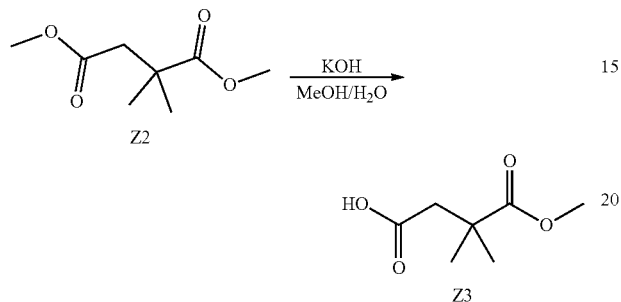

To a solution of dimethyl 2,2-dimethylsuccinate (1.74 g, 10 mmol) in MeOH (20 mL) were added KOH (0.56 g, 10 mmol) and water (10 mL) at room temperature. After addition, the reaction mixture was stirred for 2 h at room temperature. It was quenched with 1.0 N HCl (aq, 30 mL), extracted with EtOAc (3×50 mL). The organic extracts were washed with brine (2×100 mL), dried over Na₂SO₄ and concentrated to give 4-methoxy-3,3-dimethyl-4-oxobutanoic acid (1.6 g, 10 mmol,) as brown oil used as the intermediate without further purification.

24.3. Preparation of Methyl 4-((2-((2-chlorobenzyl) amino)-5-methoxyphenyl) amino)-2,2-dimethyl-4-oxobutanoate

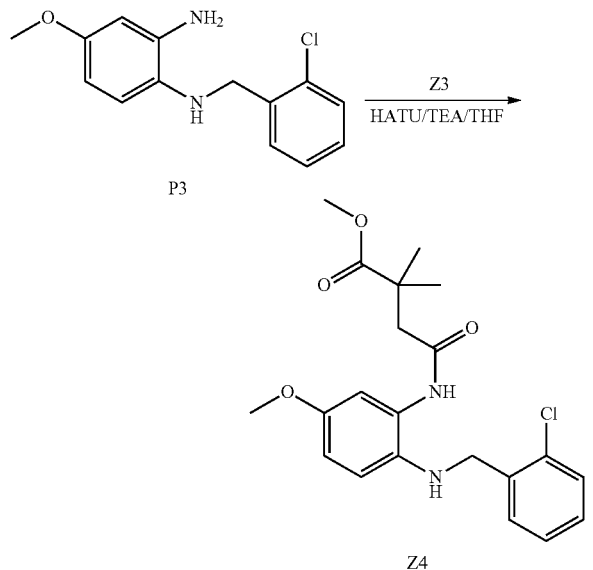

To a solution of N1-(2-chlorobenzyl)-4-methoxybenzene-1,2-diamine (2.62 g, 10 mmol) in THF (50 mL) were added 4-methoxy-3,3-dimethyl-4-oxobutanoic acid (1.6 g, 10 mmol), TEA (4.2 mL, 30 mmol) and HATU (5.7 g, 15 mmol) at room temperature. After addition, the reaction mixture was stirred for 24 h at room temperature. The mixture was concentrated, and the residue was purified by column chromatography on silica gel (PE:EA=10:1) to give methyl 4-((2-((2-chlorobenzyl) amino)-5-methoxyphenyl) amino)-2,2-dimethyl-4-oxobutanoate (1.2 g, 3 mmol, 30% yield over three steps) as brown solid. LCMS (ESI): m/z 405.3 [M+1]⁺.

24.4. Preparation of Methyl 3-(1-(2-chlorobenzyl)-5-methoxy-1H-benzo[d] imidazol-2-yl)-2,2-dimethylpropanoate

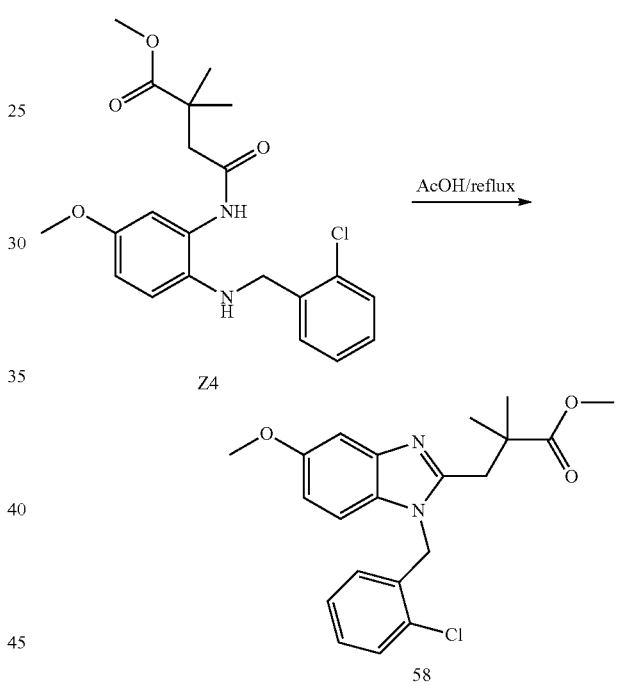

The mixture of methyl 4-((2-((2-chlorobenzyl)amino)-5-methoxyphenyl)amino)-2,2-dimethyl-4-oxobutanoate (1.2 g, 3.0 mmol) in AcOH (30 mL) was stirred for 16 h at 120° C. After cooling to room temperature, the mixture was concentrated, and the residue was purified by column chromatography on silica gel (PE:EA=15:1) to give 1-(2-chlorobenzyl)-2-(1-(4-isobutylphenyl)ethyl)-5-methoxy-1H-benzo[d]imidazole (0.6 g, 1.6 mmol, 53% yield). LCMS (ESI): m/z 405.3[M+1]⁺. ¹HNMR (400 MHz, CDCl₃): δ (ppm) 1.39 (s, 6H), 3.02 (s, 2H), 3.67 (s, 3H), 3.85 (s, 3H), 5.42 (s, 2H), 6.36 (d, J=7.6 Hz, 1H), 6.82 (dd, J=8.8, 2.4 Hz, 1H), 7.00 (d, J=8.8 Hz, 1H), 7.07 (t, J=7.6 Hz, 1H), 7.22 (t, J=7.2 Hz, 1H), 7.28 (dd, J=7.6, 2.0 Hz, 1H 1H), 7.43 (d, J=8.0 Hz, 1H).

24.5. Preparation of 3-(1-(2-chlorobenzyl)-5-methoxy-1H-benzo[d]imidazol-2-yl)-2,2-dimethylpropanoic Acid

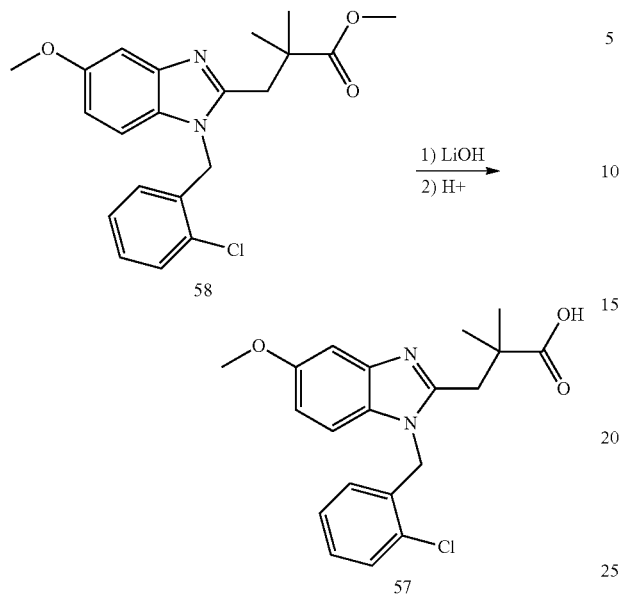

To a mixture of 1-(2-chlorobenzyl)-2-(1-(4-isobutylphenyl)ethyl)-5-methoxy-1H-benzo[d]imidazole (600 mg, 1.55 mmol) in THF (10 mL) and MeOH (10 mL) were added LiOH·H₂O (653 mg, 15.5 mmol) and H₂O (20 mL). The mixture was stirred for 5 h at 65° C. After cooling to room temperature, the mixture was concentrated. The residue was diluted with water (30 mL) and the solution was acidified with 2.0 N HCl (aq) to pH=4~5. The mixture was extracted with DCM (3×20 mL). The organic extracts were combined and dried over anhydrous $Na_2SO_4$, filtered and concentrated. The residue was recrystallizated from EtOAc:PE=1:3 to give 3-(1-(2-chlorobenzyl)-5-methoxy-1H-benzo[d]imidazol-2-yl)-2,2-dimethylpropanoic acid (250 mg, 0.67 mmol, 43% yield) as white solid. LCMS (E SI): m/z 373.3[M+1]⁺. ¹H-NMR (400 MHz, DMSO-d₆): δ (ppm) 1.26 (s, 6H), 2.97 (s, 2H), 3.77 (s, 3H), 5.53 (s, 2H), 6.42 (d, J=7.6 Hz, 1H), 6.77 (dd, J=8.8, 2.4 Hz, 1H), 7.14 (d, J=2.4 Hz, 1H), 7.17-7.24 (m, 2H), 7.32 (t, J=7.6 Hz, 1H), 7.53 (d, J=8.0 Hz, 1H), 12.21 (br s, 1H).

Biological Analysis

To test the effect of the novel compounds on the proliferation of tumor cell, we isolated tumor cells from medulloblastoma developed from mice with deficiency in Patched1 gene. Tumor cells were plated in vitro as previously described, and treated with various concentration of compounds for 48 hours. Tumor cells cultured were then harvested to measure cell survival based on MTT assay. The $IC_{50}$ value for each compound was calculated using Prism the statistical software.

Table 1 below summarizes the $IC_{50}$ data obtained using MB assay for exemplary compounds of the invention. $IC_{50}$ values are shown as A, B, C, or D. A represents $IC_{50}$ value between 1.0 μM and 5.0 μM; B is between 5.0 μM and 10 μM; C is between 10 μM to 20 μM; and D indicates greater than 20 μM.

TABLE 1

$IC_{50}$ results of exemplary compounds

| Compound Number | Structure | $IC_{50}$ |
|---|---|---|
| 1 | 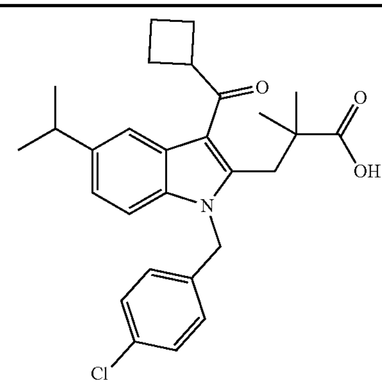 | A |
| 2 | 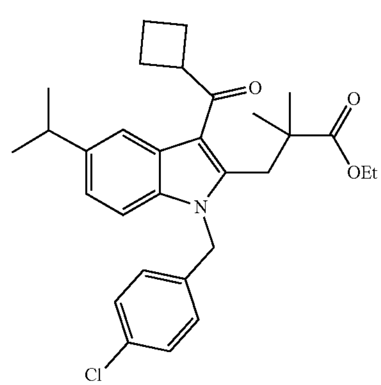 [SMILES: CCOC(=O)C(C)(C)Cc1c(C(=O)C2CCC2)c2cc(C(C)C)ccc2n1Cc1ccc(Cl)cc1] | D |

TABLE 1-continued
| | IC$_{50}$ results of exemplary compounds | |
|---|---|---|
| Compound Number | Structure | IC$_{50}$ |
| 3 | 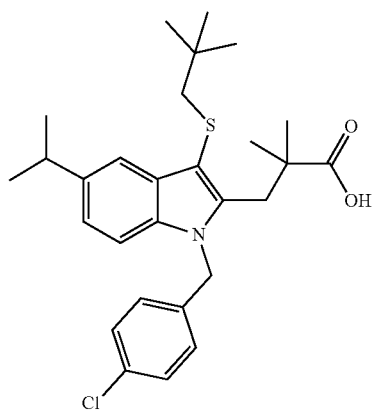 [SMILES: CC(C)c1ccc2c(c1)c(SCC(C)(C)C)c(CC(C)(C)C(=O)O)n2Cc1ccc(Cl)cc1] | A |
| 4 | 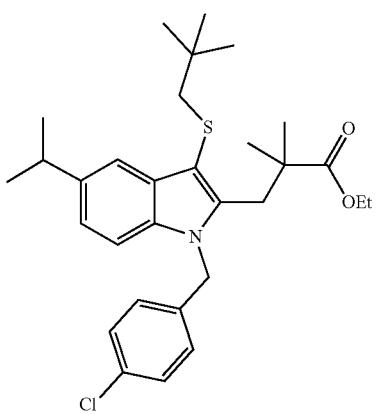 [SMILES: CCOC(=O)C(C)(C)Cc1c(SCC(C)(C)C)c2cc(C(C)C)ccc2n1Cc1ccc(Cl)cc1] | D |
| 5 | 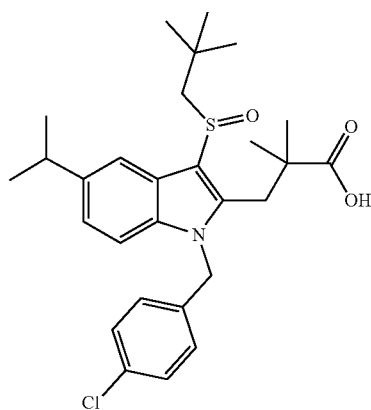 [SMILES: CC(C)c1ccc2c(c1)c(S(=O)CC(C)(C)C)c(CC(C)(C)C(=O)O)n2Cc1ccc(Cl)cc1] | D |

TABLE 1-continued

| IC$_{50}$ results of exemplary compounds | | |
|---|---|---|
| Compound Number | Structure | IC$_{50}$ |
| 6 | *(structure)* | C |
| 7 | *(structure)* | C |
| 8 | *(structure)* | C |

TABLE 1-continued

IC$_{50}$ results of exemplary compounds

| Compound Number | Structure | IC$_{50}$ |
|---|---|---|
| 9 | (structure) | C |
| 10 | (structure) | D |
| 11 | (structure) | B |
| 12 | (structure) | D |

TABLE 1-continued

IC$_{50}$ results of exemplary compounds

| Compound Number | Structure | IC$_{50}$ |
|---|---|---|
| 13 | (structure) | C |
| 14 | (structure) | D |
| 15 | (structure) | D |
| 16 | (structure) | C |

TABLE 1-continued
IC$_{50}$ results of exemplary compounds
| Compound Number | Structure | IC$_{50}$ |
|---|---|---|
| 17 | 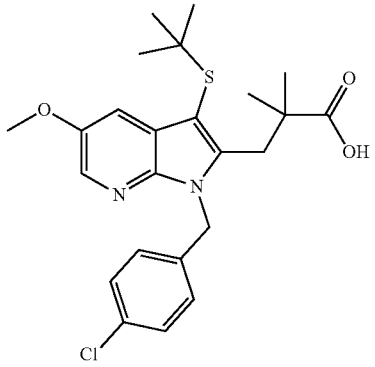 [SMILES: COc1cnc2c(c1)c(SC(C)(C)C)c(CC(C)(C)C(=O)O)n2Cc1ccc(Cl)cc1] | D |
| 18 | 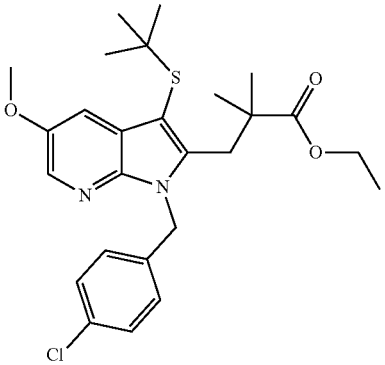 [SMILES: CCOC(=O)C(C)(C)Cc1c(SC(C)(C)C)c2cc(OC)cnc2n1Cc1ccc(Cl)cc1] | D |
| 19 | 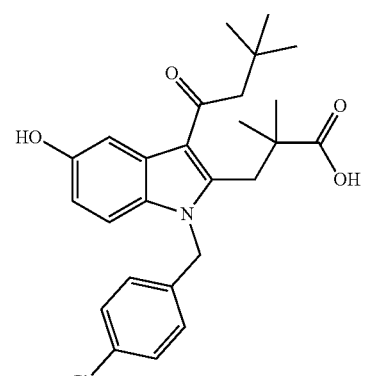 | D |
| 20 | 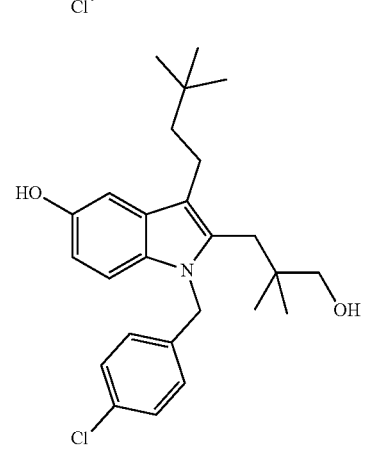 | A |

TABLE 1-continued

IC$_{50}$ results of exemplary compounds

| Compound Number | Structure | IC$_{50}$ |
|---|---|---|
| 21 | (1-(4-chlorobenzyl)-5-methoxy-3-(3,3-dimethylbutanoyl)-1H-indol-2-yl)methyl 2,2-dimethyl-propanoate methyl ester | D |
| 22 | corresponding carboxylic acid (OH) | D |
| 23 | corresponding alcohol (CH$_2$OH) | B |
| 24 | 5-OH analog, methyl ester | A |

TABLE 1-continued

IC$_{50}$ results of exemplary compounds

| Compound Number | Structure | IC$_{50}$ |
|---|---|---|
| 25 | 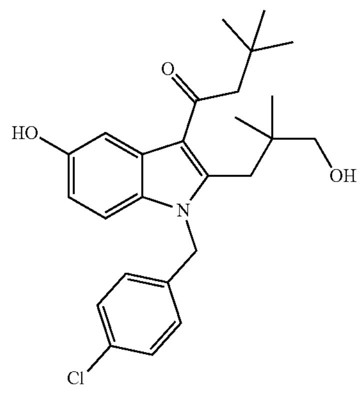 [SMILES: CC(C)(C)CC(=O)c1c(CC(C)(C)CO)n(Cc2ccc(Cl)cc2)c2ccc(O)cc12] | D |
| 26 | 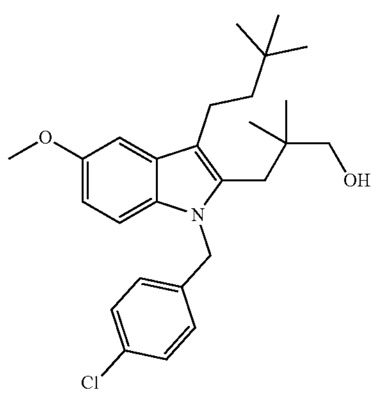 [SMILES: COc1ccc2c(c1)c(CCC(C)(C)C)c(CC(C)(C)CO)n2Cc1ccc(Cl)cc1] | A |
| 27 | 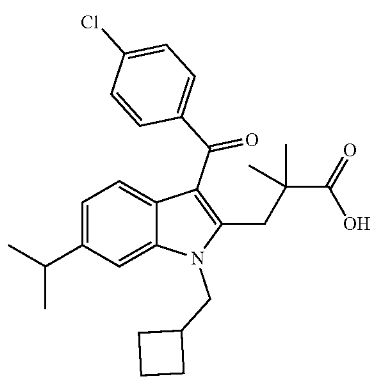 [SMILES: CC(C)c1ccc2c(C(=O)c3ccc(Cl)cc3)c(CC(C)(C)C(=O)O)n(CC3CCC3)c2c1] | B |
| 28 | 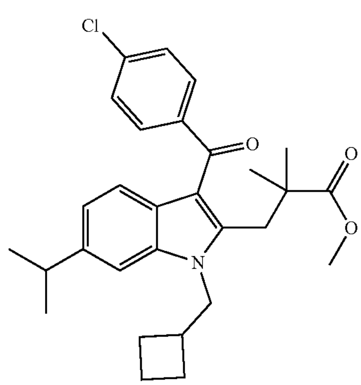 [SMILES: COC(=O)C(C)(C)Cc1c(C(=O)c2ccc(Cl)cc2)c2ccc(C(C)C)cc2n1CC1CCC1] | D |

TABLE 1-continued

| IC$_{50}$ results of exemplary compounds | | |
|---|---|---|
| Compound Number | Structure | IC$_{50}$ |
| 29 | *(structure)* | D |
| 30 | *(structure)* | D |
| 31 | *(structure)* | D |
| 32 | *(structure)* | A |

TABLE 1-continued

IC$_{50}$ results of exemplary compounds

| Compound Number | Structure | IC$_{50}$ |
|---|---|---|
| 33 | (structure) | D |
| 34 | (structure) | B |
| 35 | (structure) or (structure) | B |

TABLE 1-continued
IC$_{50}$ results of exemplary compounds
| Compound Number | Structure | IC$_{50}$ |
|---|---|---|
| 36 | 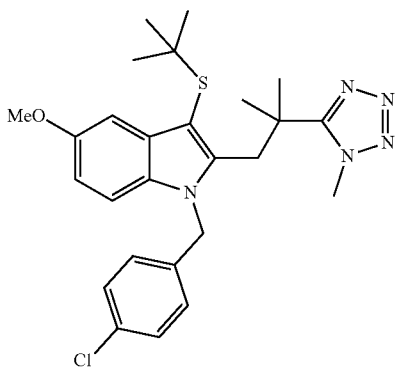 [SMILES: COc1ccc2c(c1)c(SC(C)(C)C)c(CC(C)(C)c1nnnn1C)n2Cc1ccc(Cl)cc1] or 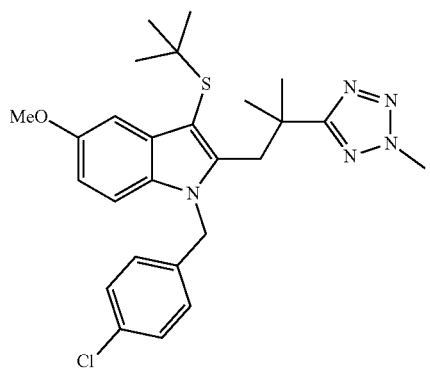 [SMILES: COc1ccc2c(c1)c(SC(C)(C)C)c(CC(C)(C)c1nnn(C)n1)n2Cc1ccc(Cl)cc1] | B |
| 37 | 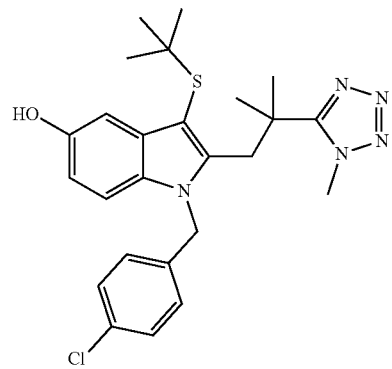 [SMILES: Cn1nnnc1C(C)(C)Cc1c(SC(C)(C)C)c2cc(O)ccc2n1Cc1ccc(Cl)cc1] or 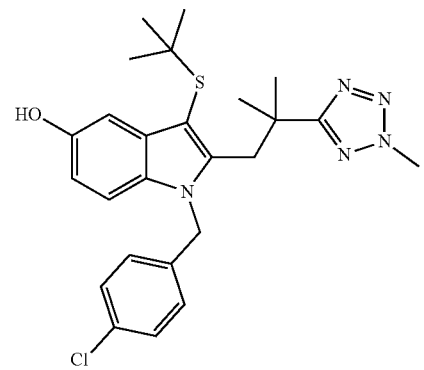 [SMILES: Cn1nnc(C(C)(C)Cc2c(SC(C)(C)C)c3cc(O)ccc3n2Cc2ccc(Cl)cc2)n1] | C |

TABLE 1-continued
| IC$_{50}$ results of exemplary compounds | | |
|---|---|---|
| Compound Number | Structure | IC$_{50}$ |
| 38 | 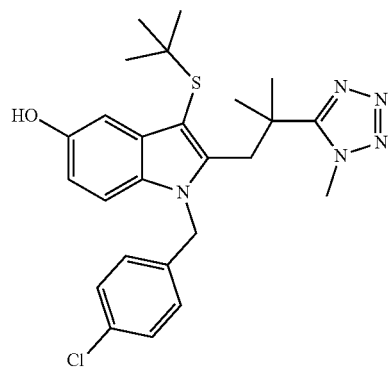 [SMILES: Cn1nnnc1C(C)(C)Cc1c(SC(C)(C)C)c2cc(O)ccc2n1Cc1ccc(Cl)cc1] or 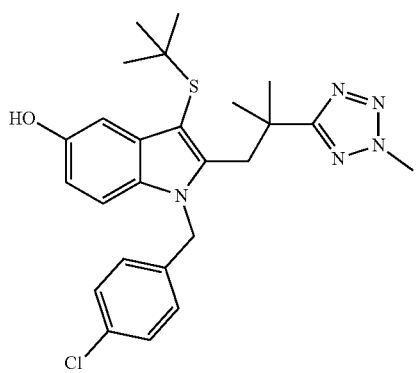 [SMILES: Cn1nnc(C(C)(C)Cc2c(SC(C)(C)C)c3cc(O)ccc3n2Cc2ccc(Cl)cc2)n1] | A |
| 39 | 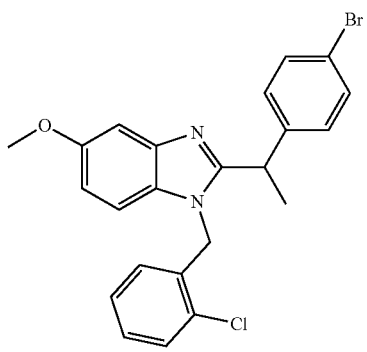 [SMILES: COc1ccc2c(c1)nc(C(C)c1ccc(Br)cc1)n2Cc1ccccc1Cl] | B |
| 40 | 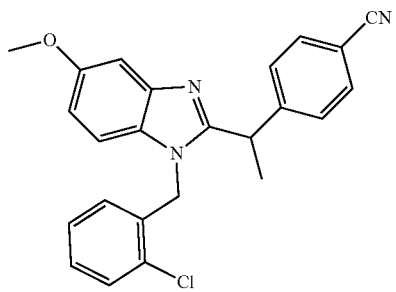 [SMILES: COc1ccc2c(c1)nc(C(C)c1ccc(C#N)cc1)n2Cc1ccccc1Cl] | D |

TABLE 1-continued

IC$_{50}$ results of exemplary compounds

| Compound Number | Structure | IC$_{50}$ |
|---|---|---|
| 41 | (5-methoxy-1-(2-chloropyridin-3-ylmethyl)-1H-benzimidazol-2-yl)ethyl-benzoic acid structure | D |
| 42 | methyl ester analog with 2-chlorobenzyl | D |
| 43 | benzyl alcohol analog with 2-chlorobenzyl | D |
| 44 | benzyl cyanide analog with 2-chlorobenzyl | D |

TABLE 1-continued

IC$_{50}$ results of exemplary compounds

| Compound Number | Structure | IC$_{50}$ |
|---|---|---|
| 45 | 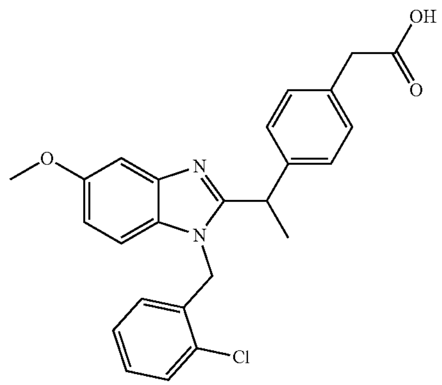 [SMILES: COc1ccc2c(c1)nc(C(C)c1ccc(CC(=O)O)cc1)n2Cc1ccccc1Cl] | D |
| 46 | 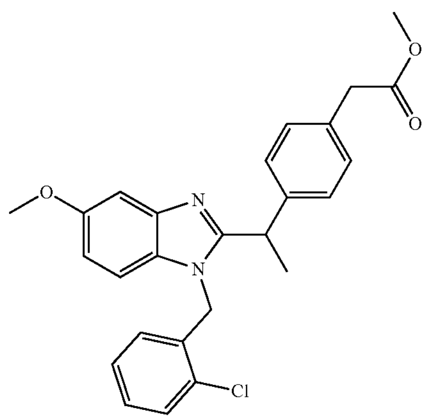 [SMILES: COC(=O)Cc1ccc(C(C)c2nc3cc(OC)ccc3n2Cc2ccccc2Cl)cc1] | C |
| 47 | 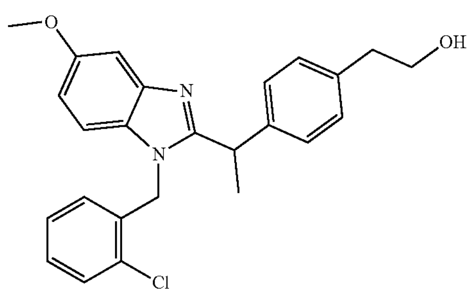 [SMILES: COc1ccc2c(c1)nc(C(C)c1ccc(CCO)cc1)n2Cc1ccccc1Cl] | D |
| 48 | 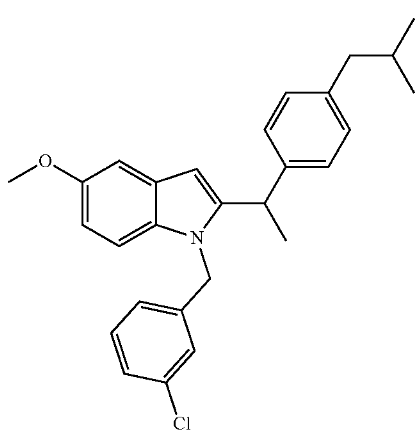 [SMILES: COc1ccc2c(c1)cc(C(C)c1ccc(CC(C)C)cc1)n2Cc1cccc(Cl)c1] | D |

TABLE 1-continued

IC$_{50}$ results of exemplary compounds

| Compound Number | Structure | IC$_{50}$ |
|---|---|---|
| 49 | (5-hydroxy-2-(1-(4-isobutylphenyl)ethyl)-1-(3-chlorobenzyl)-1H-indole) | A |
| 50 | (5-methoxy-2-(4-isobutylphenyl)-1-(2-chlorobenzyl)-1H-benzimidazole) | C |
| 51 | (5-hydroxy-2-(4-isobutylphenyl)-1-(2-chlorobenzyl)-1H-benzimidazole) | B |
| 52 | (6-bromo-2-(1-(4-isobutylphenyl)ethyl)-1-(2-chlorobenzyl)-1H-benzimidazole · CF$_3$COOH) | D |
| 53 | (1-(2-chlorobenzyl)-2-(1-(4-isobutylphenyl)ethyl)-1H-benzimidazole-5-carboxylic acid) | C |

TABLE 1-continued
IC$_{50}$ results of exemplary compounds
| Compound Number | Structure | IC$_{50}$ |
|---|---|---|
| 54 | 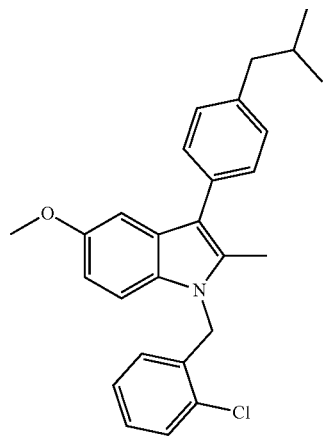 [SMILES: COc1ccc2c(c1)c(-c1ccc(CC(C)C)cc1)c(C)n2Cc1ccccc1Cl] | D |
| 55 | 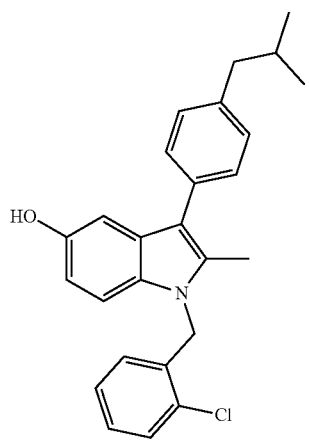 [SMILES: Cc1c(-c2ccc(CC(C)C)cc2)c2cc(O)ccc2n1Cc1ccccc1Cl] | A |
| 56 | 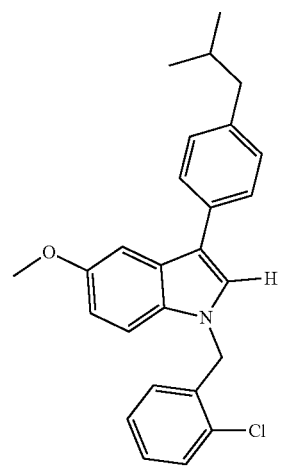 [SMILES: COc1ccc2c(c1)c(-c1ccc(CC(C)C)cc1)cn2Cc1ccccc1Cl] | D |

TABLE 1-continued

IC$_{50}$ results of exemplary compounds

| Compound Number | Structure | IC$_{50}$ |
|---|---|---|
| 57 | 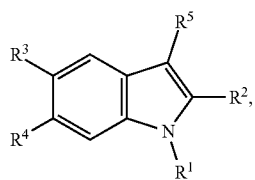 | D |
| 58 | 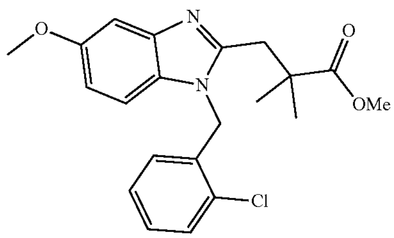 [SMILES: COC(=O)C(C)(C)Cc1nc2cc(OC)ccc2n1Cc1ccccc1Cl] | D |

It will be understood by those of skill in the art that the various embodiments and examples of the present invention described herein are illustrative only and are not intended to limit the scope of the present invention and numerous modifications can be made without departing from the spirit and scope of the present invention.

What is claimed is:

1. A compound of formula (II):

(II)

or a pharmaceutically acceptable salt, solvate or prodrug thereof, wherein:

R$^1$ is

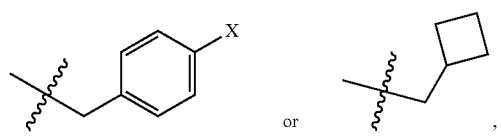

wherein X is Cl;
R$^2$ is selected from

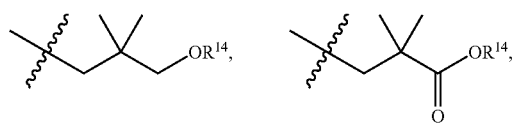

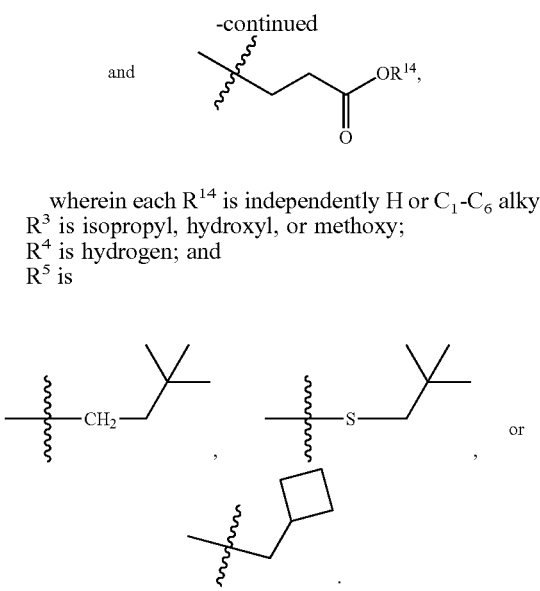

wherein each R$^{14}$ is independently H or C$_1$-C$_6$ alkyl;
R$^3$ is isopropyl, hydroxyl, or methoxy;
R$^4$ is hydrogen; and
R$^5$ is 2. A compound selected from:

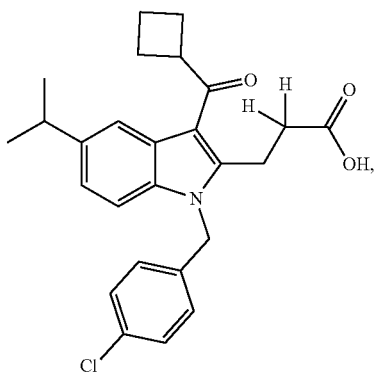

-continued
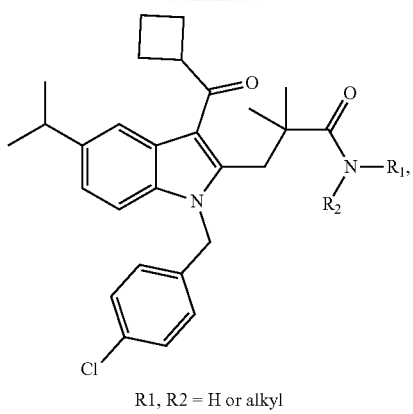
R1, R2 = H or alkyl
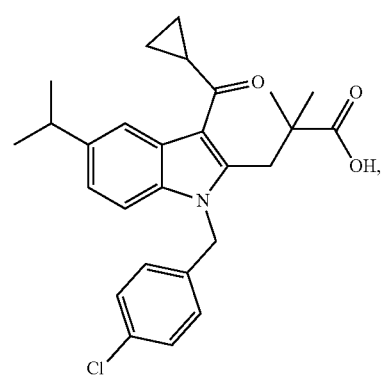
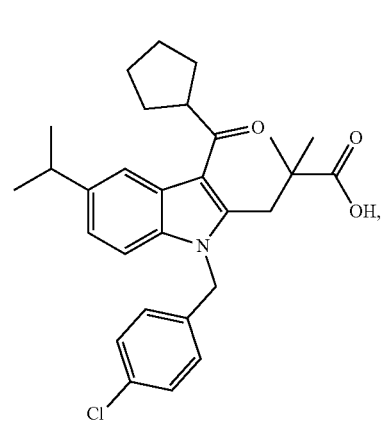
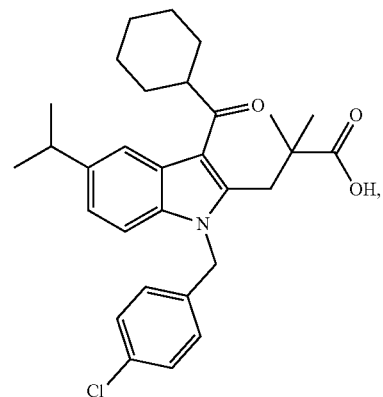
-continued
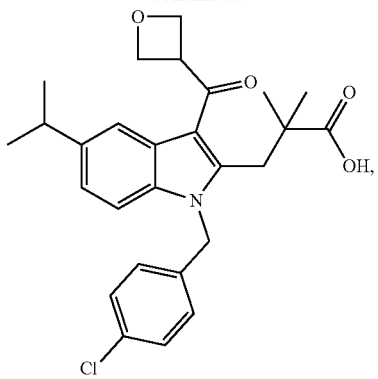
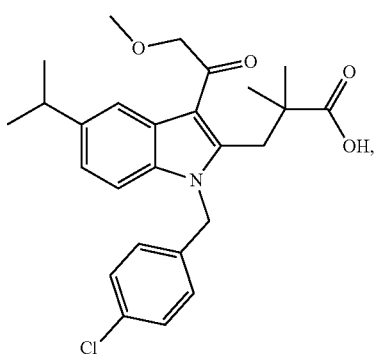
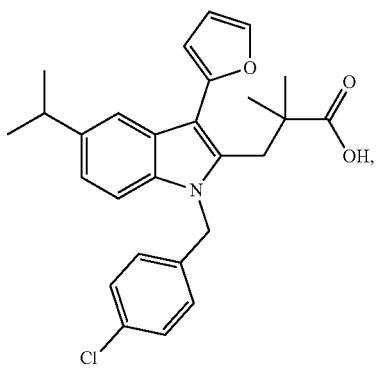
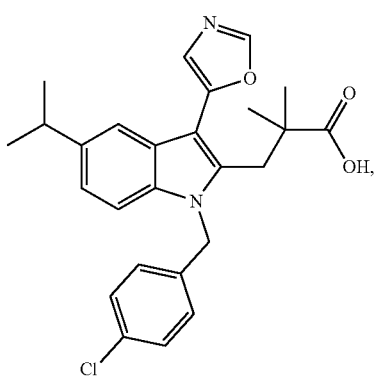

-continued
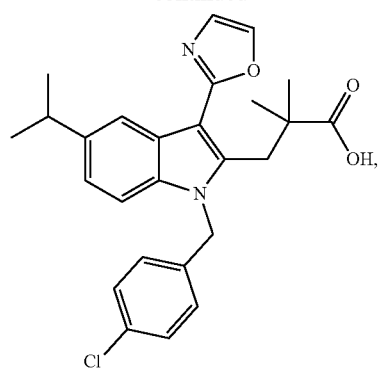
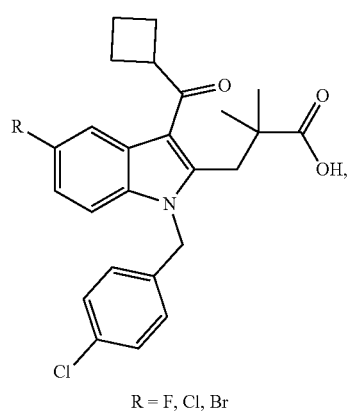
R = F, Cl, Br
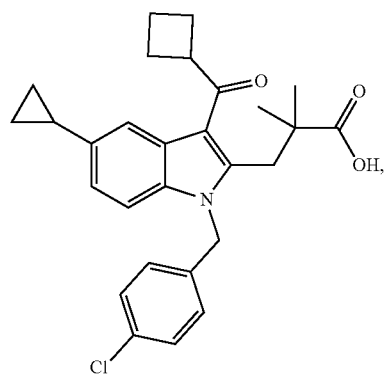
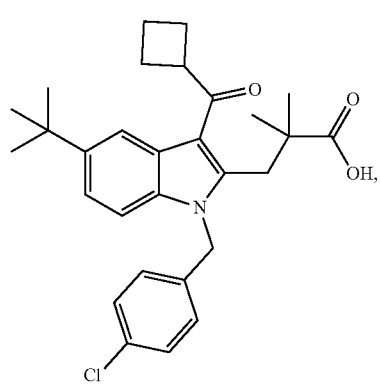
-continued
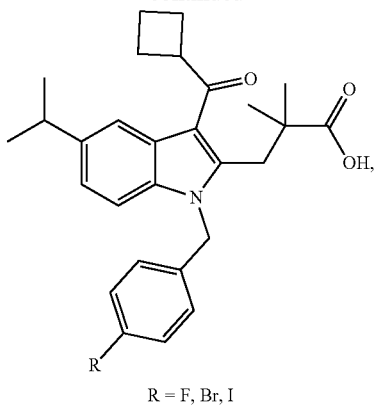
R = F, Br, I
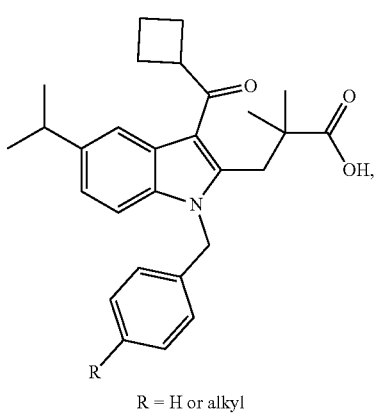
R = H or alkyl
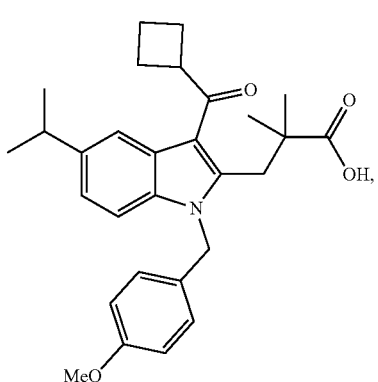
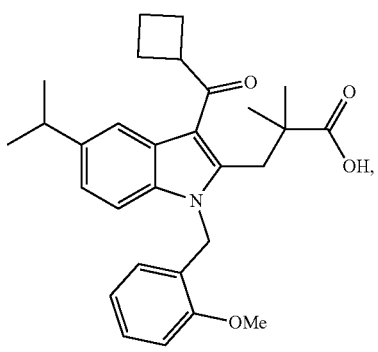

179
-continued
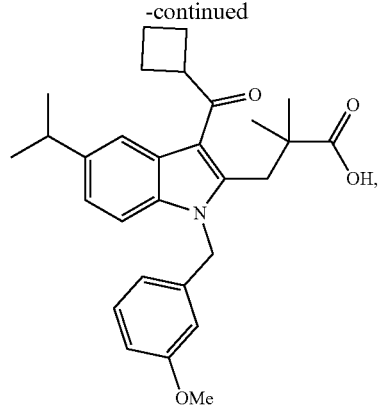
180
-continued
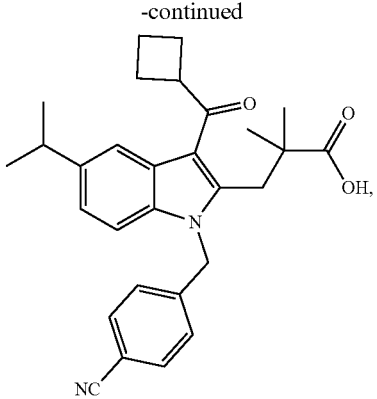
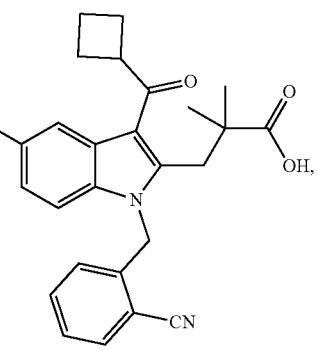
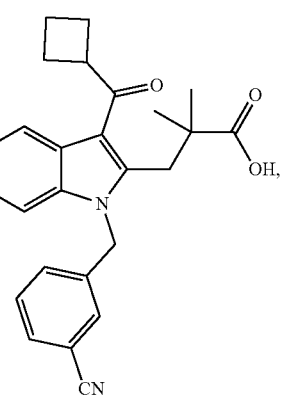
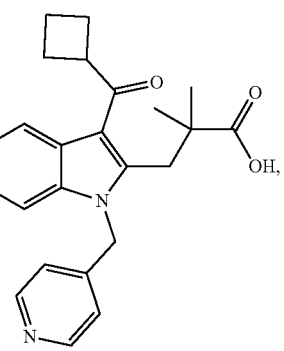

181 -continued
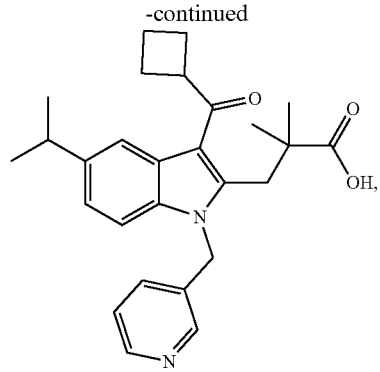
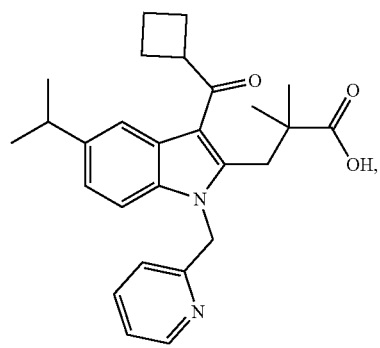
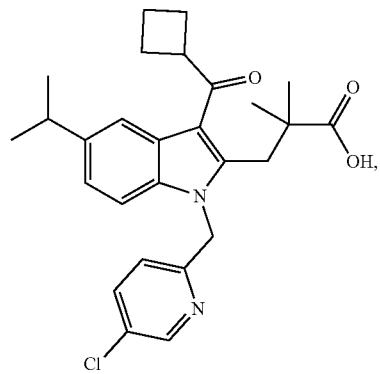
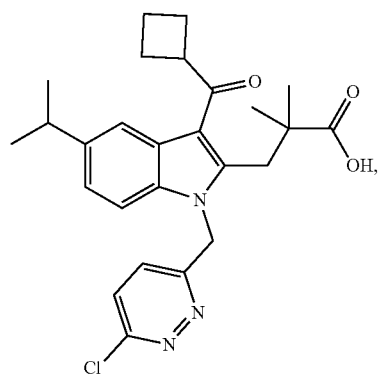
182 -continued
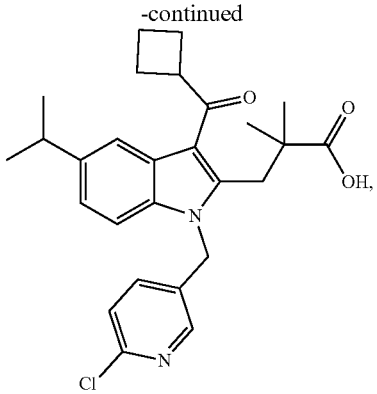
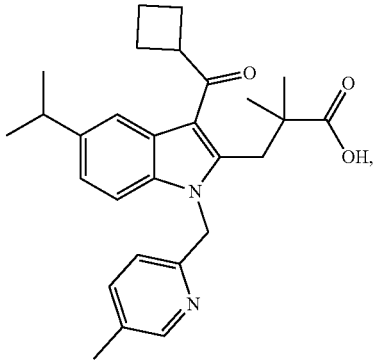
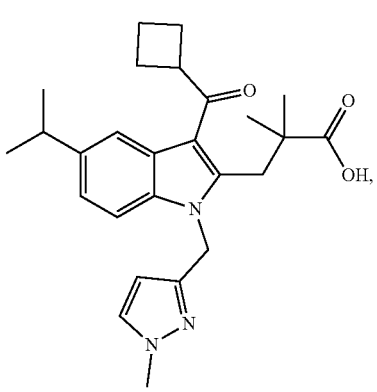
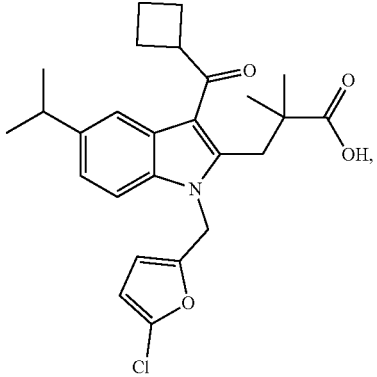

-continued
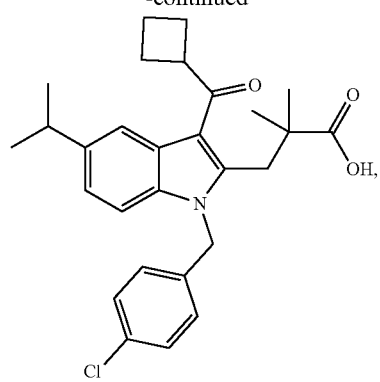
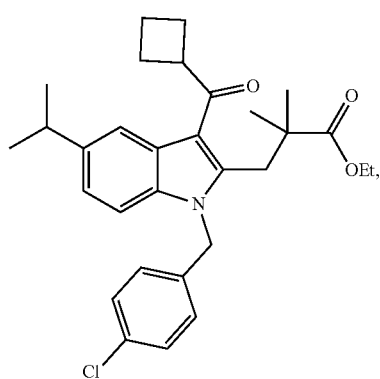
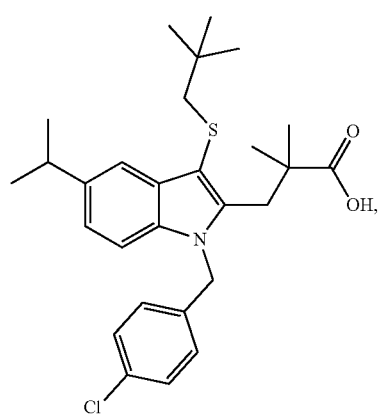
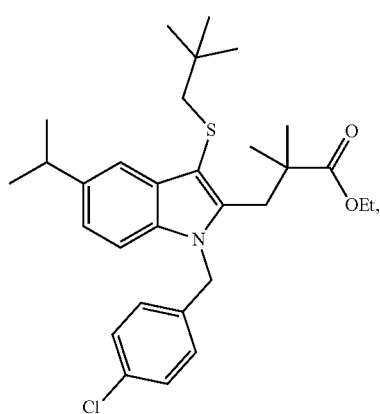
-continued
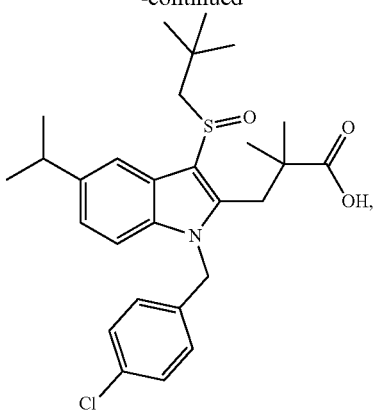
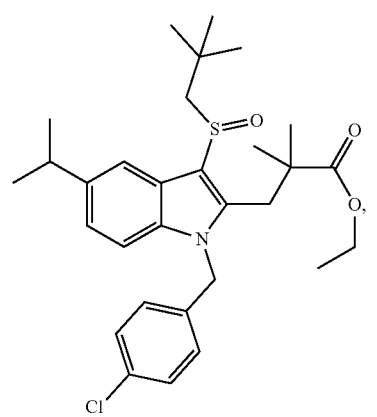
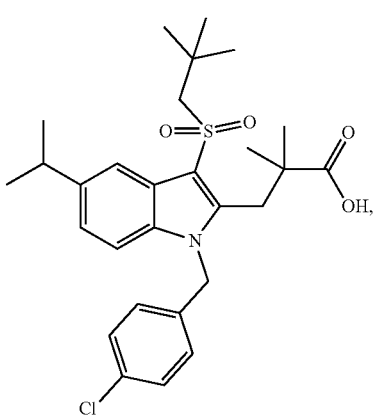
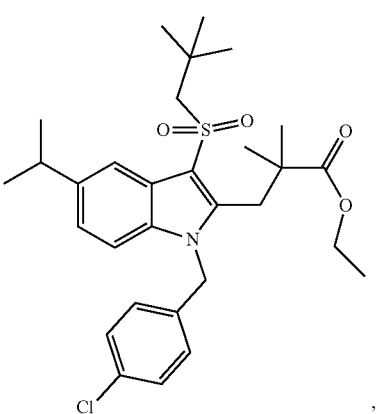

185
-continued
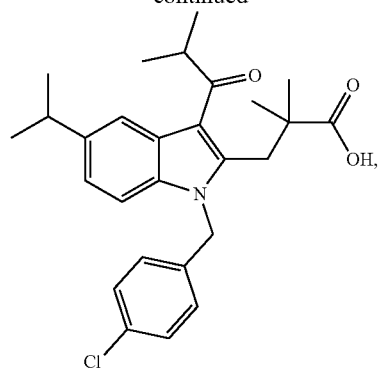
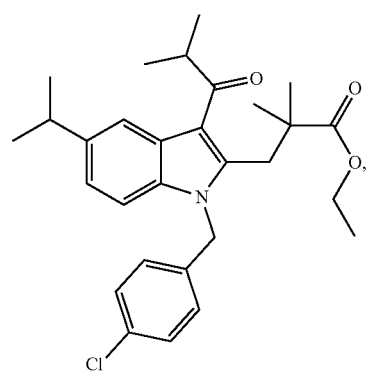
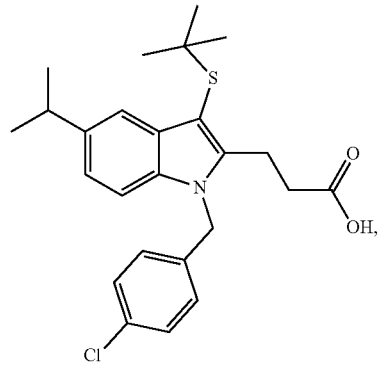
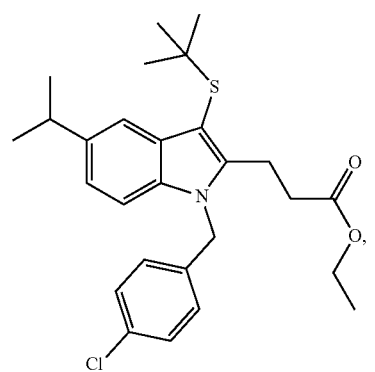
186
-continued
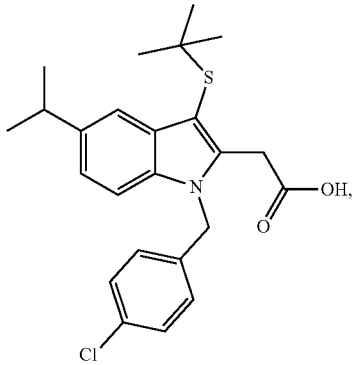
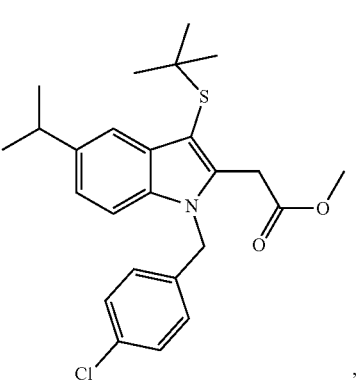
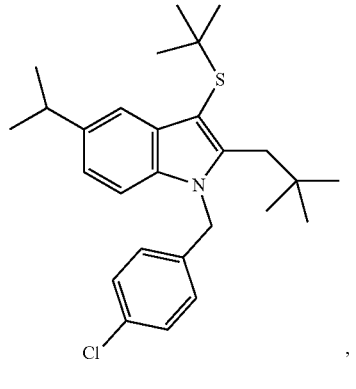
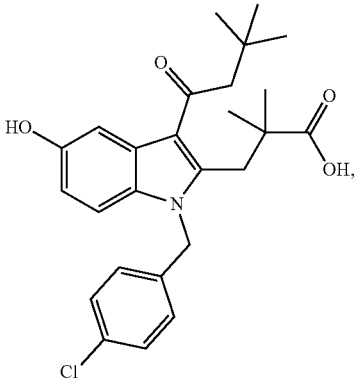

187
-continued
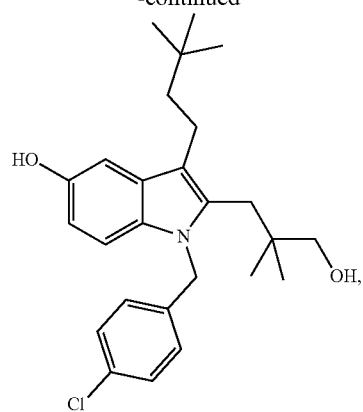
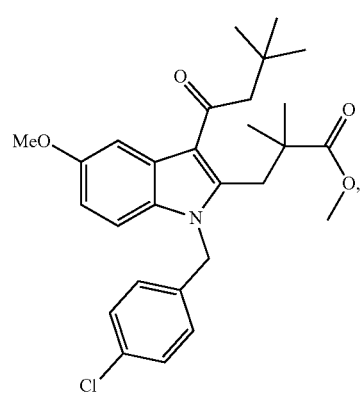
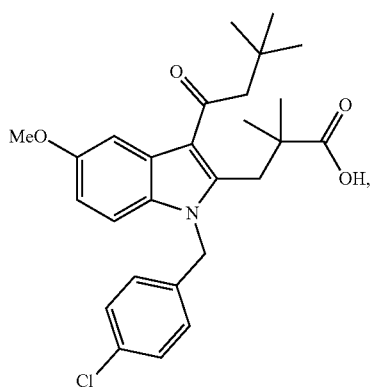
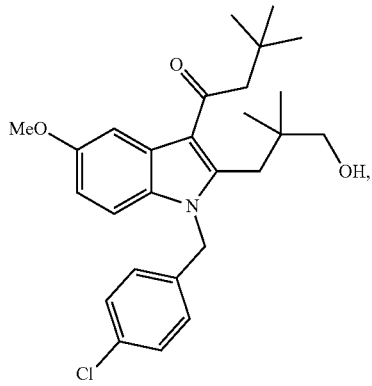
188
-continued
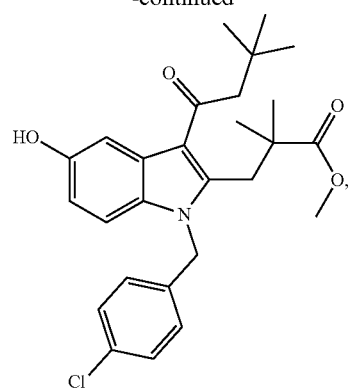
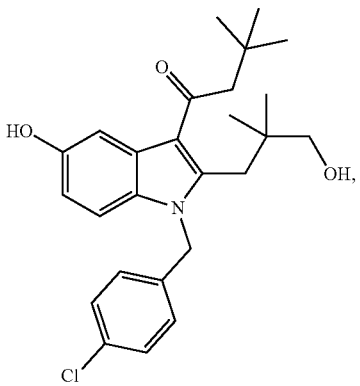
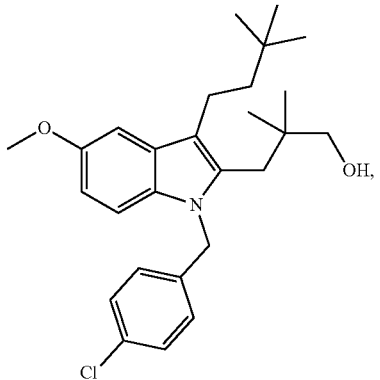
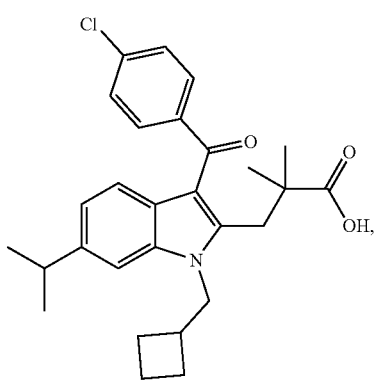

189
-continued
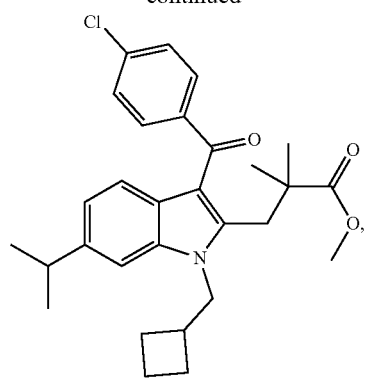
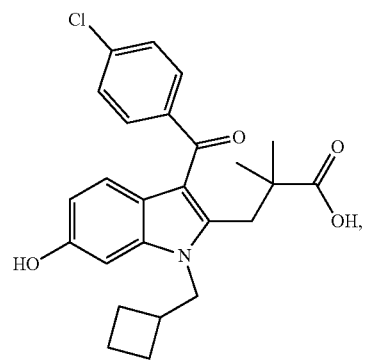
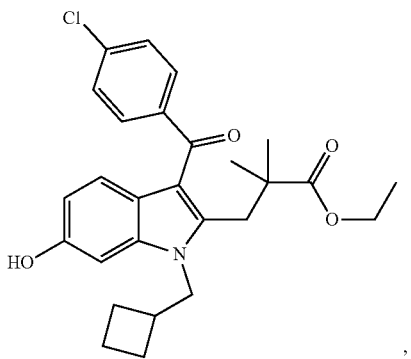
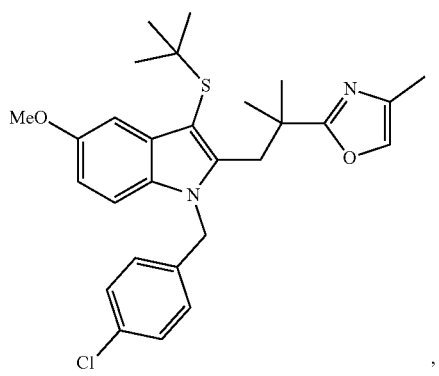
190
-continued
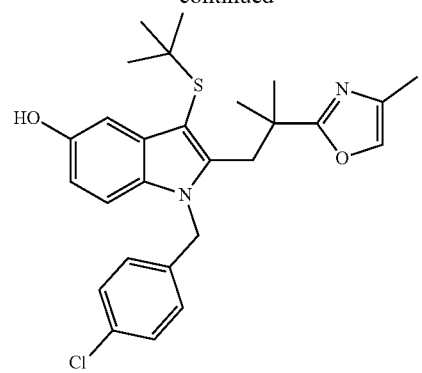
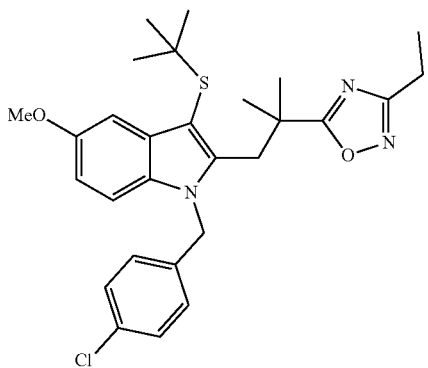
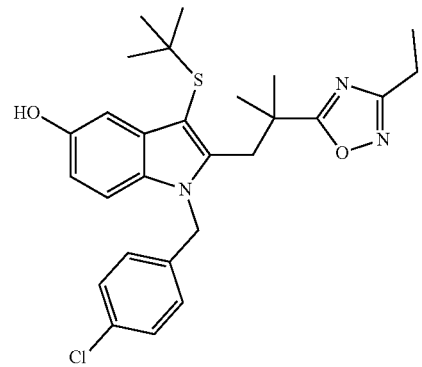
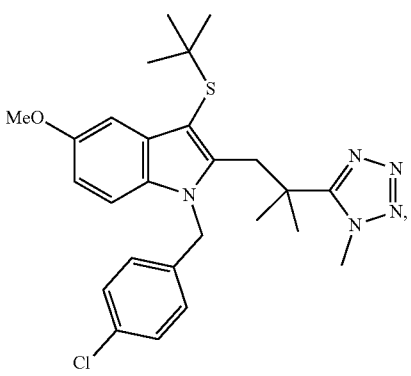

191
-continued
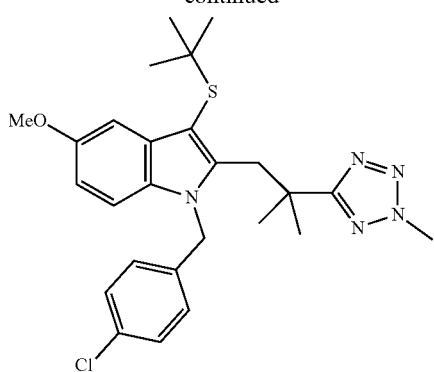
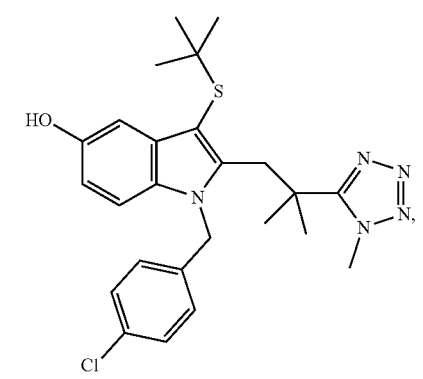
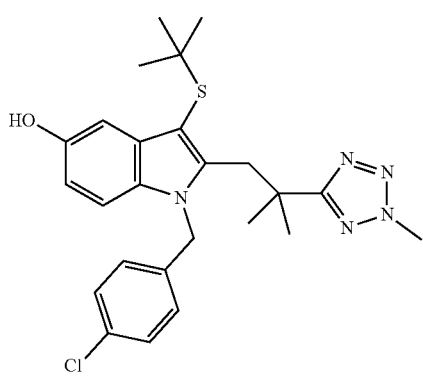
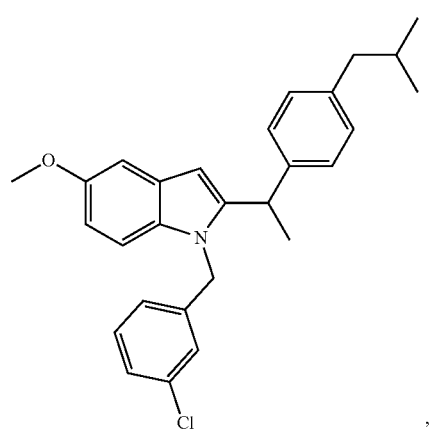
192
-continued
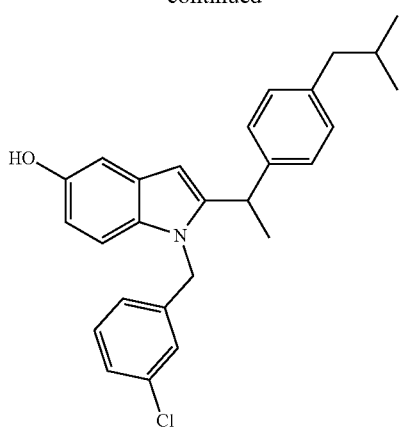
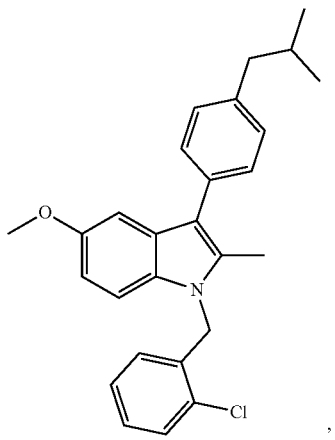
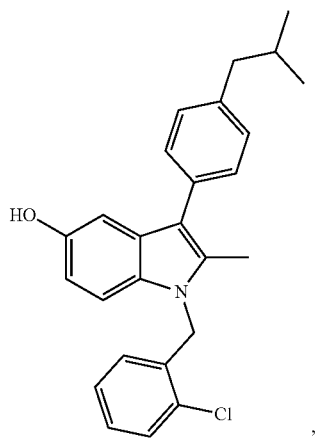
, and -continued

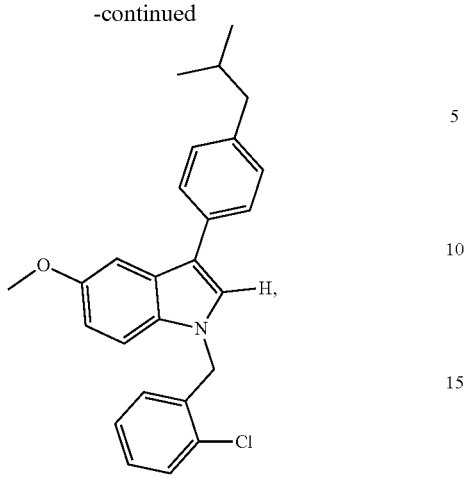

or a pharmaceutically acceptable salt, solvate, or prodrug thereof.

3. A composition comprising a compound of claim 1, or a pharmaceutically acceptable salt, solvate or prodrug thereof, and a pharmaceutically acceptable carrier.

4. A composition comprising a compound of claim 2, or a pharmaceutically acceptable salt, solvate or prodrug thereof, and a pharmaceutically acceptable carrier.

* * * * *